US012172982B2

(12) United States Patent
Lim et al.

(10) Patent No.: US 12,172,982 B2
(45) Date of Patent: Dec. 24, 2024

(54) SYNTHESIS OF QUINAZOLINE COMPOUNDS

(71) Applicants: Genentech, Inc., South San Francisco, CA (US); Hoffmann-La Roche Inc., Little Falls, NJ (US)

(72) Inventors: Ngiap-Kie Lim, Dublin, CA (US); Jeff Shen, Foster City, CA (US); Lauren Elizabeth Sirois, San Francisco, CA (US); Jacob C. Timmerman, San Mateo, CA (US); Etienne Trachsel, Basel (CH); Nicholas Andrew White, San Francisco, CA (US); Jie Xu, San Mateo, CA (US); Haiming Zhang, San Mateo, CA (US); Stephan Bachmann, Allschwil (CH); Raphael Bigler, Basel (CH); Kyle Bradley Pascual Clagg, San Francisco, CA (US); Antonio Giovanni Dipasquale, San Bruno, CA (US); Francis Gosselin, San Mateo, CA (US); Ugo Jonathan Orcel, Basel (CH); Roland Christoph Meier, Basel (CH)

(73) Assignees: Genentech, Inc., South San Francisco, CA (US); Hoffmann-La Roche Inc., Little Falls, NJ (US)

( * ) Notice: Subject to any disclaimer, the term of this patent is extended or adjusted under 35 U.S.C. 154(b) by 42 days.

(21) Appl. No.: 17/398,345

(22) Filed: Aug. 10, 2021

(65) Prior Publication Data

US 2022/0081413 A1 Mar. 17, 2022

Related U.S. Application Data

(60) Provisional application No. 63/064,746, filed on Aug. 12, 2020.

(51) Int. Cl.
*C07D 401/04* (2006.01)
*C07D 401/14* (2006.01)

(52) U.S. Cl.
CPC .................. *C07D 401/14* (2013.01)

(58) Field of Classification Search
CPC ...... C07D 401/14; C07D 401/04; Y02P 20/55
USPC ........................................ 544/284
See application file for complete search history.

(56) References Cited

U.S. PATENT DOCUMENTS

| 5,597,992 | A | 1/1997 | Walker | |
| 5,994,542 | A | 11/1999 | Asada et al. | |
| 6,344,559 | B1 | 5/2002 | Omori et al. | |
| 6,686,471 | B2 * | 2/2004 | Chiu | C07D 487/04 |
| | | | | 544/350 |
| 8,362,263 | B2 * | 1/2013 | Cho | A61P 9/00 |
| | | | | 546/321 |
| 11,236,068 | B2 * | 2/2022 | Malhotra | C07D 405/14 |
| 2017/0190672 | A1 * | 7/2017 | Mani | C07F 3/06 |

FOREIGN PATENT DOCUMENTS

| CN | 102686581 | | 9/2012 | |
| JP | 2013-107855 | | 6/2013 | |
| JP | 2016-532656 | A | 10/2016 | |
| JP | 2018-533611 | A | 11/2018 | |
| JP | 2023-531269 | A | 7/2023 | |
| WO | 03/033478 | | 4/2003 | |
| WO | 2006/051290 | A2 | 5/2006 | |
| WO | 2007/071055 | A1 | 6/2007 | |
| WO | 2010/146173 | | 12/2010 | |
| WO | 2012/058671 | | 5/2012 | |
| WO | 2015/054572 | | 4/2015 | |
| WO | 2015/054572 | A1 | 5/2015 | |
| WO | WO-2017087528 | A1 * | 5/2017 | ........... A61K 31/517 |
| WO | 2019/215203 | A1 | 11/2019 | |
| WO | 2020/097537 | A2 | 5/2020 | |
| WO | 2022/002102 | A1 | 1/2022 | |

OTHER PUBLICATIONS

Colombe et al., Org. Lett., vol. 15, No. 22, 2013, 5754-5757, "Synthesis of Solid 2 Pyridylzinc Reagents and Their Application in Negishi Reactions") (Year: 2013).*
Keinan et al., Isr. J. Chem. 2018, 58, 7-10, "Organic Synthesis: From Glorious Past to Brilliant Future" (Year: 2018).*
Colombe et al. Org. Lett., vol. 15, No. 22, 2013, 5754-5757, Synthesis of Solid 2 Pyridylzinc Reagents and Their Application in Negishi Rea (Year: 2013).*
International Search Report for PCT/US2021/045297 mailed Oct. 14, 2021; pp. 1-6.
Genov et al., "Asymmetric Negishi reaction for sterically hindered couplings: synthesis of chiral binaphthalenes" Tetrahedron: Asymmetry 17:2593-2595 ( 2006).
Genov et al., "Microwave assisted asymmetric Suzuki-Miyaura and Negishi cross-coupling reactions: synthesis of chiral binaphthalenes" Tetrahedron: Asymmetry 18:625-627 (Mar. 1, 2007).
Patel et al., "Computationally Assisted Mechanistic Investigation and Development of Pd-Catalyzed Asymmetric Suzuki-Miyaura and Negishi Cross-Coupling Reactions for Tetra-ortho-Substituted Biaryl Synthesis" ACS Catal 8:10190-10209 ( 2018).
Wang et al., "Quinazoline derivatives: synthesis and bioactivities" Chemistry Central Journal 7(95):1-15 (2013).
Yang et al., "Hindered Biaryl Bond Construction and Subsequent Diastereomeric Crystallization to Produce an Atropisomeric Covalent KRAS$^{G12C}$ Inhibitor ARS-2102" Org. Process Res. Dev. 27:206-216 ( 2023).
"International Preliminary Report on Patentability—PCT/US2021/045297" (Report Issuance Date: Feb. 7, 2023; Chapter I),:pp. 1-7 (Feb. 23, 2023).
Kubasov Chemical kinetics and catalysis. "Chapter 1" Moscow:Moscow University Press,:2-3 ( 2004).
Smit, W., et al., "Organieskij sintez. Nauka i iskusstvo" Organic synthesis. Science and art, Moscow, Mir 573:64 ( 2001).

* cited by examiner

*Primary Examiner* — Jared Barsky
*Assistant Examiner* — Liyuan Mou
(74) *Attorney, Agent, or Firm* — Genentech, Inc.

(57) ABSTRACT

Provided herein are methods of synthesizing quinazoline compounds comprising at least one atropisomeric center.

52 Claims, 6 Drawing Sheets

SYNTHESIS OF QUINAZOLINE COMPOUNDS

CROSS REFERENCE TO RELATED APPLICATIONS

This application claims the benefit of U.S. Provisional Patent Application No. 63/064,746, filed 12 Aug. 2020, which is incorporated herein by reference in its entirety and for all purposes.

FIELD OF INVENTION

Provided herein are processes to synthesize atropisomers of quinazolinyl compounds via atropselective synthetic methods/techniques.

BACKGROUND

The configuration at a biaryl axis often plays an important role for pharmacological properties of bioactive compounds and is a fundamental basis for useful reagents and catalysts in asymmetric synthesis. Highly atroposelective cross-couplings, especially those of heterocycles for the synthesis of biheteroaryls, remain a challenging and unsolved problem. The present disclosure provides improved processes for the atroposelective synthesis of aminopyridinyl-quinazolinyl compounds via Negishi coupling utilizing a chiral ligand such as chiraphite or walphos.

SUMMARY

Provided herein are solutions to the problems above and other problems in the art.

Disclosed herein are compounds and processes for making compounds of formula (I) as described herein.

In one aspect provided herein is a process for the synthesis of compounds of formula (I) as described herein, the process comprising (a) contacting a compound of formula (II) as described herein with an organomagnesium compound and a zinc complex and (b) contacting the mixture of step (a) with a compound of formula (III) as described herein, a transition metal (e.g. Pd or Ni) catalyst precursor, and a chiral ligand, thereby synthesizing a compound of formula (I).

In one aspect provided herein are compounds of formula (I) as described herein or a solvate, tautomer, stereoisomer, atropisomer, or salt thereof. In one aspect provided herein the compound of formula (I) has formula Ia, Ib, Ib1, Ib2, Ib3, Ic1, Ic2, Id, 1a, 1b, 1c, or 1 as described herein.

In another aspect provided herein are processes for the preparation of a compound of formula (I) comprising: (a) contacting a compound of formula (II) as described herein or a tautomer, stereoisomer, or salt thereof with an organomagnesium compound and a zinc complex; and (b) contacting the mixture of step (a) with a compound of formula (III) as described herein or a stereoisomer or salt thereof, a transition metal (e.g. Pd or Ni) catalyst precursor, and a chiral ligand, thereby synthesizing a compound of formula (I) or a solvate, tautomer, stereoisomer, atropisomer, or salt thereof.

Further provided herein is a process (P2) as described herein for the preparation of a compound of formula (II) as described herein or a tautomer, stereoisomer, or salt thereof.

In another aspect provided herein is a process (P3) as described herein for the preparation of a compound of formula (III) as described herein or a salt thereof.

In another aspect provided herein is a process (P4) as described herein for the preparation of a compound of formula (III) as described herein or a salt thereof.

In another aspect provided herein is a process (P5) as described herein for the preparation of a compound of formula (III) as described herein or a salt thereof.

In another aspect provided herein is a process (P6) as described herein for the preparation of a compound of formula (G) as described herein or a tautomer, stereoisomer, atropisomer, or pharmaceutically acceptable salt thereof.

In another aspect provided herein is a process (P7) as described herein for the preparation of a compound of formula (H) as described herein or a tautomer, stereoisomer, atropisomer, or pharmaceutically acceptable salt thereof.

In another aspect provided herein is a process (P8) as described herein for the preparation of a compound of formula (F) as described herein or a tautomer, stereoisomer, atropisomer, or pharmaceutically acceptable salt thereof.

In another aspect provided herein is a process (P8) as described herein for the preparation of a compound of formula (F) as described herein or a pharmaceutically acceptable salt thereof.

DETAILED DESCRIPTION

Definitions

Figure 1:
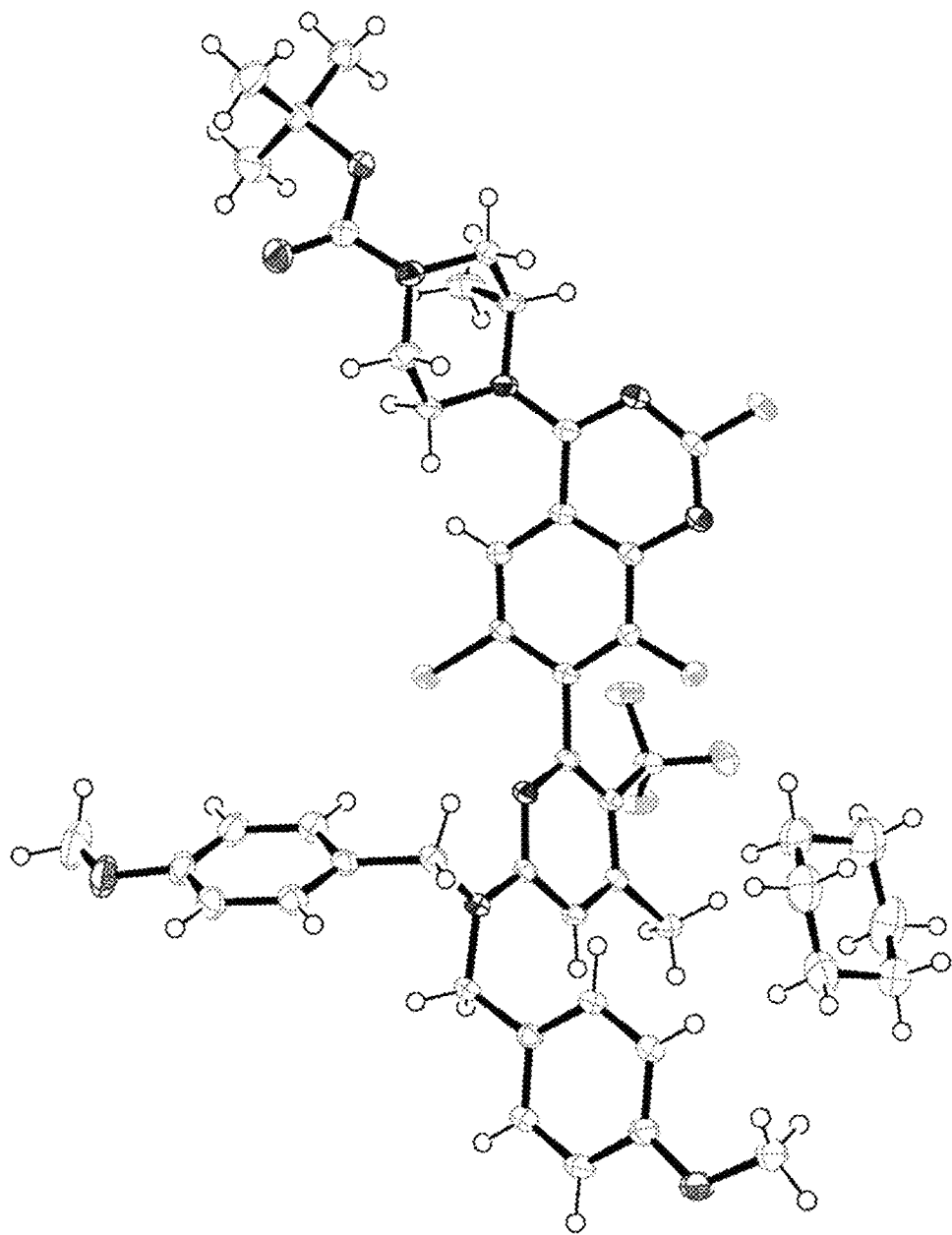
FIG. 1 shows the single crystal structure of a cyclohexane crystalline solvate of compound 1.

The terms "halogen" and "halo" are used interchangeably herein and refer to F, Cl, Br, or I.

The term "alkyl" refers to a saturated linear or branched-chain monovalent hydrocarbon group. In one example, the alkyl group is one to eighteen carbon atoms ($C_{1-18}$). In other examples, the alkyl group is $C_{1-12}$, $C_{1-10}$, $C_{1-8}$, $C_{1-6}$, $C_{1-5}$, $C_{1-4}$, or $C_{1-3}$. Examples of alkyl groups include methyl (Me, —$CH_3$), ethyl (Et, —$CH_2CH_3$), 1-propyl (n-Pr, n-propyl, —$CH_2CH_2CH_3$), 2-propyl (i-Pr, i-propyl, —$CH(CH_3)_2$), 1-butyl (n-Bu, n-butyl, —$CH_2CH_2CH_2CH_3$), 2-methyl-1-propyl (i-Bu, i-butyl, —$CH_2CH(CH_3)_2$), 2-butyl (s-Bu, s-butyl, —$CH(CH_3)CH_2CH_3$), 2-methyl-2-propyl (t-Bu, t-butyl, —$C(CH_3)_3$), 1-pentyl (n-pentyl, —$CH_2CH_2CH_2CH_2CH_3$), 2-pentyl (—$CH(CH_3)CH_2CH_2CH_3$), 3-pentyl (—$CH(CH_2CH_3)_2$), 2-methyl-2-butyl (—$C(CH_3)_2CH_2CH_3$), 3-methyl-2-butyl (—$CH(CH_3)CH(CH_3)_2$), 3-methyl-1-butyl (—$CH_2CH_2CH(CH_3)_2$), 2-methyl-1-butyl (—$CH_2CH(CH_3)CH_2CH_3$), 1-hexyl (—$CH_2CH_2CH_2CH_2CH_2CH_3$), 2-hexyl (—$CH(CH_3)CH_2CH_2CH_2CH_3$), 3-hexyl (—$CH(CH_2CH_3)(CH_2CH_2CH_3)$), 2-methyl-2-pentyl (—$C(CH_3)_2CH_2CH_2CH_3$), 3-methyl-2-pentyl (—$CH(CH_3)CH(CH_3)CH_2CH_3$), 4-methyl-2-pentyl (—$CH(CH_3)CH_2CH(CH_3)_2$), 3-methyl-3-pentyl (—$C(CH_3)(CH_2CH_3)_2$), 2-methyl-3-pentyl (—CH(CH$_2$CH$_3$)CH(CH$_3$)$_2$), 2,3-dimethyl-2-butyl (—C(CH$_3$)$_2$CH(CH$_3$)$_2$), 3,3-dimethyl-2-butyl (—CH(CH$_3$)C(CH$_3$)$_3$), 1-heptyl and 1-octyl.

The term "haloalkyl" refers to an alkyl chain in which one or more hydrogen has been replaced by a halogen. Examples of haloalkyls are trifluoromethyl, difluoromethyl, and fluoromethyl. A "fluoroalkyl" refers to an alkyl chain in which one or more hydrogen has been replaced by F.

The term "amino" refers to —NH$_2$.

The term "oxo" refers to =O.

The term "carboxy" refers to —C(=O)OH.

The term "alkoxy" refers to —O-alkyl.

The terms "cyano" and "nitrile" are used interchangeably herein and refer to —C≡N or —CN.

The term "cyanoalkyl" refers to alkyl substituted with one cyano substituent.

The term "haloalkoxy" refers to —O-haloalkyl.

The term "hydroxy" refers to —OH.

The term "hydroxyalkyl" refers to alkyl substituted with one hydroxy substituent.

The term "aryl" refers to a carbocyclic aromatic group, whether or not fused to one or more groups, having the number of carbon atoms designated, or if no number is designated, up to 14 carbon atoms. One example includes aryl groups having 6-14 carbon atoms. Another example includes aryl groups having 6-10 carbon atoms. Another example includes aryl groups having 5-7 carbon atoms. Examples of aryl groups include phenyl, naphthyl, biphenyl, phenanthrenyl, naphthacenyl, 1,2,3,4-tetrahydronaphthalenyl, 1H-indenyl, 2,3-dihydro-1H-indenyl, and the like (see, e.g., Lang's Handbook of Chemistry (Dean, J. A., ed.) 13$^{th}$ ed. Table 7-2 [1985]). A particular aryl is phenyl.

The term "cycloalkyl" refers to a saturated hydrocarbon ring group. Cycloalkyl encompasses mono-, bi-, tricyclic, spiro and bridged, saturated ring systems. In one example, the cycloalkyl group is 3 to 12 carbon atoms (C$_{3-12}$). In other examples, cycloalkyl is C$_{3-7}$, C$_{3-8}$, C$_{3-10}$, or C$_{5-10}$. In other examples, the cycloalkyl group, as a monocycle, is C$_{3-8}$, C$_{3-6}$, or C$_{5-6}$. In another example, the cycloalkyl group, as a bicycle, is C$_7$-C$_{12}$. In another example, the cycloalkyl group, as a spiro system, is C$_{5-12}$. Examples of monocyclic cycloalkyl include cyclopropyl, cyclobutyl, cyclopentyl, cyclohexyl, cycloheptyl, cyclooctyl, cyclononyl, cyclodecyl, cycloundecyl and cyclododecyl. Exemplary arrangements of bicyclic cycloalkyls having 7 to 12 ring atoms include, but are not limited to, [4,4], [4,5], [5,5], [5,6] or [6,6] ring systems. Exemplary bridged bicyclic cycloalkyls include, but are not limited to, bicyclo[2.2.1]heptane, bicyclo[2.2.2]octane and bicyclo[3.2.2]nonane. Examples of spirocycloalkyl include, spiro[2.2]pentane, spiro[2.3]hexane, spiro[2.4]heptane, spiro[2.5]octane and spiro[4.5]decane.

The terms "heterocyclic group", "heterocyclic", "heterocycle", "heterocyclyl", or "heterocyclo" are used interchangeably and refer to any mono-, bi-, tricyclic, spiro or bridged, saturated, partially saturated or unsaturated, non-aromatic ring system, having 3 to 20 ring atoms, where the ring atoms are carbon, and at least one atom in the ring or ring system is a heteroatom selected from nitrogen, sulfur or oxygen. If any ring atom of a cyclic system is a heteroatom, that system is a heterocycle, regardless of the point of attachment of the cyclic system to the rest of the molecule. In one example, heterocyclyl includes 3-11 ring atoms ("members") and includes monocycles, bicycles, tricycles, spiro, and bridged ring systems, wherein the ring atoms are carbon, where at least one atom in the ring or ring system is a heteroatom selected from nitrogen, sulfur or oxygen. In other examples, heterocyclyl includes 4-10 or 5-10 ring atoms. In one example, heterocyclyl includes 1 to 4 heteroatoms. In one example, heterocyclyl includes 1 to 3 heteroatoms. In another example, heterocyclyl includes 3- to 7-membered monocycles having 1-2, 1-3 or 1-4 heteroatoms selected from nitrogen, sulfur or oxygen. In another example, heterocyclyl includes 4- to 6-membered monocycles having 1-2, 1-3 or 1-4 heteroatoms selected from nitrogen, sulfur or oxygen. In another example, heterocyclyl includes 3-membered monocycles. In another example, heterocyclyl includes 4-membered monocycles. In another example, heterocyclyl includes 5-6 membered monocycles. In some embodiments, a heterocycloalkyl includes at least one nitrogen. In one example, the heterocyclyl group includes 0 to 3 double bonds. Any nitrogen or sulfur heteroatom may optionally be oxidized (e.g., NO, SO, SO$_2$), and any nitrogen heteroatom may optionally be quaternized (e.g., [NR$_4$]$^+$Cl$^-$, [NR$_4$]$^+$OH$^-$). Example heterocycles are oxiranyl, aziridinyl, thiiranyl, azetidinyl, oxetanyl, thietanyl, 1,2-dithietanyl, 1,3-dithietanyl, pyrrolidinyl, dihydro-1H-pyrrolyl, dihydrofuranyl, tetrahydrofuranyl, dihydrothienyl, tetrahydrothienyl, imidazolidinyl, piperidinyl, piperazinyl, isoquinolinyl, tetrahydroisoquinolinyl, morpholinyl, thiomorpholinyl, 1,1-dioxo-thiomorpholinyl, dihydropyranyl, tetrahydropyranyl, hexahydrothiopyranyl, hexahydropyrimidinyl, oxazinanyl, thiazinanyl, thioxanyl, homopiperazinyl, homopiperidinyl, azepanyl, oxepanyl, thiepanyl, oxazepinyl, oxazepanyl, diazepanyl, 1,4-diazepanyl, diazepinyl, thiazepinyl, thiazepanyl, tetrahydrothiopyranyl, oxazolidinyl, thiazolidinyl, isothiazolidinyl, 1,1-dioxoisothiazolidinonyl, 1,1-dioxoisothiazolyl, oxazolidinonyl, imidazolidinonyl, 4,5,6,7-tetrahydro[2H]indazolyl, tetrahydrobenzoimidazolyl, 4,5,6,7-tetrahydrobenzo[d]imidazolyl, thiazinyl, oxazinyl, thiadiazinyl, oxadiazinyl, dithiazinyl, dioxazinyl, oxathiazinyl, thiatriazinyl, oxatriazinyl, dithiadiazinyl, imidazolinyl, dihydropyrimidyl, tetrahydropyrimidyl, 1-pyrrolinyl, 2-pyrrolinyl, 3-pyrrolinyl, indolinyl, thiapyranyl, 2H-pyranyl, 4H-pyranyl, dioxanyl, 1,3-dioxolanyl, pyrazolinyl, pyrazolidinyl, dithianyl, dithiolanyl, pyrimidinonyl, pyrimidindionyl, pyrimidin-2,4-dionyl, piperazinonyl, piperazindionyl, pyrazolidinylimidazolinyl, 3-azabicyclo[3.1.0]hexanyl, 3,6-diazabicyclo[3.1.1]heptanyl, 6-azabicyclo[3.1.1]heptanyl, 3-azabicyclo[3.1.1]heptanyl, 3-azabicyclo[4.1.0]heptanyl, azabicyclo[2.2.2]hexanyl, 2-azabicyclo[3.2.1]octanyl, 8-azabicyclo[3.2.1]octanyl, 2-azabicyclo[2.2.2]octanyl, 8-azabicyclo[2.2.2]octanyl, 7-oxabicyclo[2.2.1]heptane, azaspiro[3.5]nonanyl, azaspiro[2.5]octanyl, azaspiro[4.5]decanyl, 1-azaspiro[4.5]decan-2-onyl, azaspiro[5.5]undecanyl, tetrahydroindolyl, octahydroindolyl, tetrahydroisoindolyl, tetrahydroindazolyl, 1,1-dioxohexahydrothiopyranyl.

The term "heteroaryl" refers to any mono-, bi-, or tricyclic aromatic ring system containing from 1 to 4 heteroatoms selected from nitrogen, oxygen, and sulfur, and in an example embodiment, at least one heteroatom is nitrogen. See, for example, Lang's Handbook of Chemistry (Dean, J. A., ed.) 13$^{th}$ ed. Table 7-2 [1985]. Included in the definition are any bicyclic groups where any of the above heteroaryl rings are fused to an aryl ring, wherein the aryl ring or the heteroaryl ring is joined to the remainder of the molecule. In one embodiment, heteroaryl includes 5-6 membered monocyclic aromatic groups where one or more ring atoms is nitrogen, sulfur or oxygen. Example heteroaryl groups include thienyl, furyl, imidazolyl, pyrazolyl, thiazolyl, isothiazolyl, oxazolyl, isoxazolyl, triazolyl, thiadiazolyl, oxadiazolyl, tetrazolyl, thiatriazolyl, oxatriazolyl, pyridyl, pyrimidyl, pyrazinyl, pyridazinyl, triazinyl, tetrazinyl, tetrazolo[1,5-b]pyridazinyl, imidazol[1,2-a]pyrimidinyl and purinyl, as well as benzo-fused derivatives, for example benzoxazolyl, benzofuryl, benzothiazolyl, benzothiadiazolyl, benzotriazolyl, benzoimidazolyl, indazolyl and indolyl.

In particular embodiments, a heterocyclyl group or a heteroaryl group is attached at a carbon atom of the heterocyclyl group or the heteroaryl group. By way of example, carbon bonded heterocyclyl groups include bonding arrangements at position 2, 3, 4, 5, or 6 of a pyridine ring, position 3, 4, 5, or 6 of a pyridazine ring, position 2, 4, 5, or 6 of a pyrimidine ring, position 2, 3, 5, or 6 of a pyrazine ring, position 2, 3, 4, or 5 of a furan, tetrahydrofuran, thiofuran, thiophene, pyrrole or tetrahydropyrrole ring, position 2, 4, or 5 of an oxazole, imidazole or thiazole ring, position 3, 4, or 5 of an isoxazole, pyrazole, or isothiazole ring, position 2 or 3 of an aziridine ring, position 2, 3, or 4 of an azetidine ring, position 2, 3, 4, 5, 6, 7, or 8 of a quinoline ring or position 1, 3, 4, 5, 6, 7, or 8 of an isoquinoline ring.

In certain embodiments, the heterocyclyl group or heteroaryl group is N-attached. By way of example, nitrogen bonded heterocyclyl or heteroaryl groups include bonding arrangements at position 1 of an aziridine, azetidine, pyrrole, pyrrolidine, 2-pyrroline, 3-pyrroline, imidazole, imidazolidine, 2-imidazoline, 3-imidazoline, pyrazole, pyrazoline, 2-pyrazoline, 3-pyrazoline, piperidine, piperazine, indole, indoline, 1H-indazole, position 2 of a isoindole, or isoindoline, position 4 of a morpholine, and position 9 of a carbazole, or β-carboline.

"Fused" refers to any ring structure described herein that shares one or more atoms (e.g., carbon or nitrogen atoms) with an existing ring structure in the compounds of the invention.

The term "acyl" refers to a carbonyl containing substituent represented by the formula —C(=O)—R in which R is a substituent such as hydrogen, alkyl, cycloalkyl, aryl or heterocyclyl, wherein the alkyl, cycloalkyl, aryl and heterocyclyl are as defined herein. Acyl groups include alkanoyl (e.g., acetyl), aroyl (e.g., benzoyl), and heteroaroyl (e.g., pyridinoyl).

A "halogenating agent" as used herein refers to any reagent that adds one or more halogens to a compound described herein. A "chlorinating agent" as used herein refers to any reagent that adds one or more chlorine (Cl) atoms to a compound described herein. A "brominating" or "iodination" agent as used herein refers to any reagent that adds one or more bromine (Br) or iodine (I) atoms, respectively, to a compound described herein.

A "haloalkylation agent" as used herein refers to any reagent that adds one or more haloalkyl groups (e.g. $CF_3$) to a compound described herein. A "fluoroalkylation agent" refers to a reagent that adds one or more fluoroalkyl groups to a compound described herein.

An "organomagnesium compound" is organometallic compound in which the metal is magnesium.

"LDA" refers to lithium diisopropylamide.

"LiTMP" or "LTMP" refers to lithium tetramethylpiperidide.

"NCS" refers to N-chlorosuccinimide. "NBS" refers to N-bromosuccinimide. "NIS" refers to N-iodosuccinimide.

A "chiral ligand" as used herein refers to one or more compounds and/or catalysts that results in the synthesis of one chiral compound such as an atropisomer over the other.

As used herein a wavy line " ~~ " that intersects a bond in a chemical structure indicates the point of attachment of the atom to which the wavy bond is connected in the chemical structure to the remainder of a molecule, or to the remainder of a fragment of a molecule.

In certain embodiments, divalent groups are described generically without specific bonding configurations. It is understood that the generic description is meant to include both bonding configurations, unless specified otherwise. For example, in the group $R^1$-$R^2$-$R^3$, if the group $R^2$ is described as —$CH_2C(O)$—, then it is understood that this group can be bonded both as $R^1$—$CH_2C(O)$—$R^3$, and as $R^1$—$C(O)$$CH_2$—$R^3$, unless specified otherwise.

The term "pharmaceutically acceptable" refers to molecular entities and compositions that do not produce an adverse, allergic or other untoward reaction when administered to an animal, such as, for example, a human, as appropriate.

Compounds of the invention may be in the form of a salt, such as a pharmaceutically acceptable salt. "Pharmaceutically acceptable salts" include both acid and base addition salts. "Pharmaceutically acceptable acid addition salt" refers to those salts which retain the biological effectiveness and properties of the free bases and which are not biologically or otherwise undesirable, formed with inorganic acids such as hydrochloric acid, hydrobromic acid, sulfuric acid, nitric acid, carbonic acid, phosphoric acid and the like, and organic acids may be selected from aliphatic, cycloaliphatic, aromatic, araliphatic, heterocyclic, carboxylic, and sulfonic classes of organic acids such as formic acid, acetic acid, propionic acid, glycolic acid, gluconic acid, lactic acid, pyruvic acid, oxalic acid, malic acid, maleic acid, malonic acid, succinic acid, fumaric acid, tartaric acid, citric acid, aspartic acid, ascorbic acid, glutamic acid, anthranilic acid, benzoic acid, cinnamic acid, mandelic acid, embonic acid, phenylacetic acid, methanesulfonic acid, ethanesulfonic acid, benzenesulfonic acid, p-toluenesulfonic acid, salicylic acid and the like.

The term "pharmaceutically acceptable base addition salts" include those derived from inorganic bases such as sodium, potassium, lithium, ammonium, calcium, magnesium, iron, zinc, copper, manganese, aluminum salts and the like. Particular base addition salts are the ammonium, potassium, sodium, calcium and magnesium salts. Salts derived from pharmaceutically acceptable organic nontoxic bases include salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, 2-diethylaminoethanol, tromethamine, dicyclohexylamine, lysine, arginine, histidine, caffeine, procaine, hydrabamine, choline, betaine, ethylenediamine, glucosamine, methylglucamine, theobromine, purines, piperazine, piperidine, N-ethylpiperidine, polyamine resins and the like. Particular organic non-toxic bases include isopropylamine, diethylamine, ethanolamine, tromethamine, dicyclohexylamine, choline, and caffeine.

In some embodiments, a salt is selected from a hydrochloride, hydrobromide, trifluoroacetate, sulfate, phosphate, acetate, fumarate, maleate, tartrate, lactate, citrate, pyruvate, succinate, oxalate, methanesulfonate, p-toluenesulfonate, bisulfate, benzenesulfonate, ethanesulfonate, malonate, xinafoate, ascorbate, oleate, nicotinate, saccharinate, adipate, formate, glycolate, palmitate, L-lactate, D-lactate, aspartate, malate, L-tartrate, D-tartrate, stearate, furoate (e.g., 2-furoate or 3-furoate), napadisylate (naphthalene-1,5-disulfonate or naphthalene-1-(sulfonic acid)-5-sulfonate), edisylate (ethane-1,2-disulfonate or ethane-1-(sulfonic acid)-2-sulfonate), isothionate (2-hydroxyethylsulfonate), 2-mesitylenesulfonate, 2-naphthalenesulfonate, 2,5-dichlorobenzenesulfonate, D-mandelate, L-mandelate, cinnamate, benzoate, adipate, esylate, malonate, mesitylate (2-mesitylenesulfonate), napsylate (2-naphthalenesulfonate), camsylate (camphor-10-sulfonate, for example (1S)-(+)-10-camphorsulfonic acid salt), glutamate, glutarate, hippurate (2-(benzoylamino)acetate), orotate, xylate (p-xylene-2-sulfonate), and pamoic (2,2'-dihydroxy-1,1'-dinaphthylmethane-3,3'-dicarboxylate).

Compounds of the invention may contain one or more chiral carbon atoms. Accordingly, the compounds may exist as diastereomers, enantiomers or mixtures thereof. The syntheses of the compounds may employ racemates, diastereomers or enantiomers as starting materials or as intermediates. Mixtures of particular diastereomeric compounds may be separated, or enriched in one or more particular diastereomers, by chromatographic or crystallization methods. Similarly, enantiomeric mixtures may be separated, or enantiomerically enriched, using the same techniques or others known in the art. Each of the asymmetric carbon or nitrogen atoms may be in the R or S configuration and both of these configurations are within the scope of the invention.

In the structures shown herein, where the stereochemistry of any particular chiral atom is not specified, then all stereoisomers are contemplated and included as the compounds of the invention. Where stereochemistry is specified by a solid wedge or dashed line representing a particular configuration, then that stereoisomer is so specified and defined. Unless otherwise specified, if solid wedges or dashed lines are used, relative stereochemistry is intended.

The term "stereoisomers" refer to compounds that have identical chemical constitution, but differ with regard to the arrangement of the atoms or groups in space. Stereoisomers include diastereomers, enantiomers, atropisomers, conformers, and the like.

The term "chiral" refers to molecules which have the property of non-superimposability of the mirror image partner, while the term "achiral" refers to molecules which are superimposable on their mirror image partner.

The term "diastereomer" refers to a stereoisomer with two or more centers of chirality and whose molecules are not mirror images of one another. Diastereomers have different physical properties, e.g., melting points, boiling points, spectral properties or biological activities. Mixtures of diastereomers may separate under high resolution analytical procedures such as electrophoresis and chromatography such as HPLC.

The term "enantiomers" refer to two stereoisomers of a compound which are non-superimposable mirror images of one another.

"Atropisomers" are stereoisomers arising because of hindered rotation around a single bond or axis, where energy differences due to steric strain or other contributors create a barrier to rotation that is high enough to allow for isolation of individual conformers.

Stereochemical definitions and conventions used herein generally follow S. P. Parker, Ed., McGraw-Hill Dictionary of Chemical Terms (1984) McGraw-Hill Book Company, New York; and Eliel, E. and Wilen, S., "Stereochemistry of Organic Compounds", John Wiley & Sons, Inc., New York, 1994. Many organic compounds exist in optically active forms, i.e., they have the ability to rotate the plane of plane-polarized light. In describing an optically active compound, the prefixes D and L, or R and S, are used to denote the absolute configuration of the molecule about its chiral center(s). The prefixes d and l or (+) and (−) are employed to designate the sign of rotation of plane-polarized light by the compound, with (−) or l meaning that the compound is levorotatory. A compound prefixed with (+) or d is dextrorotatory. For a given chemical structure, these stereoisomers are identical except that they are mirror images of one another. A specific stereoisomer may also be referred to as an enantiomer, and a mixture of such isomers is often called an enantiomeric mixture. A 50:50 mixture of enantiomers is referred to as a racemic mixture or a racemate, which may occur where there has been no stereoselection or stereospecificity in a chemical reaction or process. The terms "racemic mixture" and "racemate" refer to an equimolar mixture of two enantiomeric species, devoid of optical activity.

The term "tautomer" or "tautomeric form" refers to structural isomers of different energies which are interconvertible via a low energy barrier. For example, proton tautomers (also known as prototropic tautomers) include interconversions via migration of a proton, such as keto-enol and imine-enamine isomerizations. Valence tautomers include interconversions by reorganization of some of the bonding electrons.

The term "amino-protecting group" as used herein refers to a derivative of the groups commonly employed to block or protect an amino group while reactions are carried out on other functional groups on the compound. Examples of such protecting groups include carbamates, amides, alkyl and aryl groups, and imines, as well as many N-heteroatom derivatives which can be removed to regenerate the desired amine group. Particular amino protecting groups are PMB (p-methoxybenzyl), Boc (tert-butyloxycarbonyl), Fmoc (9-fluorenylmethyloxycarbonyl), Cbz (carbobenzyloxy), Ac (acetyl), trifluoroacetyl, phthalimide, Bn (benzyl), Tr (triphenylmethyl or trityl), benzylidenyl, p-toluenesulfonyl, or DMB (dimethoxybenzyl). In some embodiments, an amino protecting group can be a group used to block or protect an amino group which results from cyclization of groups attached to the amino group but which can be later removed or replaced. Such examples include 1,3,5-dioxazinane, 2,4-dimethyl-1,3,5-dioxazinane, 2,2,5,5-tetramethyl-1,2,5-azadisilolidine, and isoindoline-1,3-dione. Further exemplary amino-protecting groups are found in T. W. Greene and P. G. M. Wuts, "Protecting Groups in Organic Synthesis, $3^{rd}$ ed., John Wiley & Sons, Inc., 1999. The term "protected amino" refers to an amino group substituted with one of the above amino-protecting groups.

The term "leaving group" refers to a portion of a first reactant in a chemical reaction that is displaced from the first reactant in the chemical reaction. Examples of leaving groups include, but are not limited to, halogen atoms, alkoxy and sulfonyloxy groups. Example sulfonyloxy groups include, but are not limited to, alkylsulfonyloxy groups (for example methyl sulfonyloxy (mesylate group) and trifluoromethylsulfonyloxy (triflate group)) and arylsulfonyloxy groups (for example p-toluenesulfonyloxy (tosylate group) and p-nitrosulfonyloxy (nosylate group)).

The terms "inhibiting" and "reducing," or any variation of these terms, includes any measurable decrease or complete inhibition to achieve a desired result. For example, there may be a decrease of about, at most about, or at least about 5%, 10%, 15%, 20%, 25%, 30%, 35%, 40%, 45%, 50%, 55%, 60%, 65%, 70%, 75%, 80%, 85%, 90%, 95%, 99%, or more, or any range derivable therein, reduction of activity compared to normal.

The terms "antagonist" and "inhibitor" are used interchangeably, and they refer to a compound having the ability to inhibit a biological function of a target protein, whether by inhibiting the activity or expression of the protein, such as K-Ras, H-Ras or N-Ras G12C. Accordingly, the terms "antagonist" and "inhibitors" are defined in the context of the biological role of the target protein. While preferred antagonists herein specifically interact with (e.g., bind to)

the target, compounds that inhibit a biological activity of the target protein by interacting with other members of the signal transduction pathway of which the target protein is a member are also specifically included within this definition. A preferred biological activity inhibited by an antagonist is associated with the development, growth, or spread of a tumor.

The term "agonist" as used herein refers to a compound having the ability to initiate or enhance a biological function of a target protein, whether by inhibiting the activity or expression of the target protein. Accordingly, the term "agonist" is defined in the context of the biological role of the target polypeptide. While preferred agonists herein specifically interact with (e.g., bind to) the target, compounds that initiate or enhance a biological activity of the target polypeptide by interacting with other members of the signal transduction pathway of which the target polypeptide is a member are also specifically included within this definition.

The terms "cancer" and "cancerous", "neoplasm", and "tumor" and related terms refer to or describe the physiological condition in mammals that is typically characterized by unregulated cell growth. A "tumor" comprises one or more cancerous cells. Examples of cancer include carcinoma, blastoma, sarcoma, seminoma, glioblastoma, melanoma, leukemia, and myeloid or lymphoid malignancies. More particular examples of such cancers include squamous cell cancer (e.g., epithelial squamous cell cancer) and lung cancer including small-cell lung cancer, non-small cell lung cancer ("NSCLC"), adenocarcinoma of the lung and squamous carcinoma of the lung. Other cancers include skin, keratoacanthoma, follicular carcinoma, hairy cell leukemia, buccal cavity, pharynx (oral), lip, tongue, mouth, salivary gland, esophageal, larynx, hepatocellular, gastric, stomach, gastrointestinal, small intestine, large intestine, pancreatic, cervical, ovarian, liver, bladder, hepatoma, breast, colon, rectal, colorectal, genitourinary, biliary passage, thyroid, papillary, hepatic, endometrial, uterine, salivary gland, kidney or renal, prostate, testis, vulval, peritoneum, anal, penile, bone, multiple myeloma, B-cell lymphoma, diffuse large B-Cell lymphoma (DLBCL), central nervous system, brain, head and neck, Hodgkin's, and associated metastases. Examples of neoplastic disorders include myeloproliferative disorders, such as polycythemia vera, essential thrombocytosis, myelofibrosis, such as primary myelofibrosis, and chronic myelogenous leukemia (CML).

A "chemotherapeutic agent" is an agent useful in the treatment of a given disorder, for example, cancer or inflammatory disorders. Examples of chemotherapeutic agents are well-known in the art and include examples such as those disclosed in U.S. Publ. Appl. No. 2010/0048557, incorporated herein by reference. Additionally, chemotherapeutic agents include pharmaceutically acceptable salts, acids or derivatives of any of chemotherapeutic agents, as well as combinations of two or more of them.

Unless otherwise stated, structures depicted herein are also meant to include compounds that differ only in the presence of one or more isotopically enriched atoms. Exemplary isotopes that can be incorporated into compounds of the invention, include isotopes of hydrogen, carbon, nitrogen, oxygen, phosphorus, sulfur, fluorine, chlorine, and iodine, such as $^{2}H$, $^{3}H$, $^{11}C$, $^{13}C$, $^{14}C$, $^{13}N$, $^{15}N$, $^{15}O$, $^{17}O$, $^{18}O$, $^{32}P$, $^{33}P$, $^{35}S$, $^{18}F$, $^{36}Cl$, $^{123}I$, and $^{125}I$, respectively. Isotopically-labeled compounds (e.g., those labeled with $^{3}H$ and $^{14}C$) can be useful in compound or substrate tissue distribution assays. Tritiated (i.e., $^{3}H$) and carbon-14 (i.e., $^{14}C$) isotopes can be useful for their ease of preparation and detectability. Further, substitution with heavier isotopes such as deuterium (i.e., $^{2}H$) may afford certain therapeutic advantages resulting from greater metabolic stability (e.g., increased in vivo half-life or reduced dosage requirements). In some embodiments, in compounds of the invention, one or more carbon atoms are replaced by $^{13}C$- or $^{14}C$-enriched carbon. Positron emitting isotopes such as 15O, $^{13}N$, $^{11}C$, and $^{18}F$ are useful for positron emission tomography (PET) studies to examine substrate receptor occupancy. Isotopically labeled compounds can generally be prepared by following procedures analogous to those disclosed in the Schemes or in the Examples herein, by substituting an isotopically labeled reagent for a non-isotopically labeled reagent.

It is specifically contemplated that any limitation discussed with respect to one embodiment of the invention may apply to any other embodiment of the invention. Furthermore, any compound or composition of the invention may be used in any method of the invention, and any method of the invention may be used to produce or to utilize any compound or composition of the invention.

Throughout this application, the term "about" is used to indicate that a value includes the standard deviation of error for the device or method being employed to determine the value.

Compounds

Provided herein are compounds of formula (I):

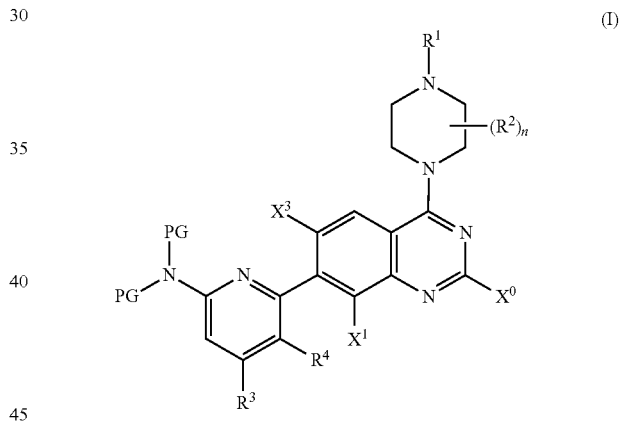

or a solvate, tautomer, stereoisomer, atropisomer, or salt thereof
wherein;
  $X^{0}$ is hydrogen, halogen, $OR^{5A}$, $SR^{5B}$, $R^{5}$-substituted or unsubstituted $C_{1-6}$ alkyl, $R^{5}$-substituted or unsubstituted $C_{1-6}$ haloalkyl, $R^{5}$-substituted or unsubstituted $C_{5-7}$ aryl, or $R^{5}$-substituted or unsubstituted $C_{5-7}$ heteroaryl;
  $X^{1}$ is hydrogen or halogen;
  $X^{3}$ is hydrogen, halogen, $R^{6}$-substituted or unsubstituted $C_{1-3}$ alkyl, $R^{6}$-substituted or unsubstituted $C_{1-3}$ haloalkyl, $R^{6}$-substituted or unsubstituted $C_{1-3}$ alkoxy, or $R^{6}$-substituted or unsubstituted cyclopropyl;
  $R^{1}$ is hydrogen or $PG^{1}$;
  each $R^{2}$ is independently halogen, cyano, unsubstituted $C_{1-6}$ alkyl, unsubstituted $C_{1-6}$ cyanoalkyl, or unsubstituted $C_{1-6}$ haloalkyl;
  $R^{3}$ is hydrogen, halogen, $R^{3A}$-substituted or unsubstituted $C_{1-3}$ alkyl, $R^{3A}$-substituted or unsubstituted $C_{1-3}$ haloalkyl, or $R^{3A}$-substituted or unsubstituted $C_{3-6}$ cycloalkyl;

$R^{3A}$ is halogen, OH, CN, unsubstituted $C_{1-3}$ alkyl or unsubstituted $C_{1-3}$ haloalkyl;

$R^4$ is $R^{4A}$-substituted or unsubstituted $C_{1-3}$ haloalkyl;

$R^{4A}$ is unsubstituted $C_{1-3}$ alkyl;

$R^5$ is halogen, cyano, OH, NO$_2$, $R^{5A}$-substituted or unsubstituted $C_{1-6}$ alkyl, $R^{5A}$-substituted or unsubstituted $C_{1-6}$ haloalkyl, $R^{5A}$-substituted or unsubstituted $C_{1-6}$ cyanoalkyl, $R^{5A}$-substituted or unsubstituted $C_{3-6}$ cycloalkyl, $R^{5A}$-substituted or unsubstituted 3-6 membered heterocycle, $R^{5A}$-substituted or unsubstituted phenyl, or $R^{5A}$-substituted or unsubstituted 6 membered heteroaryl;

$R^{5A}$ and $R^{5B}$ are each independently $R^{5C}$-substituted or unsubstituted $C_{1-6}$ alkyl, $R^{5C}$-substituted or unsubstituted $C_{1-6}$ haloalkyl, $R^{5C}$-substituted or unsubstituted $C_{3-7}$ cycloalkyl; $R^{5C}$-substituted or unsubstituted 3-7 membered heterocycle; $R^{5C}$-substituted or unsubstituted $C_{5-7}$ aryl, or $R^{5C}$-substituted or unsubstituted $C_{5-7}$ heteroaryl;

$R^{5C}$ is independently hydrogen, halogen, OH, CN, NO$_2$, $R^{5D}$-substituted or unsubstituted $C_{1-6}$ alkyl, $R^{5D}$-substituted or unsubstituted $C_{1-6}$ haloalkyl, $R^{5D}$-substituted or unsubstituted $C_{3-7}$ cycloalkyl; $R^{5D}$-substituted or unsubstituted $C_{3-7}$ heterocycle; $R^{5D}$-substituted or unsubstituted $C_{5-7}$ aryl, or $R^{5D}$-substituted or unsubstituted $C_{5-7}$ heteroaryl;

$R^{5D}$ is independently hydrogen, halogen, OH, CN, NO$_2$, unsubstituted $C_{1-6}$ alkyl, unsubstituted $C_{1-6}$ haloalkyl, unsubstituted $C_{3-7}$ cycloalkyl; unsubstituted $C_{3-7}$ heterocycle; unsubstituted $C_{5-7}$ aryl, or unsubstituted $C_{5-7}$ heteroaryl; $R^6$ is hydrogen, halogen, OH, CN, NO$_2$, unsubstituted $C_{1-6}$ alkyl, unsubstituted $C_{1-6}$ haloalkyl, or unsubstituted $C_{3-7}$ cycloalkyl;

n is 1 or 2;

each PG is independently an amino protecting group, or wherein two PG together form a $C_{3-8}$ nitrogen heterocycle; and $PG^1$ is an amino protecting group.

In one embodiment of the compounds of formula (I) or a solvate, tautomer, stereoisomer, atropisomer, or salt thereof described herein, $X^0$ is halogen, $OR^{5A}$, $SR^{5B}$, $R^5$-substituted or unsubstituted $C_{1-6}$ alkyl, $R^5$-substituted or unsubstituted $C_{1-6}$ haloalkyl, $R^5$-substituted or unsubstituted $C_{5-7}$ aryl, or $R^5$-substituted or unsubstituted $C_{5-7}$ heteroaryl. In one embodiment of the compounds of formula (I) or a solvate, tautomer, stereoisomer, atropisomer, or salt thereof described herein, $X^0$ is hydrogen, halogen, or $OR^{5A}$. In another embodiment of the compounds of formula (I) or a solvate, tautomer, stereoisomer, atropisomer, or salt thereof described herein, $X^0$ is $SR^{5B}$, $R^5$-substituted or unsubstituted $C_{1-6}$ alkyl, $R^5$-substituted or unsubstituted $C_{1-6}$ haloalkyl, $R^5$-substituted or unsubstituted $C_{5-7}$ aryl, or $R^5$-substituted or unsubstituted $C_{5-7}$ heteroaryl. In another embodiment of the compounds of formula (I) or a solvate, tautomer, stereoisomer, atropisomer, or salt thereof described herein, $X^0$ is hydrogen, halogen, $CF_3$, $CHF_2$, or $CH_2F$. In one preferred embodiment, $X^0$ is halogen. In one such embodiment of the compounds of formula (I) or a solvate, tautomer, stereoisomer, atropisomer, or salt thereof described herein, $X^0$ is F.

In still another embodiment of the compounds of formula (I) or a solvate, tautomer, stereoisomer, atropisomer, or salt thereof described herein, $X^0$ is hydrogen, halogen, $CF_3$, $CHF_2$, $CH_2F$, or a moiety having structure:

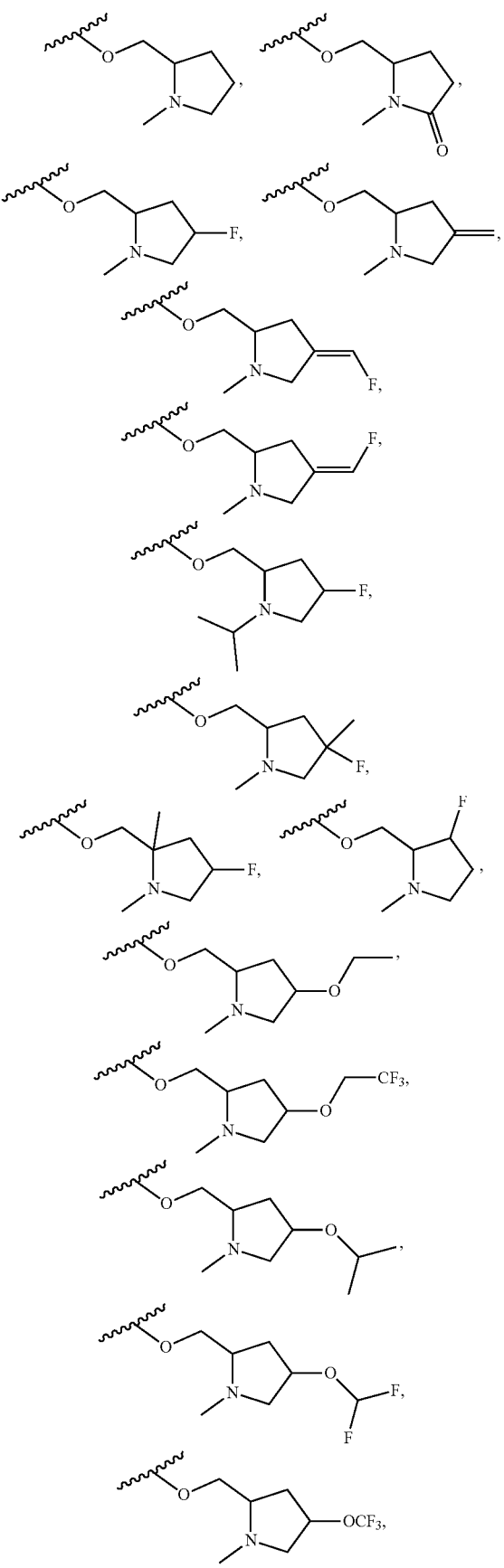

-continued
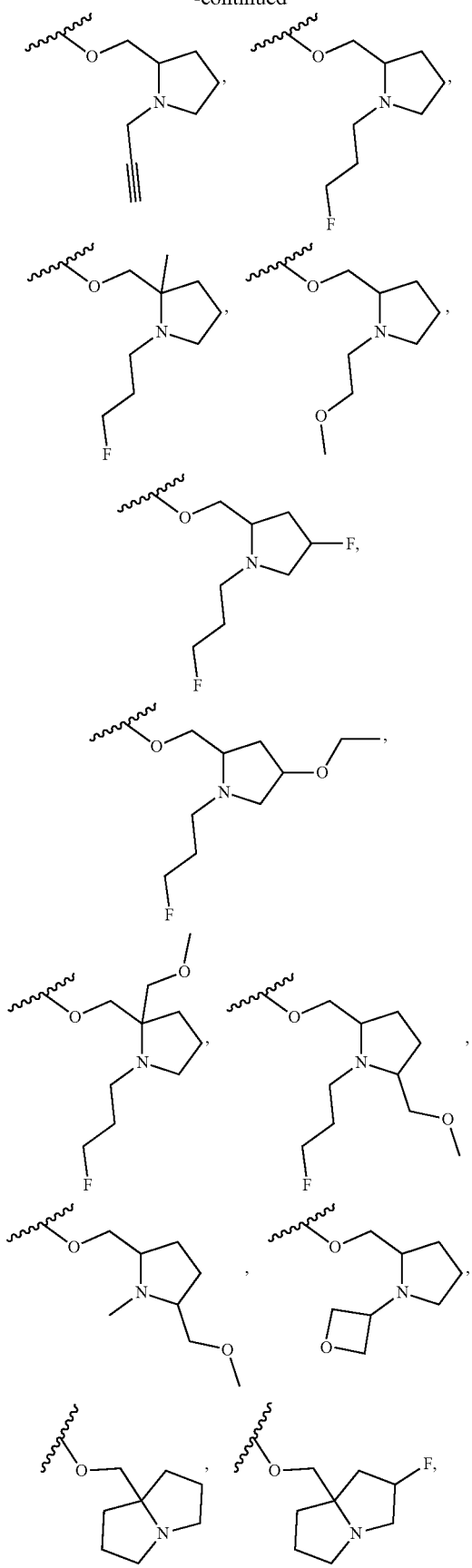
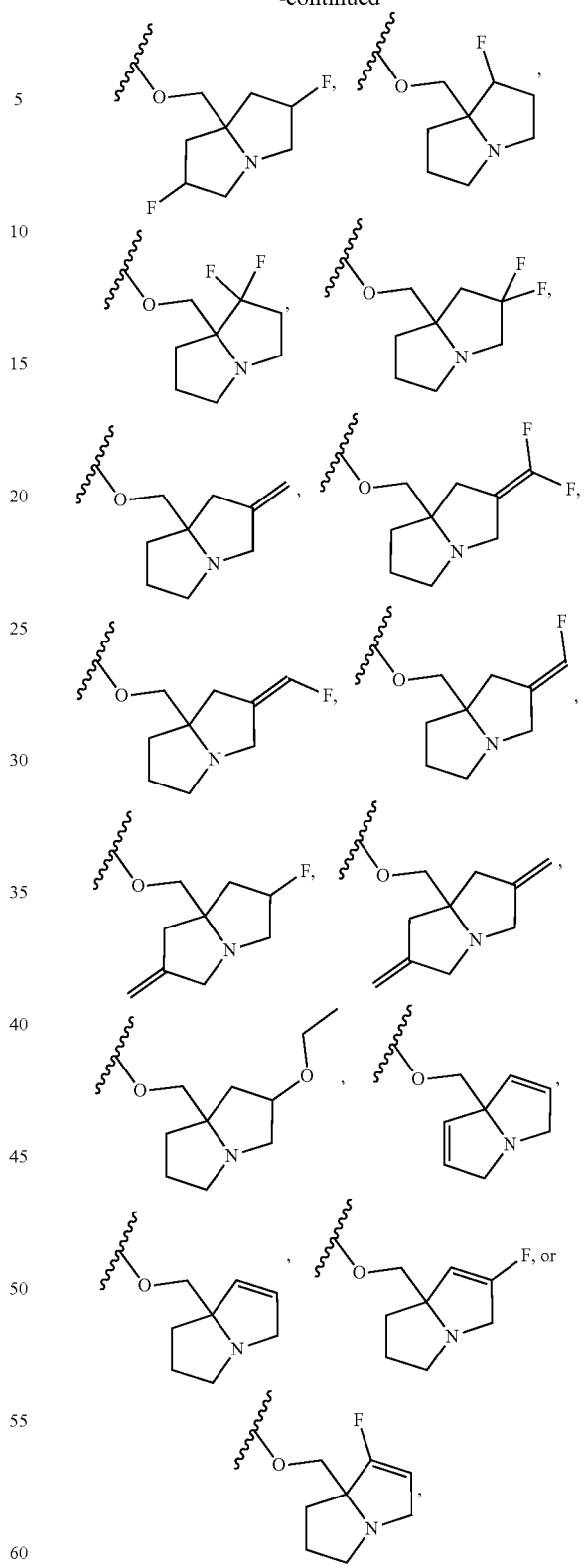
or a stereoisomer thereof.
In one embodiment of the compounds of formula (I) or a solvate, tautomer, stereoisomer, atropisomer, or salt thereof described herein, $R^5$ is halogen, cyano, OH, or $NO_2$. In one embodiment of the compounds of formula (I) or a solvate, tautomer, stereoisomer, atropisomer, or salt thereof described herein, $R^5$ is $R^{5A}$-substituted or unsubstituted $C_{1-6}$ alkyl, $R^{5A}$-substituted or unsubstituted $C_{1-6}$ haloalkyl, or $R^{5A}$-substituted or unsubstituted $C_{1-6}$ cyanoalkyl. In one embodiment of the compounds of formula (I) or a solvate, tautomer, stereoisomer, atropisomer, or salt thereof described herein, $R^5$ is $R^{5A}$-substituted or unsubstituted $C_{3-6}$ cycloalkyl, $R^{5A}$-substituted or unsubstituted 3-6 membered heterocycle, $R^{5A}$-substituted or unsubstituted phenyl, or $R^{5A}$-substituted or unsubstituted 6 membered heteroaryl.

In one embodiment, $R^{5A}$ and $R^{5B}$ are each independently $R^{5C}$-substituted or unsubstituted $C_{1-6}$ alkyl or $R^{5C}$-substituted or unsubstituted $C_{1-6}$ haloalkyl. In another embodiment, $R^{5A}$ and $R^{5B}$ are each independently $R^{5C}$-substituted or unsubstituted $C_{3-7}$ cycloalkyl; $R^{5C}$-substituted or unsubstituted 3-7 membered heterocycle, $R^{5C}$-substituted or unsubstituted $C_{5-7}$ aryl, or $R^{5C}$-substituted or unsubstituted $C_{5-7}$ heteroaryl. In one preferred embodiment, $R^{5A}$ and $R^{5B}$ are each independently $R^{5C}$-substituted or unsubstituted $C_{1-6}$ alkyl.

In one embodiment, $R^{5C}$ is independently halogen, OH, CN, or $NO_2$. In one embodiment, $R^{5C}$ is independently $R^{5D}$-substituted or unsubstituted $C_{1-6}$ alkyl or $R^{5D}$-substituted or unsubstituted $C_{1-6}$ haloalkyl. In one embodiment, $R^{5C}$ is independently $R^{5D}$-substituted or unsubstituted $C_{3-7}$ cycloalkyl or $R^{5D}$-substituted or unsubstituted $C_{3-7}$ heterocycle. In one embodiment, $R^{5C}$ is independently $R^{5D}$-substituted or unsubstituted $C_{5-7}$ aryl or $R^{5D}$-substituted or unsubstituted $C_{5-7}$ heteroaryl. In another embodiment, $R^{5C}$ is independently $R^{5D}$-substituted or unsubstituted $C_{3-7}$ heterocycle or $R^{5D}$-substituted or unsubstituted $C_{5-7}$ heteroaryl. In another embodiment, $R^{5C}$ is $R^{5D}$-substituted pyrrolidinyl.

In one embodiment, $R^{5D}$ is independently halogen, OH, or CN. In another embodiment, $R^{5D}$ is unsubstituted $C_{1-6}$ alkyl. In another embodiment, $R^{5D}$ is unsubstituted $C_{1-6}$ haloalkyl. In still another embodiment, $R^{5D}$ is unsubstituted $C_{3-7}$ cycloalkyl, unsubstituted $C_{3-7}$ heterocycle, unsubstituted $C_{5-7}$ aryl, or unsubstituted $C_{5-7}$ heteroaryl. In one embodiment, $R^{5D}$ is methyl, ethyl, or propyl.

In one embodiment, $R^{5A}$ and $R^{5B}$ are each independently

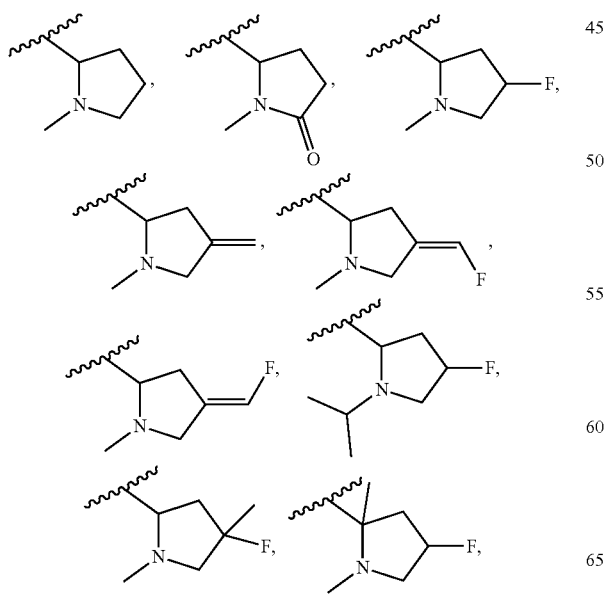

-continued

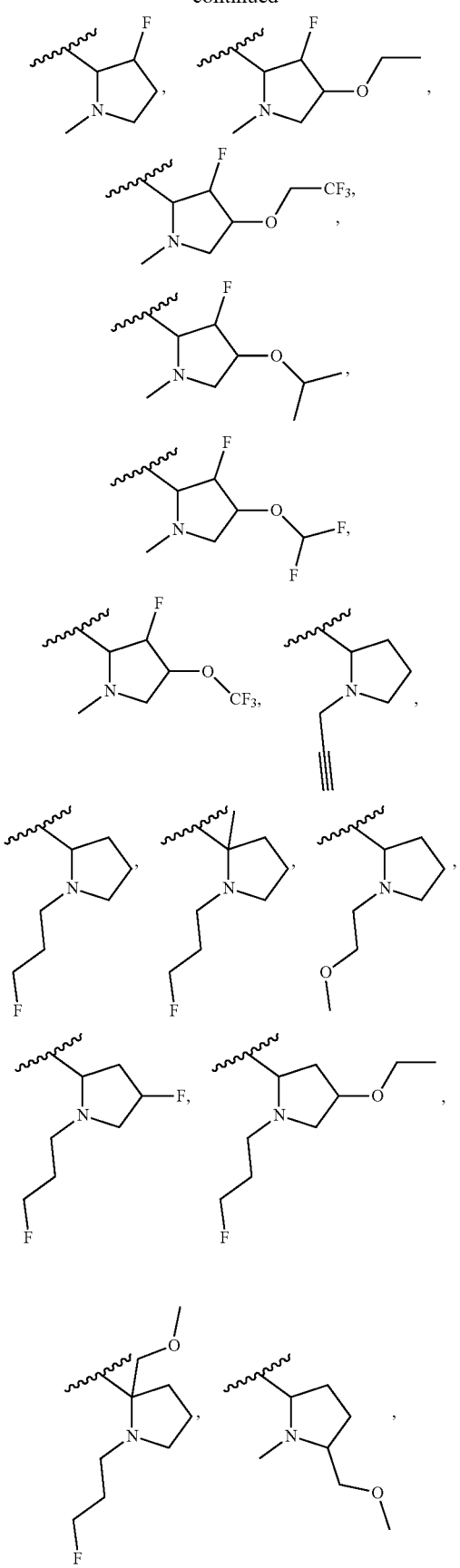

-continued
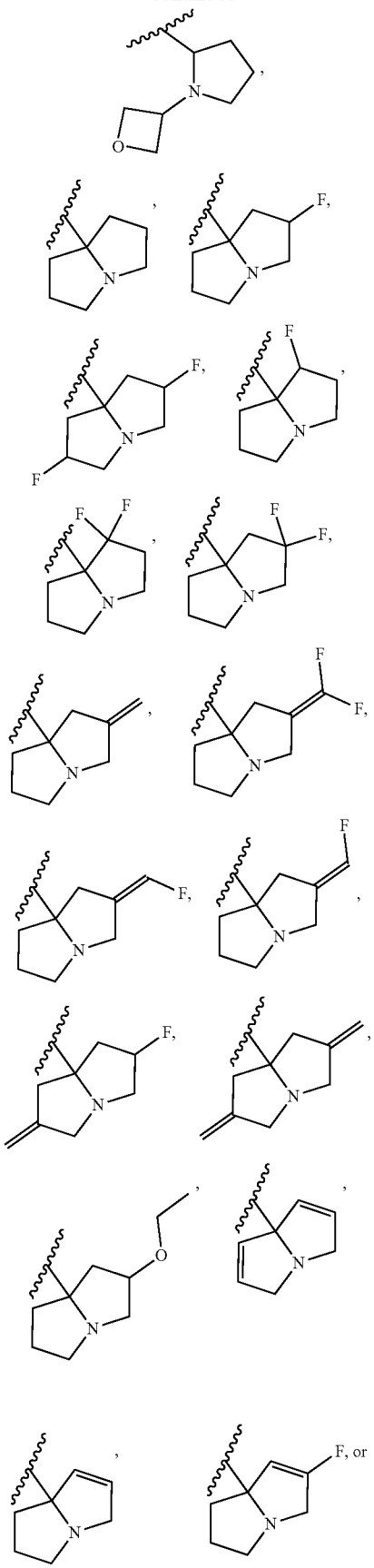
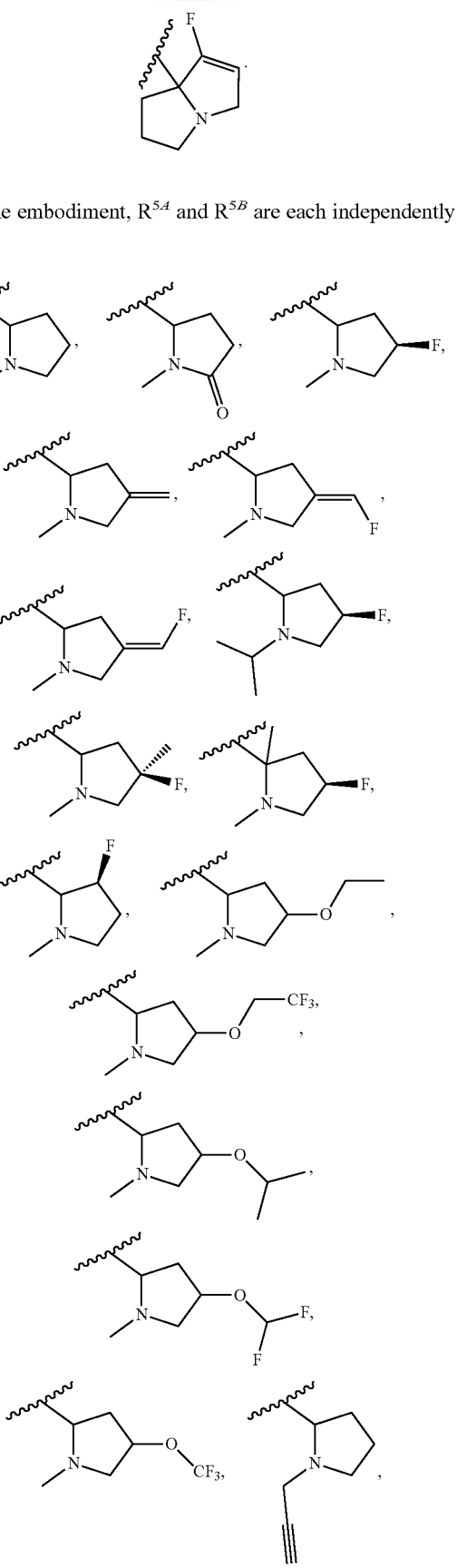
In one embodiment, $R^{5A}$ and $R^{5B}$ are each independently

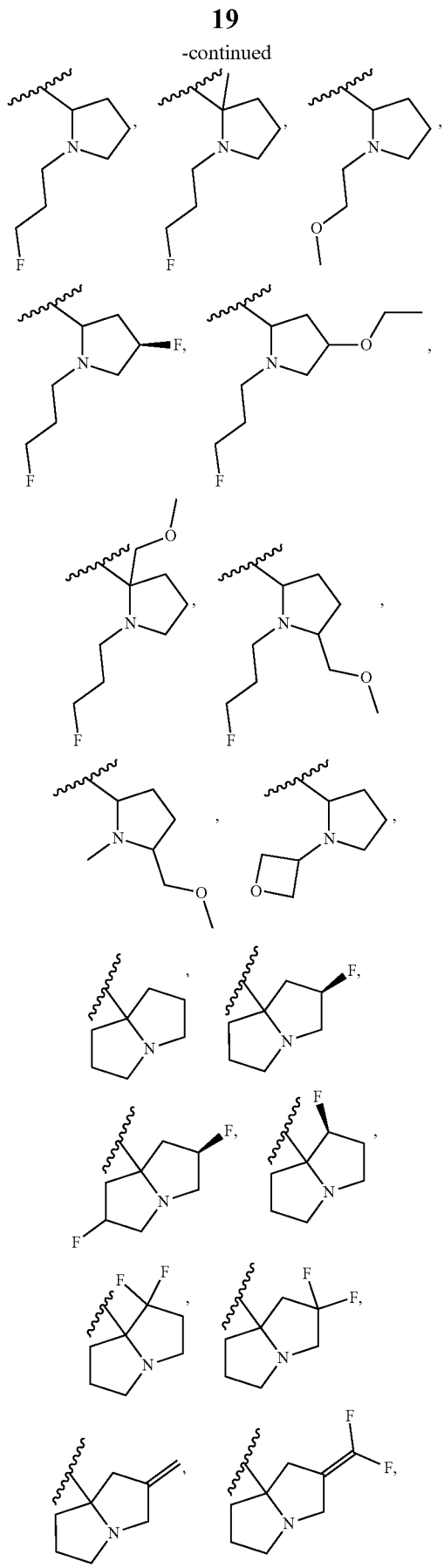
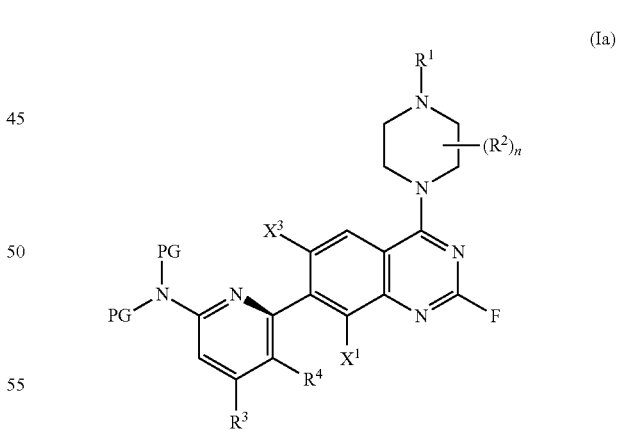
In another aspect provided herein is a compound of formula (Ia):
(Ia)
or a solvate, tautomer, stereoisomer, or salt thereof wherein;
- $X^0$ is hydrogen, halogen, or $OR^{5A}$;
- $X^1$ and $X^3$ are independently halogen or methyl;
- $R^1$ is hydrogen or $PG^1$;
- each $R^2$ is independently halogen, cyano, methyl, ethyl, propyl, —$CH_2CN$, $(CH_2)_2CN$, $CF_3$, $CHF_2$, or $CH_2F$;
- $R^3$ is hydrogen or methyl;

$R^{5A}$ is
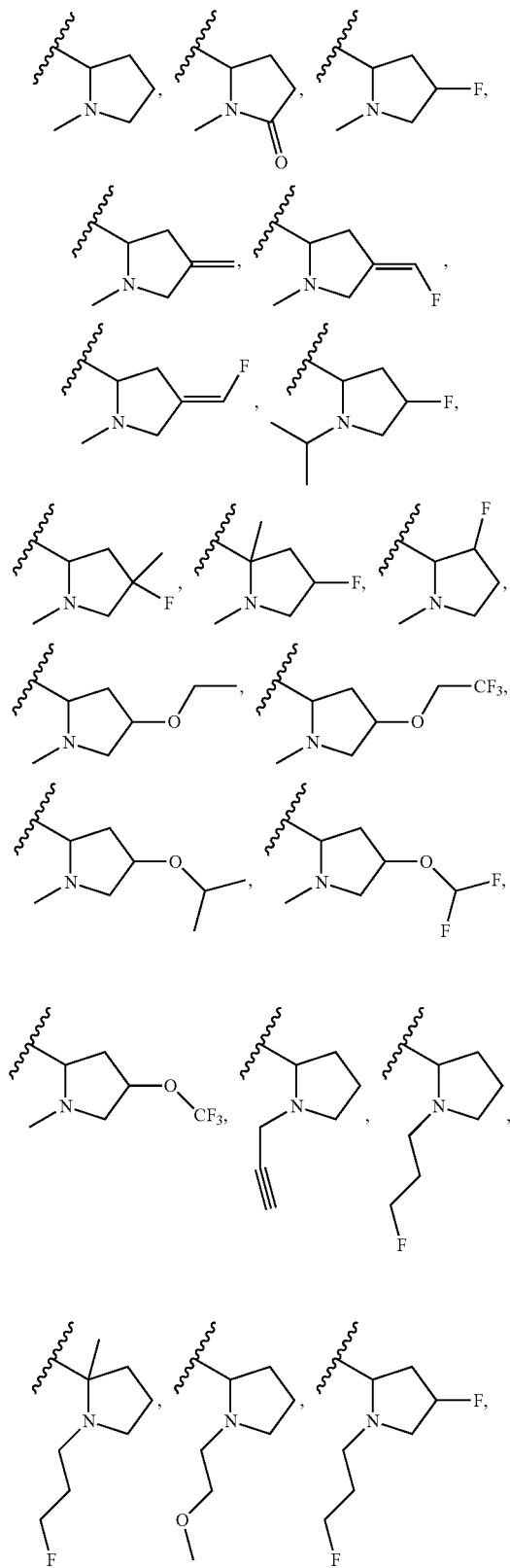
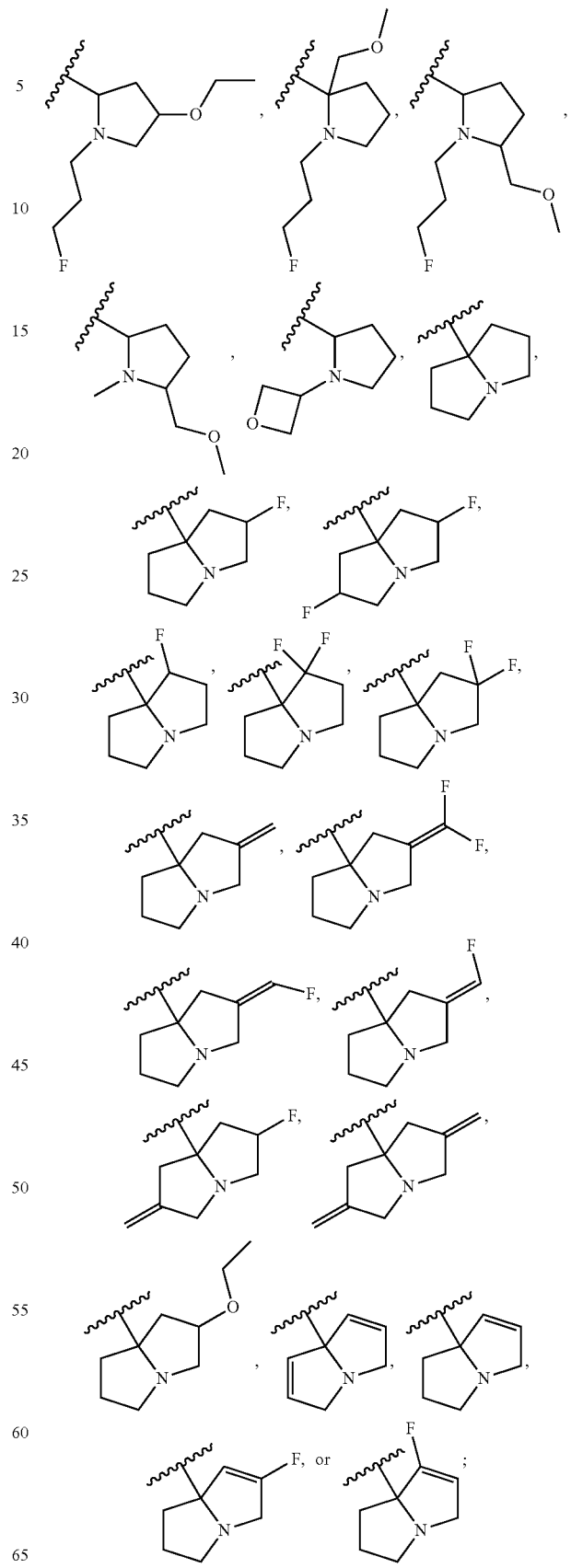

n is 0, 1, or 2;
each PG is independently an amino protecting group, or wherein two PG together form a $C_{3-8}$ nitrogen heterocycle; and $PG^1$ is an amino protecting group.

Further provided herein are compounds of formula (Ib):

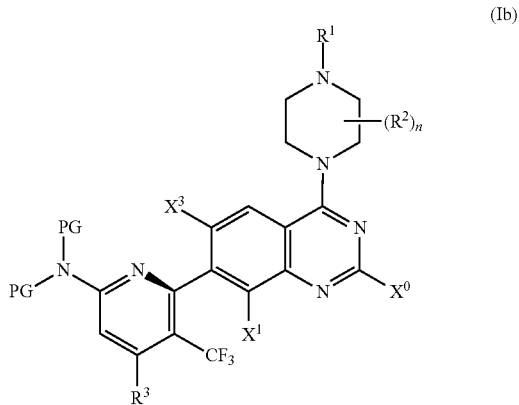

(Ib)

or a solvate, tautomer, stereoisomer, atropisomer, or salt thereof
wherein;
$X^1$ is hydrogen or halogen;
$X^3$ is hydrogen, halogen, $R^6$-substituted or unsubstituted $C_{1-3}$ alkyl, $R^6$-substituted or unsubstituted $C_{1-3}$ haloalkyl, $R^6$-substituted or unsubstituted $C_{1-3}$ alkoxy, or $R^6$-substituted or unsubstituted cyclopropyl;
$R^1$ is hydrogen or $PG^1$;
each $R^2$ is independently halogen, cyano, unsubstituted $C_{1-6}$ alkyl, unsubstituted $C_{1-6}$ cyanoalkyl, or unsubstituted $C_{1-6}$ haloalkyl;
$R^3$ is hydrogen, halogen, $R^{3A}$-substituted or unsubstituted $C_{1-3}$ alkyl, $R^{3A}$-substituted or unsubstituted $C_{1-3}$ haloalkyl, or $R^{3A}$-substituted or unsubstituted $C_{3-6}$ cycloalkyl;
$R^{3A}$ is halogen, OH, CN, unsubstituted $C_{1-3}$ alkyl or unsubstituted $C_{1-3}$ haloalkyl;
$R^4$ is $R^{4A}$-substituted or unsubstituted $C_{1-3}$ haloalkyl;
$R^{4A}$ is unsubstituted $C_{1-3}$ alkyl;
$R^6$ is hydrogen, halogen, OH, CN, $NO_2$, unsubstituted $C_{1-6}$ alkyl, unsubstituted $C_{1-6}$ haloalkyl, or unsubstituted $C_{3-7}$ cycloalkyl;
n is 0, 1, or 2;
each PG is independently an amino protecting group, or wherein two PG together form a $C_{3-8}$ nitrogen heterocycle; and
$PG^1$ is an amino protecting group.

In one embodiment, $X^1$ is hydrogen. In one embodiment, $X^1$ is halogen. In one embodiment, $X^1$ is F or Cl. In another embodiment, when $X^1$ is halogen $X^3$ is halogen. In another embodiment, when $X^1$ is F, $X^3$ is not F. In another embodiment, when $X^1$ is F, $X^3$ is Cl.

In one embodiment, $X^3$ is hydrogen, halogen, $R^6$-substituted or unsubstituted $C_{1-3}$ alkyl, or $R^6$-substituted or unsubstituted $C_{1-3}$ haloalkyl. In another embodiment, $X^3$ is $R^6$-substituted or unsubstituted $C_{1-3}$ alkoxy or $R^6$-substituted or unsubstituted cyclopropyl. In another embodiment, $X^3$ is hydrogen or halogen. In another embodiment, $X^3$ is halogen, unsubstituted $C_{1-4}$ alkyl, or unsubstituted $C_{1-3}$ haloalkyl. In still another embodiment, $X^3$ is halogen or unsubstituted $C_{1-3}$ haloalkyl. In still another embodiment, $X^3$ is unsubstituted $C_{1-3}$ alkoxy, or unsubstituted cyclopropyl. In one preferred embodiment, $X^3$ is halogen. In one such embodiment, $X^3$ is Cl or F. In another embodiment, $X^3$ is Cl, F, $CF_3$, $CHF_2$, or $CH_2F$. In still another embodiment, $X^3$ is $CF_3$, $CHF_2$, or $CH_2F$.

In one embodiment, $R^1$ is hydrogen. In a preferred embodiment, $R^1$ is $PG^1$. In one such embodiment, $PG^1$ is Ac (acetyl), trifluoroacetyl, Bn (benzyl), Tr (triphenylmethyl or trityl), benzylidenyl, p-toluenesulfonyl, PMB (p-methoxybenzyl), Boc (tert-butyloxycarbonyl), Fmoc (9-fluorenylmethyloxycarbonyl) or Cbz (carbobenzyloxy). In another embodiment, $PG^1$ is Boc (tert-butyloxycarbonyl). In a preferred embodiment, $R^1$ is Boc (tert-butyloxycarbonyl).

In one embodiment, each $R^2$ is independently halogen or cyano. In one embodiment, each $R^2$ is independently halogen or unsubstituted $C_{1-6}$ cyanoalkyl. In another embodiment, each $R^2$ is independently unsubstituted $C_{1-6}$ alkyl, unsubstituted $C_{1-6}$ cyanoalkyl, or unsubstituted $C_{1-6}$ haloalkyl. In one such embodiment n is 1. In one preferred embodiment, each $R^2$ is independently unsubstituted $C_{1-6}$ alkyl or unsubstituted $C_{1-6}$ cyanoalkyl. In one such embodiment, each $R^2$ is methyl or ethyl. In one such embodiment, n is 1. In another such embodiment, $R^2$ is methyl and n is 1. In another such embodiment, each $R^2$ is $CF_3$, $CHF_2$, or $CH_2F$. In another embodiment, $R^2$ is methyl, ethyl, CN, $CH_2CN$, $CF_3$, $CHF_2$, or $CH_2F$. In another embodiment, $R^2$ is methyl, ethyl, CN, or $CH_2CN$. In such embodiments, n is 1. In another such embodiment, $R^2$ is $CH_2CN$ and n is 1. In another embodiment, n is 0.

In one embodiment, $R^3$ is hydrogen or halogen. In one embodiment, $R^3$ is hydrogen. In another embodiment, $R^3$ is hydrogen, $R^{3A}$-substituted or unsubstituted $C_{1-3}$ alkyl, $R^{3A}$-substituted or unsubstituted $C_{1-3}$ haloalkyl, cyclopropyl. In another embodiment, $R^3$ is $R^{3A}$-substituted or unsubstituted $C_{1-3}$ alkyl or $R^{3A}$-substituted or unsubstituted $C_{1-3}$ haloalkyl. In another embodiment, $R^3$ is hydrogen or $R^{3A}$-substituted or unsubstituted $C_{1-3}$ alkyl In still another embodiment, $R^3$ is $R^{3A}$-substituted or unsubstituted $C_{1-3}$ alkyl. In one such embodiment, $R^3$ is hydrogen or methyl. In another such embodiment, $R^3$ is methyl.

In one embodiment, $R^3$ is $R^{3A}$-substituted or unsubstituted $C_{1-3}$ alkyl, $R^{3A}$-substituted or unsubstituted $C_{1-3}$ haloalkyl where $R^{3A}$ is halogen, OH, CN, or unsubstituted $C_{1-3}$ haloalkyl. In one such embodiment, is $R^{3A}$-substituted or unsubstituted $C_{1-3}$ alkyl, $R^{3A}$-substituted or unsubstituted $C_{1-3}$ haloalkyl where $R^{3A}$ is F, OH, CN, $CF_3$, $CHF_2$, or $CH_2F$.

In a preferred embodiment, $R^4$ is unsubstituted $C_{1-3}$ haloalkyl. In one such embodiment, $R^4$ is $CF_3$, $CHF_2$, or $CH_2F$. In one such embodiment, $R^4$ is $CF_3$.

In one embodiment, $R^6$ is halogen. In another embodiment, $R^6$ is OH, CN, $NO_2$, unsubstituted $C_{1-6}$ alkyl, unsubstituted $C_{1-6}$ haloalkyl, or unsubstituted $C_{3-7}$ cycloalkyl.

In one embodiment, each PG is independently an amino protecting group. In one embodiment, each PG is the same. In one such embodiment, each PG is Ac (acetyl), trifluoroacetyl, Bn (benzyl), Tr (triphenylmethyl or trityl), benzylidenyl, p-toluenesulfonyl, DMB (dimethoxybenzyl), PMB (p-methoxybenzyl), Boc (tert-butyloxycarbonyl), Fmoc (9-fluorenylmethyloxycarbonyl) or Cbz (carbobenzyloxy). In another embodiment, each PG is PMB, DMB, or Boc. In one preferred embodiment, each PG is PMB.

In still another embodiment, two PG together form a $C_{3-8}$ nitrogen heterocycle. In one embodiment, two PG together form a moiety having the structure:

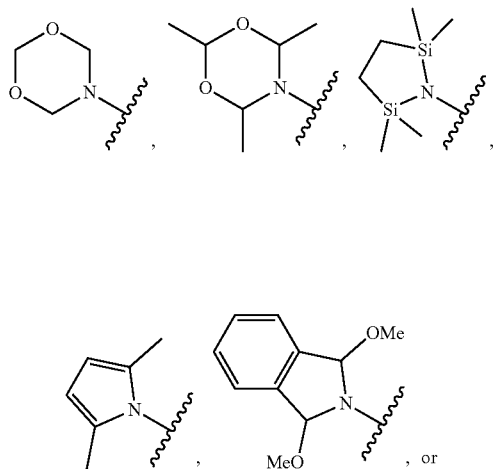

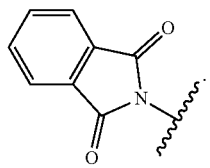

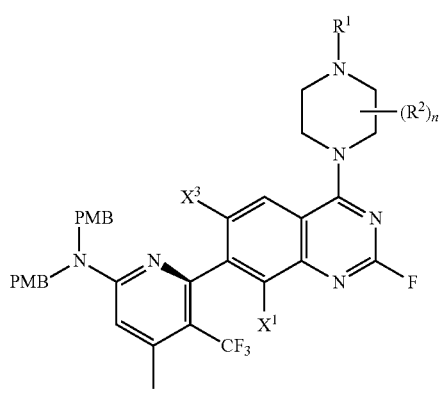

In another aspect provided herein is a compound of formula (Ib1):

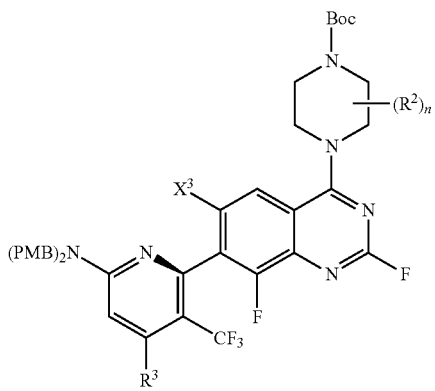

(Ib1)

or a solvate, tautomer, stereoisomer, atropisomer, or salt thereof
wherein;
X$^1$ and X$^3$ are independently halogen or methyl;
R$^1$ is hydrogen or PG$^1$;
each R$^2$ is independently halogen, cyano, methyl, ethyl, propyl, —CH$_2$CN, (CH$_2$)$_2$CN, CF$_3$, CHF$_2$, or CH$_2$F;
n is 1 or 2; and
PG$^1$ is an amino protecting group.

In one embodiment, the compound of formula (I) or a solvate, tautomer, stereoisomer, atropisomer, or salt thereof described herein comprises a compound of formula (Ib2):

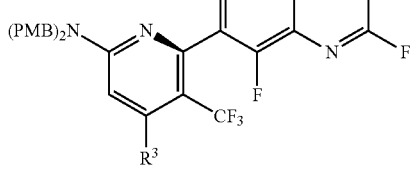

(Ib2)

or a solvate, tautomer, stereoisomer, atropisomer, or salt thereof.

In one embodiment, the compound of formula (I) or a solvate, tautomer, stereoisomer, atropisomer, or salt thereof described herein comprises a compound of formula (Ib3):

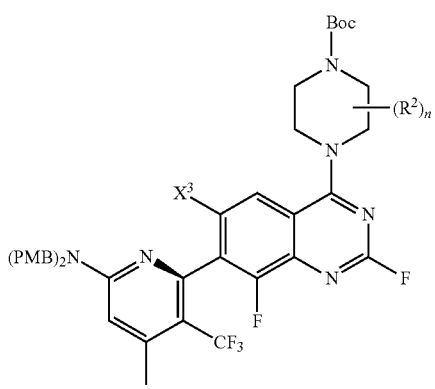

(Ib3)

or a solvate, tautomer, stereoisomer, or salt thereof.

In one embodiment, the compound of formula (I) or a solvate, tautomer, stereoisomer, or salt thereof described herein comprises a compound of formula:

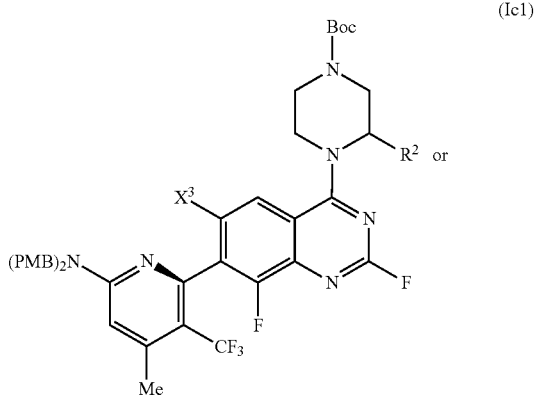

(Ic1)

or

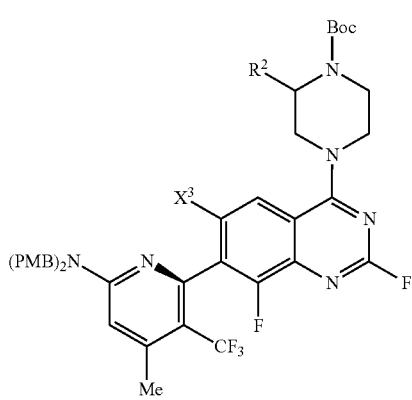
(Ic2)

or a solvate, tautomer, stereoisomer, or salt thereof.

In one embodiment, the compound of formula (I) or a solvate, tautomer, stereoisomer, or salt thereof described herein comprises a compound of formula:

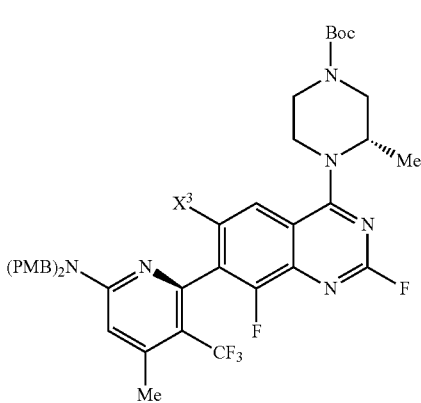
(Id)

or a solvate, tautomer, stereoisomer, or salt thereof.

In one embodiment, the compound of formula (I) or a solvate, tautomer, stereoisomer, or salt thereof described herein comprises a compound of formula:

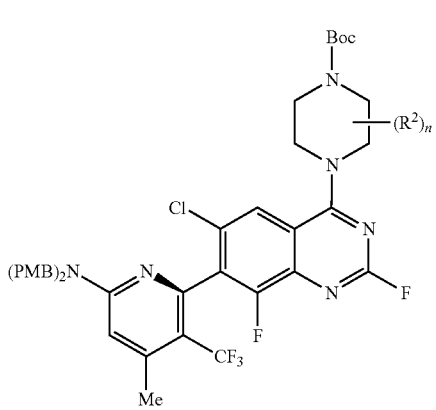
(Ia)

or a solvate, tautomer, stereoisomer, or salt thereof.

In one embodiment, the compound of formula (I) or a solvate, tautomer, stereoisomer, or salt thereof described herein comprises a compound of formula:

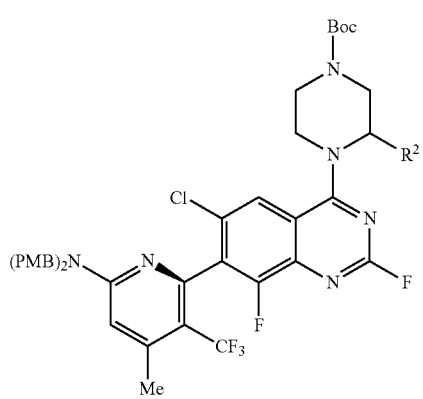
(Ib)

or a solvate, tautomer, stereoisomer, or salt thereof.

In one embodiment, the compound of formula (I) or a solvate, tautomer, stereoisomer, or salt thereof described herein comprises a compound of formula:

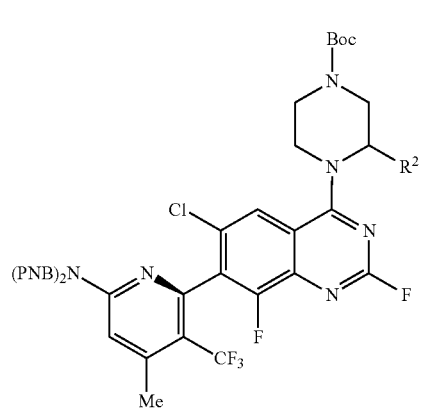
(Ic)

or a solvate, tautomer, stereoisomer, or salt thereof.

In one embodiment, the compound of formula (I) or a solvate, tautomer, stereoisomer, or salt thereof described herein is a compound of formula 1:

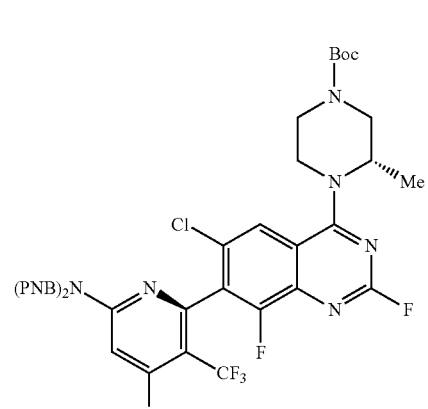
(1)

or a solvate, tautomer, stereoisomer, or salt thereof.

Further provided herein are crystalline solvates of the compounds of formula (I). In one embodiment, the compound of formula (I) is a cyclohexane, methylcyclohexane, chlorobenzene, ethylbenzene, m-xylene, or toluene solvate.

In one embodiment, the compound of formula (I) is a crystalline solvate of compound of formula 1:

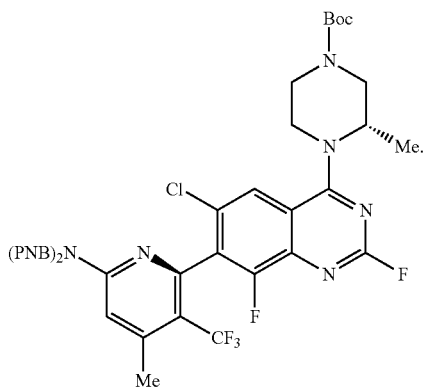

(1)

Figure 2:
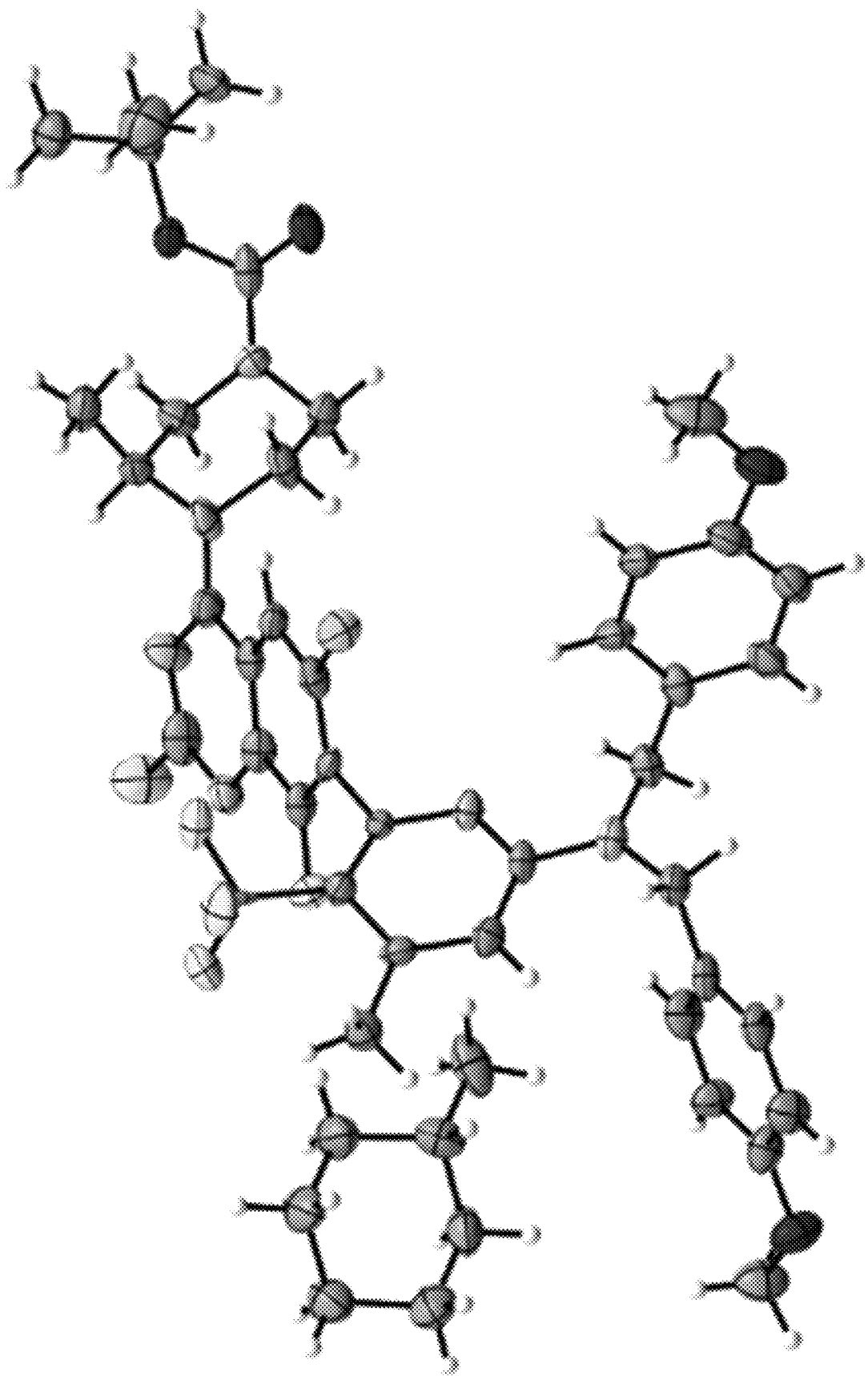
FIG. 2 shows the single crystal structure of a methylcyclohexane crystalline solvate of compound 1.
Figure 3:
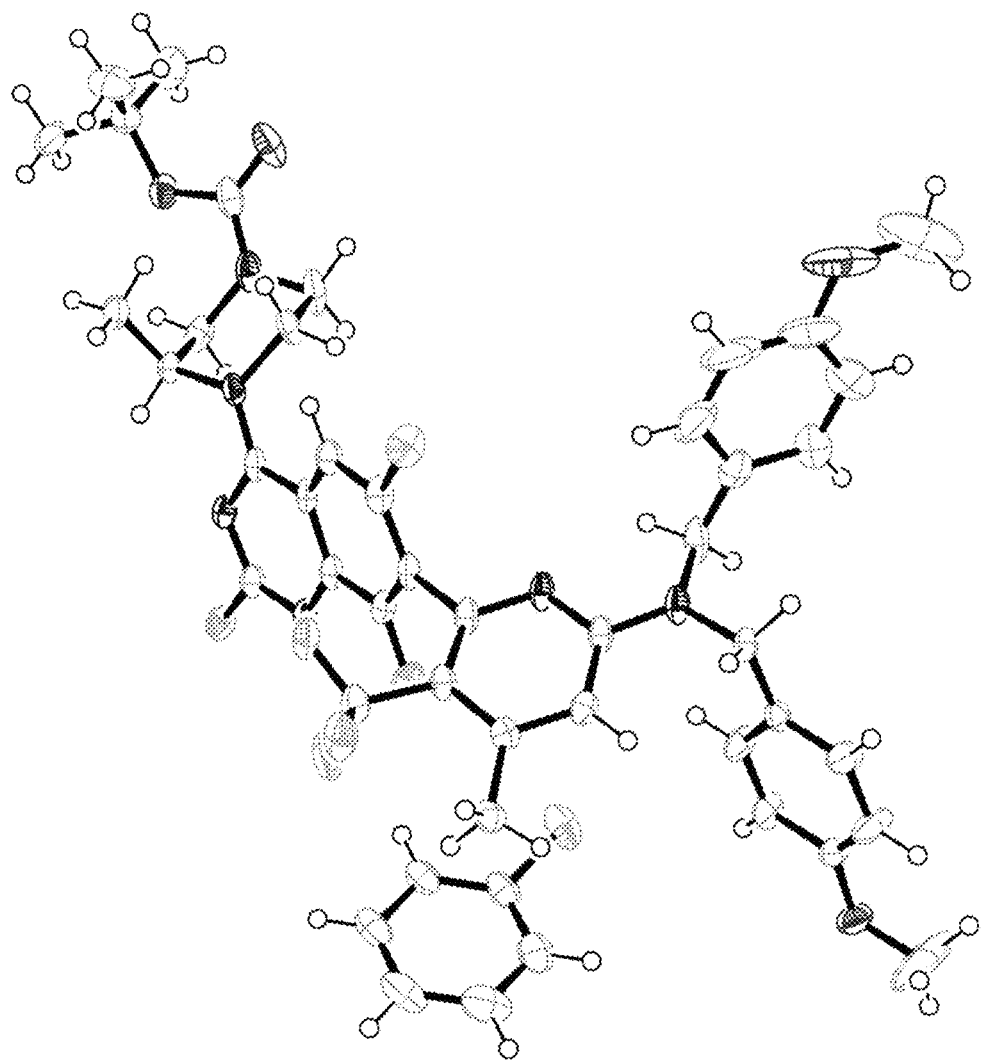
FIG. 3 shows the single crystal structure of a chlorobenzene crystalline solvate of compound 1.
Figure 4:
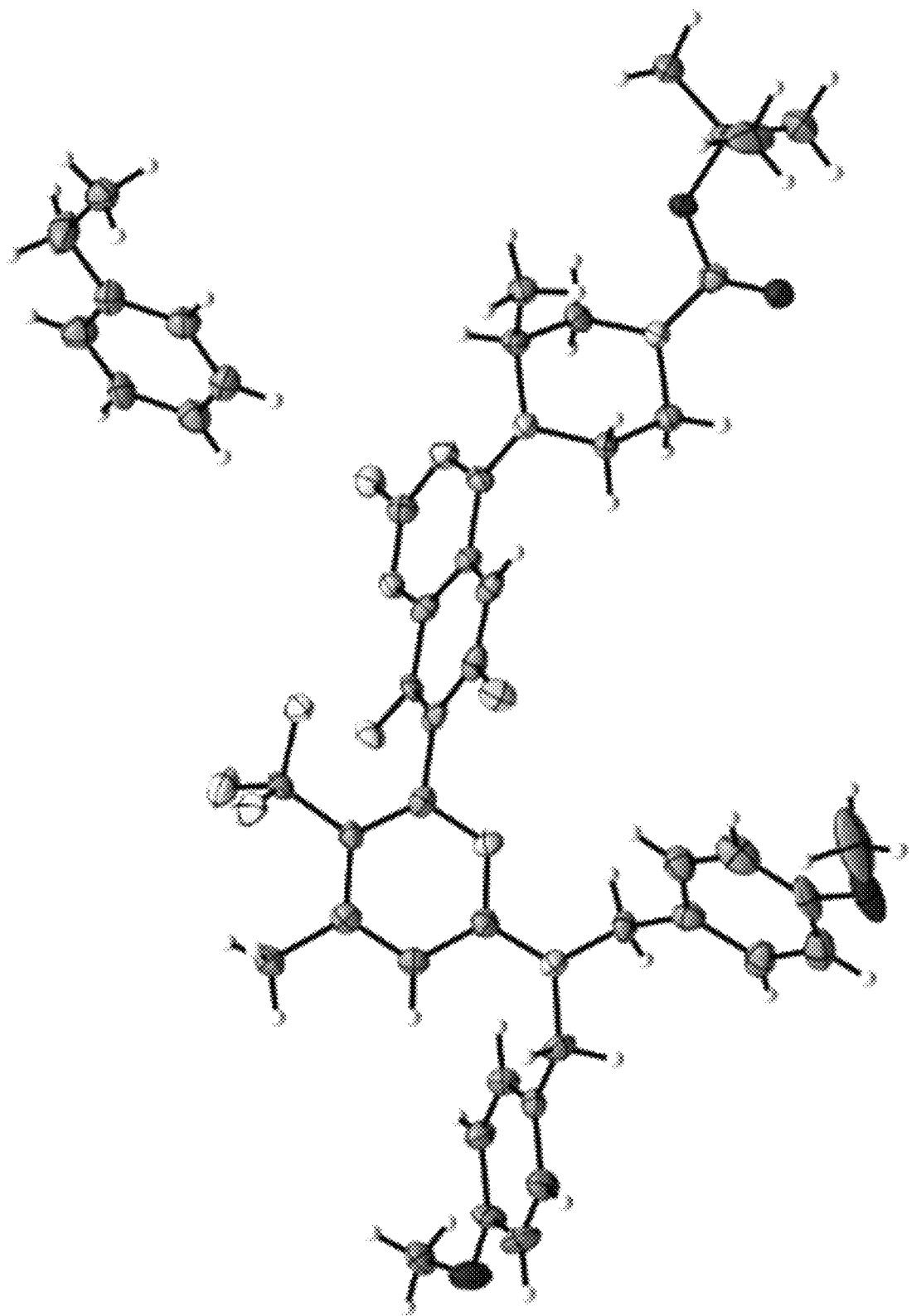
FIG. 4 shows the single crystal structure of an ethylbenzene crystalline solvate of compound 1.
Figure 5:
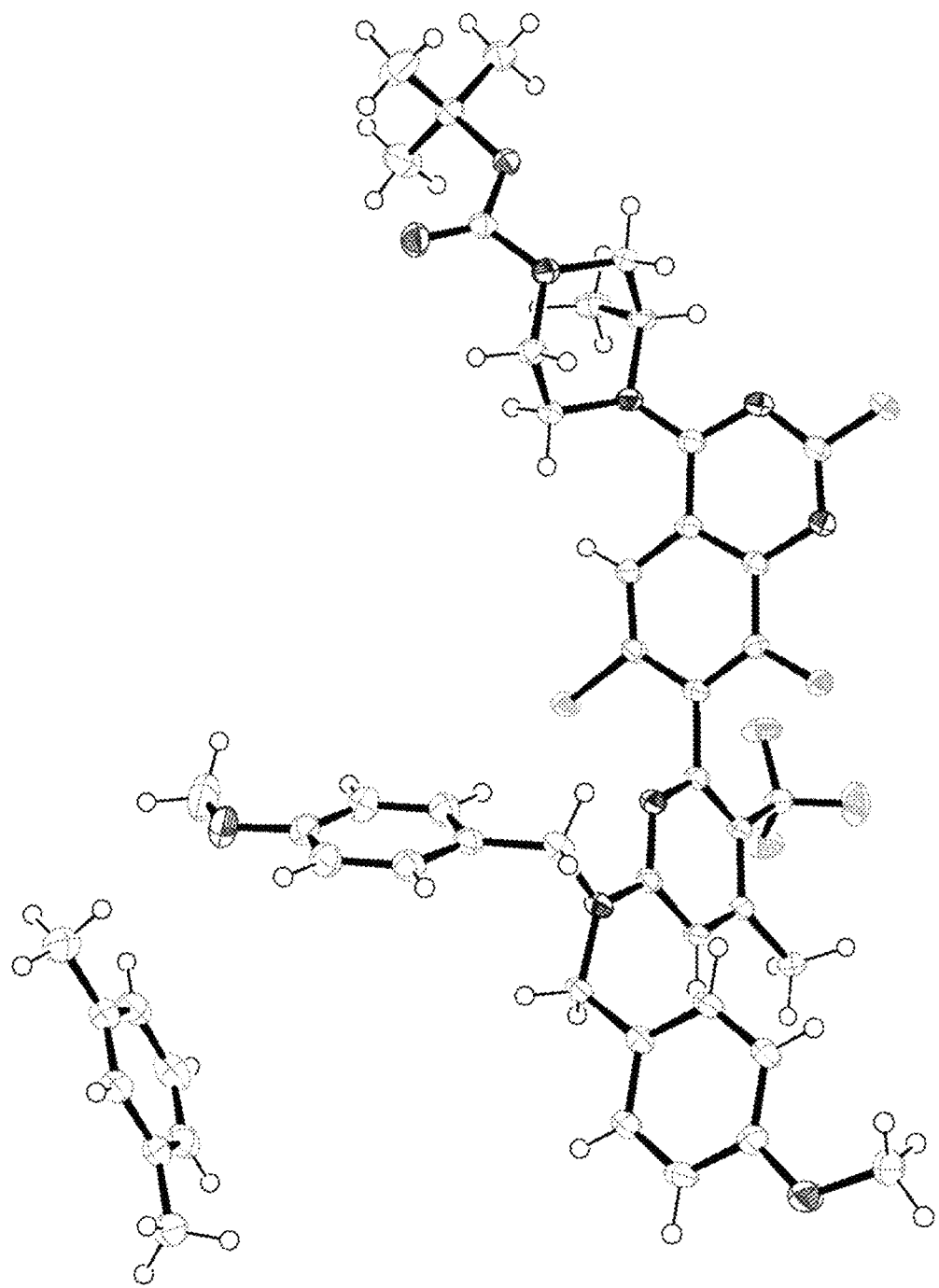
FIG. 5 shows the single crystal structure of a m-xylene crystalline solvate of compound 1.
Figure 6:
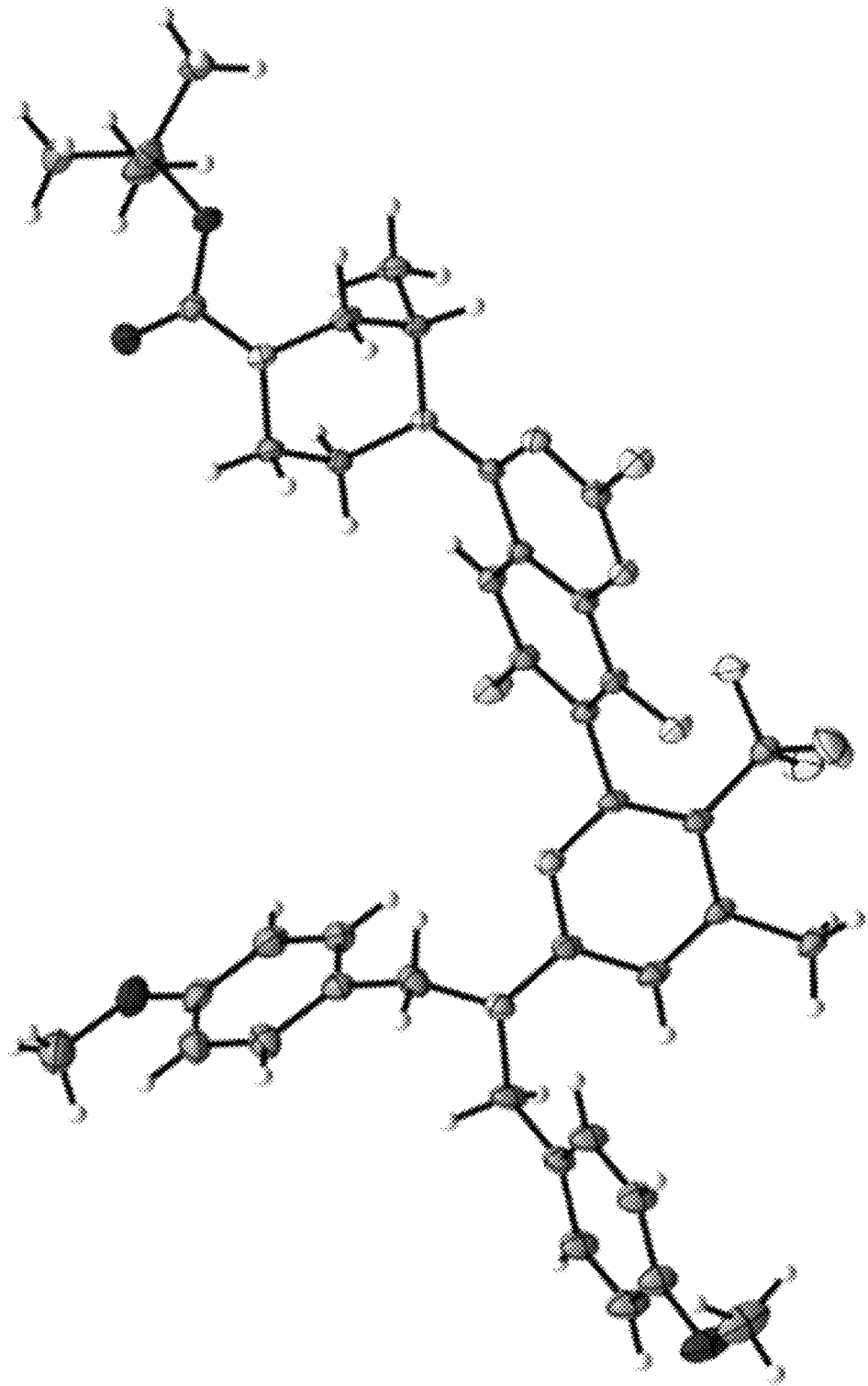
FIG. 6 shows the single crystal structure of a toluene crystalline solvate of compound 1.

In one embodiment, the compound of formula (1) is a cyclohexane, methylcyclohexane, chlorobenzene, ethylbenzene, m-xylene, or toluene solvate. In one embodiment, the compound of formula (1) is a crystalline cyclohexane solvate. In one such embodiment, the crystalline cyclohexane solvate of the compound of formula (1) is substantially as shown in FIG. 1. In another embodiment, the compound of formula (1) is a crystalline methylcyclohexane solvate. In one such embodiment, the crystalline methylcyclohexane solvate of the compound of formula (1) is substantially as shown in FIG. 2. In another embodiment, the compound of formula (1) is a crystalline chlorobenzene solvate. In one such embodiment, the crystalline chlorobenzene solvate of the compound of formula (1) is substantially as shown in FIG. 3. In another embodiment, the compound of formula (1) is a crystalline ethylbenzene solvate. In one such embodiment, the crystalline ethylbenzene solvate of the compound of formula (1) is substantially as shown in FIG. 4. In another embodiment, the compound of formula (1) is a crystalline m-xylene solvate. In one such embodiment, the crystalline m-xylene solvate of the compound of formula (1) is substantially as shown in FIG. 5. In another embodiment, the compound of formula (1) is a crystalline toluene solvate. In one such embodiment, the crystalline toluene solvate of the compound of formula (1) is substantially as shown in FIG. 6.

In another aspect provided herein are crystalline solvate solid forms of Compound (1).

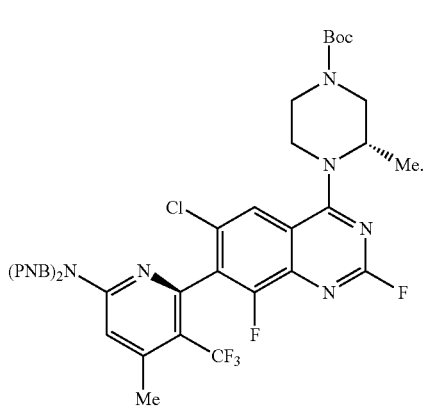

(1)

In certain embodiments, the crystalline solvate is a crystalline cyclohexane solvate of Compound 1. In one embodiment, the cyclohexane crystalline solvate of Compound 1 is obtained from a hot cyclohexane solution allowed to cool to about room temperature. In one such embodiment, the solution is allowed to cool for about 72 h. In one embodiment, the cyclohexane crystalline solvate of Compound 1 is substantially as shown in FIG. 1. In another embodiment, the cyclohexane crystalline solvate of Compound 1 has the unit cell dimensions as set forth in Table 2.

In certain embodiments, the crystalline solvate is a crystalline methylcyclohexane solvate of Compound 1. In one embodiment, the methylcyclohexane crystalline solvate of Compound 1 is obtained from a hot methylcyclohexane solution allowed to cool to about room temperature. In one such embodiment, the solution is allowed to cool for about 48 h. In one embodiment, the methylcyclohexane crystalline solvate of Compound 1 is substantially as shown in FIG. 2. In another embodiment, the methylcyclohexane crystalline solvate of Compound 1 has the unit cell dimensions as set forth in Table 3.

In certain embodiments, the crystalline solvate is a crystalline chlorobenzene solvate of Compound 1. In one embodiment, the chlorobenzene crystalline solvate of Compound 1 is obtained from a saturated chlorobenzene solution followed by slow vapor diffusion of heptane. In one embodiment, the chlorobenzene crystalline solvate of Compound 1 is substantially as shown in FIG. 3. In another embodiment, the chlorobenzene crystalline solvate of Compound 1 has the unit cell dimensions as set forth in Table 4.

In certain embodiments, the crystalline solvate is a crystalline ethylbenzene solvate of Compound 1. In one embodiment, the ethylbenzene crystalline solvate of Compound 1 is obtained from a saturated ethylbenzene solution followed by slow vapor diffusion of heptane. In one embodiment, the ethylbenzene crystalline solvate of Compound 1 is substantially as shown in FIG. 4. In another embodiment, the ethylbenzene crystalline solvate of Compound 1 has the unit cell dimensions as set forth in Table 5.

In certain embodiments, the crystalline solvate is a crystalline m-xylene solvate of Compound 1. In one embodiment, the m-xylene crystalline solvate of Compound 1 is obtained from a saturated m-xylene solution followed by slow vapor diffusion of heptane. In one embodiment, the m-xylene crystalline solvate of Compound 1 is substantially as shown in FIG. 5. In another embodiment, the m-xylene crystalline solvate of Compound 1 has the unit cell dimensions as set forth in Table 6.

In certain embodiments, the crystalline solvate is a crystalline toluene solvate of Compound 1. In one embodiment, the toluene crystalline solvate of Compound 1 is obtained from a saturated toluene solution followed by slow vapor diffusion of heptane. In one embodiment, the toluene crystalline solvate of Compound 1 is substantially as shown in FIG. 6. In another embodiment, the toluene crystalline solvate of Compound 1 has the unit cell dimensions as set forth in Table 7.

In another embodiment, the compound of formula (I) or a solvate, tautomer, stereoisomer, atropisomer, or salt thereof described herein is a compound or solvate, tautomer, stereoisomer, atropisomer, or salt thereof having formula as set forth in Table 1.

TABLE 1
| Cmpd No | Structure |
|---|---|
| 101 | 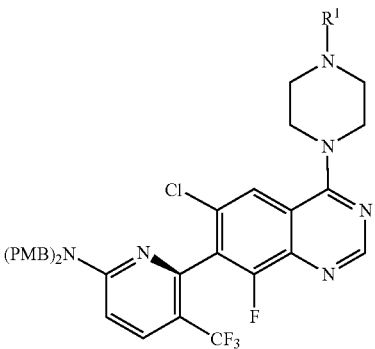 |
| 102 | 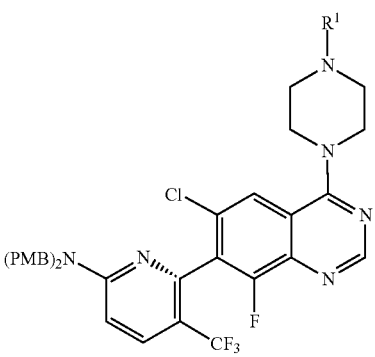 |
| 103 | 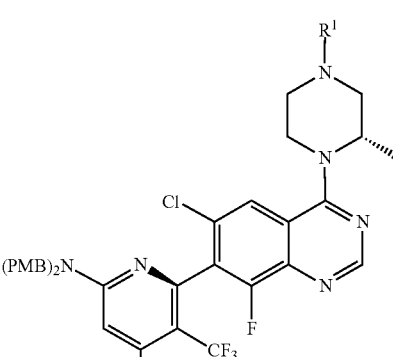 |
| 104 | 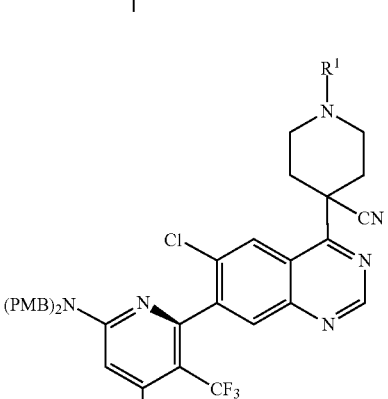 |
TABLE 1-continued
| Cmpd No | Structure |
|---|---|
| 105 | 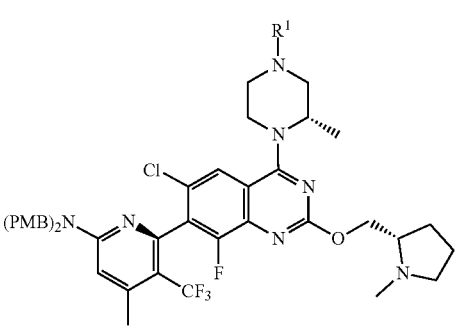 |
| 106 | 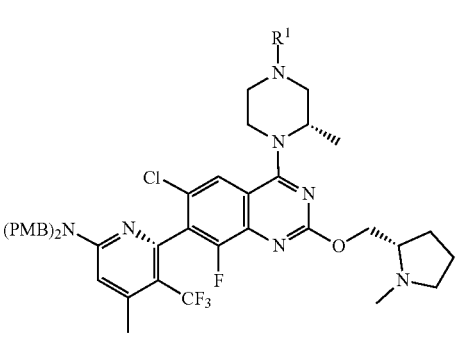 |
| 107 | 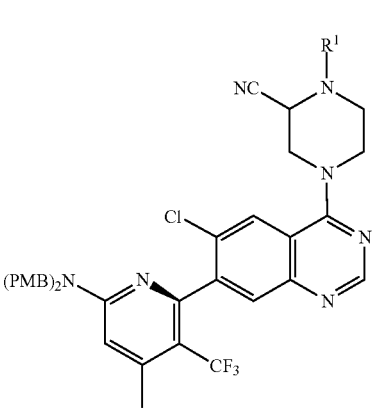 |
| 108 | 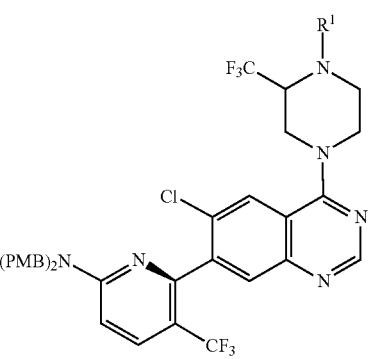 |

TABLE 1-continued

| Cmpd No | Structure |
|---|---|
| 109 | (structure) |
| 110 | (structure) |
| 111 | (structure) |
| 112 | (structure) |
| 113 | (structure) |
| 114 | (structure) |
| 115 | (structure) |
| 116 | (structure) |

TABLE 1-continued

| Cmpd No | Structure |
|---|---|
| 117 | 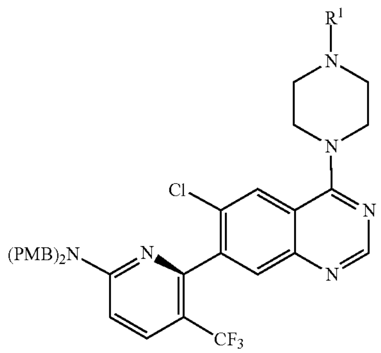 |
| 118 | 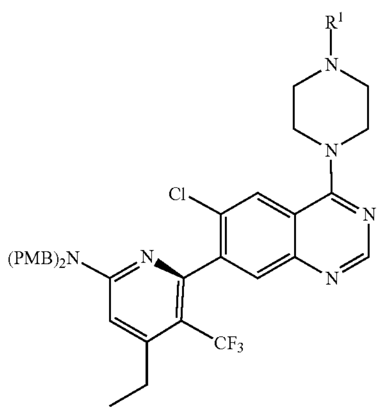 |
| 119 | 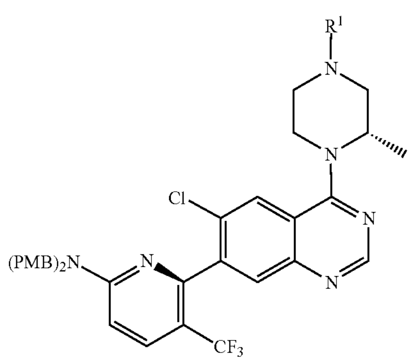 |
| 120 | 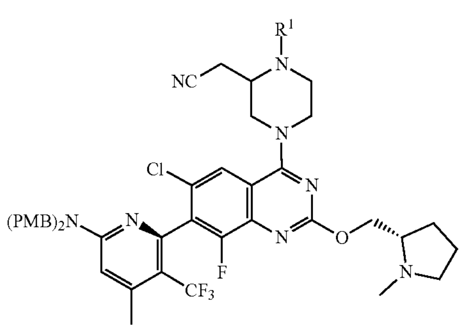 |
| 121 | |
| 122 | |
| 123 | |
| 124 | |

TABLE 1-continued

| Cmpd No | Structure |
|---|---|
| 125 | |
| 126 | |
| 127 | |
| 128 | |
| 129 | 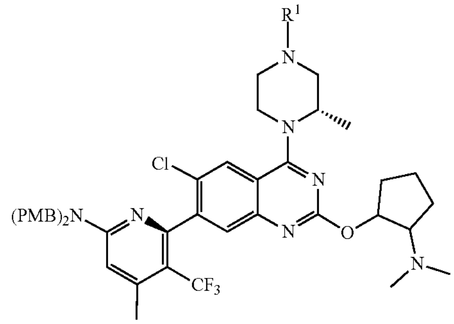 |
| 130 | 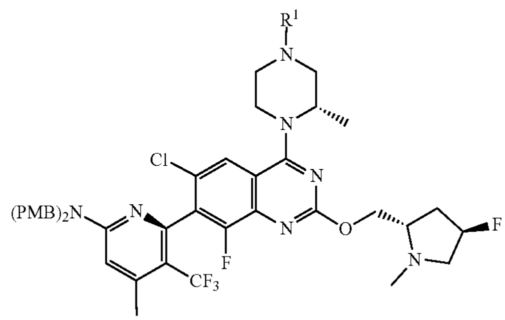 |
| 131 | 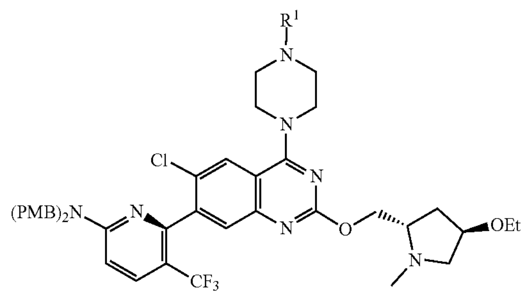 |
| 132 | 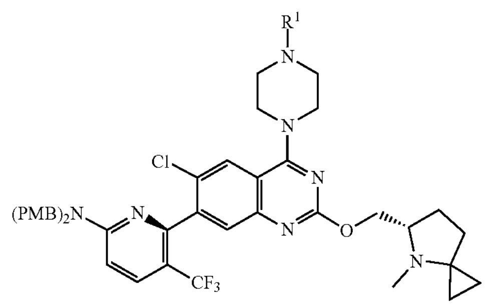 |
| 133 | 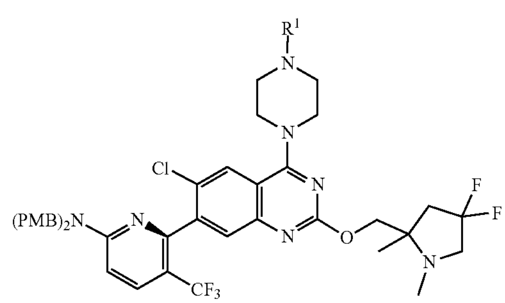 |

TABLE 1-continued

| Cmpd No | Structure |
|---|---|
| 134 | 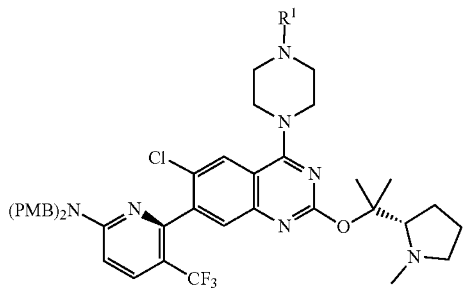 |
| 135 | 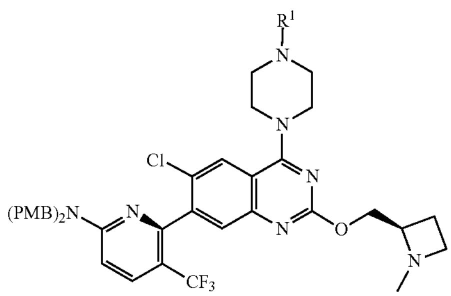 |
| 136 | 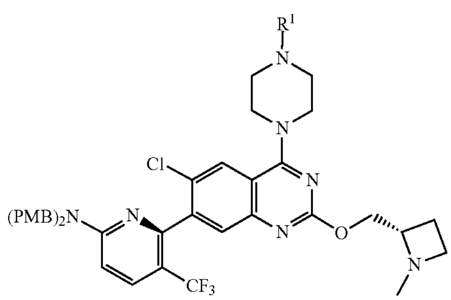 |
| 137 | 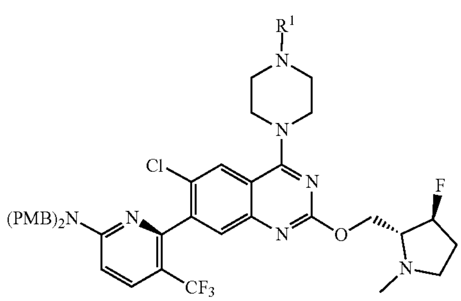 |
| 138 | 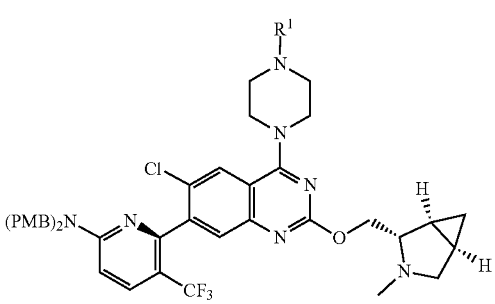 |
| 139 | |
| 140 | |
| 141 | |
| 142 | |
| 143 | |

TABLE 1-continued

| Cmpd No | Structure |
|---|---|
| 144 | |
| 145 | |
| 146 | |
| 147 | |
| 148 | 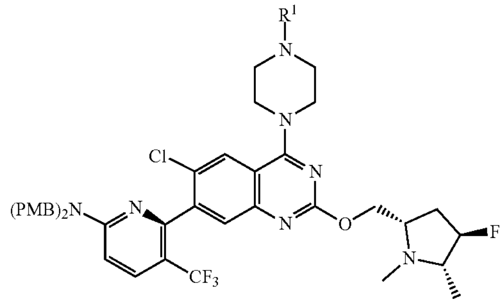 |
| 149 | 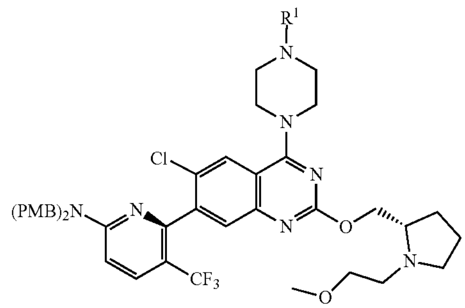 |
| 150 | 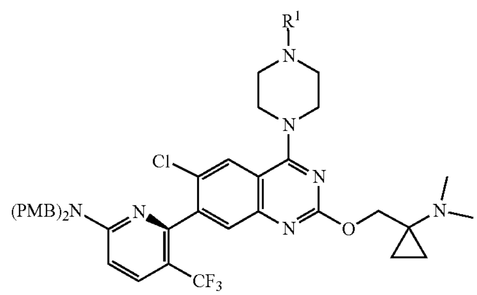 |
| 151 | 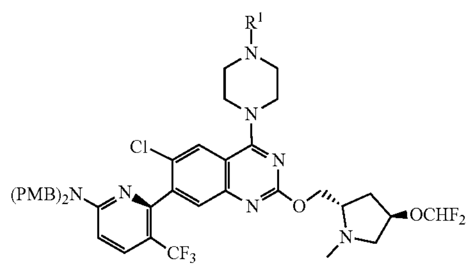 |
| 152 | 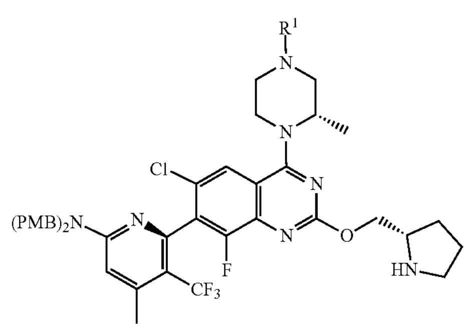 |

TABLE 1-continued

| Cmpd No | Structure |
|---|---|
| 153 | 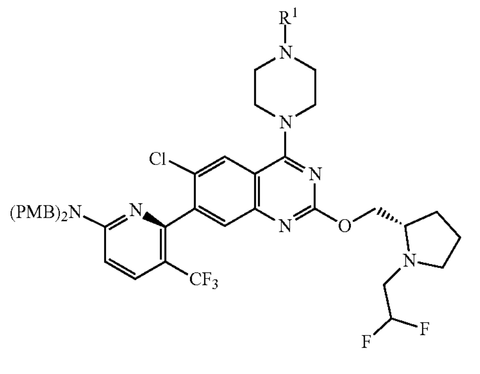 |
| 154 | 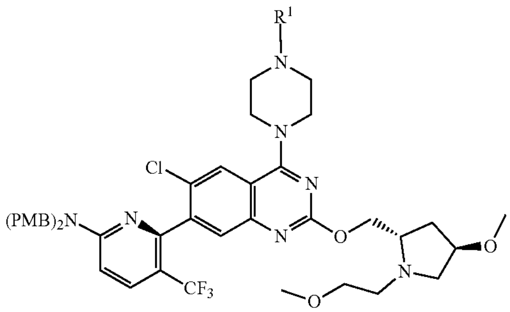 |
| 155 | 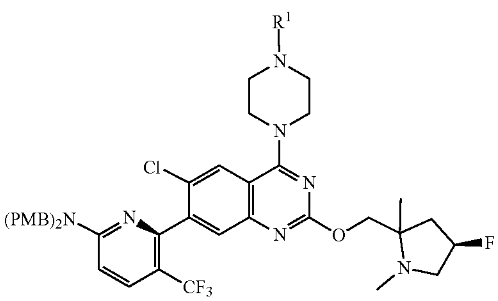 |
| 156 | 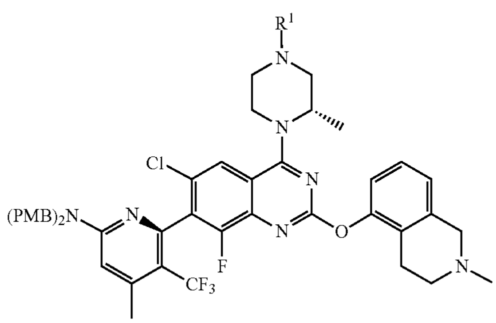 |

In one embodiment, the compound of formula (I) or a solvate, tautomer, stereoisomer, atropisomer, or salt thereof comprises a compound of formula 103, 104, 105, 106, 107, 110, 113, 120, 121, 122, 125, 126, 127, 128, 129, 131, 137, 144, 145, 143, or 148. In another embodiment, the compound of formula (I) or a solvate, tautomer, stereoisomer, atropisomer, or salt thereof is a compound of formula 105, 106, 120, 126, 128, 129, 131, 137, 143, or 148. In still another embodiment, the compound of formula (I) or a solvate, tautomer, stereoisomer, atropisomer, or salt thereof is a compound of formula 105, 126, 128, 129, 131, or 143.

In one preferred embodiment, the compound is a compound of formula 105, 105, 126, 128, 129, 131, or 143 of table 1, where $R^1$ is Boc.

In another embodiment, the compound of formula (I) is a crystalline solvate of a compound of formula 103, 104, 105, 106, 107, 110, 113, 120, 121, 122, 125, 126, 127, 128, 129, 131, 137, 144, 145, 143, or 148. In still another embodiment, the compound of formula (I) is a crystalline solvate of a compound of formula 105, 126, 128, 129, 131, or 143. In such embodiments, the solvate is a cyclohexane, methylcyclohexane, chlorobenzene, ethylbenzene, m-xylene, or toluene solvate of the compound of formula (1). In one embodiment, the compound of formula (I) is a crystalline solvate of a compound of formula 105, 126, 128, 129, 131, or 143 where $R^1$ is Boc. In one embodiment, the compound of formula (I) is a crystalline solvate of a compound of formula 105 where $R^1$ is Boc.

Process of Preparation

Further provided herein are processes for the preparation of a compound of formula (I):

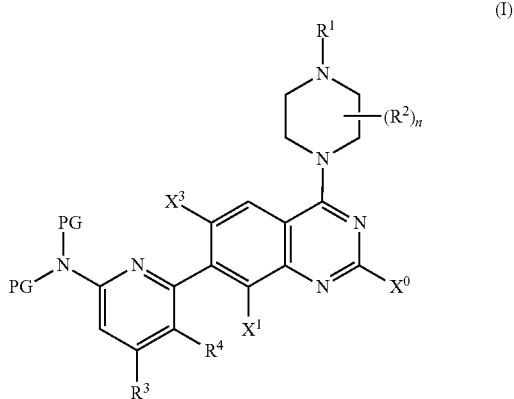

(I)

or a solvate, tautomer, stereoisomer, atropisomer, or salt thereof, wherein $X^0$, $X^1$, $X^3$, $R^1$, $R^2$, $R^3$, $R^4$, n, and PG are as described herein. In one embodiment, the compound of formula (I) synthesized according to the methods described herein is a crystalline solvate. In one embodiment, the compound of formula (I) is a cyclohexane, methylcyclohexane, chlorobenzene, ethylbenzene, m-xylene, or toluene solvate.

In one aspect provided herein is a process (P1) for the preparation of a compound of formula (I) or a solvate, tautomer, stereoisomer, atropisomer, or salt thereof, the process comprising:

(a) contacting a compound of formula (II)

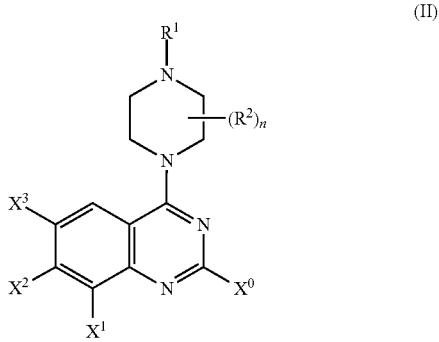

(II)

or a tautomer, stereoisomer, or salt thereof wherein $X^0$, $X^1$, $X^3$, $R^1$, and $R^2$ are as described herein; and $X^2$ is halogen or $ZnY^1$, where $Y^1$ is halogen (e.g. Cl, Br, or I), OAc, TFA, OTf, or OPiv;

with an organomagnesium compound and a zinc complex; and (b) contacting the mixture of step (a) with a compound of formula (III),

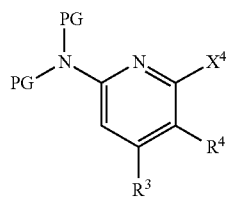

(III)

or a stereoisomer or salt thereof wherein $X^4$ is halogen; a transition metal (e.g. Pd or Ni) catalyst precursor, and a chiral ligand, thereby synthesizing a compound of formula (I) or a solvate, tautomer, stereoisomer, atropisomer, or salt thereof.

In one preferred embodiment of the process (P1) described herein, $X^0$ is halogen. In one such embodiment, $X^0$ is F. In another embodiment, $X^0$ is a moiety selected from the group consisting of:

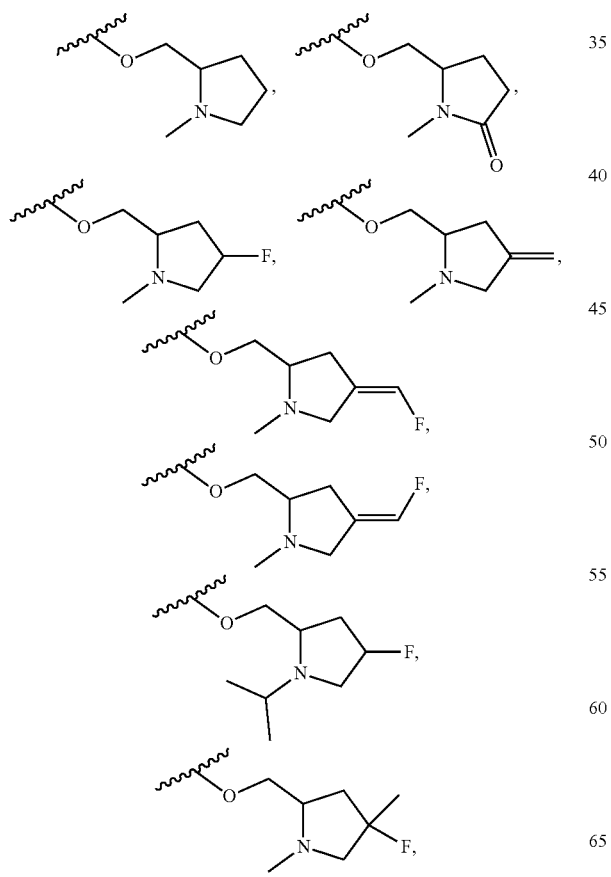

-continued

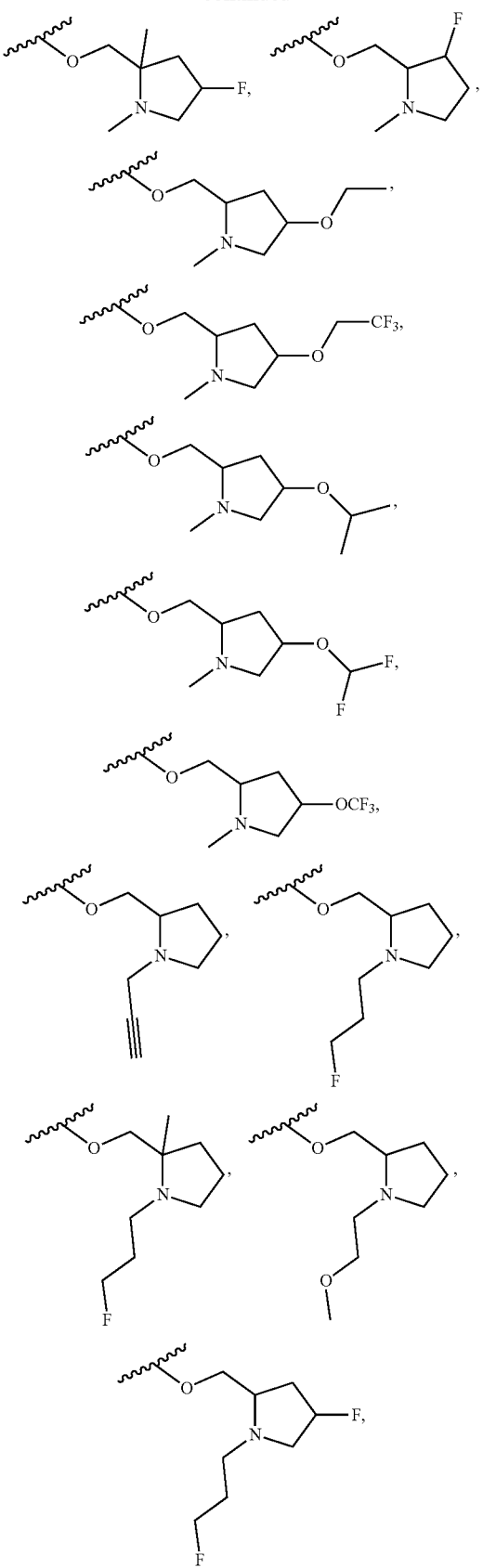

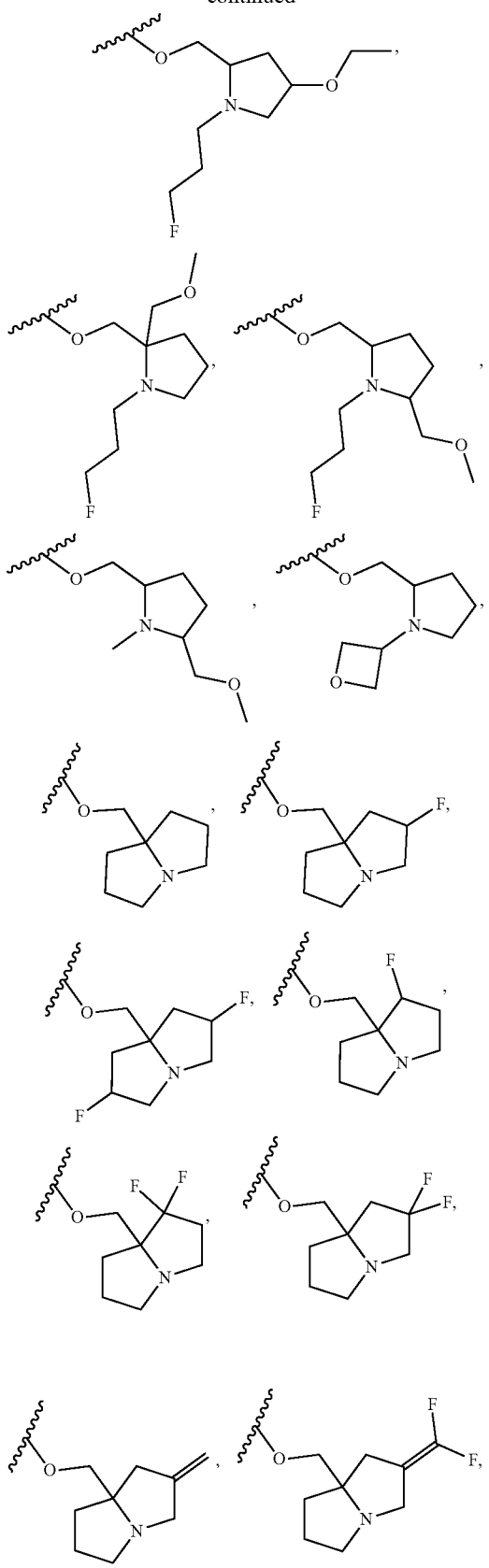
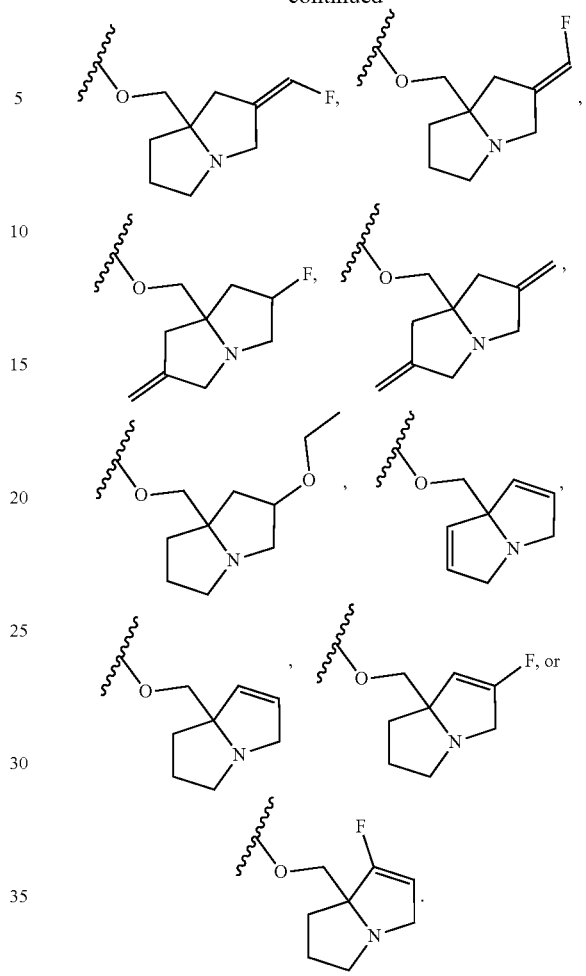

In one embodiment of the process (P1) described herein, the organomagnesium compound is selected from the group consisting of isopropylmagnesium chloride, isopropylmagnesium bromide, isopropylmagnesium iodide, isopropylmagnesium chloride lithium chloride complex, sec-butylmagnesium chloride, lithium tri-n-butylmagnesiate, lithium triisopropylmagnesiate, and lithium (isopropyl)(di-n-butyl)magnesiate). In one such embodiment, the organomagnesium compound is isopropylmagnesium chloride, isopropylmagnesium bromide, or isopropylmagnesium iodide. In another embodiment, the organomagnesium compound is isopropylmagnesium chloride lithium chloride complex. In one embodiment, the reaction with the organomagnesium compound is performed at a temperature of about −100 to about −40° C. In one such embodiment, the temperature is about −80 to about −60° C. In still another embodiment, the temperature is about −70±5° C.

In one embodiment of the process (P1) described herein, the zinc complex is selected from the group consisting of $ZnCl_2$, $ZnBr_2$, $ZnI_2$, $Zn(OAc)_2$, $Zn(TFA)_2$, $Zn(OTf)_2$, and $Zn(OPiv)_2$. In another embodiment, the zinc complex is $ZnCl_2$, $ZnBr_2$ or $ZnI_2$. In one such embodiment, the zinc complex is $ZnCl_2$. In another embodiment, the zinc complex is $Zn(OAc)_2$, $Zn(TFA)_2$, $Zn(OTf)_2$, or $Zn(OPiv)_2$.

In one embodiment of the process (P1) described herein, the process is performed in a polar aprotic solvent. In one such embodiment, the polar aprotic solvent is dichloromethane (DCM), tetrahydrofuran (THF), 2-methyltetrahydrofuran (MeTHF), ethyl acetate (EtOAc), acetonitrile (ACN or MeCN), N,N-dimethylformamide (DMF), dimethyl sulfoxide (DMSO), acetone, or hexamethylphosphoric triamide (HMPA), or a combination thereof. In another embodiment, the process is performed in THF. In another embodiment, the process is performed in 2-MeTHF. In still another embodiment, the process is performed in THF and MeTHF.

In one embodiment of the process (P1) described herein, the transition metal catalyst precursor is a Pd or Ni catalyst precursor. In one embodiment of the process (P1) described herein, the Pd or Ni catalyst precursor is selected from the group consisting of $Pd(OAc)_2$, $PdCl_2$, $PdCl_2(MeCN)_2$, $Pd(benzonitrile)_2Cl_2$, $Pd(dba)_2$, $Pd_2(dba)_3$, $Pd(PPh_3)_4$, $Pd(PCy_3)_2$, $Pd(PtBu_3)_2$, $Pd(TFA)_2$, $[Pd(allyl)Cl]_2$, $[Pd(cinammyl)Cl]_2$, $[PdCl(crotyl)]_2$, $PdCl(\eta 5\text{-cyclopentadienyl})$, $[(\eta 3\text{-allyl})(\eta 5\text{-cyclopentadienyl})palladium(II)]$, $[Ni(\eta 5\text{-cyclopentadienyl})(allyl)]$, $[bis(1,5\text{-cyclooctadiene})nickel(0)]$, $NiCl_2$, $NiBr_2$, $Ni(OAc)_2$, and Nickel(II) acetylacetonate.

In one such embodiment of the process (P1) described herein, the Pd or Ni catalyst precursor is a Pd catalyst precursor. In one embodiment, the Pd catalyst precursor is $Pd(OAc)_2$, $PdCl_2$, $PdCl_2(MeCN)_2$, $Pd(dba)_2$, $Pd_2(dba)_3$, $Pd(TFA)_2$, $[Pd(allyl)Cl]_2$, $[Pd(cinammyl)Cl]_2$, $[PdCl(crotyl)]_2$, $PdCl(\eta 5\text{-cyclopentadienyl})$, or $[(\eta 3\text{-allyl})(\eta 5\text{-cyclopentadienyl})palladium(II)]$. In another embodiment of the process (P1) described herein, the Pd catalyst precursor is $Pd(OAc)_2$, or $PdCl_2$. In another embodiment of the process (P1) described herein, the Pd catalyst precursor is $[PdCl(crotyl)]_2$, $PdCl(\eta 5\text{-cyclopentadienyl})$, $PdCl_2(MeCN)_2$, $Pd(dba)_2$, $Pd_2(dba)_3$, or $Pd(TFA)_2$. In another embodiment of the process (P1) described herein, the Pd catalyst precursor is $[Pd(allyl)Cl]_2$, $[Pd(cinammyl)Cl]_2$, or $(\eta 3\text{-allyl})(\eta 5\text{-cyclopentadienyl})palladium(II)$. In one embodiment, the Pd catalyst precursor is $[Pd(allyl)Cl]_2$ or $[Pd(cinammyl)Cl]2$. In one embodiment, the Pd catalyst precursor is $[Pd(cinammyl)Cl]_2$.

In another embodiment of the process (P1) described herein, the Pd or Ni catalyst precursor is a Ni catalyst precursor. In one embodiment, the Ni catalyst precursor is NiCp(allyl), bis(1,5-cyclooctadiene)nickel(0), $NiCl_2$, $NiBr_2$, $Ni(OAc)_2$, or Nickel(II) acetylacetonate. In one embodiment, the Ni catalyst precursor is $NiCl_2$, $NiBr_2$, or $Ni(OAc)_2$. In another embodiment, the Ni catalyst precursor is NiCp(allyl), bis(1,5-cyclooctadiene)nickel(0), or Nickel(II) acetylacetonate.

In one embodiment, step 1 of the process of P1 is run using continuous flow mode comprising one or more continuous stir reactors (CSTRs). In one embodiment, a Pd precursor described herein and a chiral ligand described herein are contacted to form a Pd-ligand complex in situ. In another embodiment, a Pd precursor described herein is treated with a chiral ligand described herein to form a Pd-ligand complex that can be isolated before use in a process described herein.

In one embodiment of the process (P1) described herein, the chiral ligand is:

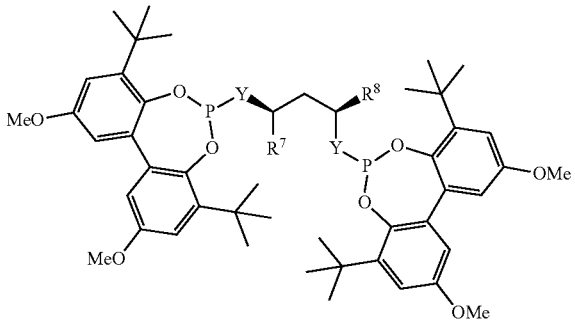

(L1)

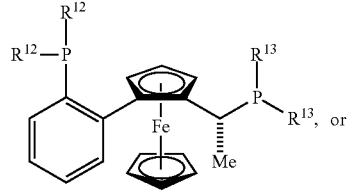

(L2)

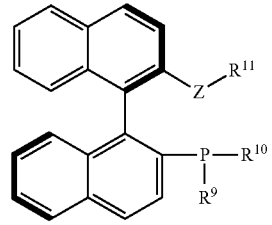

(L3)

wherein

Y is O or NR;

Z is O or N;

each $R^7$ and $R^8$ are independently unsubstituted $C_{1-6}$ alkyl or unsubstituted phenyl;

or wherein $R^7$ and $R^8$ together form a unsubstituted $C_{5-6}$ cycloalkyl or unsubstituted $C_{6-10}$ aryl; or wherein $R^8$ together with the adjacent methylene can form $R^{8A}$ substituted or unsubstituted $C_{5-8}$ cycloalkyl or $R^{8A}$-substituted or unsubstituted 5-8 membered heterocycle comprising at least one O atom, wherein $R^{8A}$ is $C_{1-3}$ unsubstituted alkyl;

$R^9$ and $R^{10}$ are independently $R^{10A}$-substituted or unsubstituted $C_{5-6}$ cycloalkyl or $R^{10A}$-substituted or unsubstituted phenyl;

each $R^{10A}$ is independently hydrogen, $C_{1-6}$ unsubstituted alkyl, or $C_{1-6}$ unsubstituted haloalkyl;

$R^{11}$ is $C_{1-4}$ unsubstituted alkyl;

$R^{12}$ and $R^{13}$ are each independently $R^{14}$-substituted or unsubstituted $C_{1-6}$ alkyl, $R^{14}$-substituted or unsubstituted $C_{3-7}$ cycloalkyl, $R^{14}$-substituted or unsubstituted aryl, or $R^{14}$-substituted or unsubstituted $C_{5-7}$ heteroaryl; and each $R^{14}$ is independently unsubstituted $C_{1-4}$ alkyl.

In one embodiment of the process (P1) described herein, the chiral ligand comprises a compound of formula:

(L1)

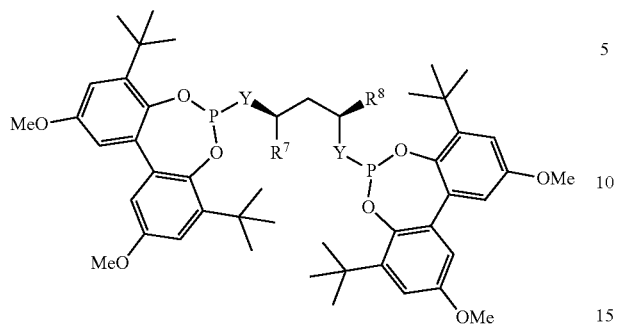

where Y, R$^7$, and R$^8$ are as described herein.

In one such embodiment, each Y is O. In one such embodiment, each Y is O and R$^7$ and R$^8$ are independently ethyl or phenyl. In one such embodiment, R$^7$ and R$^8$ are the same. In one such embodiment, each Y is NR$^7$ where each R$^7$ is independently methyl, ethyl, or propyl. In another embodiment, each Y is NR$^7$ where each R$^7$ is methyl.

In one such embodiment of the compounds of L1, R$^7$ and R$^8$ are the same. In another such embodiment of the compounds of L1, R$^7$ and R$^8$ are each methyl, ethyl, or propyl. In another such embodiment, R$^7$ and R$^8$ together form an unsubstituted cyclopentyl, cyclohexyl, or indenyl moiety. In another such embodiment, R$^8$ together with the adjacent methylene form a tetrahydrofuro-dioxolyl moiety.

In one such embodiment of the process (P1) described herein, the chiral ligand is:

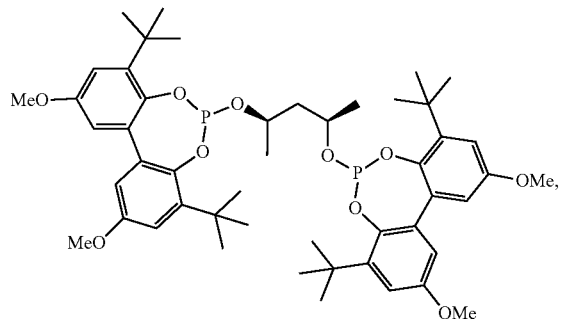

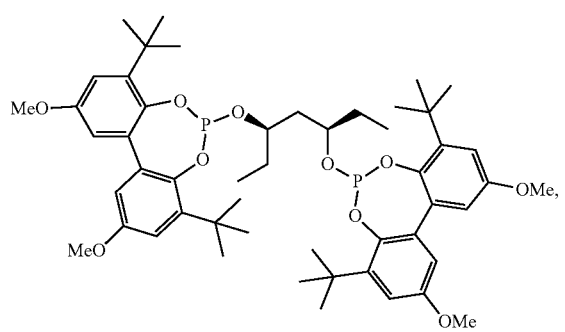

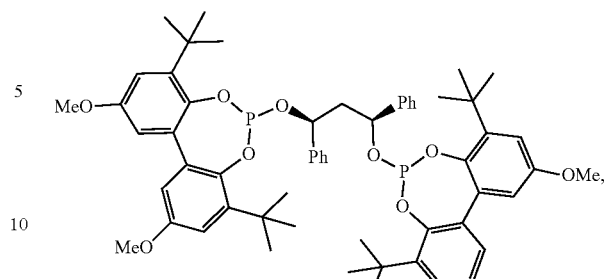

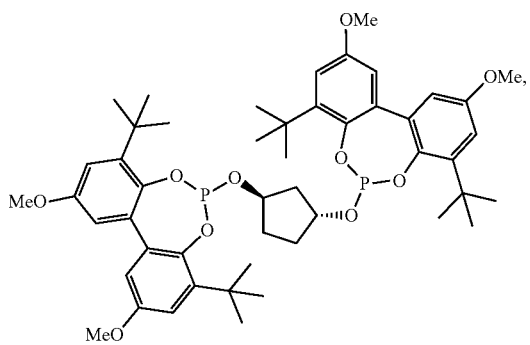

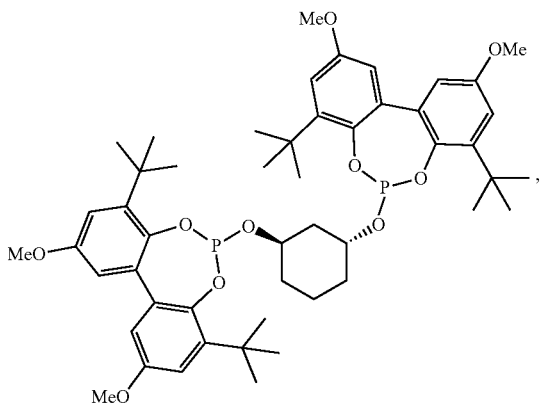

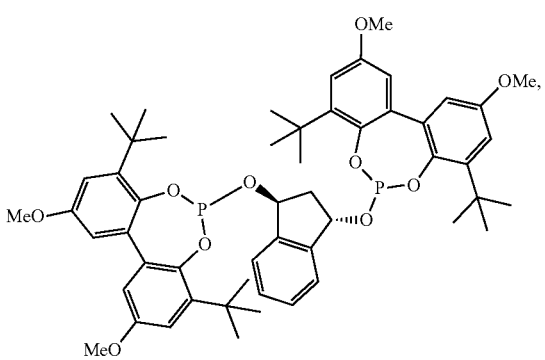

-continued
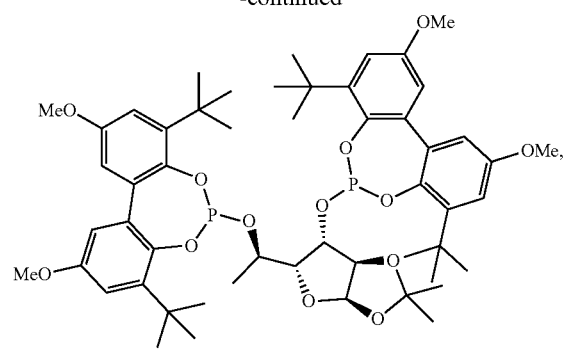
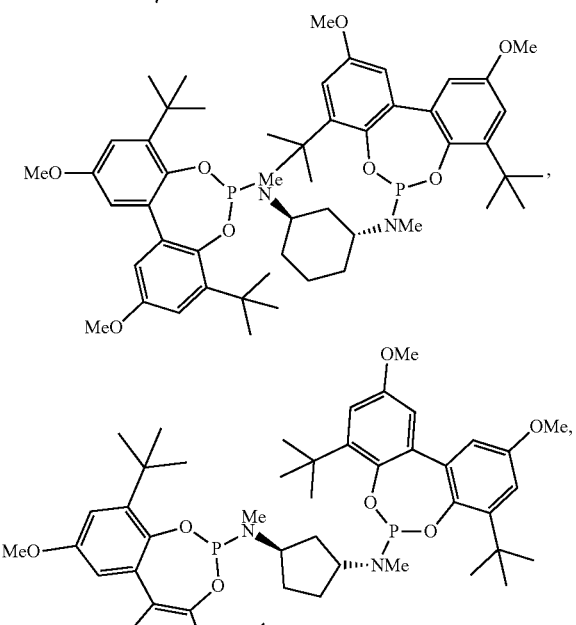
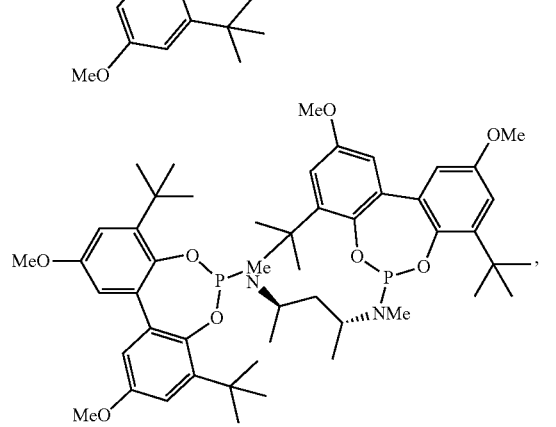
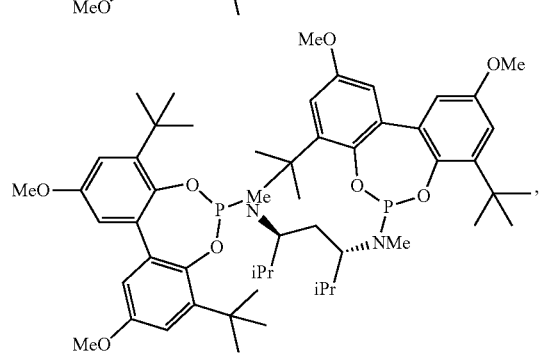
-continued
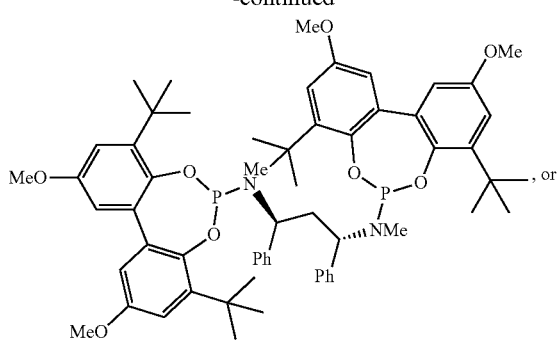
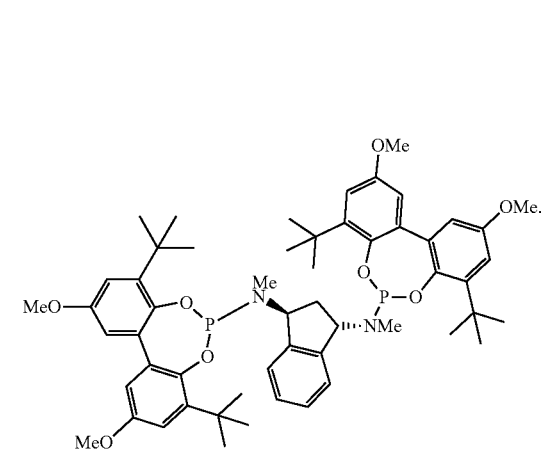
In one such embodiment of the process (P1) described herein, the chiral ligand is:
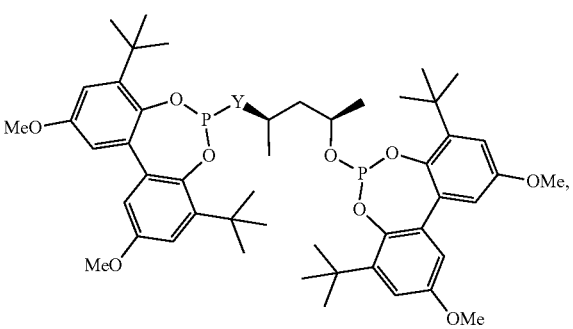
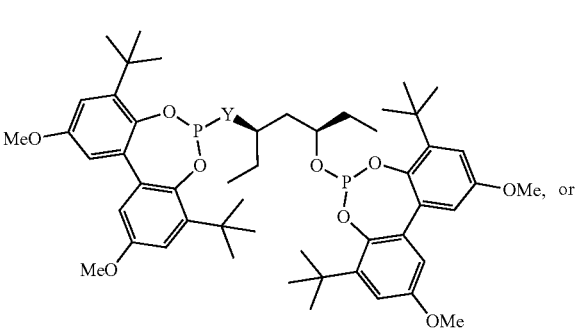

-continued

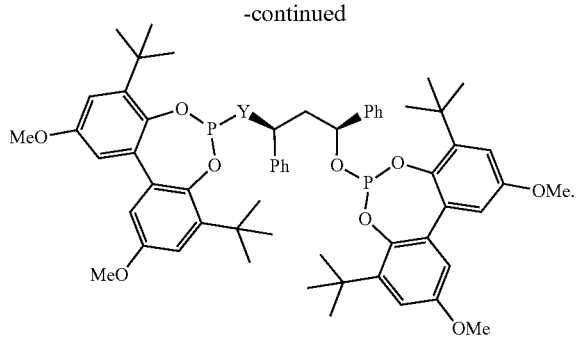

In one such embodiment of the process (P1) described herein, the chiral ligand is:

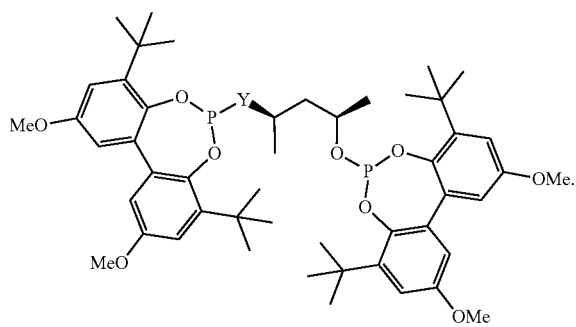

In another embodiment of the process (P1) described herein, the chiral ligand comprises a compound of formula:

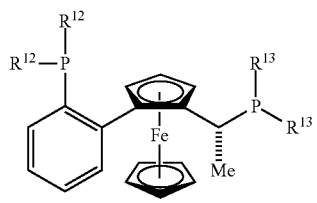

(L2)

where $R^{12}$ and $R^{13}$ are as described herein.

In one such embodiment of the compounds of L2, $R^{12}$ and $R^{13}$ are each independently $R^{14}$-substituted or unsubstituted $C_{1-6}$ alkyl. In another embodiment of the compounds of L2, $R^{12}$ and $R^{13}$ are each independently $R^{14}$-substituted or unsubstituted $C_{3-7}$ cycloalkyl or $R^{14}$-substituted or unsubstituted aryl. In one embodiment of the compounds of L2, $R^{12}$ and $R^{13}$ are each independently phenyl or unsubstituted $C_{3-7}$ cycloalkyl. In another embodiment of the compounds of L2, each $R^{12}$ phenyl and each $R^{13}$ is unsubstituted $C_{3-7}$ cycloalkyl. In one embodiment of the compounds of L2, $R^{13}$ is norbornanyl.

In one such embodiment of the process (P1) described herein, the chiral ligand is L2 having structure:

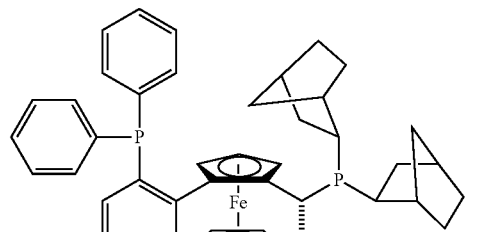

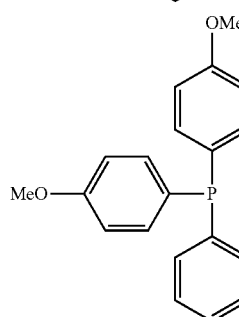

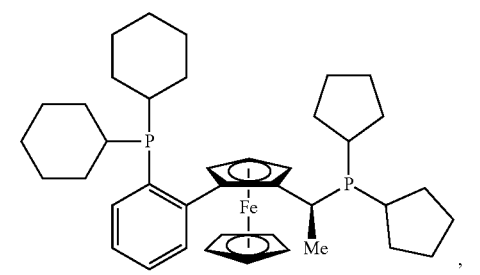

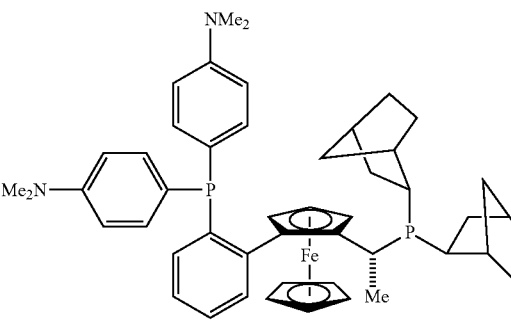

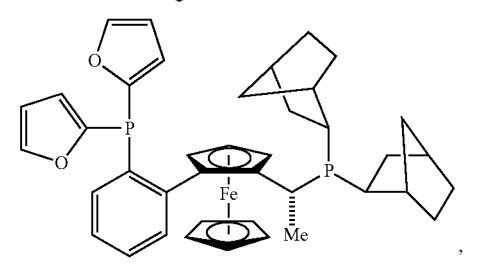

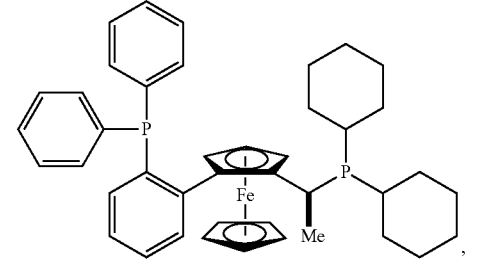

-continued
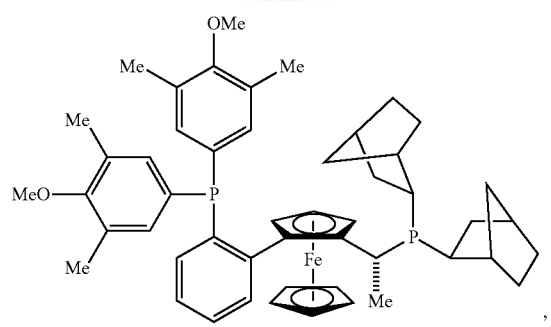
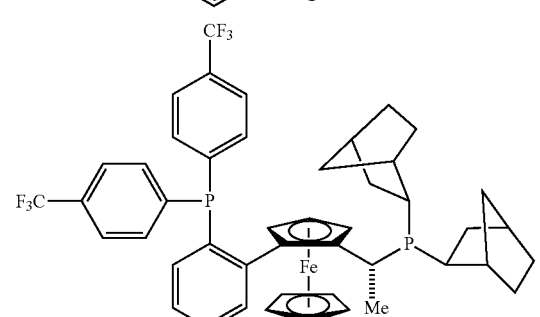
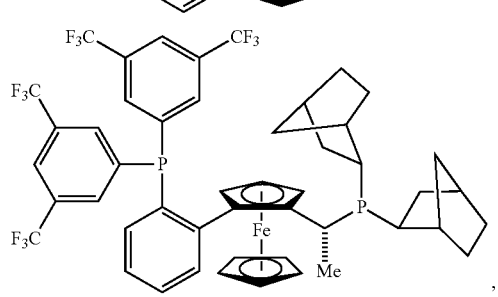
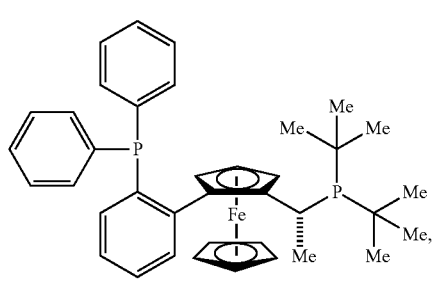
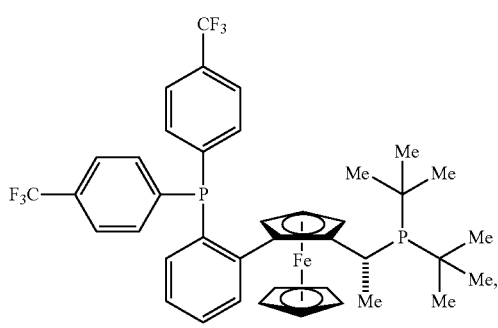
-continued
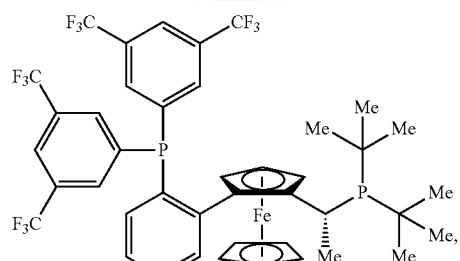
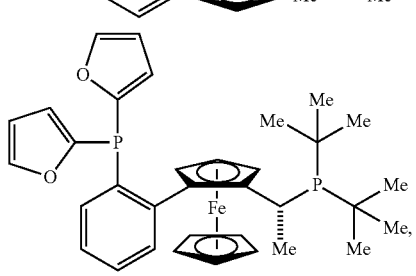
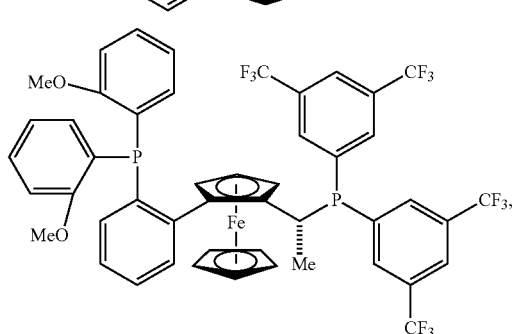
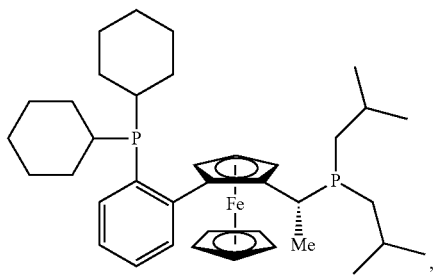
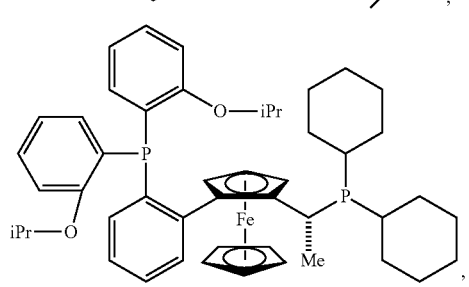
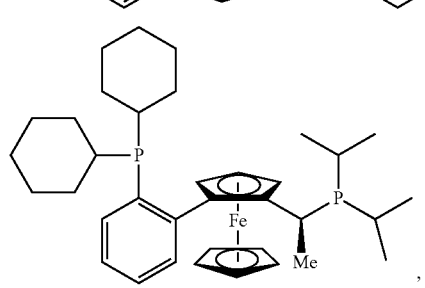

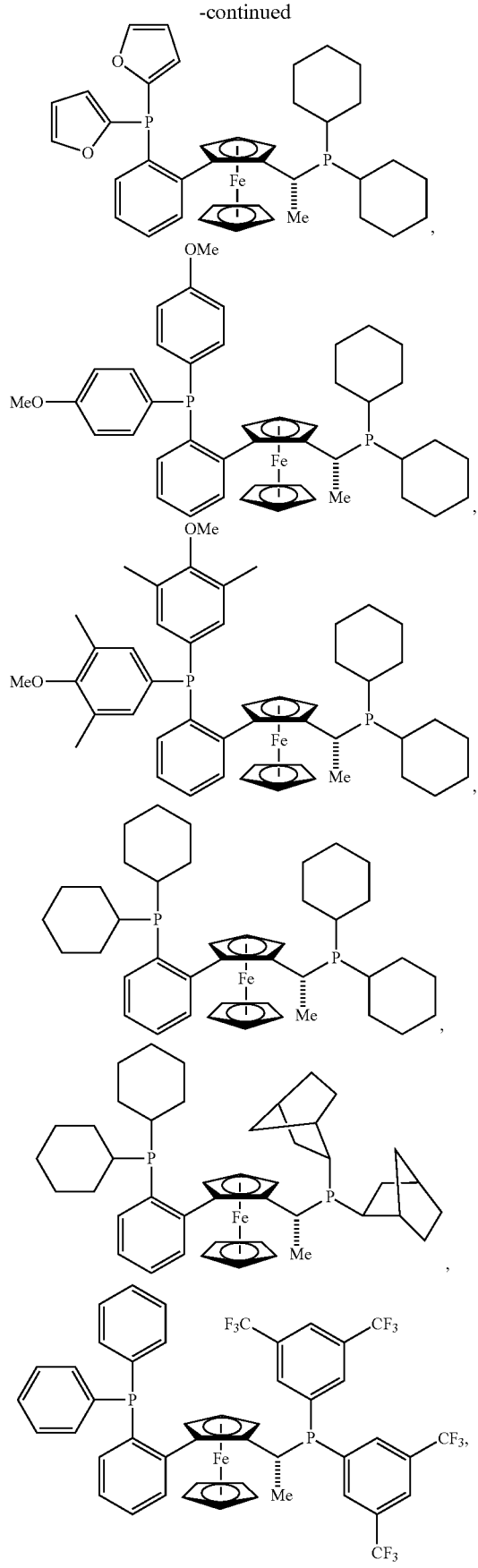
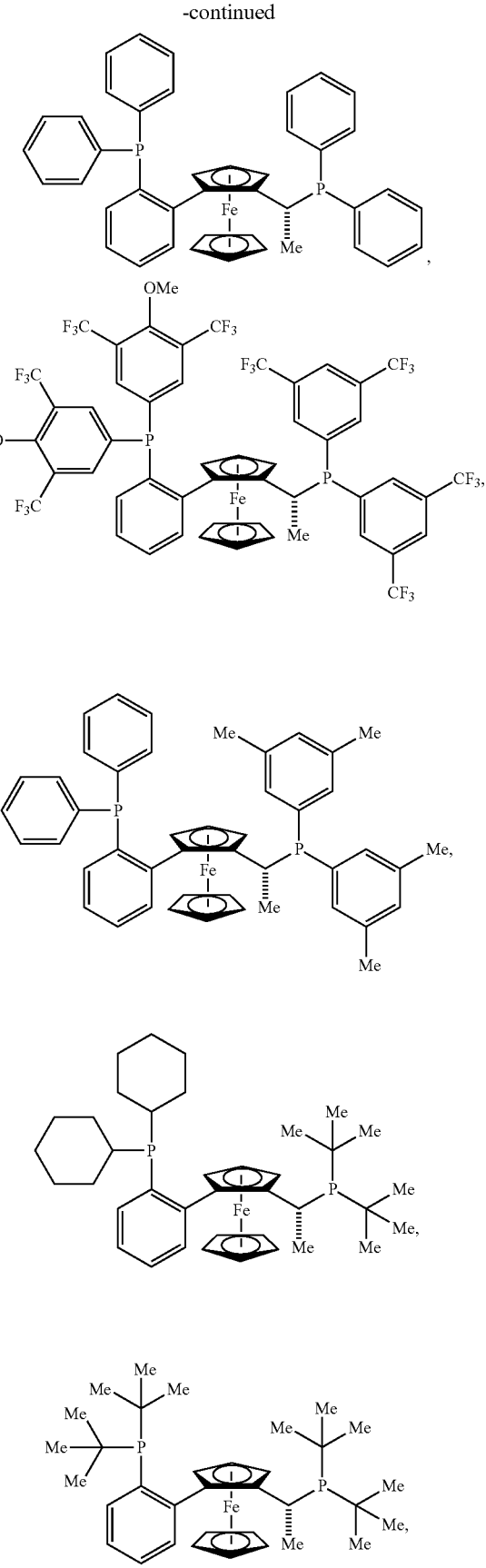

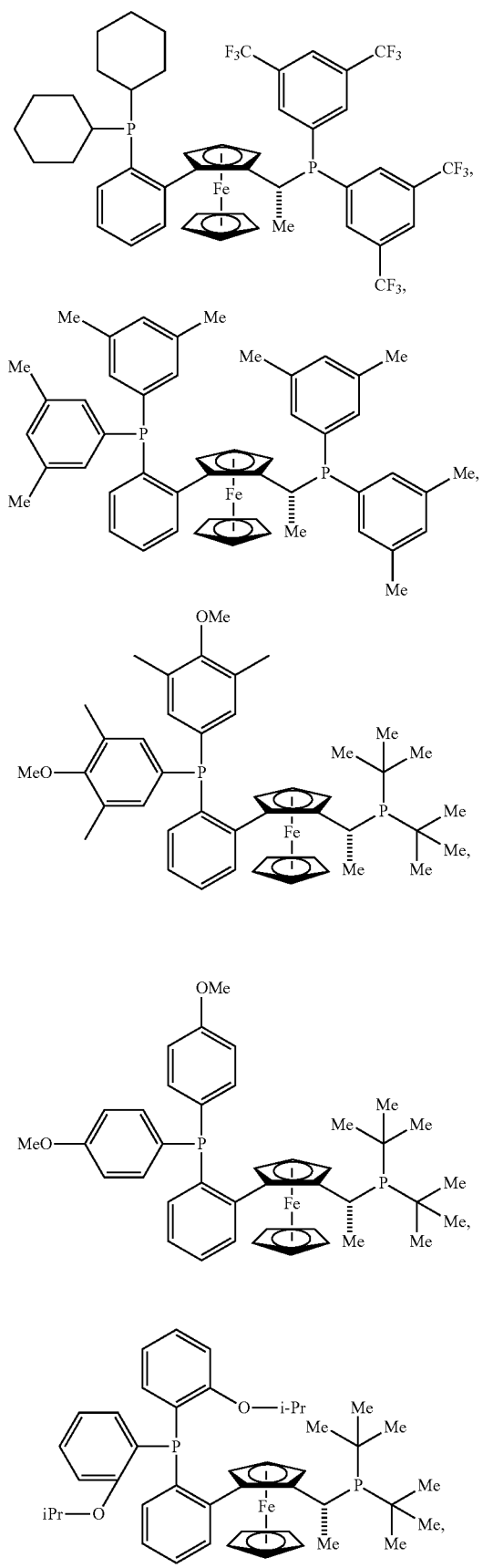
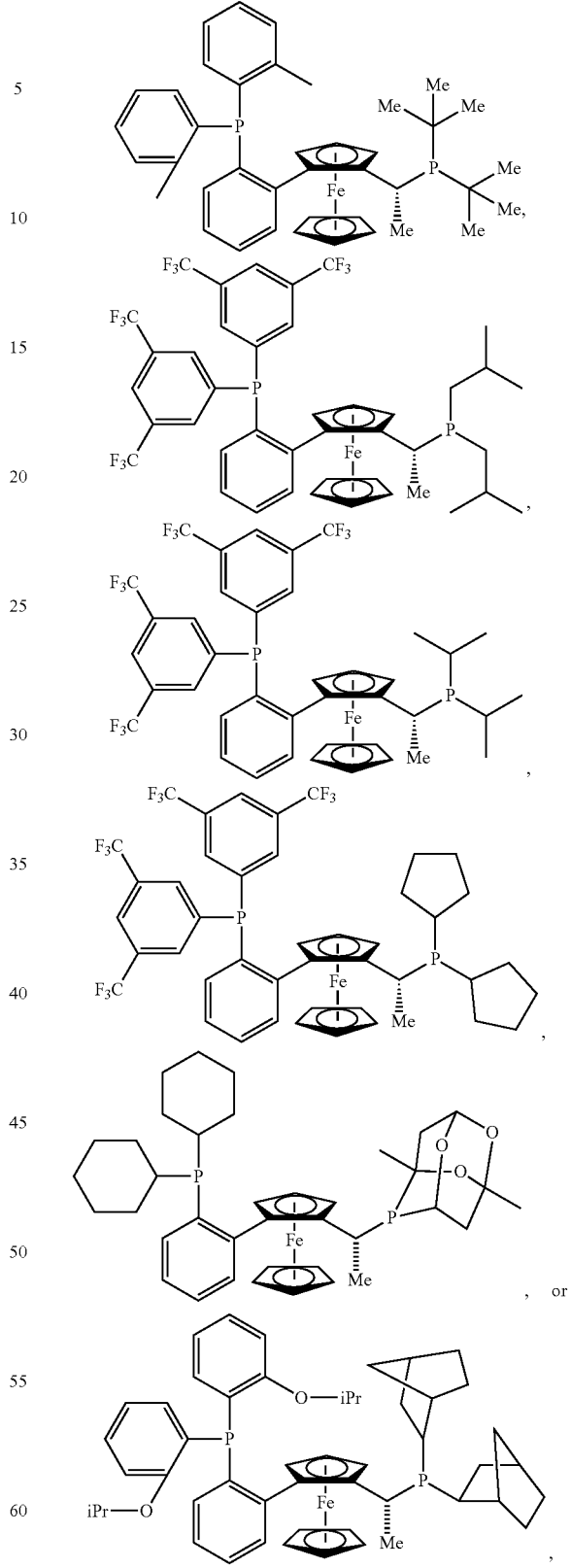
or a stereoisomer thereof.
In one embodiment of the process (P1) described herein, the chiral ligand is L2 having structure:

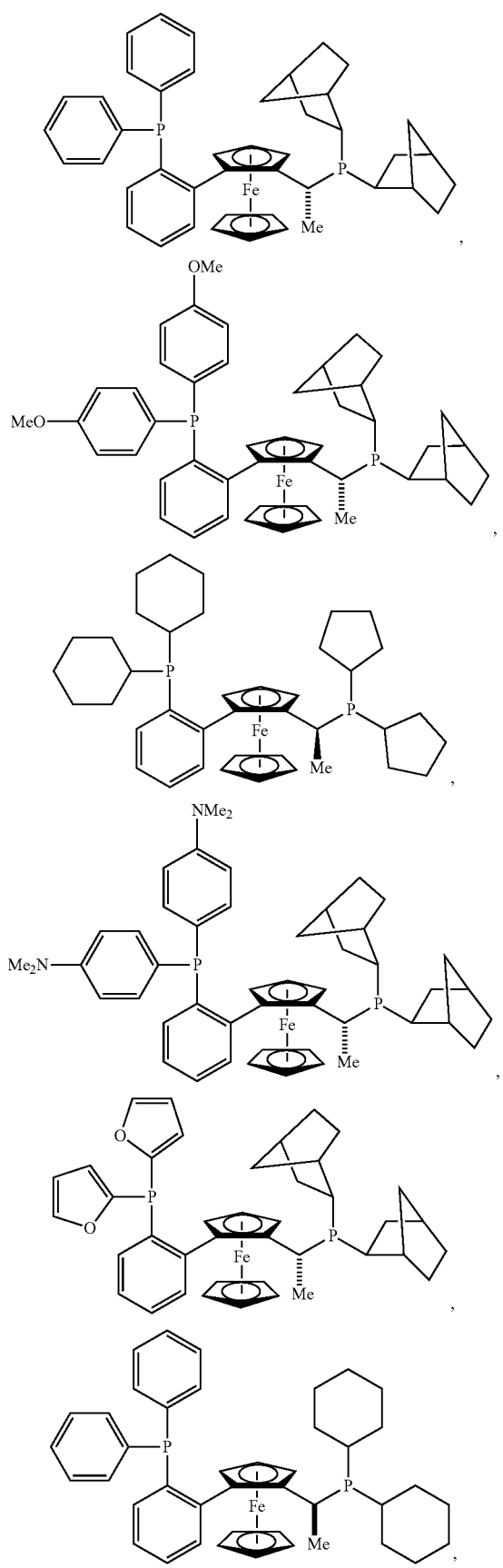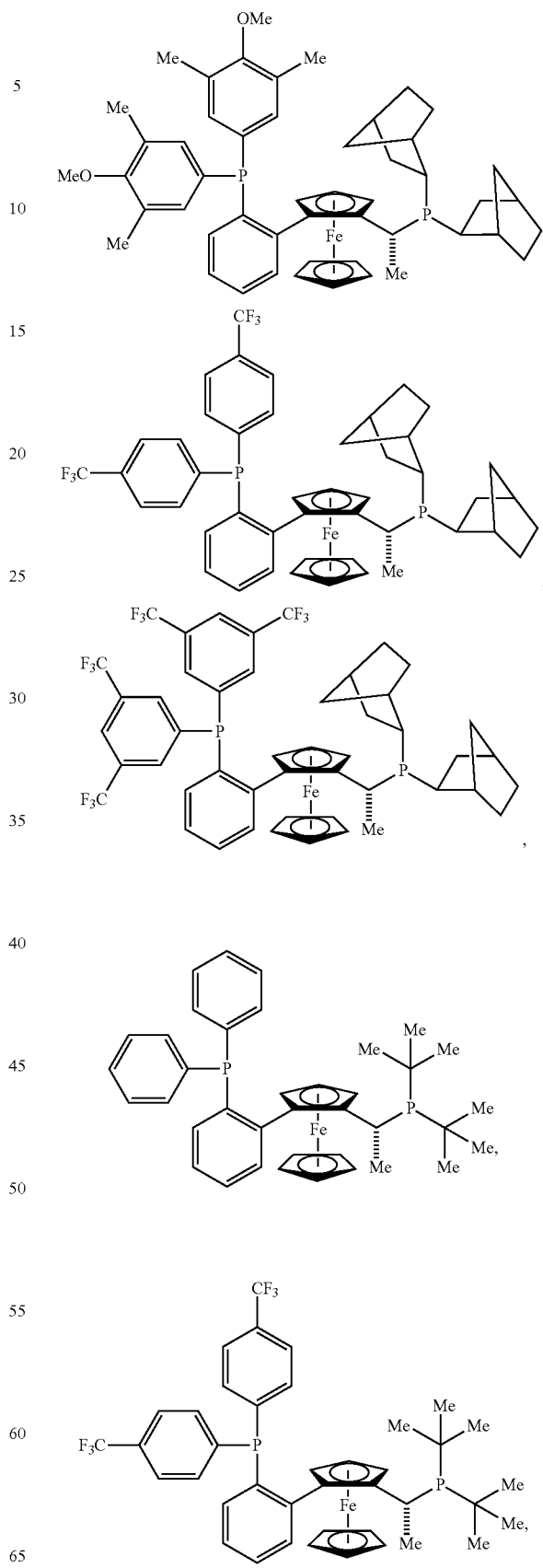

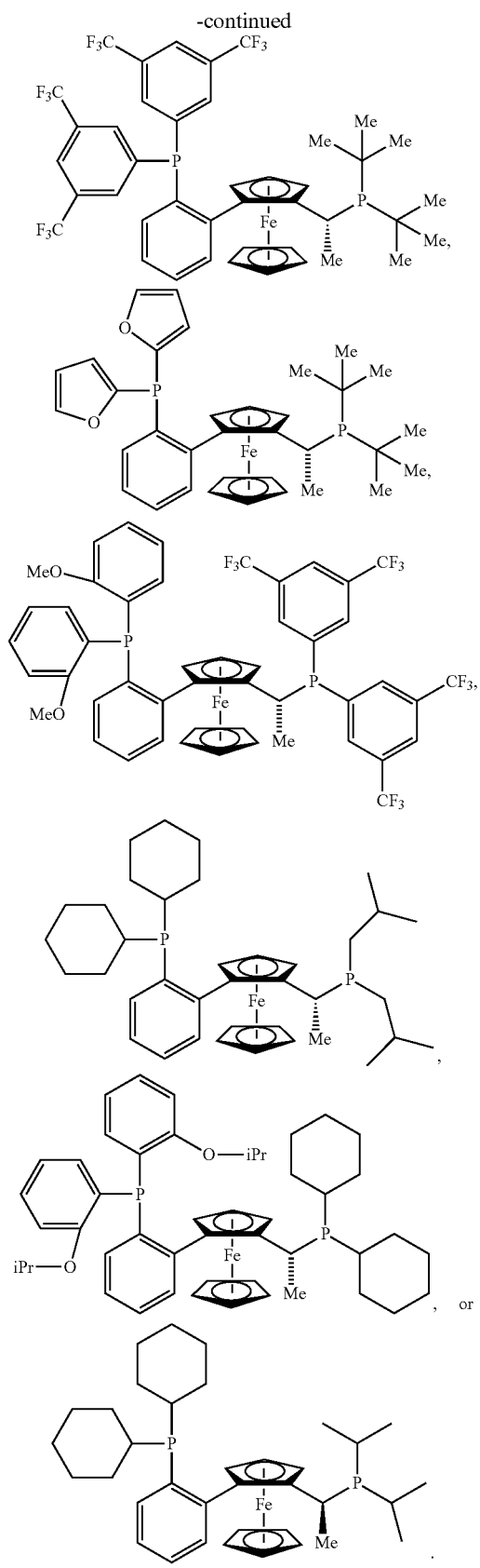

In another embodiment of the process (P1) described herein, the chiral ligand is L2 having structure:

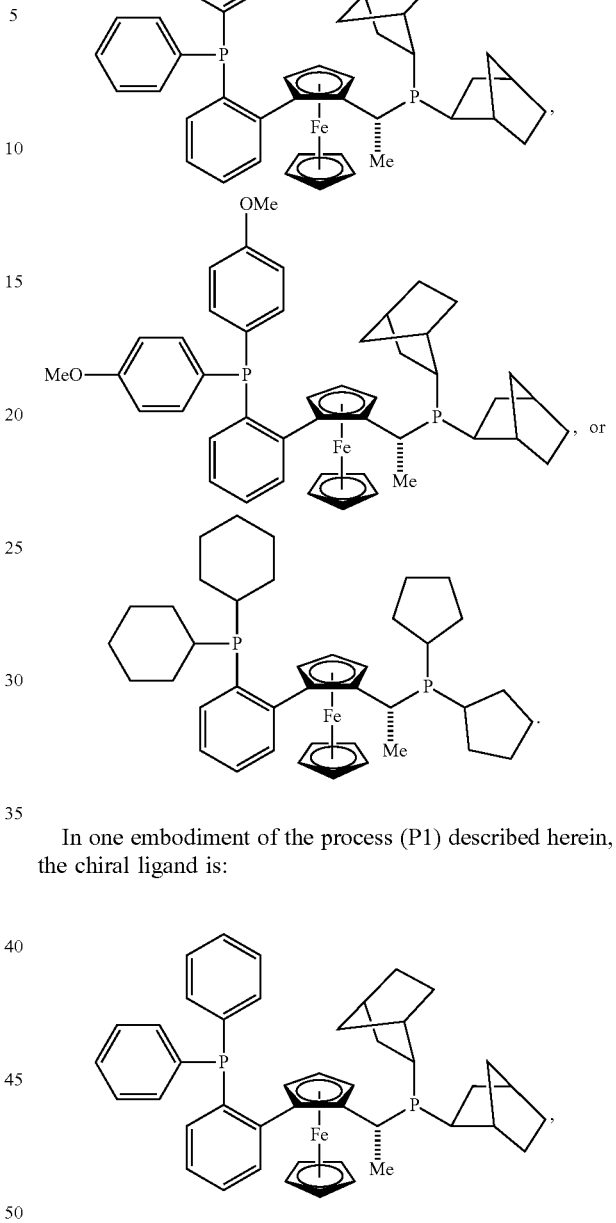

In one embodiment of the process (P1) described herein, the chiral ligand is:

In one embodiment of the process (P1) described herein, the reaction with the chiral ligand is performed at a temperature of: about 30° C. to about 65° C.; about 35° C. to about 55° C.; about 40° C. to about 50° C.; about 35° C. to about 45° C.; or about 40° C. to about 55° C. In another embodiment, the reaction with the chiral ligand is performed at a temperature of about 40, 41, 42, 43, 44, 45, 46, 47, 48, 49, or 50° C. In another embodiment, the reaction with the chiral ligand is performed at a temperature of about 40, 41, 42, 43, 44, 45, 46, 47, 48, 49, or 50° C. In another embodiment, the reaction with the chiral ligand is performed at a temperature of about 50, 52, 54, 56, 58, 60, 62, or 64° C.

In one embodiment of the process (P1) described herein, the reaction with the chiral ligand is performed for: about 1 to about 15 hrs; about 1 to about 10 hrs; about 2 to about 10 hrs; about 4 to about 10 hrs; about 10 to about 30 hrs; about 15 to about 30 hrs; about 15 to about 25 hrs; about 10 to about 20 hrs; about 16 to about 24 hrs; or about 16 to about 20 hours. In one embodiment of the process (P1) described herein, the reaction with the chiral ligand is performed for: about 1, 2, 3, 4, 5, 6, 8, 10, 12, 14, or 16 hrs.

In one embodiment of the process (P1) described herein, the compound of formula (II) or a tautomer, stereoisomer, or salt thereof and the compound of formula (III) or a stereoisomer or salt thereof are present at about an equal amount of molar equivalents. In another embodiment of the process (P1) described herein, the compound of formula (II) or a tautomer, stereoisomer, or salt thereof and the compound of formula (III) or a stereoisomer or salt thereof are present at about 1:1, 1.1:1, or 1.2:1 equivalents.

In one embodiment of the process (P1) described herein, the process is performed using a Pd catalyst precursor described herein at a mol % ratio to the chiral ligand of: about 0.1 to about 1; about 0.5 to about 1.1; about 1:1 to about 1:5; about 1:1 to about 1:4; about 1:1 to about 1:3; or about 1:1 to about 1:2. In one embodiment, the process is performed using a Pd catalyst precursor described herein at a mol % ratio to the chiral ligand of about 0.5:1. In another embodiment, the process is performed using a Pd catalyst precursor described herein at a mol % ratio to the chiral ligand of about 1:2. In another embodiment, the process is performed using a Pd catalyst precursor described herein at a mol % ratio to the chiral ligand of about 1:1.1.

In one embodiment of the process (P1) described herein, the process is performed using a Pd catalyst precursor described herein wherein the catalyst loading (e.g. with respect to the limiting reagent of the reaction) is about: 0.1 mol % to 10 mol %, 0.1 mol % to 5 mol %, 0.1 mol % to 2 mol %, 0.1 mol % to 1.5 mol %, 0.1 mol % to 1 mol %, 0.5 mol % to 10 mol %, 0.5 mol % to 5 mol %, 0.5 mol % to 2 mol %, 0.7 mol % to 10 mol %, 0.7 mol % to 5 mol %, 0.7 mol % to 2 mol %, or 0.7 mol % to 1.5 mol %. In one such embodiment, the catalyst loading is about 0.1 mol % to 10 mol %. In another embodiment, the catalyst loading is about 0.5 mol % to 2 mol %. In another embodiment, the catalyst loading is about 0.7-1.5 mol %.

In one embodiment, the process (P1) further comprises addition of a salt additive during step 2. In one embodiment, the additive is NaTFA, NaOAc, or NaOTf.

In another embodiment of the process (P1) described herein, the chiral ligand

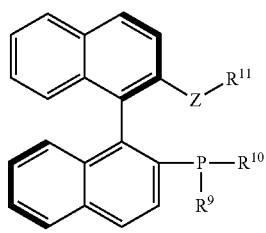

(L3)

where $R^9$, $R^{10}$, and $R^{11}$ are as described herein.

In one embodiment of the compounds of L3, $R^9$ and $R^{10}$ are the same. In one such embodiment of the compounds of L3, $R^9$ and $R^{10}$ are $R^{10A}$-substituted or unsubstituted $C_{5-6}$ cycloalkyl. In one such embodiment of the compounds of L3, $R^9$ and $R^{10}$ are each unsubstituted cyclohexyl. In another embodiment of the compounds of L3, $R^9$ and $R^{10}$ are $R^{10A}$-substituted or unsubstituted phenyl. In one such embodiment of the compounds of L3, $R^9$ and $R^{10}$ are unsubstituted phenyl. In another such embodiment of the compounds of L3, $R^9$ and $R^{10}$ are $R^{10A}$-substituted phenyl where $R^{10A}$ is methyl, ethyl, tert-butyl or $CF_3$.

In one embodiment of the compounds of L3, Z is O and $R^{11}$ is methyl, ethyl, or tert-butyl. In another embodiment of the compounds of L3, Z is N and $R^{11}$ is dimethyl, diethyl, or di-tertbutyl.

In one embodiment, the chiral ligand is a compound of formula:

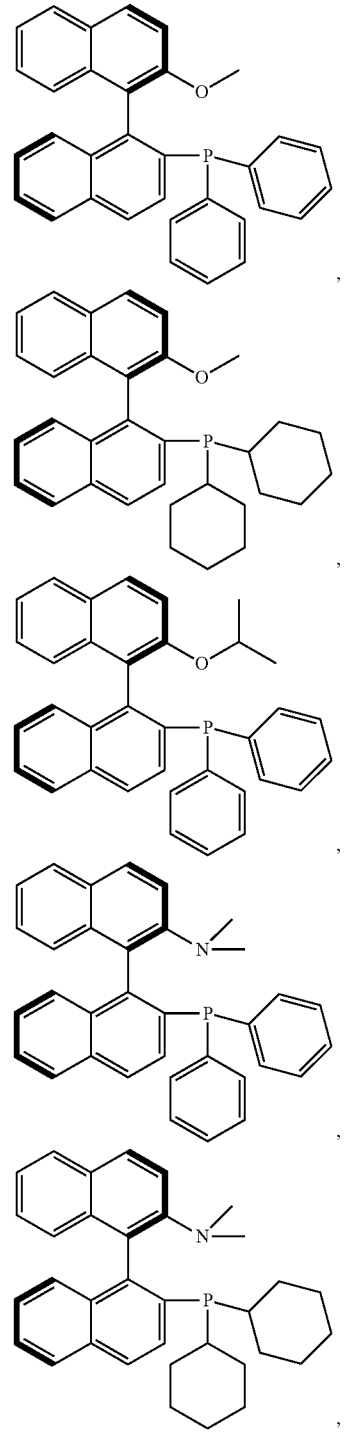

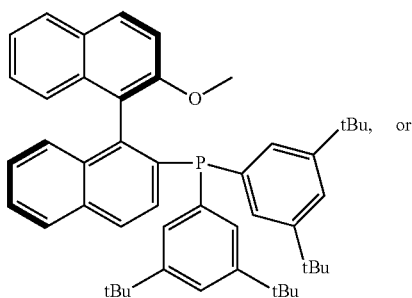

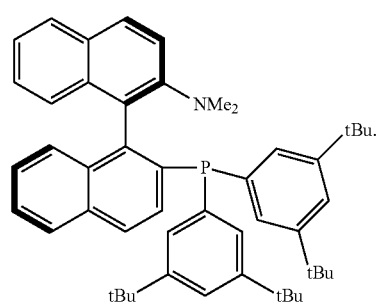

In another embodiment of the process (P1) described herein, the chiral ligand is a compound of formula:

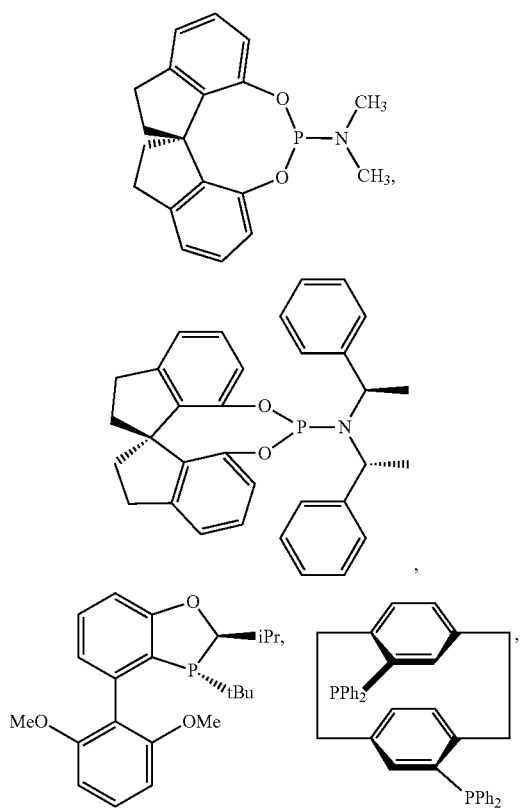

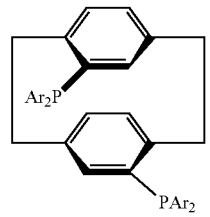

Ar = 3,5-xylyl , or

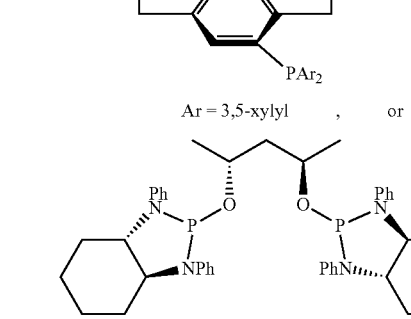

In one embodiment, the compound of formula (II)

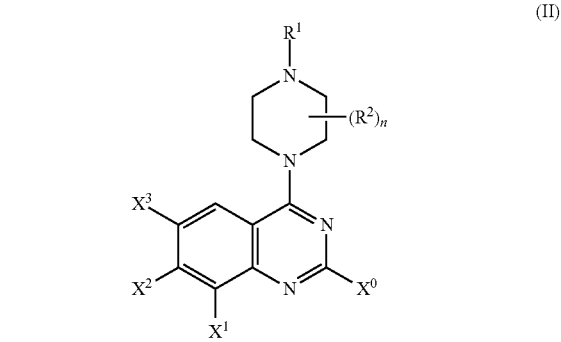

or a tautomer, stereoisomer, or salt thereof is prepared according to a process (P2) comprising the steps:

(a) contacting a compound of formula (IVa)

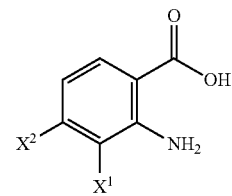

or a stereoisomer or salt thereof with a halogenating agent having formula or

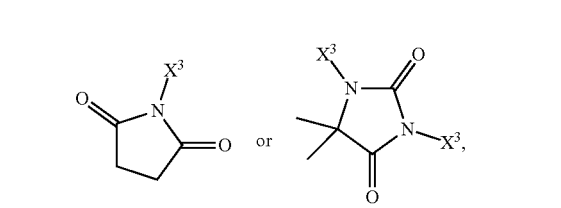

wherein $X^3$ is halogen, to make a compound of formula (IVb)

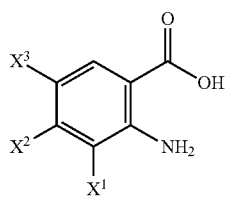

or a stereoisomer or salt thereof;
(c) cyclizing the compound of formula (IVb) to a compound of formula (V)

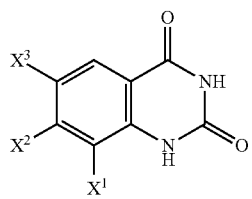

or a stereoisomer or salt thereof;
(d) contacting the compound of formula (V) with a chlorinating agent to make a compound of formula (Va)

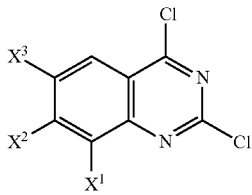

or a stereoisomer or salt thereof;
(e) contacting the compound of formula (Va) with a piperazinyl moiety having formula (VI)

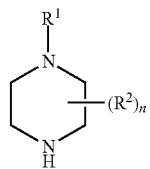

to make a compound of formula (IIa)

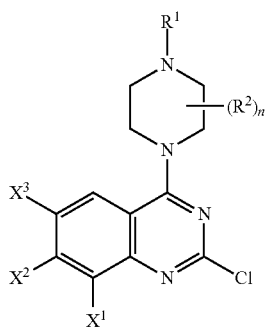

or a stereoisomer or salt thereof; and
(f) contacting the compound of formula (IIa) with a salt of $X^0$ for form a compound of formula (II) or a tautomer, stereoisomer, or salt thereof.

In one embodiment, the compound of formula (II) or a tautomer, stereoisomer, or salt thereof comprises a compound of formula:

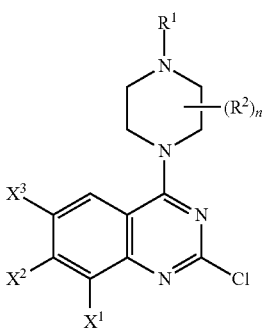

(IIa)

or a tautomer, stereoisomer, or salt thereof.

In one embodiment, the compound of formula (II) or a tautomer, stereoisomer, or salt thereof comprises a compound of formula:

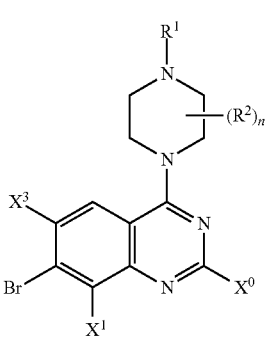

(IIb)

or a tautomer, stereoisomer, or salt thereof.

In one embodiment, the compound of formula (II) or a tautomer, stereoisomer, or salt thereof comprises a compound of formula:

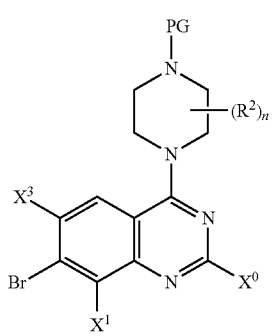

(IIb1)

or a tautomer, stereoisomer, or salt thereof.

In one embodiment, the compound of formula (II) or a tautomer, stereoisomer, or salt thereof comprises a compound of formula:

(IIb2)

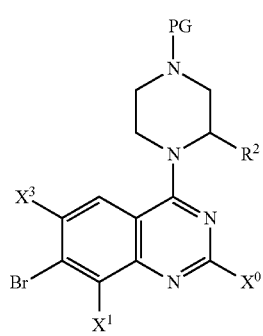

or a tautomer, stereoisomer, or salt thereof.

In one embodiment, the compound of formula (II) or a tautomer, stereoisomer, or salt thereof comprises a compound of formula:

(IIb3)

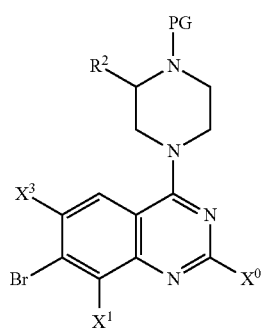

or a tautomer, stereoisomer, or salt thereof.

In one embodiment, the compound of formula (II) or a tautomer, stereoisomer, or salt thereof comprises a compound of formula:

(IIc)

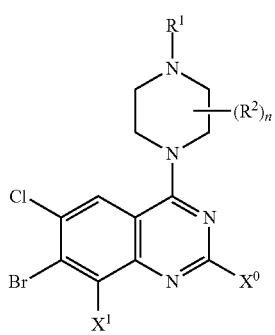

or a tautomer, stereoisomer, or salt thereof.

In one embodiment, the compound of formula (II) or a tautomer, stereoisomer, or salt thereof comprises a compound of formula:

(IIc1)

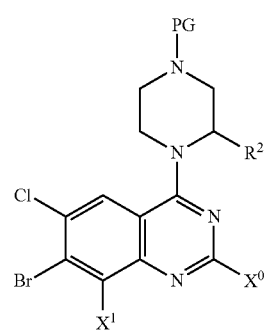

or a tautomer, stereoisomer, or salt thereof.

In one embodiment, the compound of formula (II) or a tautomer, stereoisomer, or salt thereof comprises a compound of formula:

(IIc2)

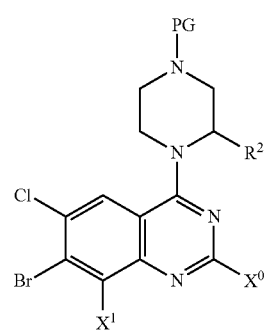

or a tautomer, stereoisomer, or salt thereof.

In one embodiment, the compound of formula (II) or a tautomer, stereoisomer, or salt thereof comprises a compound of formula:

(IIc3)

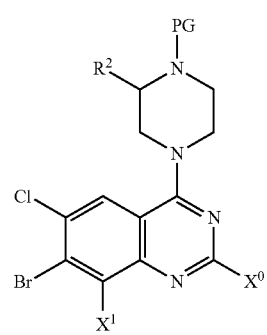

or a tautomer, stereoisomer, or salt thereof.

In one embodiment, the compound of formula (II) or a tautomer, stereoisomer, or salt thereof comprises a compound of formula:

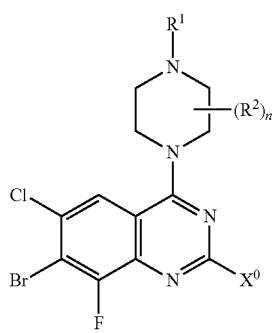

(IId)

or a tautomer, stereoisomer, or salt thereof.

In one embodiment, the compound of formula (II) or a tautomer, stereoisomer, or salt thereof comprises a compound of formula:

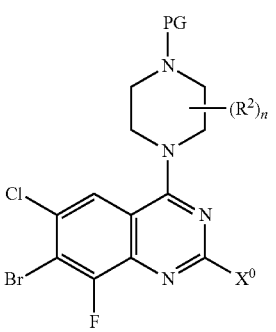

(IId1)

or a tautomer, stereoisomer, or salt thereof.

In one embodiment, the compound of formula (II) or a tautomer, stereoisomer, or salt thereof comprises a compound of formula:

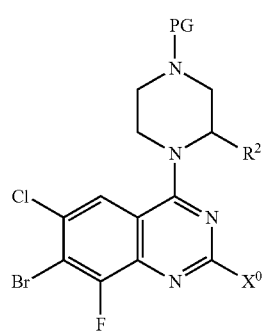

(IId2)

or a tautomer, stereoisomer, or salt thereof.

In one embodiment, the compound of formula (II) or a tautomer, stereoisomer, or salt thereof comprises a compound of formula:

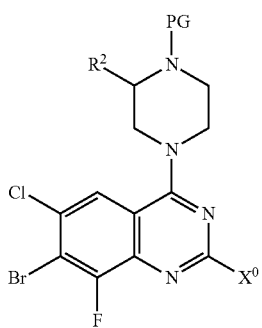

(IId3)

or a tautomer, stereoisomer, or salt thereof.

In one embodiment, the compound of formula (II) or a tautomer, stereoisomer, or salt thereof comprises a compound of formula:

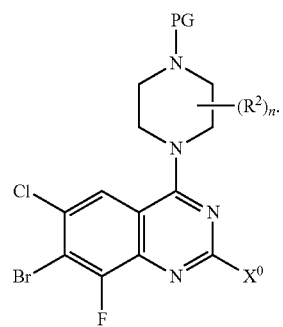

(IId1)

or a tautomer, stereoisomer, or salt thereof.

In one embodiment, the compound of formula (II) or a tautomer, stereoisomer, or salt thereof comprises a compound of formula:

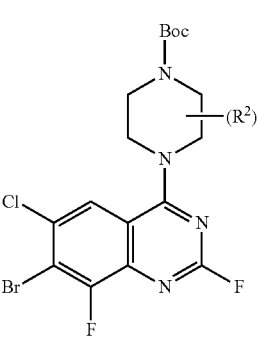

(2a)

or a tautomer, stereoisomer, or salt thereof.

In one embodiment, the compound of formula (II) or a tautomer, stereoisomer, or salt thereof comprises a compound of formula:

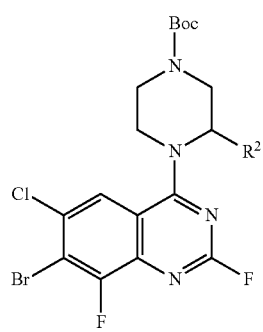
(2b)

or a tautomer, stereoisomer, or salt thereof.

In one embodiment, the compound of formula (II) or a tautomer, stereoisomer, or salt thereof comprises a compound of formula:

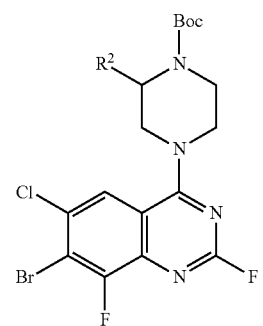
(2c)

or a tautomer, stereoisomer, or salt thereof.

In one embodiment, the compound of formula (II) or a tautomer, stereoisomer, or salt thereof comprises a compound of formula:

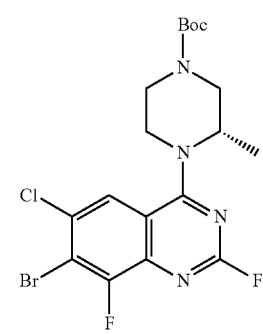
(2)

or a salt thereof.

In one embodiment, the compound of formula (II) is contacted as described herein with an organomagnesium compound and a zinc complex (process P1), thereby forming a compound of formula (IIz):

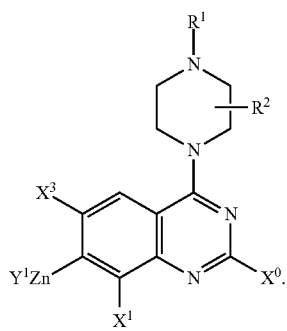
(IIz)

In one embodiment, the compound of formula (IIb), (IIb1), (IIb2), (IIb3), (IIc), (IIc1), (IIc2), (IIc3), (IId), (IId1), (IId2), (IId3), (IIa1), (IIa2), or (IIa3), is contacted as described herein with a zinc complex and an organomagnesium compound (process P1), thereby forming a compound of formula:

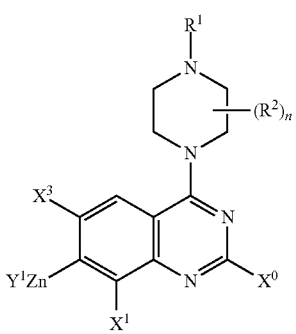
IIz1

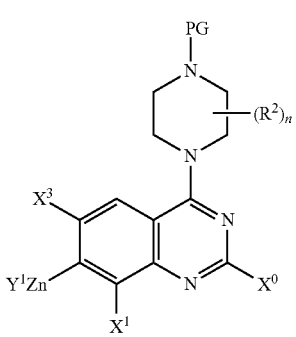
IIz2

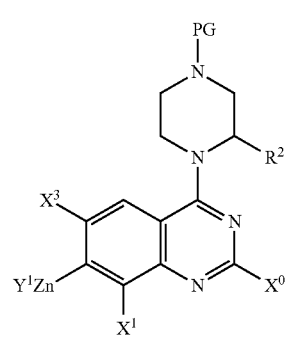
IIz3

-continued
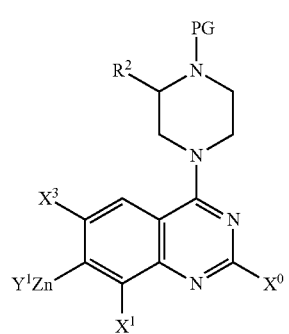
IIz4
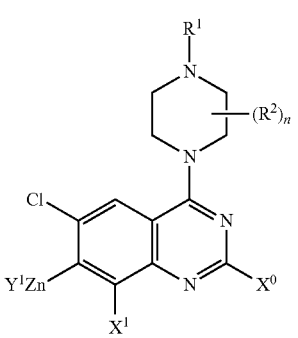
IIz5
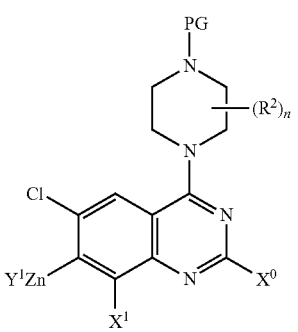
IIz6
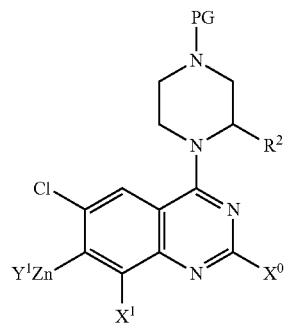
IIz7
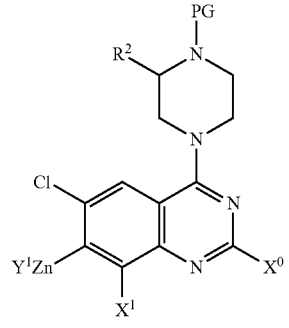
IIz8
-continued
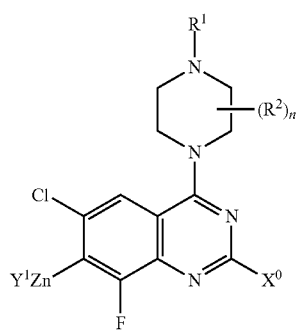
IIz9
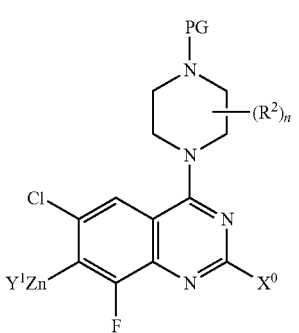
IIz10
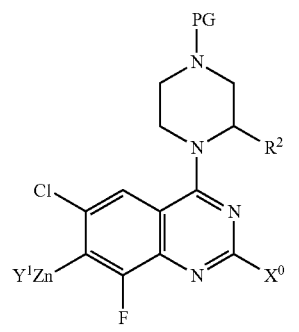
IIz11
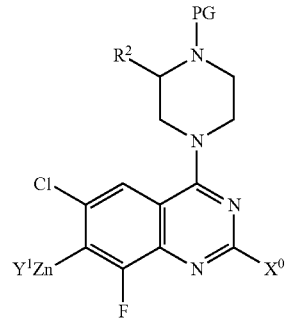
IIz12
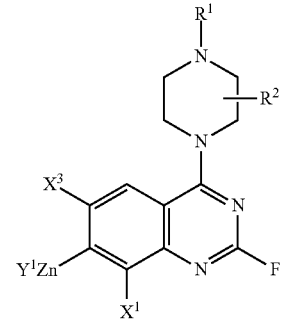
IIz13

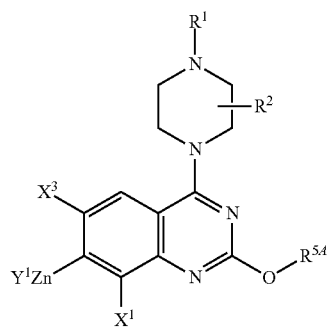

IIz14

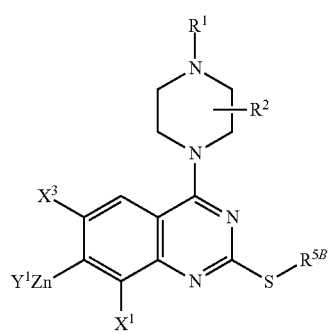

IIz15 where Y¹ is halogen (e.g. Cl, Br, or I), OAc, TFA, OTf, or OPiv.

In one embodiment, Y¹ is Cl. In one embodiment, the compound of step a as described herein in the process P1 carried over to step b as described herein is a compound of formula IIz1, IIz2, IIz3, IIz4, IIz5, IIz6, IIz7, IIz8, IIz9, IIz10, IIz11, IIz12, IIz13, IIz14, IIz15, 2az, 2bz, 2cz, or 2z.

In another embodiment, the compound of formula (2a), is contacted as described herein with a zinc complex and an organomagnesium compound (process P1), thereby forming a compound of formula-:

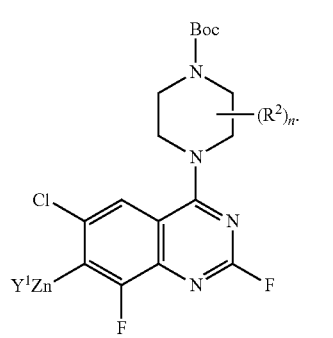

(2az)

In another embodiment, the compound of formula (2b), is contacted as described herein with a zinc complex and an organomagnesium compound (process P1), thereby forming a compound of formula:

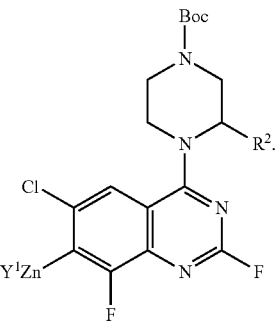

(2bz)

In another embodiment, the compound of formula (2c), is contacted as described herein with a zinc complex and an organomagnesium compound (process P1), thereby forming a compound of formula:

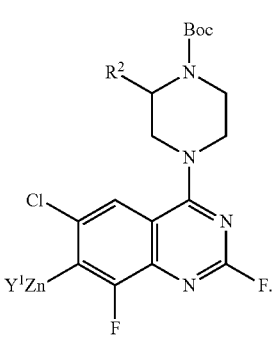

(2cz)

In another embodiment, the compound of formula (2), is contacted as described herein with a zinc complex and an organomagnesium compound (process P1), thereby forming a compound of formula:

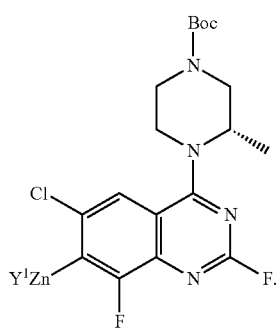

(2z)

In such embodiments, Y¹ is halogen (e.g. Cl, Br, or I), OAc, TFA, OTf, or OPiv. In one such embodiment, Y¹ is Cl. In one such embodiment, Y¹ is OPiv.

In one embodiment of the process (P2) described herein, the process further comprises:

(a0) contacting a compound of formula (IV)

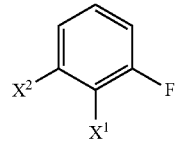

with a base in the presence of $CO_2$ gas and aminating the compound to form the compound of formula (IVa)

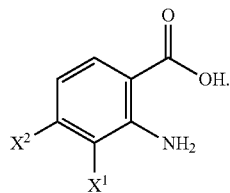

In one embodiment of the process (P2) described herein, the base of step (a0) is n-butyllithium, LDA or LiTMP. In another embodiment, the base is LDA.

In one embodiment of the process (P2) described herein, the halogenating agent of step (b) has formula

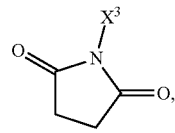

where $X^3$ is Cl, Br, or I. In one such embodiment, $X^3$ is Cl. In another embodiment, $X^3$ is Br. In still another embodiment, $X^3$ is I.

In one embodiment of the process (P2) described herein, the halogenating agent of step (b) has formula

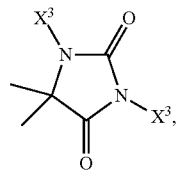

where each $X^3$ is the same and is Cl, Br, or I. In one embodiment, each $X^3$ is Cl. In another embodiment, each $X^3$ is Br. In still another embodiment, each $X^3$ is I.

In one embodiment of the process (P2) described herein, the halogenating agent of step (b) is NCS or 1,3-dichloro-5,5-dimethylhydantoin. In another embodiment, the halogenating agent is NCS. In another embodiment, the halogenating agent is 1,3-dichloro-5,5-dimethylhydantoin.

In one embodiment of the process (P2) described herein, the cyclizing the compound of formula (IVb) to a compound of formula (V) of step (c) is performed using KOCN in aqueous base (e.g. NaOH or KOH) following by contacting with an acid (e.g. HCl).

In one embodiment of the process (P2) described herein, the chlorinating agent of step (d) is $POCl_3$, $PCl_3$, $PCl_5$, or $SOCl_2$. In another embodiment, the chlorinating agent is $POCl_3$.

In one embodiment of the process (P2) described herein, $X^0$ of the compound of formula (II) is F and step (f) comprises contacting the compound of formula (IIa) with CsF to make a compound of formula (IIa1):

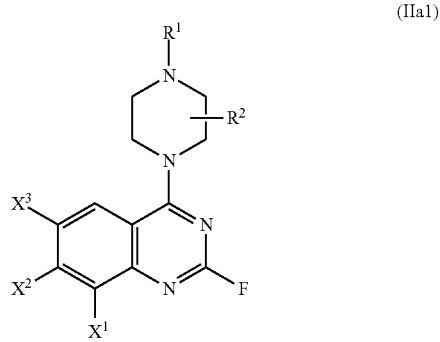

or a tautomer, stereoisomer, or salt thereof.

In one embodiment of the process (P2) described herein, $X^0$ of the compound of formula (II) or a tautomer, stereoisomer, or salt thereof is F and step (f) comprises contacting the compound of formula (IIa) with CsF to make a compound of formula (IIa2):

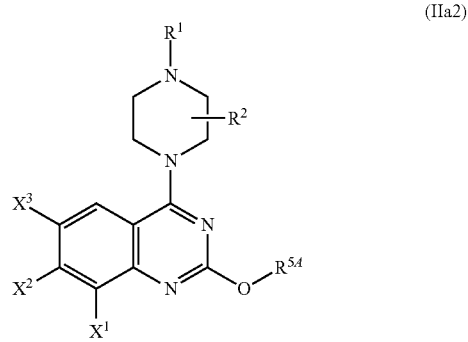

or a tautomer, stereoisomer, or salt thereof.

In one embodiment of the process (P2) described herein, $X^0$ of the compound of formula (II) or a tautomer, stereoisomer, or salt thereof is F and step (f) comprises contacting the compound of formula (IIa) with CsF to make a compound of formula (IIa3):

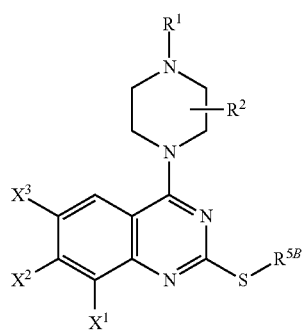
(IIa3)

or a tautomer, stereoisomer, or salt thereof.

In one embodiment of the process (P2) described herein, the compound of formula (IV) has formula:

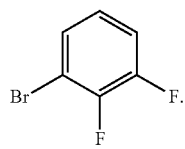
(4)

In one embodiment of the process (P2) described herein, the compound of formula (IVa) has formula:

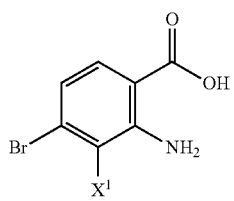
(IVa1)

or a salt thereof.

In one embodiment of the process (P2) described herein, the compound of formula (IVa) has formula:

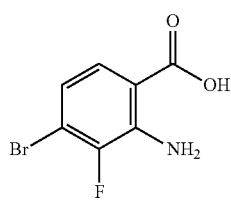
(4a)

or a salt thereof.

In one embodiment of the process (P2) described herein, the compound of formula (IVb) has formula:

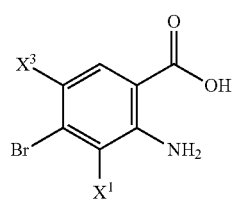
(IVb1)

or a salt thereof.

In one embodiment of the process (P2) described herein, the compound of formula (IVb) has formula:

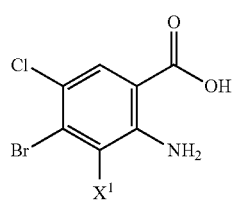
(IVb2)

or a salt thereof.

In one embodiment of the process (P2) described herein, the compound of formula (IVb) has formula:

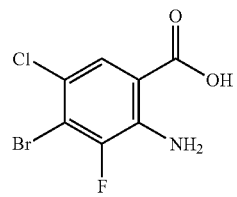
(4b)

or a salt thereof.

In one embodiment of the process (P2) described herein, the compound of formula (V) has formula:

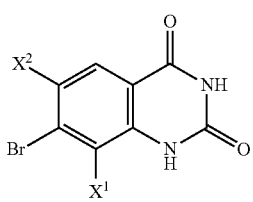
(V1)

or a salt thereof.

In one embodiment of the process (P2) described herein, the compound of formula (V) has formula:

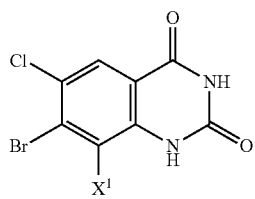

(V2)

or a salt thereof.

In one embodiment of the process (P2) described herein, the compound of formula (V) has formula:

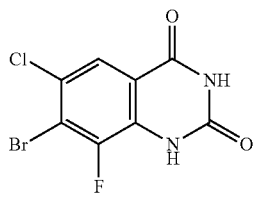

(5)

or a salt thereof.

In one embodiment the compound of formula (III)

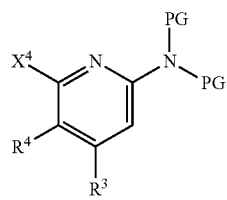

(III)

or a salt thereof of the processes described herein is prepared according to a process (P3) comprising:

(a) contacting a compound of formula (VII)

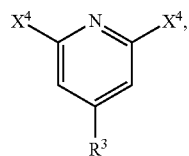

wherein $X^4$ is halogen, with a compound having formula $NH_2(PG)$ thereby making a compound of formula (VIIa)

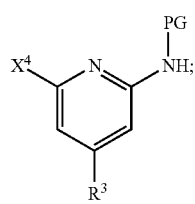

(b) contacting the compound of formula (VIIa) with a compound having formula $X^aPG$, wherein $X^a$ is halogen, to make a compound of formula (VIIb)

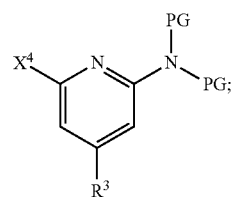

(c) contacting the compound of formula (VIIb) with a halogenating agent having formula

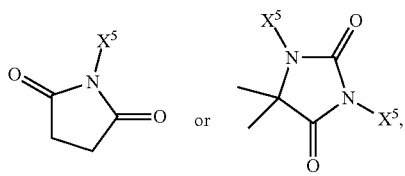

wherein $X^5$ is halogen, to make a compound of formula (VIIc)

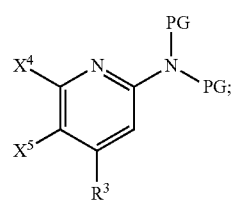

(d) haloalkylating the compound of formula (VIIc) with a haloalkylation agent to make a compound of formula (VIId)

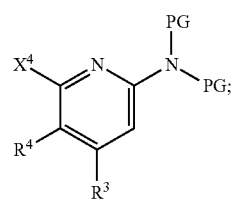

(e) brominating the compound of formula (VIId) to make a compound of formula (VIIe)

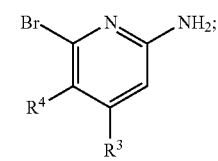

and (f) contacting the compound of formula (VIIe) with $X^aPG$ to make a compound of formula (III) or a salt thereof.

In one embodiment of the process (P3) described herein, each PG is the same. In one embodiment, each PG is the same and is PMB, DMB, or Boc. In another embodiment, each PG is PMB (p-methoxybenzyl). In one embodiment, $X^a$ is Cl or Br. In another embodiment, $X^a$ is Cl.

In one embodiment of the process (P3) described herein, the halogenating agent of step (c) is

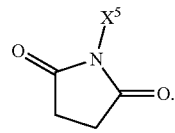

In one such embodiment, $X^5$ is Cl, Br, or I. In another embodiment, $X^5$ is I. In another embodiment, $X^5$ is Cl. In still another embodiment, $X^5$ is Br.

In one embodiment of the process (P3) described herein, the halogenating agent of step (c) is

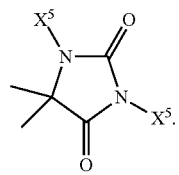

In one such embodiment, $X^5$ is Cl, Br, or I. In another embodiment, $X^5$ is I. In another embodiment, $X^5$ is Cl. In still another embodiment, $X^5$ is Br.

In another embodiment of the process (P3) described herein, the halogenating agent of step (c) is NIS or 1,3-diiodo-5,5-dimethylhydantoin. In one such embodiment, the halogenating agent is NIS. In another embodiment, the halogenating agent is 1,3-diiodomo-5,5-dimethylhydantoin.

In one embodiment of the process (P3) described herein, the haloalkylation agent of step (d) is a fluoroalkylation agent. In one such embodiment, the haloalkylation agent is methyl 2,2-difluoro-2-(fluorosulfonyl)acetate.

In one embodiment of the process (P3) described herein, the brominating step (e) further comprises contacting the compound of formula (VIId) with HBr.

In one such embodiment of the process (P3) described herein, the brominating step (e) further comprises contacting the compound of formula (VIId) with AcBr to make the compound of formula (VIIe).

In one embodiment, the $X^4$ of the compound of formula (VII) is Cl or I. In another embodiment, $X^4$ of the compound of formula (VII) is Cl.

In one embodiment, the compound of formula (VII) has formula:

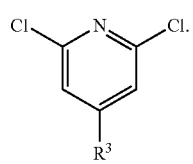

(VII1)

In one embodiment, the compound of formula (VII) has formula:

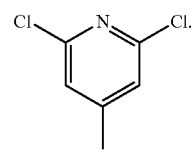

(7)

In one embodiment, the compound of formula (VIIa) has formula:

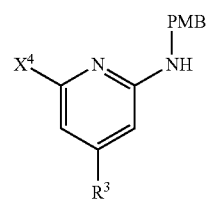

(VIIa1)

or a salt thereof.

In one embodiment, the compound of formula VIIa has formula:

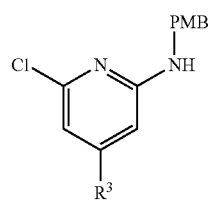

(VIIa2)

or a salt thereof.

In one embodiment, the compound of formula (VIIa) has formula:

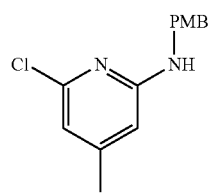

(7a)

or a salt thereof.

In one embodiment, the compound of formula (VIIb) has formula:

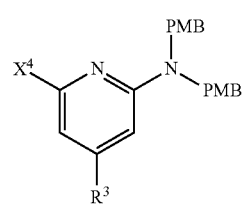

(VIIb1)

or a salt thereof.

In one embodiment, the compound of formula (VIIb) has formula:

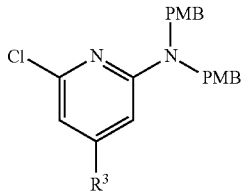
(VIIb2)

or a salt thereof.

In one embodiment, the compound of formula (VIIb) has formula:

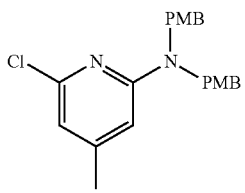
(7b)

or a salt thereof.

In one embodiment, the compound of formula (VIIc) has formula:

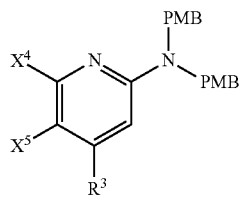
(VIIc1)

or a salt thereof.

In one embodiment, the compound of formula (VIIc) has formula:

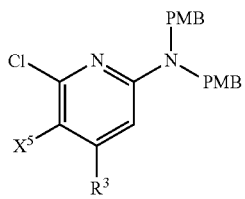
(VIIc2)

or a salt thereof.

In one embodiment, the compound of formula (VIIc) has formula:

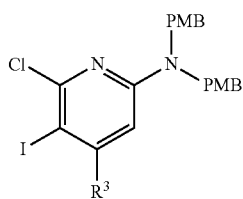
(VIIc3)

or a salt thereof.

In one embodiment, the compound of formula (VIIc) has formula:

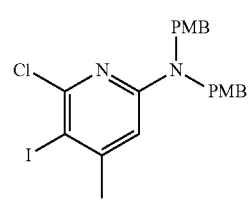
(7c)

or a salt thereof.

In one embodiment, the compound of formula (VIId) has formula:

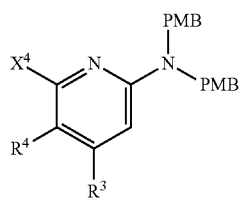
(VIId1)

or a salt thereof.

In one embodiment, the compound of formula (VIId) has formula:

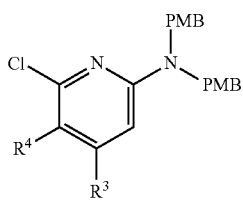
(VIId2)

or a salt thereof.

In one embodiment, the compound of formula (VIId) has formula:

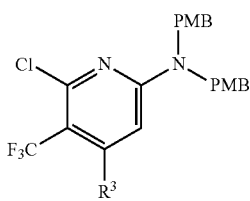
(VIId3)

or a salt thereof.

In one embodiment, the compound of formula (VIId) has formula:

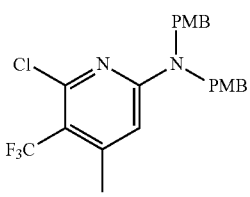
(7d)

or a salt thereof.

In one embodiment, the compound of formula (VIIe) has formula:

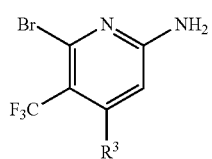
(VIIe1)

or a salt thereof.

In one embodiment, the compound of formula (VIIe) has formula:

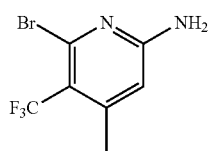
(7e)

or a salt thereof.

In another embodiment, the compound of formula (III)

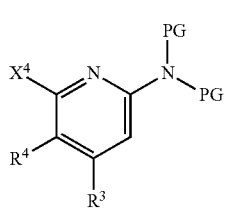
(III)

or a salt thereof of the processes described herein is prepared according to a process (P4) comprising:

(a) contacting a compound of formula (VIII)

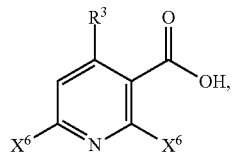

wherein $X^6$ is Cl or I, with a halogenating agent to form a compound of formula (VIIIa)

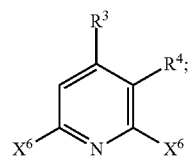

(b) brominating the compound of formula (VIIIa) to form a compound of formula (VIIIb)

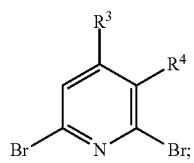

and (c) contacting the compound of formula (VIII) with a compound having formula $NH(PG)_2$ thereby making a compound of formula (III) or a salt thereof.

In one embodiment of the process (P4) described herein, each $X^6$ is the same. In one such embodiment, each $X^6$ is Cl. In another embodiment, each $X^6$ is I.

In still another embodiment, the compound of formula (III)

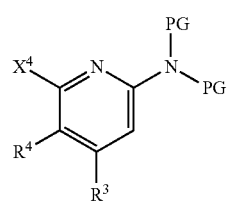
(III)

or a salt thereof of the processes described herein is prepared according to a process (P5) comprising:

(a) contacting a compound of formula (VIIIc)

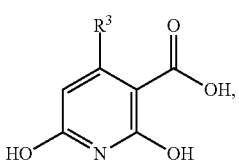

with a brominating agent to form a compound of formula (VIIId)

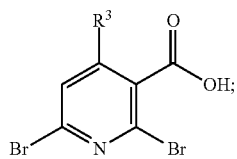

(b) contacting the compound of formula (VIIId) with a halogenating agent to form a compound of formula (VIIIb)

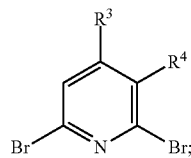

(c) contacting the compound of formula (VIIIb) with a compound having formula NH(PG)$_2$ thereby making a compound of formula (III).

In one embodiment of the process (P4) or (P5) as described herein, the halogenating agent is SF$_4$ in HF.

In one such embodiment, the compound of formula (VIII) has formula:

(VIII1)

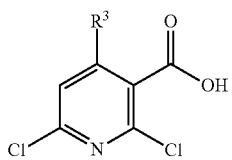

or a salt thereof.

In one such embodiment, the compound of formula (VIII) has formula:

(8)

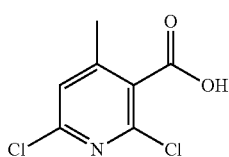

or a salt thereof.

In one such embodiment, the compound of formula (VIIIa) has formula:

(VIIIa1)

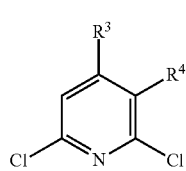

or a salt thereof.

In one such embodiment, the compound of formula (VIIIa) has formula:

(VIIIa2)

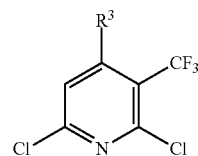

or a salt thereof.

In one such embodiment, the compound of formula (VIIIa) has formula:

(8a)

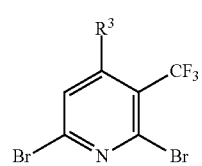

or a salt thereof.

In one such embodiment, the compound of formula (VIIIb) has formula:

(VIIIb1)

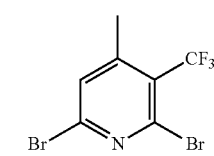

or a salt thereof.

In one such embodiment, the compound of formula (VIIIb) has formula:

(8b)

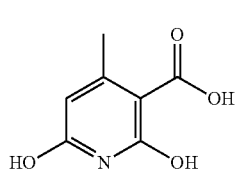

or a salt thereof.

In one such embodiment, the compound of formula (VIIIc) has formula:

(8c)

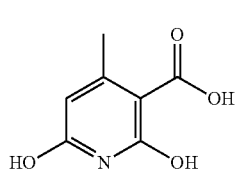

or a salt thereof.

In one such embodiment, the compound of formula (VIIId) has formula:

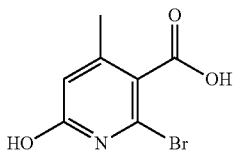

or a salt thereof.

In one such embodiment, the compound of formula (III) has formula:

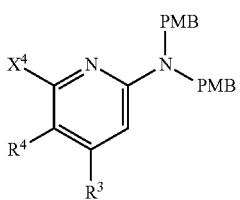

or a salt thereof.

In one such embodiment, the compound of formula (III) has formula:

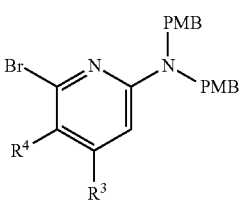

or a salt thereof.

In one such embodiment, the compound of formula (III) has formula:

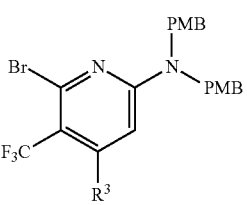

or a salt thereof.

In one such embodiment, the compound of formula (III) has formula:

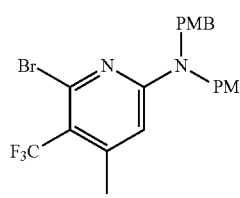

or a salt thereof.

In one embodiment of the processes described herein, $X^1$ is hydrogen. In one embodiment of the processes described herein, $X^1$ is halogen. In one embodiment, $X^1$ is F or Cl. In another embodiment of the processes described herein, when $X^1$ is halogen $X^3$ is halogen. In another embodiment of the processes described herein, when $X^1$ is F, $X^3$ is not F. In another embodiment of the processes described herein, when $X^1$ is F, $X^3$ is Cl. In another embodiment of the processes described herein, when $X^1$ is H, $X^3$ is Cl.

In one embodiment of the processes described herein, $X^2$ is Br. In one embodiment of the processes described herein, $X^2$ is ZnCl, ZnBr, ZnI, ZnOAc, ZnTFA, ZnOTf, or ZnOPiv. In one embodiment of the processes described herein, $X^2$ is ZnCl.

In one embodiment of the processes described herein, $X^3$ is hydrogen, halogen, $R^6$-substituted or unsubstituted $C_{1-3}$ alkyl, or $R^6$-substituted or unsubstituted $C_{1-3}$ haloalkyl. In another embodiment of the processes described herein, $X^3$ is $R^6$-substituted or unsubstituted $C_{1-3}$ alkoxy or $R^6$-substituted or unsubstituted cyclopropyl. In another embodiment of the processes described herein, $X^3$ is hydrogen or halogen. In another embodiment of the processes described herein, $X^3$ is halogen, unsubstituted $C_{1-4}$ alkyl, or unsubstituted $C_{1-3}$ haloalkyl. In still another embodiment of the processes described herein, $X^3$ is halogen or unsubstituted $C_{1-3}$ haloalkyl. In still another embodiment of the processes described herein, $X^3$ is unsubstituted $C_{1-3}$ alkoxy, or unsubstituted cyclopropyl. In one preferred embodiment of the processes described herein, $X^3$ is halogen. In one such embodiment of the processes described herein, $X^3$ is Cl or F. In another embodiment, $X^3$ is Cl, F, $CF_3$, $CHF_2$, or $CH_2F$. In still another embodiment of the processes described herein, $X^3$ is $CF_3$, $CHF_2$, or $CH_2F$.

In one embodiment of the processes described herein, $R^1$ is hydrogen. In a preferred embodiment of the processes described herein, $R^1$ is $PG^1$. In one such embodiment of the processes described herein, $PG^1$ is Ac (acetyl), trifluoroacetyl, Bn (benzyl), Tr (triphenylmethyl or trityl), benzylidenyl, p-toluenesulfonyl, PMB (p-methoxybenzyl), Boc (tert-butyloxycarbonyl), Fmoc (9-fluorenylmethyloxycarbonyl) or Cbz (carbobenzyloxy). In another embodiment of the processes described herein, $PG^1$ is Boc (tert-butyloxycarbonyl). In a preferred embodiment of the processes described herein, $R^1$ is Boc (tert-butyloxycarbonyl).

In one embodiment of the processes described herein, each $R^2$ is independently halogen or cyano. In another embodiment of the processes described herein, each $R^2$ is independently unsubstituted $C_{1-6}$ alkyl, unsubstituted $C_{1-6}$ cyanoalkyl, or unsubstituted $C_{1-6}$ haloalkyl. In another embodiment of the processes described herein, each $R^2$ is independently unsubstituted $C_{1-6}$ alkyl, or unsubstituted $C_{1-6}$ cyanoalkyl. In one such embodiment of the processes described herein is 1. In one preferred embodiment of the processes described herein, each $R^2$ is independently unsubstituted $C_{1-6}$ alkyl or unsubstituted $C_{1-6}$ cyanoalkyl. In one such embodiment of the processes described herein, each $R^2$ is methyl or ethyl. In one such embodiment of the processes described herein, n is 1. In another such embodiment of the processes described herein, $R^2$ is methyl and n is 1. In another such embodiment of the processes described herein, each $R^2$ is $CF_3$, $CHF_2$, or $CH_2F$. In another such embodiment of the processes described herein, $R^2$ is methyl, ethyl, CN, $CH_2CN$, $CF_3$, $CHF_2$, or $CH_2F$. In another embodiment of the processes described herein, $R^2$ is methyl, ethyl, CN, or $CH_2CN$. In such embodiments of the processes described herein, n is 1. In another such embodiment of the processes described herein, $R^2$ is $CH_2CN$ and n is 1. In still another embodiment, n is 0.

In one embodiment of the processes described herein, $R^3$ is hydrogen or halogen. In one embodiment of the processes described herein, $R^3$ is hydrogen. In another embodiment of the processes described herein, $R^3$ is $R^{3A}$-substituted or unsubstituted $C_{1-3}$ alkyl, $R^{3A}$-substituted or unsubstituted $C_{1-3}$ haloalkyl, cyclopropyl. In another embodiment of the processes described herein, $R^3$ is $R^{3A}$-substituted or unsubstituted $C_{1-3}$ alkyl or $R^{3A}$-substituted or unsubstituted $C_{1-3}$ haloalkyl. In still another embodiment of the processes described herein, $R^3$ is $R^{3A}$-substituted or unsubstituted $C_{1-3}$ alkyl. In one such embodiment of the processes described herein, $R^3$ is hydrogen or methyl. In another such embodiment of the processes described herein, $R^3$ is methyl.

In one embodiment of the processes described herein, $R^3$ is $R^{3A}$-substituted or unsubstituted $C_{1-3}$ alkyl, $R^{3A}$-substituted or unsubstituted $C_{1-3}$ haloalkyl where $R^{3A}$ is halogen, OH, CN, or unsubstituted $C_{1-3}$ haloalkyl. In one such embodiment of the processes described herein, is $R^{3A}$-substituted or unsubstituted $C_{1-3}$ alkyl, $R^{3A}$-substituted or unsubstituted $C_{1-3}$ haloalkyl where $R^{3A}$ is F, OH, CN, $CF_3$, $CHF_2$, or $CH_2F$.

In a preferred embodiment of the processes described herein of the processes described herein, $R^4$ is unsubstituted $C_{1-3}$ haloalkyl. In one such embodiment of the processes described herein, $R^4$ is $CF_3$, $CHF_2$, or $CH_2F$.

In one embodiment, $R^5$ is halogen, cyano, or OH. In another embodiment, $R^5$ is $R^{5A}$-substituted or unsubstituted $C_{1-6}$ alkyl, $R^{5A}$-substituted or unsubstituted $C_{1-6}$ haloalkyl, or $R^{5A}$-substituted or unsubstituted $C_{1-6}$ cyanoalkyl. In another embodiment, $R^5$ is $R^{5A}$-substituted or unsubstituted $C_{3-6}$ cycloalkyl, $R^{5A}$-substituted or unsubstituted 3-6 membered heterocycle, $R^{5A}$-substituted or unsubstituted phenyl, or $R^{5A}$-substituted or unsubstituted 6 membered heteroaryl.

In one embodiment of the processes described herein, $R^{5A}$ and $R^{5B}$ are each independently $R^{5C}$-substituted or unsubstituted $C_{1-6}$ alkyl or $R^{5C}$-substituted or unsubstituted $C_{1-6}$ haloalkyl. In another embodiment of the processes described herein, $R^{5A}$ and $R^{5B}$ are each independently $R^{5C}$-substituted or unsubstituted $C_{3-7}$ cycloalkyl; $R^{5C}$-substituted or unsubstituted 3-7 membered heterocycle, $R^{5C}$-substituted or unsubstituted $C_{5-7}$ aryl, or $R^{5C}$-substituted or unsubstituted $C_{5-7}$ heteroaryl. In one preferred embodiment of the processes described herein, $R^{5A}$ and $R^{5B}$ are each independently $R^{5C}$-substituted or unsubstituted $C_{1-6}$ alkyl.

In one embodiment of the processes described herein, $R^{5C}$ is independently halogen, OH, CN, or $NO_2$. In one embodiment of the processes described herein, $R^{5C}$ is independently $R^{5D}$-substituted or unsubstituted $C_{1-6}$ alkyl or $R^{5D}$-substituted or unsubstituted $C_{1-6}$ haloalkyl. In one embodiment of the processes described herein, $R^{5C}$ is independently $R^{5D}$-substituted or unsubstituted $C_{3-7}$ cycloalkyl or $R^{5D}$-substituted or unsubstituted $C_{3-7}$ heterocycle. In one embodiment, $R^{5C}$ is independently $R^{5D}$-substituted or unsubstituted $C_{5-7}$ aryl or $R^{5D}$-substituted or unsubstituted $C_{5-7}$ heteroaryl. In another embodiment of the processes described herein, $R^{5C}$ is independently $R^{5D}$-substituted or unsubstituted $C_{3-7}$ heterocycle or $R^{5D}$-substituted or unsubstituted $C_{5-7}$ heteroaryl. In another embodiment of the processes described herein, $R^{5C}$ is $R^{5D}$-substituted pyrrolidinyl.

In one embodiment of the processes described herein, $R^{5D}$ is independently halogen, OH, or CN. In another embodiment, $R^{5D}$ is unsubstituted $C_{1-6}$ alkyl. In another embodiment of the processes described herein, $R^{5D}$ is unsubstituted $C_{1-6}$ haloalkyl. In still another embodiment of the processes described herein, $R^{5D}$ is unsubstituted $C_{3-7}$ cycloalkyl, unsubstituted $C_{3-7}$ heterocycle, unsubstituted $C_{5-7}$ aryl, or unsubstituted $C_{5-7}$ heteroaryl. In one embodiment of the processes described herein, $R^{5D}$ is methyl, ethyl, or propyl.

In one embodiment of the processes described herein, $R^{5A}$ and $R^{5B}$ are each independently:

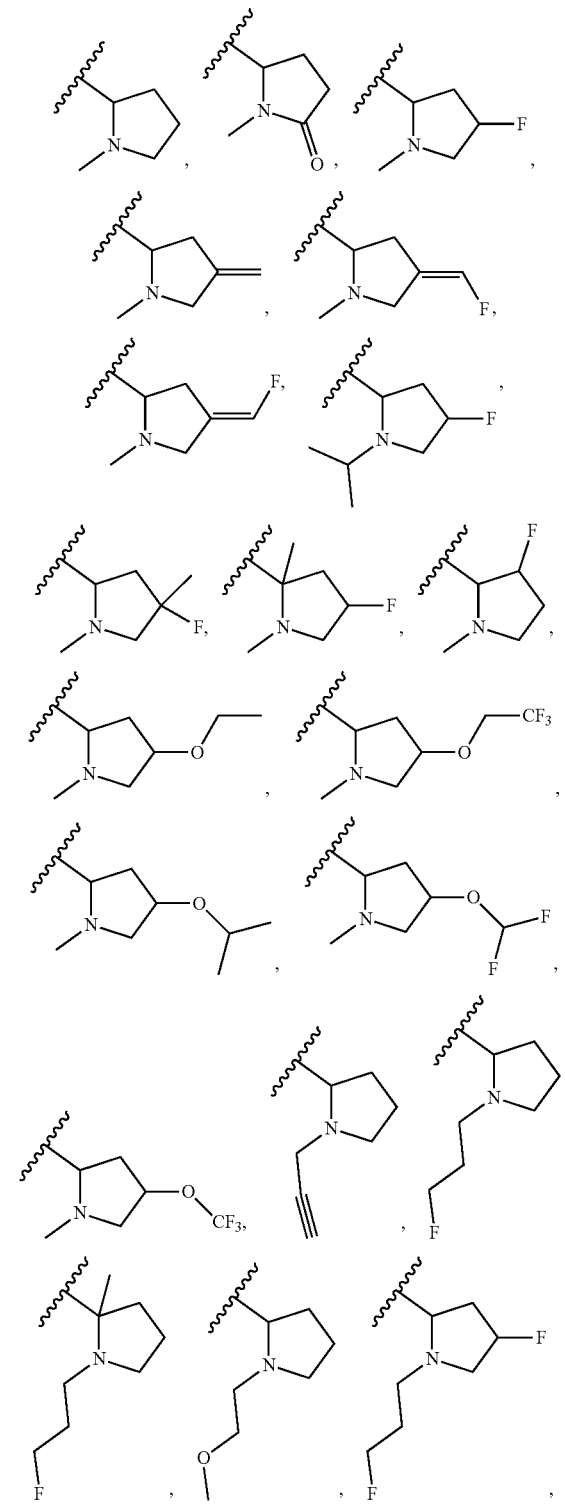

-continued

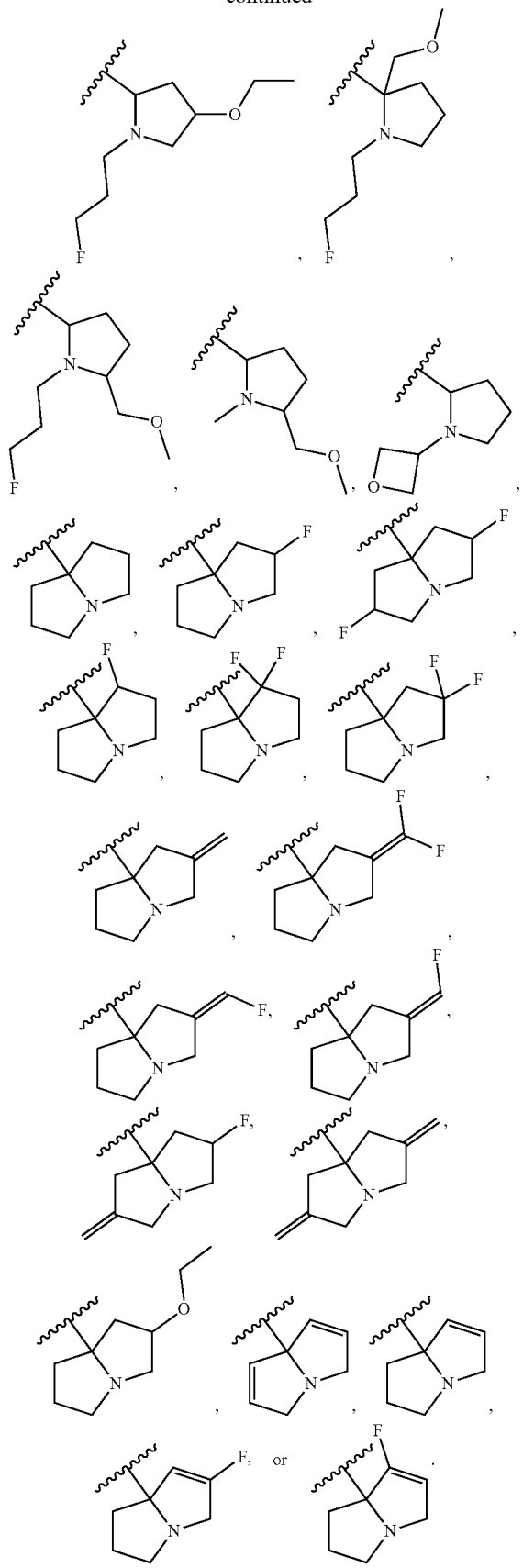

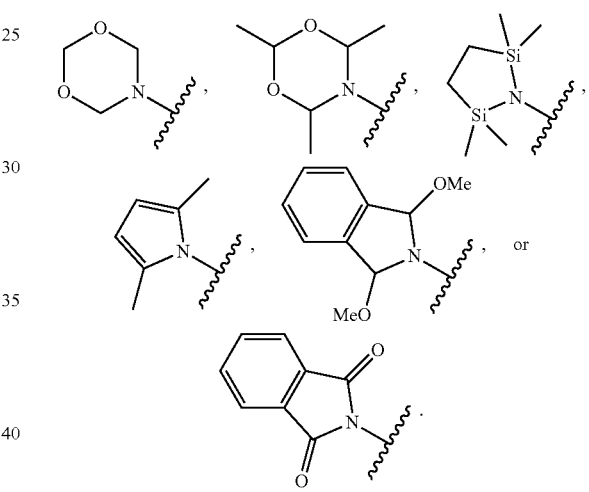

In one embodiment of the processes described herein, $R^6$ is halogen. In another embodiment of the processes described herein, $R^6$ is OH, ON, $NO_2$, unsubstituted $C_{1-6}$ alkyl, unsubstituted $C_{1-6}$ haloalkyl, or unsubstituted $C_{3-7}$ cycloalkyl.

In one embodiment of the processes described herein, each PG is independently an amino protecting group. In one embodiment, each PG is the same. In one such embodiment of the processes described herein, each PG is Ac (acetyl), trifluoroacetyl, Bn (benzyl), Tr (triphenylmethyl or trityl), benzylidenyl, p-toluenesulfonyl, DMB (dimethoxybenzyl), PMB (p-methoxybenzyl), Boc (tert-butyloxycarbonyl), Fmoc (9-fluorenylmethyloxycarbonyl) or Cbz (carbobenzyloxy). In another embodiment, each PG is PMB, DMB, or Boc. In one preferred embodiment of the processes described herein, each PG is PMB.

In still another embodiment of the processes described herein, two PG together form a $C_{3-8}$ nitrogen heterocycle. In one embodiment of the processes described herein, two PG together form a moiety having the structure:

In one embodiment of the processes described herein, $X^0$ is hydrogen, halogen, or $OR^{5A}$. In another embodiment of the processes described herein, $X^0$ is $SR^{5B}$, $R^5$-substituted or unsubstituted $C_{1-6}$ alkyl, $R^5$-substituted or unsubstituted $C_{1-6}$ haloalkyl, $R^5$-substituted or unsubstituted $C_{5-7}$ aryl, or $R^5$-substituted or unsubstituted $C_{5-7}$ heteroaryl. In another embodiment of the processes described herein, $X^0$ is hydrogen, halogen, $CF_3$, $CHF_2$, or $CH_2F$. In one preferred embodiment of the processes described herein, $X^0$ is halogen. In one such embodiment of the processes described herein, $X^0$ is F. In still another embodiment of the processes described herein, $X^0$ is hydrogen, halogen, $CF_3$, $CHF_2$, $CH_2F$, or a moiety having structure:

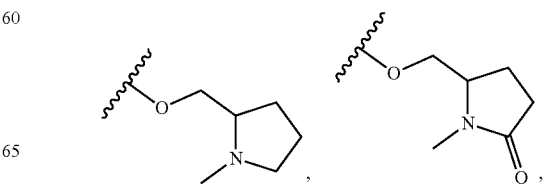

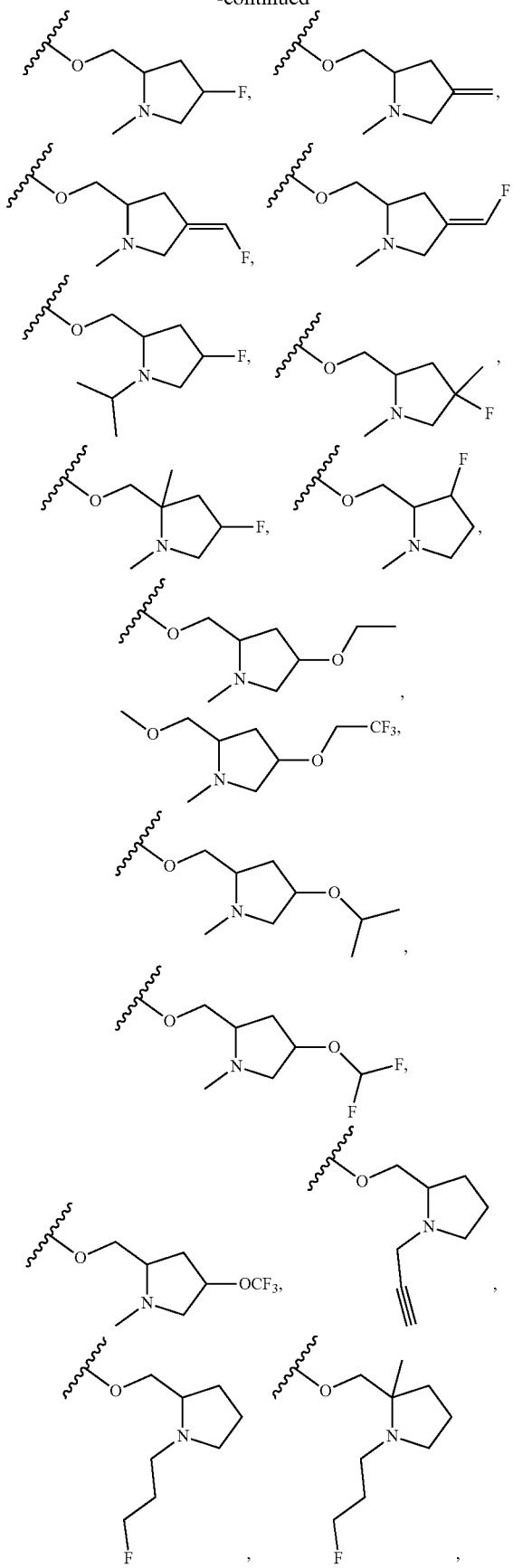
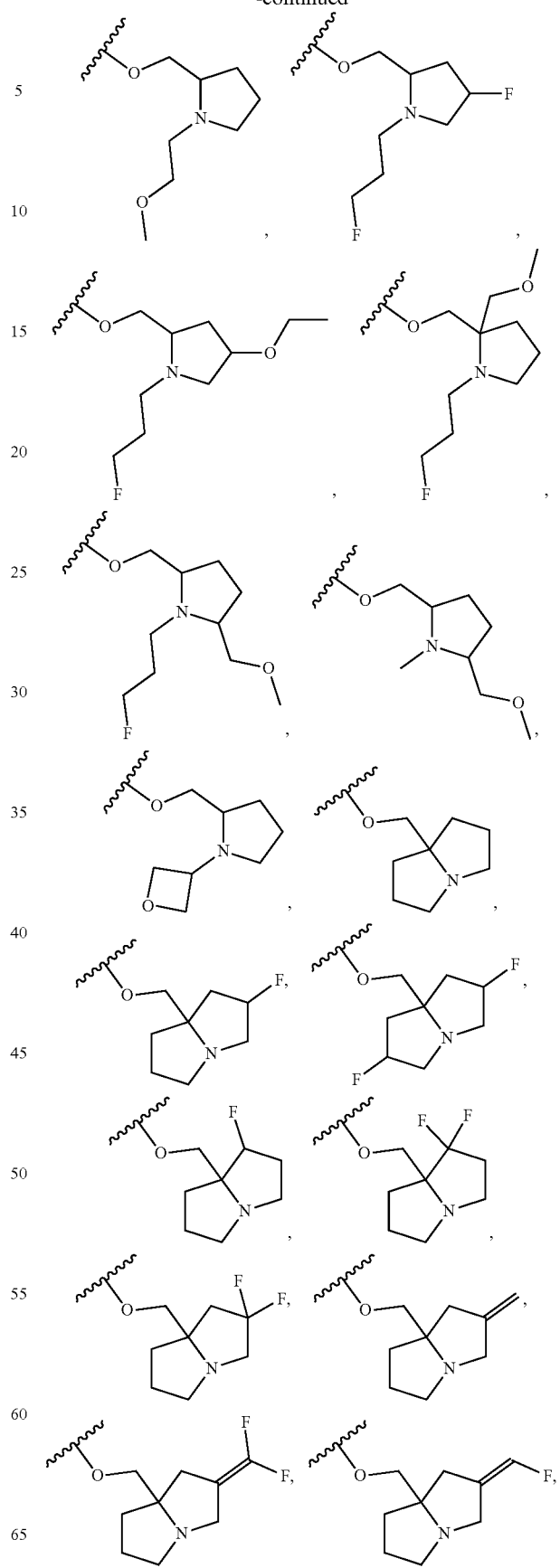

-continued

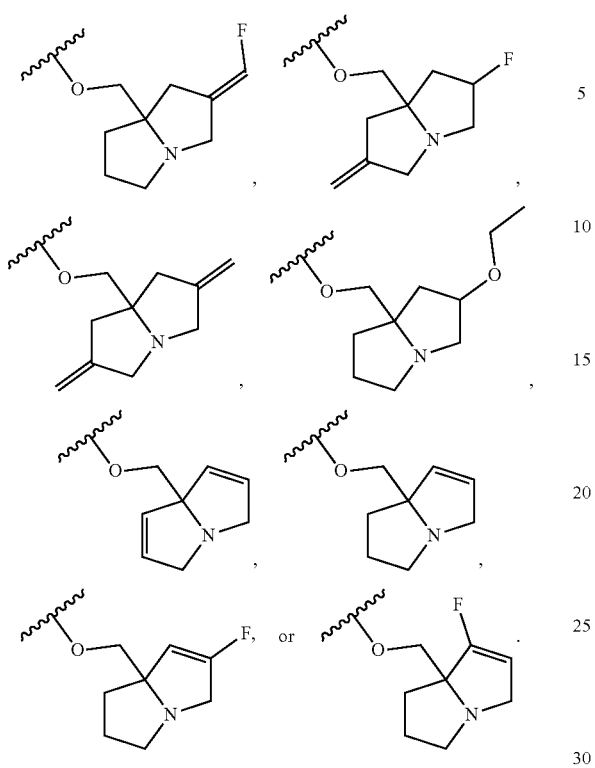

In one embodiment of the process (P1) described herein, the compound of formula (III) has formula (III1), (III2), (III3), or (3) as described herein.

In one embodiment of the process (P2) described herein, the process comprises:

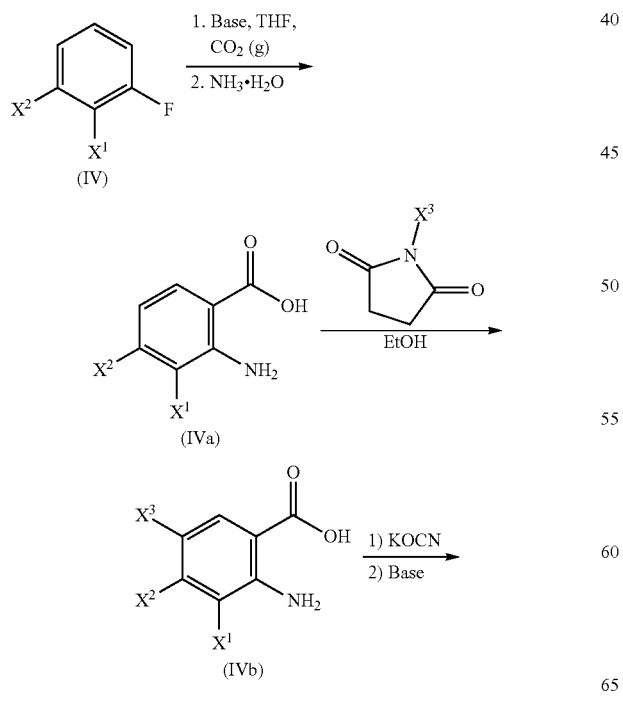

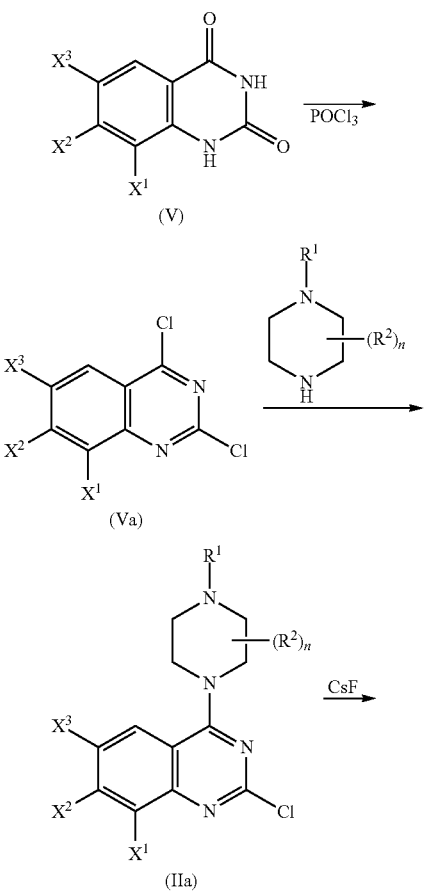

where $X^1$, $X^2$, $X^3$, $R^1$, $R^2$, and n are as described herein. In one such embodiment, $R^1$ is $PG^1$ and $R^2$ is methyl.

In one embodiment of the process (P3) described herein, the process comprises:

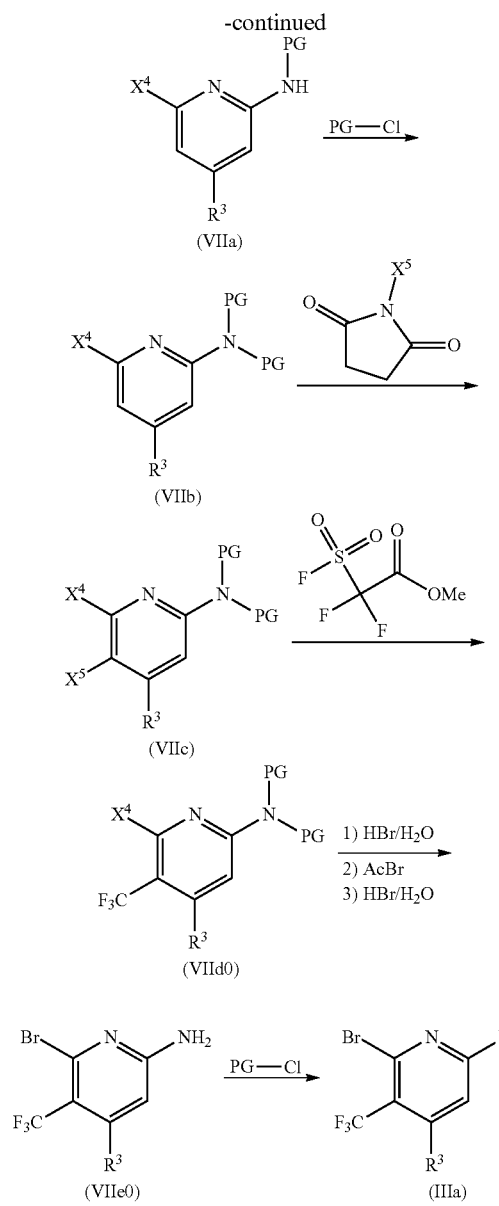

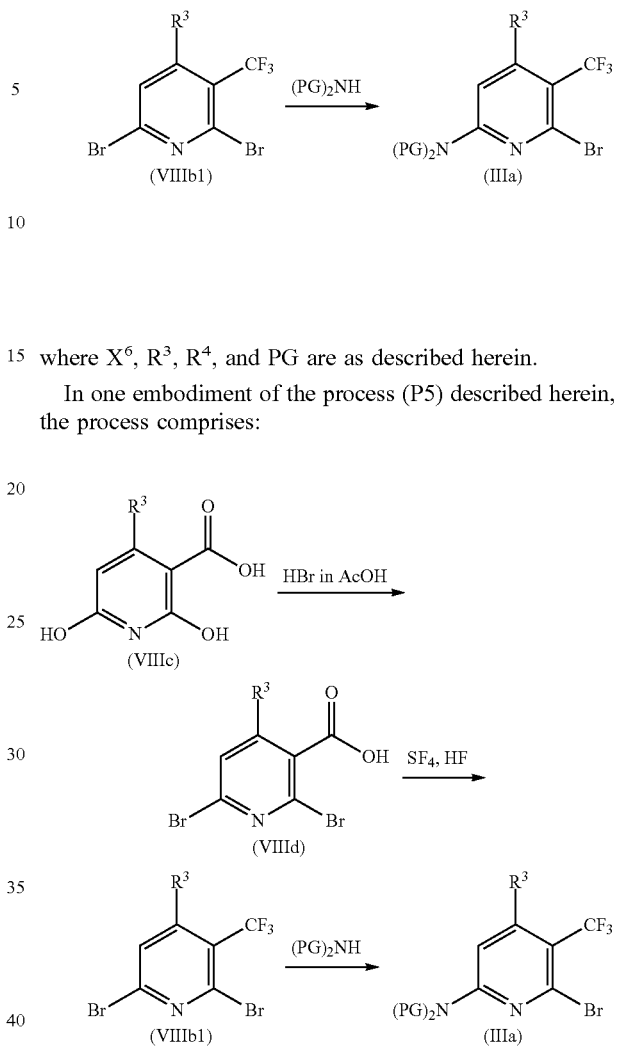

where $X^4$, $X^5$, $R^3$, and PG are as described herein.

In one embodiment of the process (P4) described herein, the process comprises:

where $X^6$, $R^3$, $R^4$, and PG are as described herein.

In one embodiment of the process (P5) described herein, the process comprises:

where $R^3$, $R^4$, and PG are as described herein.

Further provided herein is a process (P6) for the synthesis of a compound of formula (G) the process comprising;

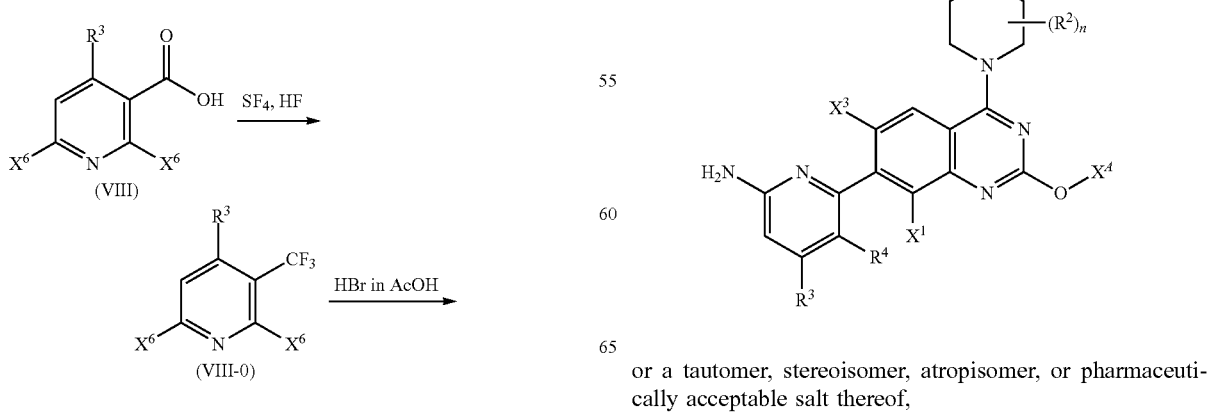

or a tautomer, stereoisomer, atropisomer, or pharmaceutically acceptable salt thereof, wherein $X^1$, $X^3$, $R^2$, $R^3$, $R^4$, and n are as described herein;
$R^{Alk}$ is a moiety selected from the group consisting of:
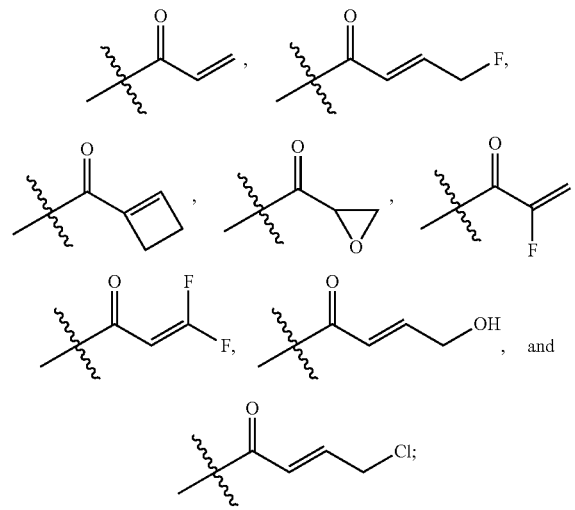
and
$X^A$ is selected from the group consisting of
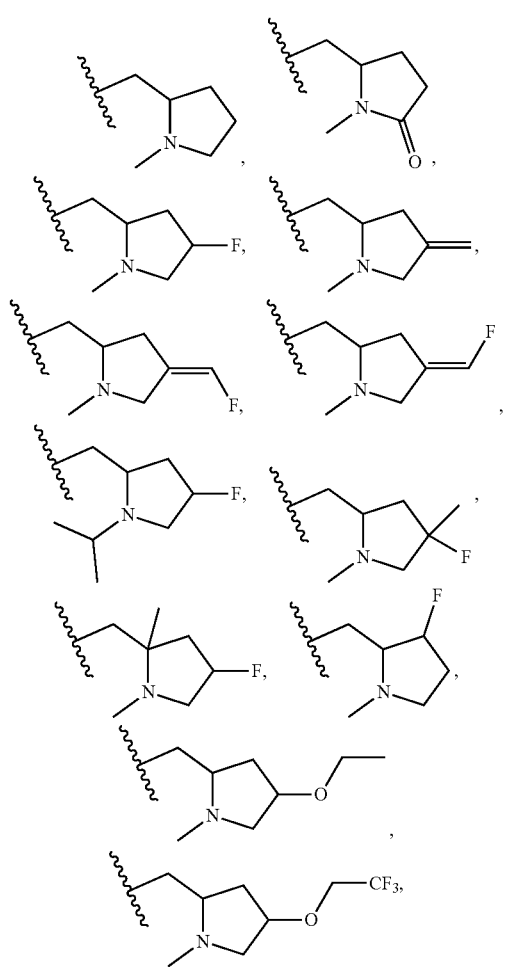
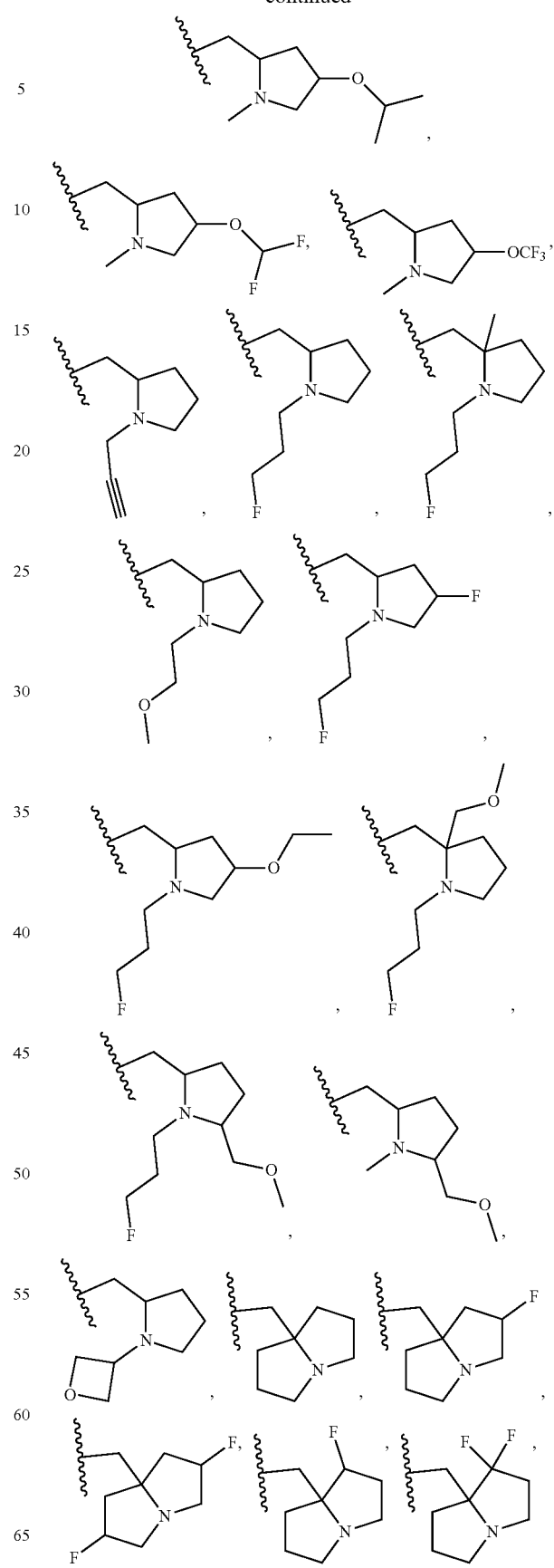

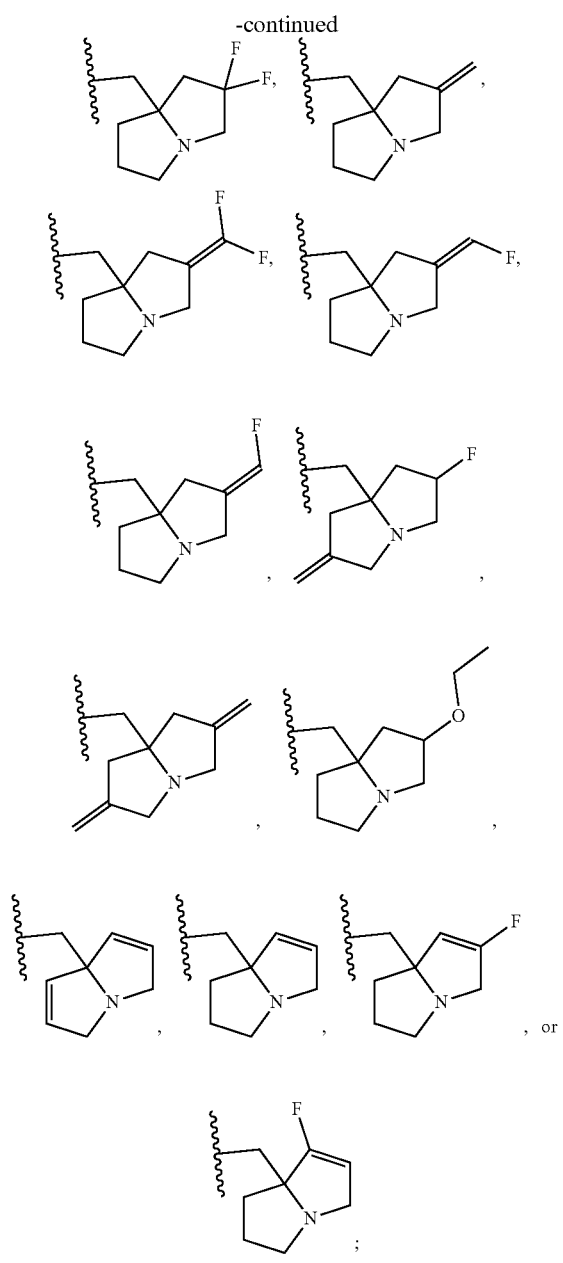

-continued

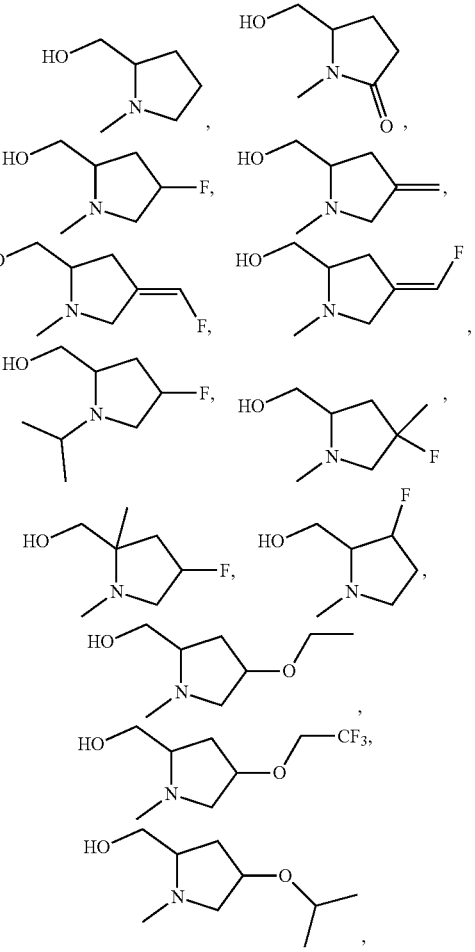

(G1)

or a solvate, tautomer, stereoisomer, atropisomer, or salt thereof, wherein PG and $R^1$ are as described herein;

(c) removing the PG groups from the compound of formula (G1); and
(d) installing the $R^{Alk}$ group, thereby synthesizing the compound of formula (G) or a tautomer, stereoisomer, atropisomer, or pharmaceutically acceptable salt thereof.

In one such embodiment, the moiety comprising $X^A$ of step (b) is:

(a) contacting a compound of formula (II), or a tautomer, stereoisomer, or salt thereof, synthesized according to the processes described herein with a compound of formula (III), or a salt thereof, synthesized according to the processes described herein to make a compound of formula (I) or a solvate, tautomer, stereoisomer, atropisomer, or salt thereof as described herein;

(b) contacting the compound of formula (I) or a solvate, tautomer, stereoisomer, atropisomer, or salt thereof with a moiety comprising $X^A$ thereby synthesizing a compound of formula (G1);

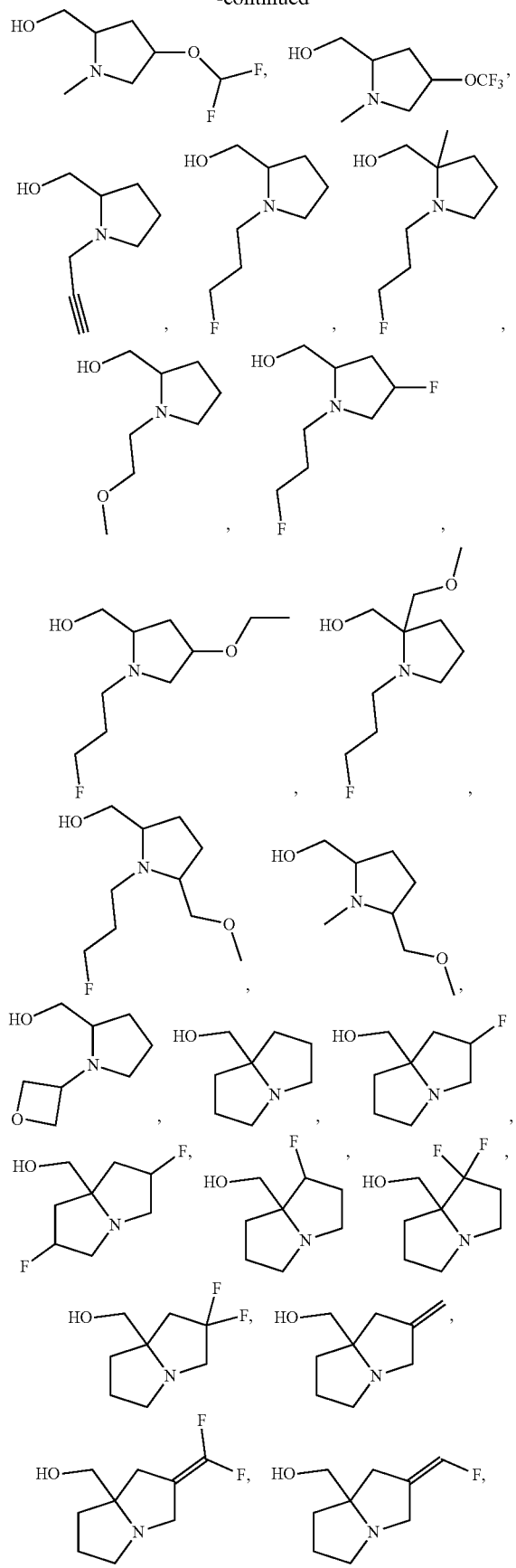

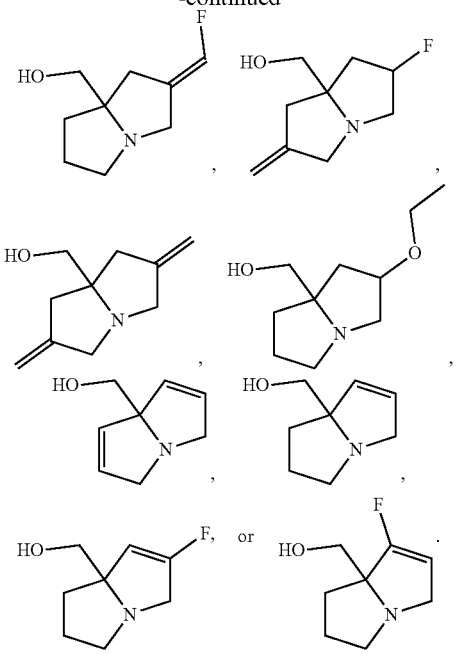

In one such embodiment, step (d) of process (P6) further comprises a base and an activating agent. In one embodiment, the activating agent is 1-ethyl-3-(3-dimethylaminopropyl)carbodiimide (EDCl), isobutyl chloroformate, ethyl chloroformate, or propylphosphonic anhydride.

In one embodiment of the process (P6) described herein, $R^{Alk}$ is

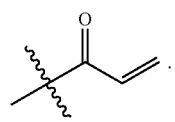 [SMILES: *C(=O)C=C]

In one embodiment of the process (P6) described herein, $R^{Alk}$ is

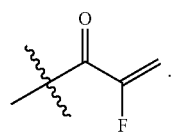 [SMILES: *C(=O)C(=C)F]

In such embodiments, the process includes a base and an activation agent as described herein.

In one embodiment of the process (P6) described herein, $R^2$ is $C_{1-3}$ alkyl or $C_{1-3}$ cyanoalkyl and n is 1. In one embodiment of the process (P6) described herein, each PG is PMB. In one embodiment of the process (P6) described herein, $X^1$ and $X^3$ are independently halogen.

Further provided herein is a process (P7) for the synthesis of a compound of formula (H):

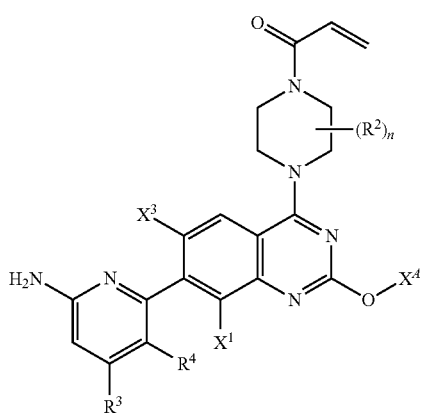

or a tautomer, stereoisomer, atropisomer, or pharmaceutically acceptable salt thereof, where $X^1$, $X^3$, $R^2$, $R^3$, $R^4$, PG, and n are as described herein, the process comprising:
(a) contacting a compound of formula (II), or a tautomer, stereoisomer, or salt thereof, synthesized according to the processes described herein with a compound of formula (III), or a salt thereof, synthesized according to the processes described herein to make a compound of formula (I) or a solvate, tautomer, stereoisomer, atropisomer, or salt thereof as described herein;
(b) contacting the compound of formula (I) or a solvate, tautomer, stereoisomer, atropisomer, or salt thereof with a compound of formula HO—$X^A$ in the presence of a base wherein said compound is selected from the group consisting of:

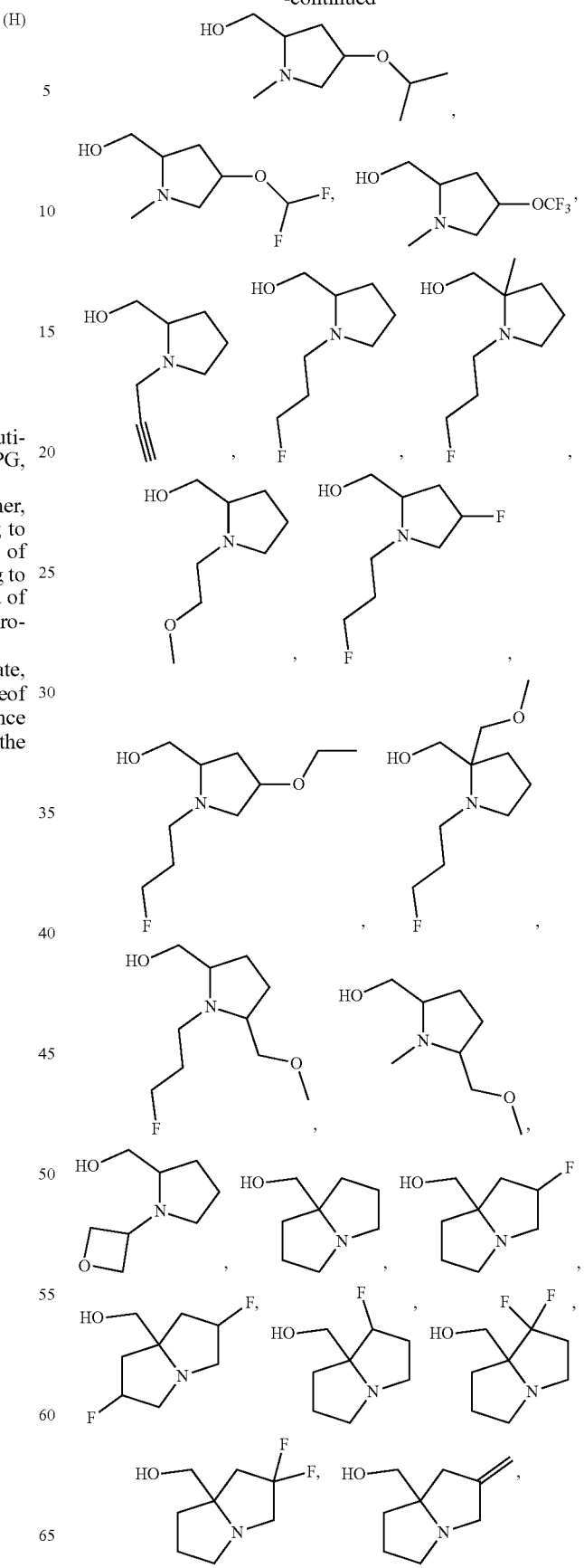

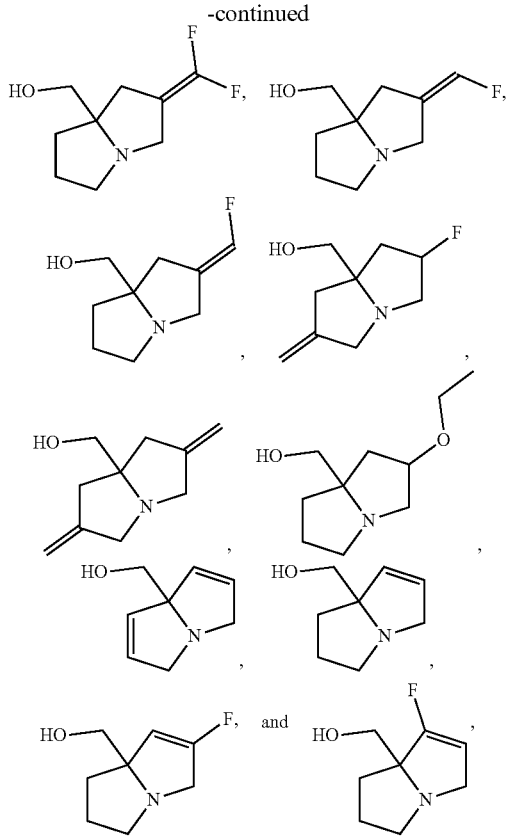

thereby making a compound of formula (G1);

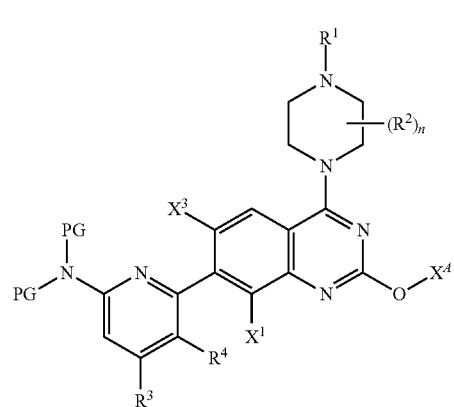

or a solvate, tautomer, stereoisomer, atropisomer, or salt thereof,
wherein PG and R¹ are as described herein; and
(c) removing the PG groups from the compound of formula (G1);
(d) contacting the compound of step (c) with

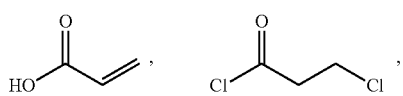

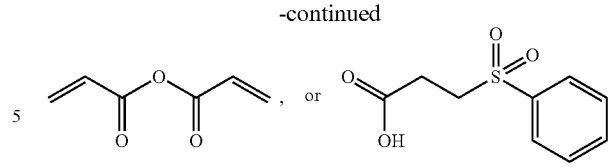

in the presence of a base and optionally an activating agent, thereby making a compound of formula (H) or a tautomer, stereoisomer, atropisomer, or pharmaceutically acceptable salt thereof.

In one embodiment of the process (P7) described herein, where R¹ is PG¹, the process further comprises step (b1): removing PG¹ from the compound of G1 before performing step (d).

In one embodiment of the process (P7) described herein, the compound of step (d) is

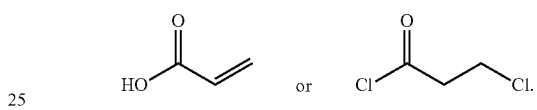

In one embodiment of the process (P7) described herein, the compound of step (d) is

and step (d) is done in the presence of a base described herein and an activating agent described herein. In one such embodiment, the activating agent is EDCl.

In one embodiment of the process (P7) described herein, the compound of step (d) is

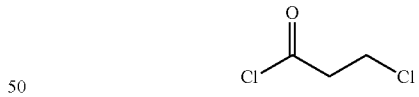

and step (d) is done in the presence of only a base described herein.

In one embodiment of the process (P7) described herein, the compound of step (d) is

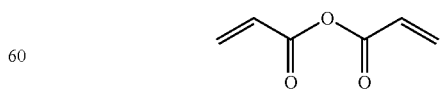

and step (d) is done in the presence of only a base described herein.

In one embodiment of the process (P7) described herein, the compound of step (d) is

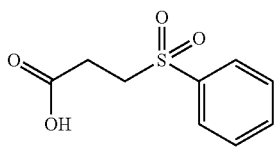 [SMILES: O=C(O)CCS(=O)(=O)c1ccccc1]

and step (d) is done in the presence of a base described herein and an activating agent described herein. In one such embodiment, the activating agent is EDCl.

In one embodiment of the process (P7) described herein, the base of step (d) is N-ethyl morpholine (NEM), triethylamine (TEA), tri(n-propyl)amine (TPA), N,N-diisopropylethylamine (DIPEA), or pyridine. In one embodiment of the process (P7) described herein, the base of step (d) is diisopropylethylamine (DIPEA). In one embodiment of the process (P7) described herein, $R^2$ is $C_{1-3}$ alkyl or $C_{1-3}$ cyanoalkyl and n is 1. In one embodiment of the process (P7) described herein, each PG is PMB. In one embodiment, $R^1$ is $PG^1$, where $PG^1$ is Boc. In one embodiment of the process (P7) described herein, $X^1$ and $X^3$ are independently halogen.

In one embodiment of the process (P7) described herein, the activating agent is a carbodiimide (e.g. dicyclohexylcarbodiimide (DCC), diisopropylcarbodiimide (DIC), or 1-ethyl-3-(3-dimethylaminopropyl)carbodiimide (EDCl)). In one embodiment of the process (P7) described herein, the activating agent is a benzo-triazol hexafluorophosphate compound (e.g. (Benzotriazol-1-yloxy)tris(dimethylamino) phosphonium hexafluorophosphate (BOP), (Benzotriazol-1-yloxy)tripyrrolidinophosphonium hexafluorophosphate (PyBOP), (7-Azabenzotriazol-1-yloxy)tripyrrolidinophosphonium hexafluorophosphate (PyAOP), Bromotripyrrolidinophosphonium hexafluorophosphate (PyBrOP), or BOP-Cl.

In one embodiment of the process (P7) described herein, the activating agent is a uronium compound (e.g. 2-(1H-7-Azabenzotriazol-1-yl)-1,1,3,3-tetramethyl uronium hexafluorophosphate (HATU), O-Benzotriazole-N,N,N',N'-tetramethyluronium-hexafluoro-phosphate (HBTU), 2-(6-Chloro-1H-benzotriazole-1-yl)-1,1,3,3-tetramethylaminium hexafluorophosphate (HCTU), O-(7-Azabenzotriazole-1-yl)-N,N,N',N'-tetramethyluronium tetrafluoroborate (TATU), or O-(Benzotriazol-1-yl)-N,N,N',N'-tetramethyluronium tetrafluoroborate (TBTU), O-[(Ethoxycarbonyl)cyanomethyleneamino]-N,N,N'N'-tetramethyluronium tetrafluoroborate (TOTU). In still another embodiment, the activating agent is O—(N-Suc-cinimidyl)-1,1,3,3-tetramethyl-uronium tetrafluoroborate (TSTU), O-(5-Norbornene-2,3-dicarboximido)-N,N,N',N'-tetramethyluronium tetrafluoroborate (TNTU) and O-(1,2-Dihydro-2-oxo-1-pyridyl-N,N,N',N'-tetramethyluronium tetrafluoroborate (TPTU). In still another embodiment, the coupling agent is 3-(Diethylphosphoryloxy)-1,2,3-benzotriazin-4(3H)-one (DEPBT).

In one embodiment of the process (P7) described herein, the activating agent is EDCl, isobutyl chloroformate, ethyl chloroformate, or propylphosphonic anhydride. In one such embodiment, the activating agent is EDCl. In another such embodiment, the activating agent is isobutyl chloroformate or ethyl chloroformate. In another such embodiment, the activating agent is propylphosphonic anhydride.

In one embodiment of the process (P7) described herein the moiety comprising $X^4$ is

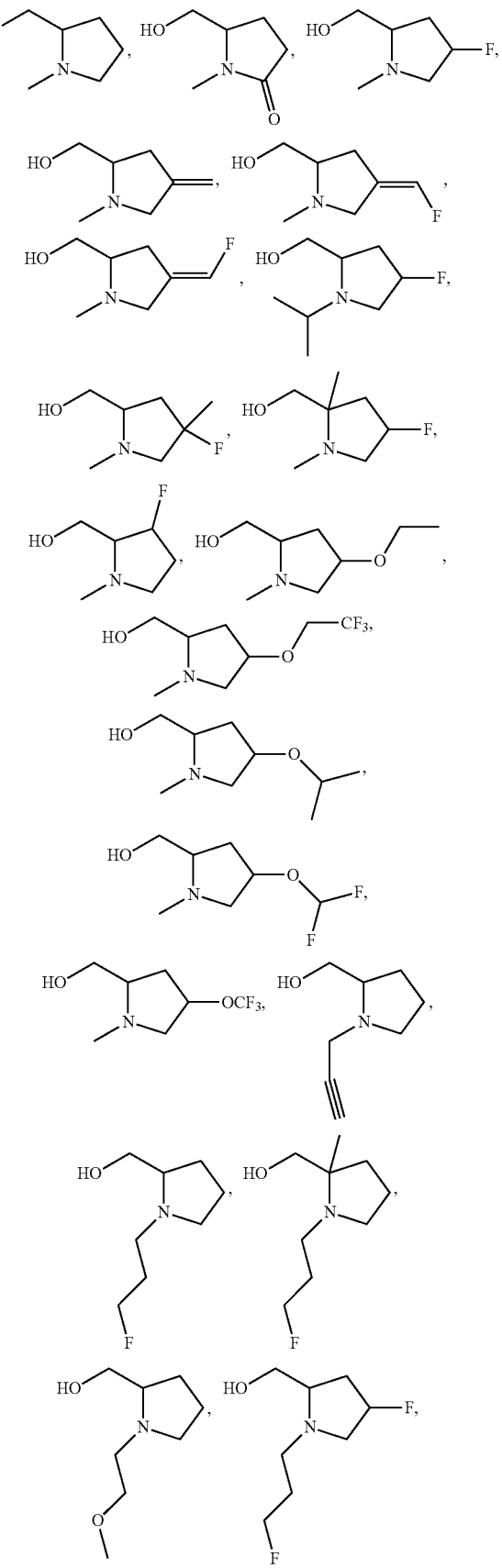

-continued

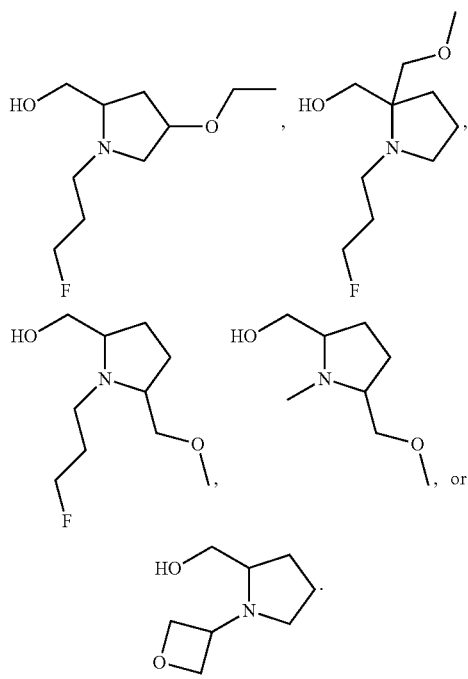

In one embodiment of the process (P7) described herein the moiety comprising $X^A$ is

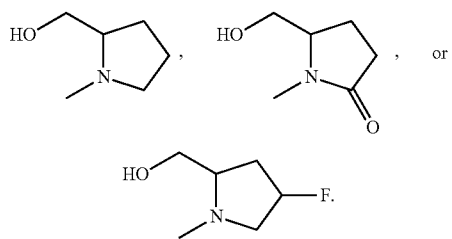

In one embodiment of the process (P7) described herein the moiety comprising $X^A$ is

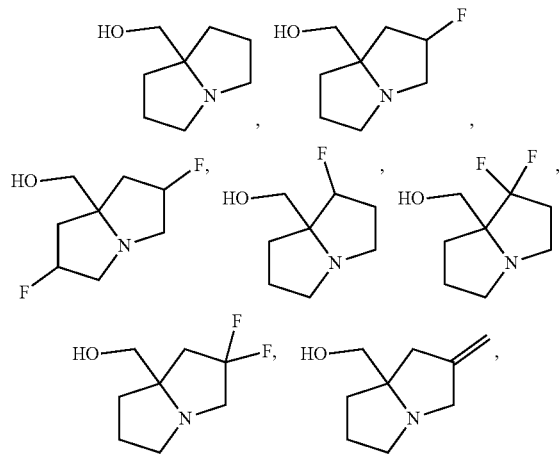

-continued

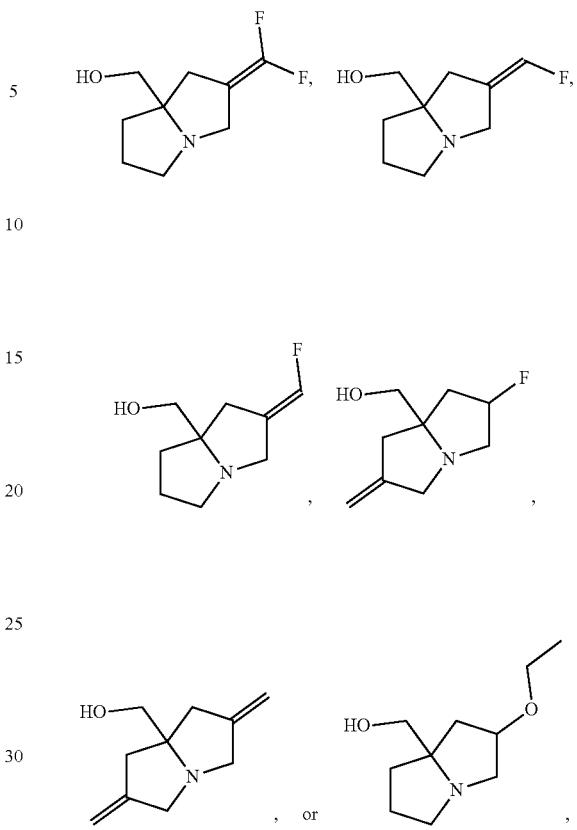

In one embodiment of the process (P7) described herein the moiety comprising

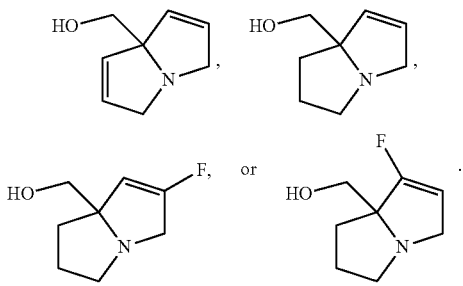

In one embodiment of the process (P6) or (P7) described herein, the compound of formula (G1) or a solvate, atropisomer, tautomer, stereoisomer, or salt thereof is a compound of Table 1. In one embodiment of the process (P6) or (P7) described herein, the compound of formula (G1) or a solvate, tautomer, stereoisomer, atropisomer, or salt thereof is a compound of formula 5, 33, 35, 37, 40, 44, 46, or 69 of Table 1. In one preferred embodiment of the process (P6) or (P7) described herein, the compound of formula (G1) or a solvate, atropisomer, tautomer, stereoisomer, or salt thereof is a compound of formula 5 of Table 1.

In another aspect provided herein is a process (P8) for the synthesis of a compound of formula (F) or a tautomer, stereoisomer, atropisomer, or pharmaceutically acceptable salt thereof,

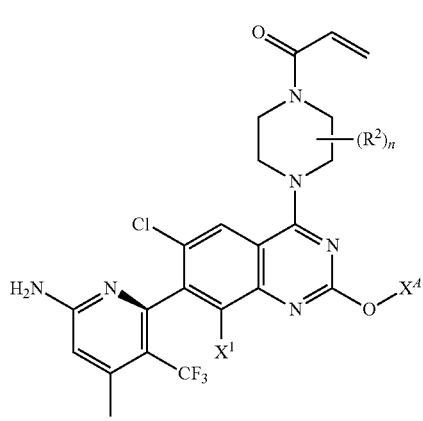

(F)

wherein R² and n are as described herein, the process comprising;
(a) contacting a compound of formula

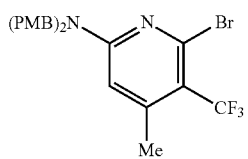

(3)

or a salt thereof with a compound of formula

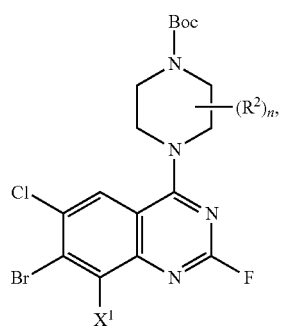

(2a)

or a tautomer, stereoisomer, or salt thereof thereby synthesizing a compound of formula (1a)

(1a)

or a solvate, tautomer, stereoisomer, atropisomer, salt thereof, (b) contacting the compound of formula (1a) or a solvate, tautomer, stereoisomer, atropisomer thereof, with a compound of formula HO—$X^A$, wherein $X^A$ has formula

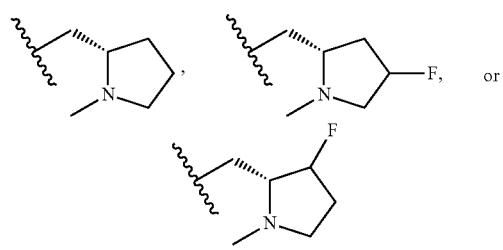

thereby synthesizing a compound of formula (F1);

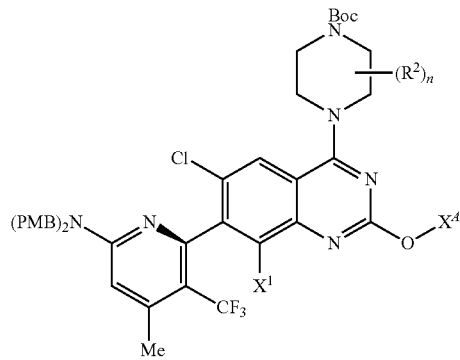

(F1)

or a solvate, tautomer, stereoisomer, or salt thereof;
(c) contacting the compound of formula (F1) or a solvate, tautomer, stereoisomer, or salt thereof with methanesulfonic acid (MsOH) in an acid thereby synthesizing a compound of formula (F2);

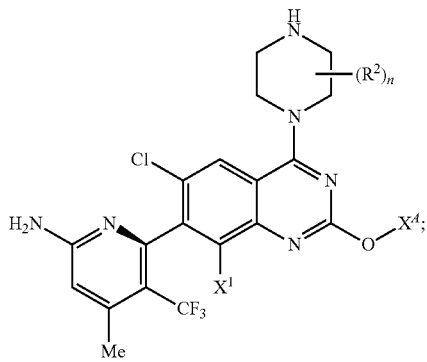

(F2)

or a solvate, tautomer, stereoisomer, or salt thereof; and
(d) contacting the compound of formula (F2) or a solvate, tautomer, stereoisomer, or salt thereof with a compound of formula

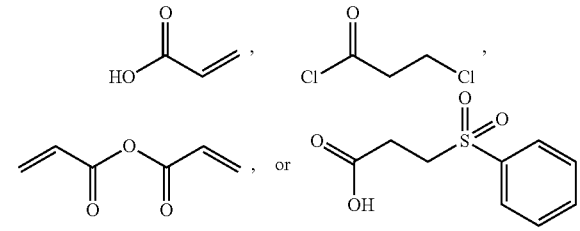

thereby making a compound of formula (F) or a tautomer, stereoisomer, or pharmaceutically acceptable salt thereof.

In one embodiment of the process (P8) described herein, the acid of step (c) is AcOH, trifluoroacetic acid, chlorosulfonic acid, sulfuric acid, HCl, HBr, p-toluenesulfonic acid, or trifluoromethanesulfonic acid. In one such embodiment, the acid of step (c) is AcOH, trifluoroacetic acid, or chlorosulfonic acid. In another such embodiment, the acid of step (c) is AcOH.

In one embodiment of the process (P8) described herein, $X^A$ is or

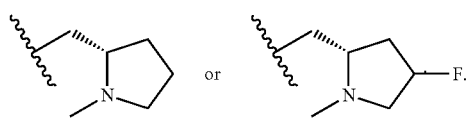

In one embodiment of the process described herein, $X^A$ is

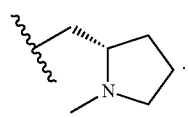 [SMILES: *C[C@@H]1CCCN1C]

In one embodiment of the process (P8), step (d) further comprises a base and optionally an activating agent. In one such embodiment, step (d) of process (P8) further comprises only a base as described herein. In another such embodiment, step (d) of process (P8) further comprises a base and an activating agent as described herein.

In one embodiment of the process (P8) described herein, the compound of step (d) is

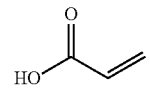

and a base.

In one embodiment of the process (P8) described herein, the compound of step (d) is

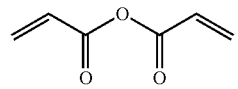

and a base.

In one embodiment of the process (P8) described herein, the compound of step (d) is

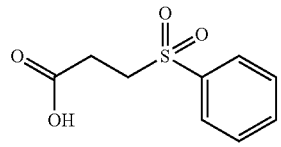 [SMILES: O=C(O)CCS(=O)(=O)c1ccccc1]

and a base and an activating as described herein.

In one embodiment of the process (P8) described herein, each $R^2$ is independently halogen or cyano. In one embodiment of the process (P8) described herein, each $R^2$ is independently halogen or unsubstituted $C_{1-6}$ cyanoalkyl. In one embodiment of the process (P8) described herein, each $R^2$ is independently unsubstituted $C_{1-6}$ alkyl, unsubstituted $C_{1-6}$ cyanoalkyl, or unsubstituted $C_{1-6}$ haloalkyl. In one embodiment of the process (P8) described herein is 1. In one embodiment of the process (P8) described herein, each $R^2$ is independently unsubstituted $C_{1-6}$ alkyl or unsubstituted $C_{1-6}$ cyanoalkyl. In one embodiment of the process (P8) described herein, each $R^2$ is methyl or ethyl. In one such embodiment, n is 1. In one embodiment of the process (P8) described herein, $R^2$ is methyl and n is 1. In one embodiment of the process (P8) described herein, each $R^2$ is $CF_3$, $CHF_2$, or $CH_2F$. In one embodiment of the process (P8) described herein, $R^2$ is methyl, ethyl, CN, $CH_2CN$, $CF_3$, $CHF_2$, or $CH_2F$. In another embodiment, $R^2$ is methyl, ethyl, CN, or $CH_2CN$. In one embodiment of the process (P8) described herein, n is 1. In one embodiment of the process (P8) described herein, $R^2$ is $CH_2CN$ and n is 1. In one embodiment of the process (P8) described herein, n is 0.

In one embodiment, the compound of formula (F) has formula (F4):

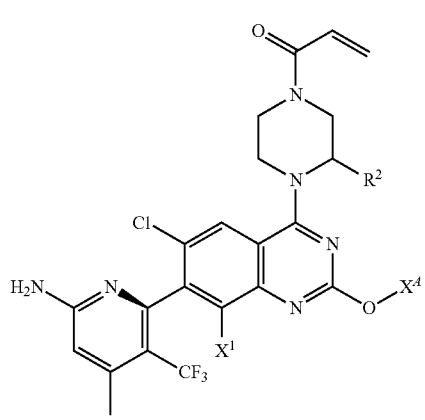

(F4)

or a tautomer, stereoisomer, or pharmaceutically acceptable salt thereof.

In one embodiment, the compound of formula (F) has formula (F5)

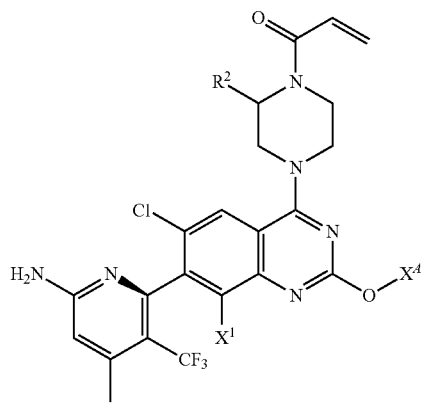

(F5)

or a tautomer, stereoisomer, or pharmaceutically acceptable salt thereof.

In one embodiment of the process (P8) described herein, the compound (F1) or a tautomer, stereoisomer, or pharmaceutically acceptable salt thereof is a compound of Table 1. In one embodiment of the process (P8) described herein, the compound of formula (F1) or a tautomer, stereoisomer, or pharmaceutically acceptable salt thereof is a compound of formula 105, 133, 135, 137, 140, 144, 146, or 169 of Table 1. In one preferred embodiment of the process (P8) described herein, the compound of formula (F1) or a tautomer, stereoisomer, or pharmaceutically acceptable salt thereof is a compound of formula 105 of Table 1.

Further provided herein is a process (P9) for the preparation of a compound of formula (A)

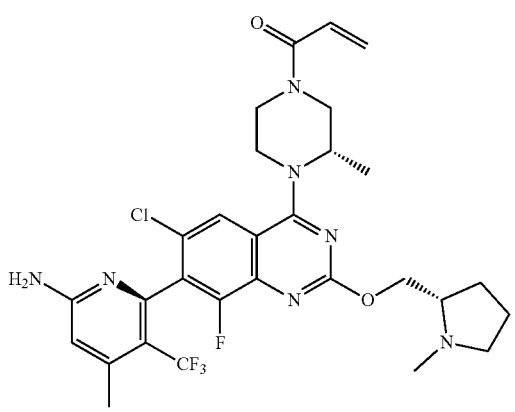

(A)

or a pharmaceutically acceptable salt thereof, the process comprising (a) contacting a compound of formula (2)

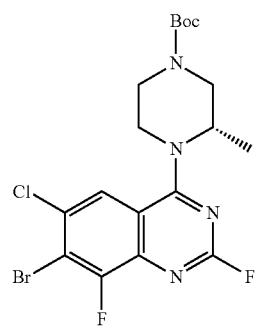 [SMILES: C[C@H]1CN(C(=O)OC(C)(C)C)CCN1c1nc(F)nc2c(F)c(Br)c(Cl)cc12]

or a salt thereof with i-PrMgCl·LiCl and ZnCl$_2$, followed by NaTFA and a compound of formula (3)

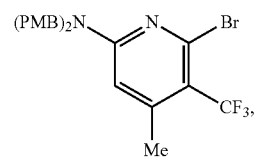

(b) contacting the mixture of step (a) or a salt thereof with a Pd or Ni catalyst precursor as described herein and a chiral ligand as described herein thereby synthesizing a compound of formula (1)

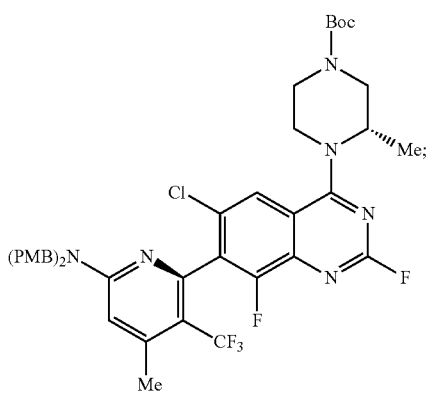

(1)

or a solvate or salt thereof, (c) contacting the compound of formula (1) or a solvate or salt thereof, with a compound of formula HO—X$^A$, wherein X$^A$ has formula

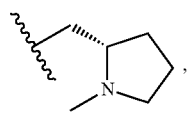 [SMILES: *C[C@@H]1CCCN1C]

and a base thereby synthesizing a compound of formula (1d);

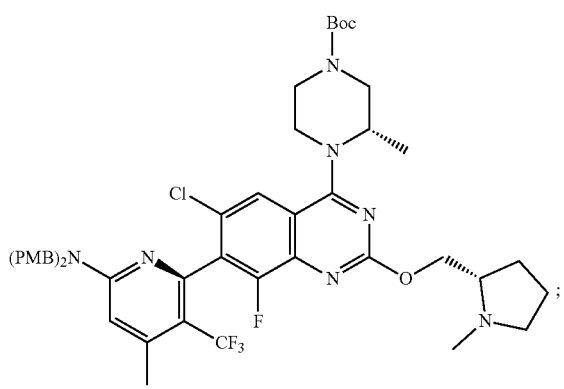

(1d)

or a solvate or pharmaceutically acceptable salt thereof;

(d) contacting the compound of formula (ad) with MsOH in an acid thereby synthesizing a compound of formula (1e);

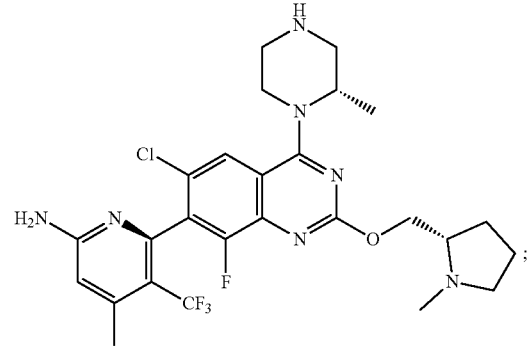

(1e)

or a solvate or pharmaceutically acceptable salt thereof; and (e) contacting the compound of formula (1e) or a solvate or pharmaceutically acceptable salt thereof with

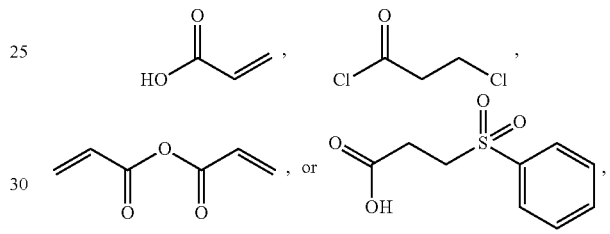

followed by a base and optionally an activating agent each as described herein, thereby making a compound of formula (A) or a pharmaceutically acceptable salt thereof.

In one embodiment, step (b) of the process (P9) further comprises a crystallization. In one such embodiment, the crystallization is performed in toluene/n-heptane.

In one embodiment, step (c) of the process (P9) further comprises washing with potassium carbonate and filtration (e.g. polishing filtration). In one such embodiment, step (c) of the process of (P9) further comprises a solvent swap to 1-PrOH. In one such embodiment, crystallization is performed from 1-PrOH/water following the solvent swap. In another embodiment, crystallization is performed from isopropanol/water, acetonitrile, acetonitrile/water, or acetone/water.

In one embodiment of the process described herein, the base of step (c) is selected from the group consisting of LiOt-Am, NaOt-Am, KOt-Am, KDMO (potassium 3,7-dimethyl-3-octanoxide), LiOt-Bu, NaOt-Bu, or KOt-Bu. In one such embodiment, the base is a base of table:

| Entry | Base | Time (h) | Conv (%)$^c$ | Product (A %) | Byproduct (A %) |
|---|---|---|---|---|---|
| 1 | LiHMDS | 4 | 67 | 55 | 7.8 |
| 2 | NaHMDS | 4 | 85 | 63 | 12 |
| 3 | KHMDS | 4 | 92 | 61 | 24 |
| 4 | LiOt-Am | 20 | 92 | 73 | 10 |
| 5 | NaOt-Am | 1 | 99 | 94 | 1.6 |
| 6 | KOt-Am | 1 | 99 | 93 | 1.8 |
| 7 | KDMO | 1 | 99 | 92 | 1.5 |

-continued

| Entry | Base | Time (h) | Conv (%)$^c$ | Product (A %) | Byproduct (A %) |
|---|---|---|---|---|---|
| 8 | LiOt-Bu | 4 | 85 | 74 | 7.0 |
| 9 | NaOt-Bu | 1 | 99 | 92 | 1.4 |
| 10 | KOt-Bu | 1 | 99 | 73 | 23 |

Byproduct is-OH at C2 position

In one such embodiment, the base is NaOt-Am or NaOt-Bu. In such embodiments, the base can be present at an amount of about 1.1 to about 1.35 equivalents relative to Compound 1.

In one embodiment of the process (P9) described herein, the acid of step (d) is AcOH, trifluoroacetic acid, chlorosulfonic acid, sulfuric acid, HCl, HBr, formic acid, p-toluenesulfonic acid, or trifluoromethanesulfonic acid. In one such embodiment, the acid of step (d) is AcOH, trifluoroacetic acid, or chlorosulfonic acid. In one such embodiment, the acid of step (d) is AcOH, formic acid, trifluoroacetic acid, or chlorosulfonic acid. In another such embodiment, the acid of step (d) is AcOH.

In one embodiment of the process (P9) described herein, the activating agent is EDCl, isobutyl chloroformate, ethyl chloroformate, or propylphosphonic anhydride. In one such embodiment, the activating agent is EDCl. In another such embodiment, the activating agent is isobutyl chloroformate or ethyl chloroformate. In another such embodiment, the activating agent is propylphosphonic anhydride.

In one embodiment, step (d) of the process (P9) further comprises quenching with a base (e.g. a hydroxide base such as, for example, NaOH) and washing with the same base (e.g. NaOH). In another such embodiment, step (d) of the process of (P9) further comprises polishing filtration. In still another embodiment, step (d) of the process of (P9) further comprises a crystallization step (e.g. with toluene/n-heptane).

In one embodiment of the process (P9) described herein, the MsOH of step (d) can be present at an amount of about 10-30 equivalents, 15-30 equivalents, 15-27 equivalents, 15-25 equivalents, 15-23 equivalents, or about 20-30 equivalents relative to the compound of formula (1d). In one such embodiment, the MsOH is present at an amount of about 15-27 equivalents relative to the compound of formula (1d). In another embodiment of the process (P9) described herein, the AcOH is present in an mount of about 1-4 vols., 1.5-3.5 vols., 1.6-3.4 vols., or 1.8-3.3 vols. In one embodiment of the process (P9) described herein, step d further comprises toluene as a cosolvent. In one such embodiment, the vol of toluene is 0-7 volumes.

In one embodiment of the process (P9) described herein, step (e) comprises contacting the compound of formula (1e) or a solvate or pharmaceutically acceptable salt thereof with

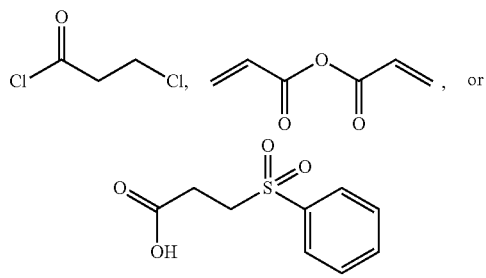

, or and a base and optionally an activating agent as described herein.

In one embodiment of the process (P9) described herein, step (e) comprises contacting the compound of formula (1e) or a solvate or pharmaceutically acceptable salt thereof with

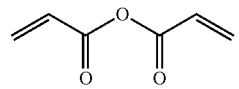

in the presence of a base.

In one embodiment of the process (P9) described herein, step (e) comprises contacting the compound of formula (1e) or a solvate or pharmaceutically acceptable salt thereof with

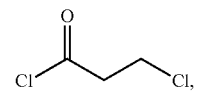

in the presence of a base.

In one embodiment of the process (P9) described herein, step (e) comprises contacting the compound of formula (1e) or a solvate or pharmaceutically acceptable salt thereof with

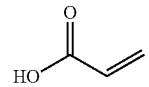

in the presence of a base and an activating agent as described herein.

In one embodiment of the process (P9) described herein, step (e) comprises contacting the compound of formula (1e) or a solvate or pharmaceutically acceptable salt thereof with

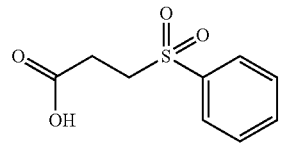 [SMILES: O=C(O)CCS(=O)(=O)c1ccccc1]

in the presence of a base and an activating agent as described herein. In one such embodiment, the reaction is performed in a solvent such as 2-Me-THF or toluene. In one embodiment, the activating agent is EDCl. In another embodiment, the activating agent includes Pivaloyl chloride (PivCl).

In one embodiment of the process described herein, the base of step (e) is NaOH, KOH, LiOH, triethylamine, or pyridine. In one such embodiment, the base is NaOH.

In one embodiment of the process (P9) described herein, the compound of formula (1) is a cyclohexane, methylcyclohexane, chlorobenzene, ethylbenzene, m-xylene, or toluene solvate. In one embodiment of the process (P9) described herein, the compound of formula (1) is a crystalline cyclohexane solvate. In one such embodiment of the process (P9) described herein, the crystalline cyclohexane solvate of the compound of formula (1) is substantially as shown in FIG. 1. In another embodiment of the process (P9) described herein, the compound of formula (1) is a crystalline methylcyclohexane solvate. In one such embodiment of the process (P9) described herein, the crystalline methylcyclohexane solvate of the compound of formula (1) is substantially as shown in FIG. 2. In another embodiment of the process (P9) described herein, the compound of formula (1) is a crystalline chlorobenzene solvate. In one such embodiment of the process (P9) described herein, the crystalline chlorobenzene solvate of the compound of formula (1) is substantially as shown in FIG. 3. In another embodiment of the process (P9) described herein, the compound of formula (1) is a crystalline ethylbenzene solvate. In one such embodiment of the process (P9) described herein, the crystalline ethylbenzene solvate of the compound of formula (1) is substantially as shown in FIG. 4. In another embodiment of the process (P9) described herein, the compound of formula (1) is a crystalline m-xylene solvate. In one such embodiment of the process (P9) described herein, the crystalline m-xylene solvate of the compound of formula (1) is substantially as shown in FIG. 5. In another embodiment of the process (P9) described herein, the compound of formula (1) is a crystalline toluene solvate. In one such embodiment of the process (P9) described herein, the crystalline toluene solvate of the compound of formula (1) is substantially as shown in FIG. 6.

In one embodiment of the process described herein, the process (P9) further comprises step (f): contacting the compound of formula (A) with adipic acid in a solvent (e.g. methylethylketone (MEK), 2-Me-THF, 2-butanol, or 2-Me-THF/2-butanol) to form a compound of formula (B). In one embodiment, step (f) comprises Scheme 1. In another embodiment, step (f) comprises Scheme 2. In another embodiment, step (f) comprises Scheme 3. In one embodiment, Scheme 3 further comprises n-heptane.

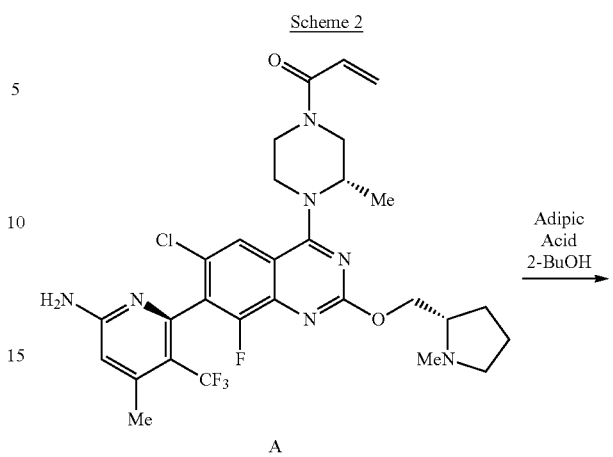

Scheme 2

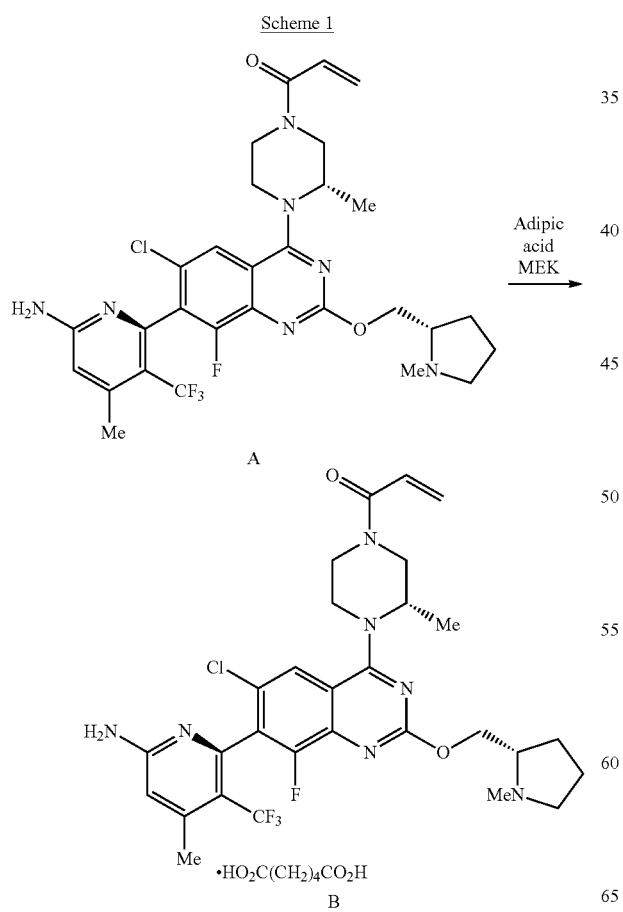

Scheme 1

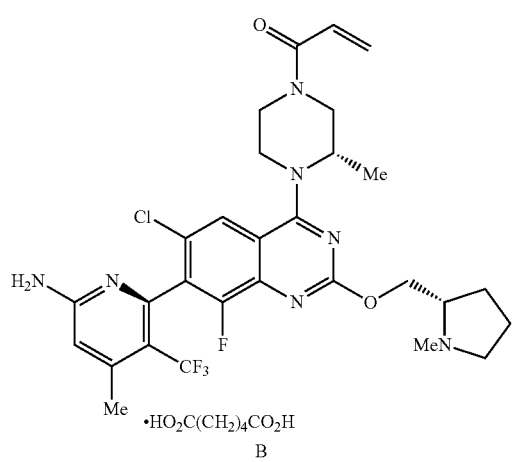

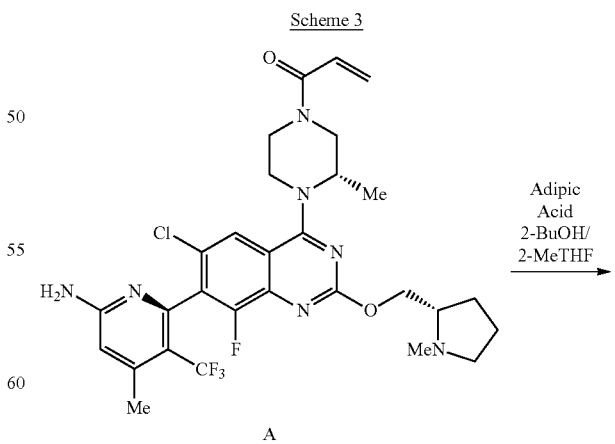

Scheme 3

-continued

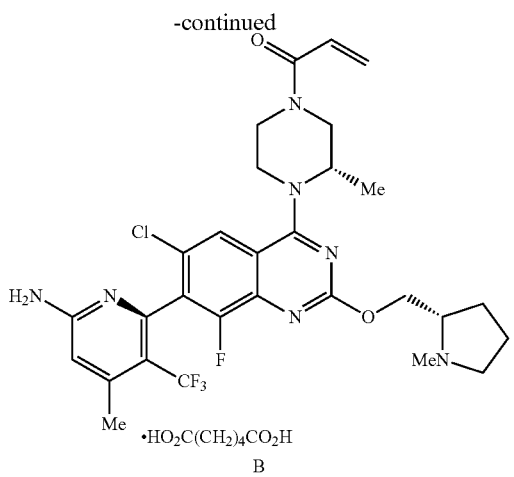

B

Methods of Treating

The processes described herein are useful in preparing compounds useful in the treatment of cancers. In one embodiment provided herein is a method of treating a cancer mediated by a KRas$^{G12C}$ mutation by administering an effective amount of Compound (A) or a pharmaceutically acceptable salt thereof synthesized according to any of the processes described herein. In one embodiment provided herein is a method of treating a cancer mediated by a KRas$^{G12C}$ mutation by administering an effective amount of Compound (B) synthesized according to any of the processes described herein. In one preferred embodiment of the methods described herein, Compound (A) or a pharmaceutically acceptable salt thereof is synthesized according to process P9 as described herein. In one preferred embodiment of the methods described herein, Compound (B) or a pharmaceutically acceptable salt thereof is synthesized according to process P9 as described herein.

Determining whether a tumor or cancer comprises a KRas$^{G12C}$ mutation can be undertaken by assessing the nucleotide sequence encoding the K-Ras protein, by assessing the amino acid sequence of the K-Ras protein, or by assessing the characteristics of a putative K-Ras mutant protein. The sequence of wild-type human K-Ras (e.g. Accession No. NP203524) is known in the art.

In certain particular embodiments, the methods include treatment of lung cancers. In one embodiment, is a method of treating lung cancer comprising a KRas$^{G12C}$ mutation in a patient having such lung cancer, the method comprising administering a therapeutically effective amount of Compound (A) or a pharmaceutically acceptable salt thereof synthesized according to process P9 as described herein to the patient. In one preferred embodiment, is a method of treating lung cancer comprising a KRas$^{G12C}$ mutation in a patient having such lung cancer, the method comprising administering a therapeutically effective amount of Compound (B) or a pharmaceutically acceptable salt thereof synthesized according to process P9 as described herein to the patient.

In certain embodiments the lung cancer is a non-small cell lung carcinoma (NSCLC), for example adenocarcinoma, squamous-cell lung carcinoma or large-cell lung carcinoma. In some embodiments, the cancer is lung adenocarcinoma. In other embodiments, the lung cancer is a small cell lung carcinoma. The NSCLC can be, for example, adenocarcinoma, squamous-cell lung carcinoma or large-cell lung carcinoma. In another embodiment, the lung cancer is small cell lung carcinoma. In still another embodiment, the lung cancer is glandular tumors, carcinoid tumors or undifferentiated carcinomas. The lung cancer can be stage I or II lung cancer. In one embodiment, the lung cancer is stage III or IV lung cancer.

In one embodiment of such methods, the patient is diagnosed with a cancer described herein. In another embodiment of such methods, the sample is a tumor sample taken from the subject. In one such embodiment, the sample is taken before administration of any therapy. In another such embodiment, the sample is taken before administration of a compound of pharmaceutically acceptable salt thereof described herein and after administration of another chemotherapeutic agent. In another embodiment of such methods, the compound or pharmaceutically acceptable salt thereof described herein is administered as provided herein (e.g. orally).

Further provided herein are methods of treating pancreatic cancer comprising a KRas$^{G12C}$ mutation in a patient having such pancreatic cancer, the method comprising administering a therapeutically effective amount of Compound (A) or a pharmaceutically acceptable salt thereof synthesized according to process P9 as described herein to the patient. Further provided herein are methods of treating pancreatic cancer comprising a KRas$^{G12C}$ mutation in a patient having such pancreatic cancer, such methods comprising administering a therapeutically effective amount of Compound (B) or a pharmaceutically acceptable salt thereof synthesized according to process P9 as described herein to the patient.

In one embodiment, the patient has been previously treated with radiation and one or more chemotherapy agents. In one embodiment, the pancreatic cancer is stage 0, I, or II. In another embodiment, the pancreatic cancer is stage III or stage IV.

Still further provided herein are methods of treating colon cancer comprising a KRas$^{G12C}$ mutation in a patient having such colon cancer, the method comprising administering a therapeutically effective amount of Compound (A) or a pharmaceutically acceptable salt thereof synthesized according to process P9 as described herein to the patient. Still further provided herein are methods of treating colon cancer comprising a KRas$^{G12C}$ mutation in a patient having such colon cancer, the method comprising administering a therapeutically effective amount of Compound (B) or a pharmaceutically acceptable salt thereof synthesized according to process P9 as described herein to the patient.

In one embodiment, the colon cancer is stage I or II. In another embodiment, the colon cancer is stage III or stage IV.

Further provided herein are methods for treating a hematological cancer comprising a KRas$^{G12C}$ mutation or MYH associated polyposis cancer comprising a KRas$^{G12C}$ mutation by administering a therapeutically effective amount of Compound (A) or a pharmaceutically acceptable salt thereof synthesized according to process P9 as described herein to a subject having such disease. Still further provided herein are methods for treating a hematological cancer comprising a KRas$^{G12C}$ mutation or MYH associated polyposis cancer comprising a KRas$^{G12C}$ mutation by administering a therapeutically effective amount of Compound (B) synthesized according to process P9 as described herein to a subject having such disease.

Further provided herein are methods of treating tumor agnostic cancer comprising a KRas$^{G12C}$ mutation. In one embodiment of such methods, the method comprises:
(a) determining the absence or presence of a KRas$^{G12C}$ mutation in a sample taken from a patient with a suspected diagnosed cancer; and (b) administering to the patient a therapeutically effective amount of effective amount of Compound (A) or a pharmaceutically acceptable salt thereof synthesized according to process P9 as described herein to a subject having such disease.

Further provided herein are methods of treating tumor agnostic cancer comprising a KRas$^{G12C}$ mutation. In one embodiment of such methods, the method comprises:
(a) determining the absence or presence of a KRas$^{G12C}$ mutation in a sample taken from a patient with a suspected diagnosed cancer; and
(b) administering to the patient a therapeutically effective amount of effective amount of Compound (B) synthesized according to process P9 as described herein to a subject having such disease.

A patient described herein can be a human. In some embodiments, administration of a compound described herein in the methods provided herein is via the oral route. In some embodiments, the administration is via injection. The methods provided herein include administration of the compound as a 1 L therapy.

Embodiments

The following are exemplary embodiments.

Embodiment No 1. A process for the preparation of a compound of formula (I) comprising;

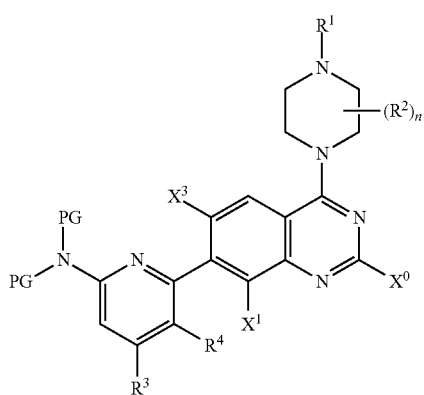

wherein;
$X^0$ is hydrogen, halogen, OR$^{5A}$, SR$^{5B}$, R$^5$-substituted or unsubstituted $C_{1-6}$ alkyl, R$^5$-substituted or unsubstituted $C_{1-6}$ haloalkyl, R$^5$-substituted or unsubstituted $C_{5-7}$ aryl, or R$^5$-substituted or unsubstituted $C_{5-7}$ heteroaryl;

$X^1$ is hydrogen or halogen;

$X^3$ is hydrogen, halogen, R$^6$-substituted or unsubstituted $C_{1-3}$ alkyl, R$^6$-substituted or unsubstituted $C_{1-3}$ haloalkyl, R$^6$-substituted or unsubstituted $C_{1-3}$ alkoxy, or R$^6$-substituted or unsubstituted cyclopropyl;

$R^1$ is hydrogen or PG$^1$;

each R$^2$ is independently halogen, cyano, unsubstituted $C_{1-6}$ alkyl, unsubstituted $C_{1-6}$ cyanoalkyl, or unsubstituted $C_{1-6}$ haloalkyl;

$R^3$ is hydrogen, halogen, R$^{3A}$-substituted or unsubstituted $C_{1-3}$ alkyl, R$^{3A}$-substituted or unsubstituted $C_{1-3}$ haloalkyl, or R$^{3A}$-substituted or unsubstituted $C_{3-6}$ cycloalkyl;

R$^{3A}$ is halogen, OH, CN, unsubstituted $C_{1-3}$ alkyl or unsubstituted $C_{1-3}$ haloalkyl;

$R^4$ is R$^{4A}$-substituted or unsubstituted $C_{1-3}$ haloalkyl;

R$^{4A}$ is unsubstituted $C_{1-3}$ alkyl;

$R^5$ is halogen, cyano, OH, NO$_2$, R$^{5A}$-substituted or unsubstituted $C_{1-6}$ alkyl, R$^{5A}$-substituted or unsubstituted $C_{1-6}$ haloalkyl, R$^{5A}$-substituted or unsubstituted $C_{1-6}$ cyanoalkyl, R$^{5A}$-substituted or unsubstituted $C_{3-6}$ cycloalkyl, R$^{5A}$-substituted or unsubstituted 3-6 membered heterocycle, R$^{5A}$-substituted or unsubstituted phenyl, or R$^{5A}$-substituted or unsubstituted 6 membered heteroaryl;

R$^{5A}$ and R$^{5B}$ are each independently R$^{5C}$-substituted or unsubstituted $C_{1-6}$ alkyl, R$^{5C}$-substituted or unsubstituted $C_{1-6}$ haloalkyl, R$^{5C}$-substituted or unsubstituted $C_{3-7}$ cycloalkyl; R$^{5C}$-substituted or unsubstituted 3-7 membered heterocycle; R$^{5C}$-substituted or unsubstituted $C_{5-7}$ aryl, or R$^{5C}$-substituted or unsubstituted $C_{5-7}$ heteroaryl;

R$^{5C}$ is independently halogen, OH, CN, NO$_2$, R$^{5D}$-substituted or unsubstituted $C_{1-6}$ alkyl, R$^{5D}$-substituted or unsubstituted $C_{1-6}$ haloalkyl, R$^{5D}$-substituted or unsubstituted $C_{3-7}$ cycloalkyl; R$^{5D}$-substituted or unsubstituted $C_{3-7}$ heterocycle; R$^{5D}$-substituted or unsubstituted $C_{5-7}$ aryl, or R$^{5D}$-substituted or unsubstituted $C_{5-7}$ heteroaryl;

R$^{5D}$ is independently halogen, OH, CN, NO$_2$, unsubstituted $C_{1-6}$ alkyl, unsubstituted $C_{1-6}$ haloalkyl, unsubstituted $C_{3-7}$ cycloalkyl; unsubstituted $C_{3-7}$ heterocycle; unsubstituted $C_{5-7}$ aryl, or unsubstituted $C_{5-7}$ heteroaryl;

$R^6$ is halogen, OH, CN, NO$_2$, unsubstituted $C_{1-6}$ alkyl, unsubstituted $C_{1-6}$ haloalkyl, or unsubstituted $C_{3-7}$ cycloalkyl;

n is 0, 1, or 2;

each PG is independently an amino protecting group, or wherein two PG together form a $C_{3-7}$ nitrogen heterocycle; and PG$^1$ is an amino protecting group;

(a) contacting a compound of formula (II)

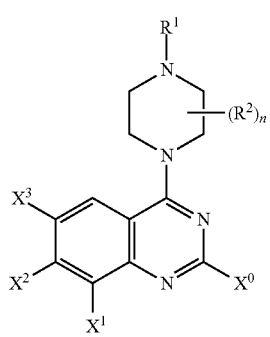

wherein $X^2$ is halogen;

with an organomagnesium compound and a zinc complex; and (b) contacting the mixture of step (a) with a compound of formula (III),

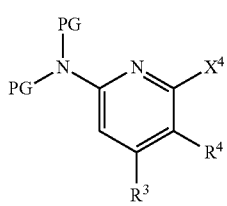

(III)

wherein $X^4$ is halogen;
a transition metal (e.g. Pd or Ni) catalyst precursor, and a chiral ligand, thereby synthesizing a compound of formula (I).

Embodiment No 2. The process of embodiment 1, wherein the compound of formula (II) is prepared according to the method:

(a) contacting the compound of formula (IVa)

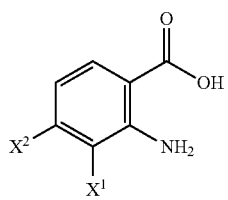

(IVa)

with a halogenating agent having formula

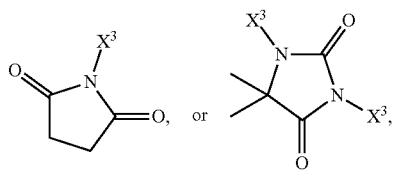

wherein $X^3$ is halogen, to make a compound of formula (IVb)

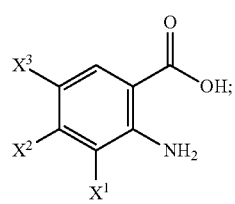

(d) cyclizing the compound of formula (IVb) to a compound of formula (V)

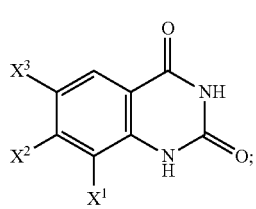

(V)

(d) contacting the compound of formula (V) with a chlorinating agent to make a compound of formula (Va)

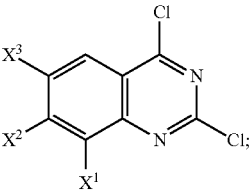

(Va)

and (e) contacting the compound of formula (Va) with a piperazinyl moiety having formula

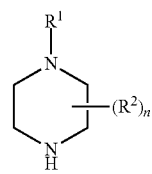

(VI)

to make a compound of formula (IIa)

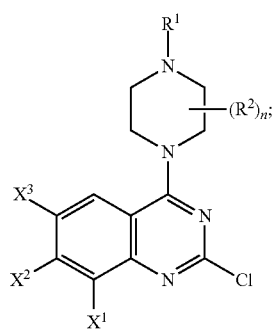

(IIa)

and (f) contacting the compound of formula (IIa) with a moiety comprising $X^0$ for form a compound of formula (II).

Embodiment No 3. The process of embodiment 2 further comprising step:

(a0) contacting a compound of formula (IV)

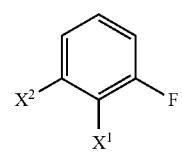

with a base in the presence of $CO_2$ gas and aminating the compound to form the compound of formula (IVa)

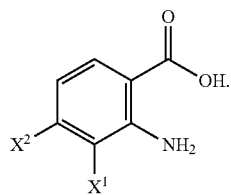

Embodiment No 4. The process of any one of embodiments 1-3, wherein the compound of formula (III) is prepared according to the method:

(a) contacting a compound of formula (VII)

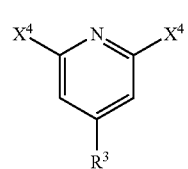

with a compound having formula $NH_2(PG)$ thereby making a compound of formula (VIIa)

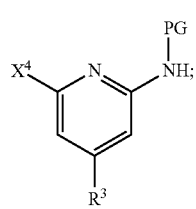

(b) contacting the compound of formula (VIIa) with a compound having formula $X^aPG$, wherein $X^a$ is halogen, to make a compound of formula (VIIb)

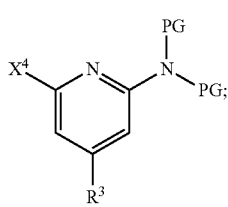

(c) contacting the compound of formula (VIIb) with a halogenating agent having formula

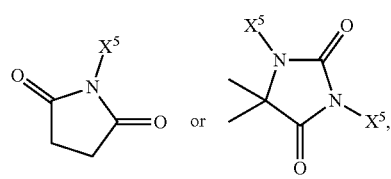

wherein $X^5$ is halogen, to make a compound of formula of formula (VIIc)

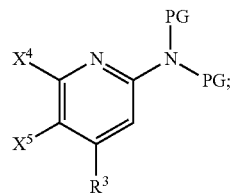

(d) haloalkylating the compound of formula (VIIc) with a haloalkylation agent to make a compound of formula (VIId)

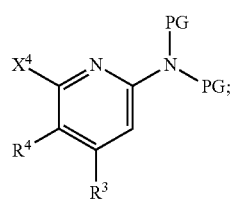

(e) brominating the compound of formula (VIId) to make a compound of formula (VIIe)

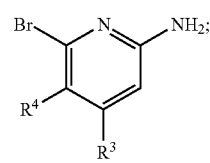

and (f) contacting the compound of formula (VIIe) with $X^aPG$ to make a compound of formula (III).

Embodiment No 5. The process of embodiment 1, wherein the compound of formula (III) is prepared according to the method:

(a) contacting a compound of formula (Viii)

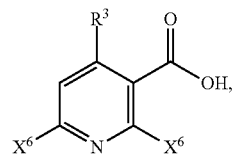

wherein $X^6$ is Cl or I, with a halogenating agent to form a compound of formula (VIIIa)

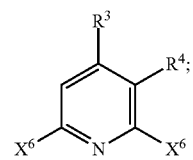

(b) brominating the compound of formula (VIIIa) to form a compound of formula (VIIIb)

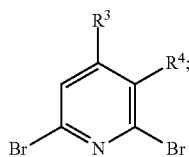

and (c) contacting the compound of formula (VIIIb) with a compound having formula NH(PG)$_2$ thereby making a compound of formula (III).

Embodiment No 6. The process of embodiment 1, wherein the compound of formula (III) is prepared according to the method:

(a) contacting a compound of formula (VIIIc)

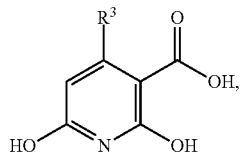

with a brominating agent to form a compound of formula (VIIId)

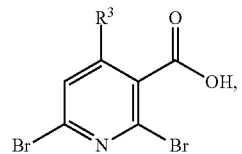

(b) contacting the compound of formula (VIIId) with a halogenating agent to form a compound of formula (VIIIb)

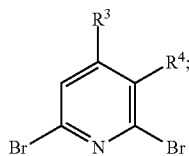

(c) contacting the compound of formula (VIIIb) with a compound having formula NH(PG)$_2$ thereby making a compound of formula (III).

Embodiment No 7. The process of any one of embodiments 1-6, wherein $X^1$ is halogen.

Embodiment No 8. The process of any one of embodiments 1-7, wherein $X^1$ is F or Cl.

Embodiment No 9. The process of any one of embodiments 1-6, wherein $X^1$ is hydrogen or halogen.

Embodiment No 10. The process of any one of embodiments 1-8, wherein $X^3$ is halogen, unsubstituted $C_{1-4}$ alkyl, or unsubstituted $C_{1-3}$ haloalkyl.

Embodiment No 11. The process of any one of embodiments 1-8, wherein $X^3$ is halogen or unsubstituted $C_{1-3}$ haloalkyl.

Embodiment No 12. The process of any one of embodiments 1-8, wherein $X^3$ is unsubstituted $C_{1-3}$ alkoxy, or unsubstituted cyclopropyl.

Embodiment No 13. The process of any one of embodiments 1-8, wherein $X^3$ is halogen.

Embodiment No 14. The process of any one of embodiments 1-8, wherein $X^3$ is Cl or F.

Embodiment No 15. The process of any one of embodiments 1-8, wherein $X^3$ is Cl, F, $CF_3$, $CHF_2$, or $CH_2F$.

Embodiment No 16. The process of any one of embodiments 1-8, wherein $X^3$ is $CF_3$, $CHF_2$, or $CH_2F$.

Embodiment No 17. The process of any one of embodiments 1-16, wherein $R^1$ is $PG^1$.

Embodiment No 18. The process of embodiment 17, wherein $PG^1$ is Ac (acetyl), trifluoroacetyl, Bn (benzyl), Tr (triphenylmethyl or trityl), benzylidenyl, p-toluenesulfonyl, PMB (p-methoxybenzyl), Boc (tert-butyloxycarbonyl), Fmoc (9-fluorenylmethyloxycarbonyl) or Cbz (carbobenzyloxy).

Embodiment No 19. The process of any one of embodiments 1-16, wherein $R^1$ is Boc (tert-butyloxycarbonyl).

Embodiment No 20. The process of any one of embodiments 1-19, wherein $R^2$ is halogen or cyano.

Embodiment No 21. The process of any one of embodiments 1-19, wherein $R^2$ is unsubstituted $C_{1-6}$ alkyl, unsubstituted $C_{1-6}$ cyanoalkyl, or unsubstituted $C_{1-6}$ haloalkyl.

Embodiment No 22. The process of any one of embodiments 1-19, wherein $R^2$ is unsubstituted $C_{1-6}$ alkyl or unsubstituted $C_{1-6}$ cyanoalkyl.

Embodiment No 23. The process of any one of embodiments 1-19, wherein $R^2$ is unsubstituted $C_{1-6}$ alkyl or unsubstituted $C_{1-6}$ haloalkyl.

Embodiment No 24. The process of any one of embodiments 1-19, wherein $R^2$ is methyl or ethyl.

Embodiment No 25. The process of any one of embodiments 1-19, wherein $R^2$ is methyl.

Embodiment No 26. The process of any one of embodiments 1-19, wherein $R^2$ is $CF_3$, $CHF_2$, or $CH_2F$.

Embodiment No 27. The process of any one of embodiments 1-19, wherein $R^2$ is $CH_2CN$.

Embodiment No 28. The process of any one of embodiments 1-27, wherein $R^3$ is hydrogen or $R^{3A}$-substituted or unsubstituted $C_{1-3}$ alkyl.

Embodiment No 29. The process of any one of embodiments 1-27, wherein $R^3$ is $R^{3A}$-substituted or unsubstituted $C_{1-3}$ alkyl, $R^{3A}$-substituted or unsubstituted $C_{1-3}$ haloalkyl, or cyclopropyl.

Embodiment No 30. The process of any one of embodiments 1-27, wherein $R^3$ is $R^{3A}$-substituted or unsubstituted $C_{1-3}$ alkyl or $R^{3A}$-substituted or unsubstituted $C_{1-3}$ haloalkyl.

Embodiment No 31. The process of any one of embodiments 1-27, wherein $R^3$ is $R^{3A}$-substituted or unsubstituted $C_{1-3}$ alkyl.

Embodiment No 32. The process of any one of embodiments 1-27, wherein $R^3$ is methyl.

Embodiment No 33. The process of any one of embodiments 1-32, wherein $R^4$ is $CF_3$, $CHF_2$, or $CH_2F$.

Embodiment No 34. The process of any one of embodiments 1-33, wherein each PG is independently a protecting group selected from the group consisting of Ac (acetyl), trifluoroacetyl, phthalimide, Bn (benzyl), Tr (triphenylmethyl or trityl), benzylidenyl, p-toluenesulfonyl, DMB (dimethoxybenzyl), PMB (p-methoxybenzyl), Boc (tert-butyloxycarbonyl), Fmoc (9-fluorenylmethyloxycarbonyl) or Cbz (carbobenzyloxy).

Embodiment No 35. The process of any one of embodiments 1-34, wherein each PG is p-methoxybenzyl.

Embodiment No 36. The process of any one of embodiments 1-34, wherein two PG together form a moiety having the structure:

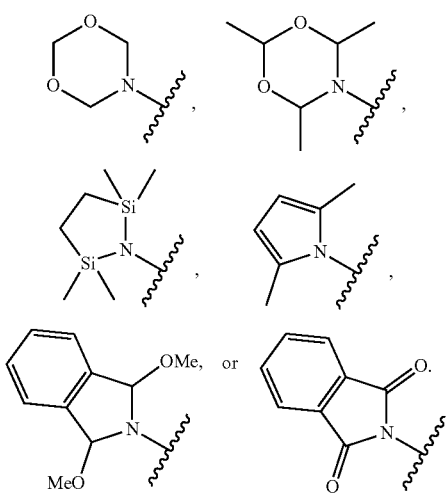

Embodiment No 37. The process of any one of embodiments 1-36, wherein $X^2$ is Br.

Embodiment No 38. The process of any one of embodiments 1-37, wherein the organomagnesium compound is selected from the group consisting of isopropylmagnesium chloride, isopropylmagnesium bromide, isopropylmagnesium iodide, isopropylmagnesium chloride lithium chloride complex, sec-butylmagnesium chloride, lithium tri-n-butylmagnesiate, lithium triisopropylmagnesiate, and lithium (isopropyl)(di-n-butyl)magnesiate).

Embodiment No 39. The process of any one of embodiments 1-38, wherein the zinc complex is selected from the group consisting of $ZnCl_2$, $ZnBr_2$, $ZnI_2$, $Zn(OAc)_2$, and $Zn(OPiv)_2$.

Embodiment No 40. The process of any one of embodiments 1-39, wherein the transition metal catalyst precursor is a Pd or Ni catalyst precursor selected from the group consisting of $Pd(OAc)_2$, $PdCl_2$, $PdCl_2(MeCN)_2$, $Pd(benzonitrile)_2Cl_2$, $Pd(dba)_2$, $Pd_2(dba)_3$, $Pd(PPh_3)_4$, $Pd(PCy_3)_2$, $Pd(PtBu_3)_2$, $Pd(TFA)_2$, $[Pd(allyl)Cl]_2$, $[Pd(cinammyl)Cl]_2$, $[PdCl(crotyl)]_2$, $PdCl(\eta5\text{-cyclopentadienyl})$, $[(\eta3\text{-allyl})(\eta5\text{-cyclopentadienyl})palladium(II)]$, $[Ni(\eta5\text{-cyclopentadienyl})(allyl)]$, $[bis(1,5\text{-cyclooctadiene})nickel(0)]$, $NiCl_2$, $NiBr_2$, $Ni(OAc)_2$, and Nickel(II) acetylacetonate.

Embodiment No 41. The process of any one of embodiments 1-40, wherein the chiral ligand is

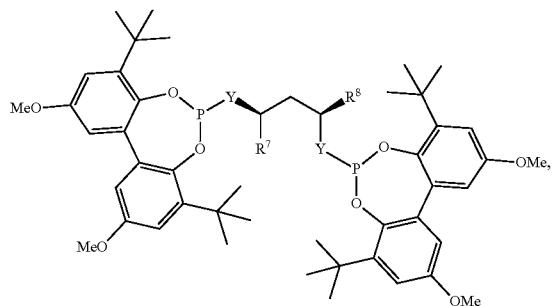

(L1)

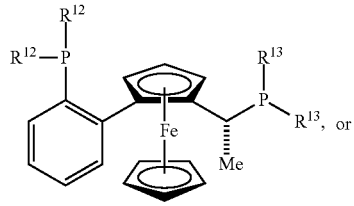

(L2)

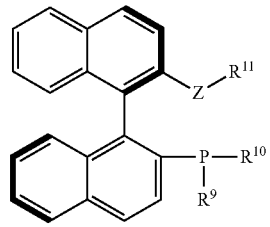

(L3)

wherein

Y is O or $NR^7$;

Z is O or N;

$R^7$ and $R^8$ are independently unsubstituted $C_{1-6}$ alkyl;

$R^9$ and $R^{10}$ are independently $R^{11}$-substituted or unsubstituted $C_{5-6}$ cycloalkyl or $R^{11}$-substituted or unsubstituted phenyl;

each $R^{11}$ is independently hydrogen, $C_{1-6}$ unsubstituted alkyl, or $C_{1-6}$ unsubstituted haloalkyl;

$R^{12}$ and $R^{13}$ are each independently $R^{14}$-substituted or unsubstituted $C_{1-6}$ alky, $R^{14}$-substituted or unsubstituted $C_{3-7}$ cycloalkyl, $R^{14}$-substituted or unsubstituted aryl, or $R^{14}$-substituted or unsubstituted $C_{5-7}$ heteroaryl;

each $R^{14}$ is independently unsubstituted $C_{1-4}$ alkyl.

Embodiment No 42. The process of embodiment 41, wherein $R^7$ and $R^8$ are the same.

Embodiment No 43. The process of embodiment 42, wherein $R^7$ and $R^8$ are each methyl, ethyl, or phenyl.

Embodiment No 44. The process of embodiment 2, wherein the base is LDA or LiTMP.

Embodiment No 45. The process of embodiment 2, wherein the halogenating agent is NCS or 1,3-dichloro-5,5-dimethylhydantoin.

Embodiment No 46. The process of embodiment 2, wherein the chlorinating agent is $POCl_3$, $PCl_3$, $PCl_5$, or $SOCl_2$.

Embodiment No 47. The process of embodiment 4, wherein the halogenating agent is NIS or 1,3-diiodomo-5,5-dimethylhydantoin.

Embodiment No 48. The process of embodiment 4, wherein the haloalkylation agent is a fluoroalkylation agent.

Embodiment No 49. The process of embodiment 4, wherein the haloalkylation agent is methyl 2,2-difluoro-2-(fluorosulfonyl)acetate.

Embodiment No 50. The process of embodiment 5 or 6, wherein the halogenating agent is $SF_4$ in HF.

Embodiment No 51. The process of embodiment 1, wherein the compound of formula (II) has the formula:

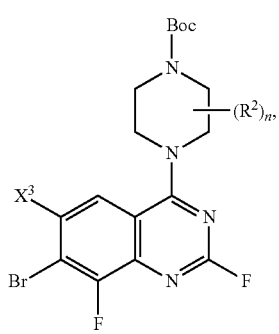

(IIe)

wherein X³ is halogen.

Embodiment No 52. The process of embodiment 1, wherein the compound of formula (II) has the formula:

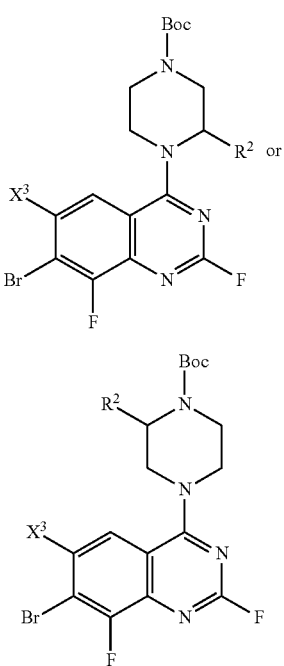

(IIe1)

(IIe2)

wherein X³ is halogen.

Embodiment No 53. The process of embodiment 1, wherein the compound of formula (II) has the formula:

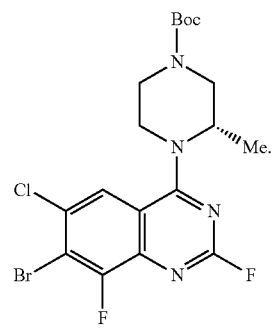

(2)

Embodiment No 54. The process of embodiment 1, wherein the compound of formula (III) has the formula:

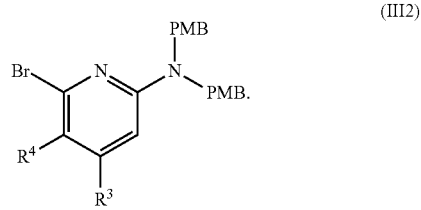

(III2)

Embodiment No 55. The process of embodiment 54, wherein $R^3$ is unsubstituted $C_{1-3}$ alkyl.

Embodiment No 56. The process of embodiment 54 or 55, wherein $R^4$ is unsubstituted $C_{1-3}$ haloalkyl.

Embodiment No 57. The process of embodiment 1, wherein the compound of formula (III) has the formula:

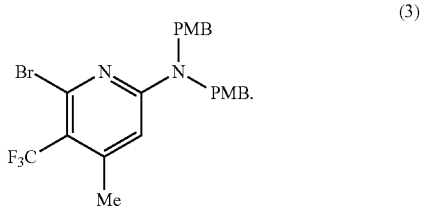

(3)

Embodiment No 58. The process of embodiment 1, wherein the compound of formula (I) has the formula:

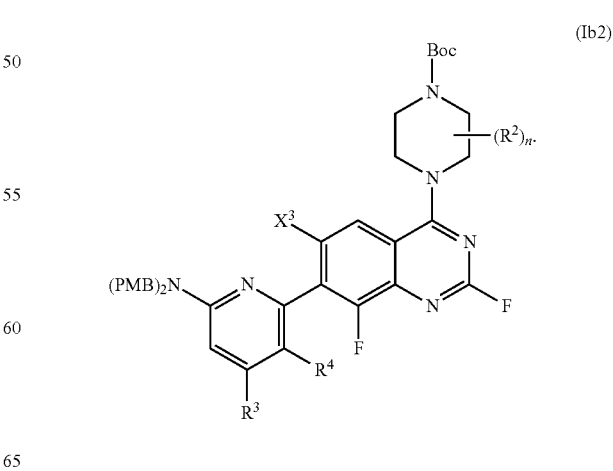

(Ib2)

Embodiment No 59. The process of embodiment 1, wherein the compound of formula (I) has the formula:

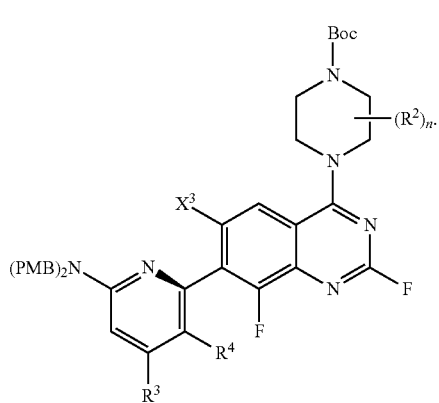

(Ib3)

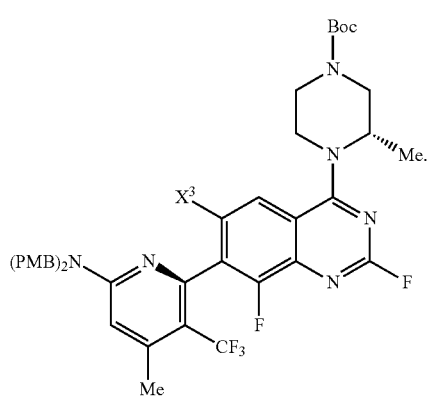

(Id)

Embodiment No 60. The process of embodiment 58 or 59, wherein $R^3$ is unsubstituted $C_{1-3}$ alkyl.

Embodiment No 61. The process of any one of embodiments 58-60, wherein $R^4$ is unsubstituted $C_{1-3}$ haloalkyl.

Embodiment No 62. The process of embodiment 1, wherein the compound of formula (I) has the formula:

wherein $X^3$ is halogen.

Embodiment No 67. The process of embodiment 1, wherein the compound of formula (I) has the formula:

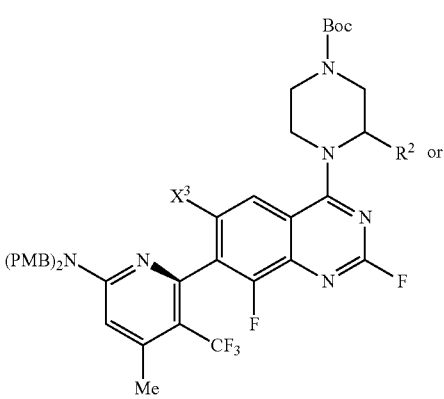

(Ic1)

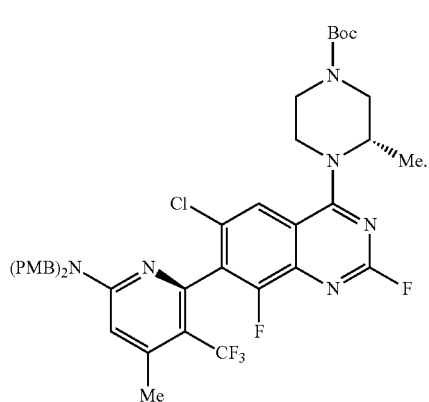

(I)

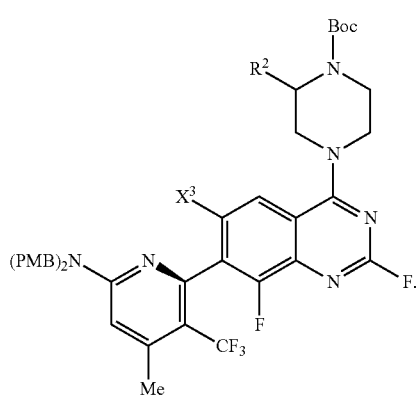

(Ic2)

Embodiment No 63. The process of any one of embodiments 58-62, wherein $R^2$ is unsubstituted $C_{1-6}$ alkyl, unsubstituted $C_{1-6}$ cyanoalkyl, or unsubstituted $C_{1-6}$ haloalkyl.

Embodiment No 64. The process of embodiment 63, wherein $R^2$ is methyl, ethyl, CN, $CH_2CN$, $CF_3$, $CHF_2$, or $CH_2F$.

Embodiment No 65. The process of embodiment 63, wherein $R^2$ is methyl, ethyl, CN, or $CH_2CN$.

Embodiment No 66. The process of embodiment 1, wherein the compound of formula (I) has the formula:

Embodiment No 68. The process of embodiment 1, wherein $X^0$ is hydrogen, halogen, $CF_3$, $CHF_2$, $CH_2F$, or a moiety having structure:

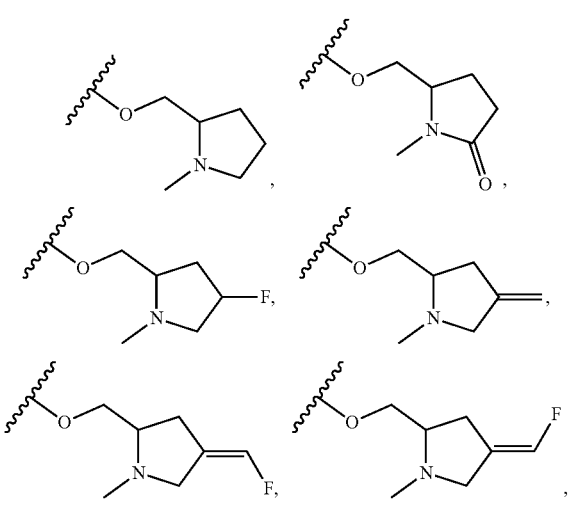

151
-continued
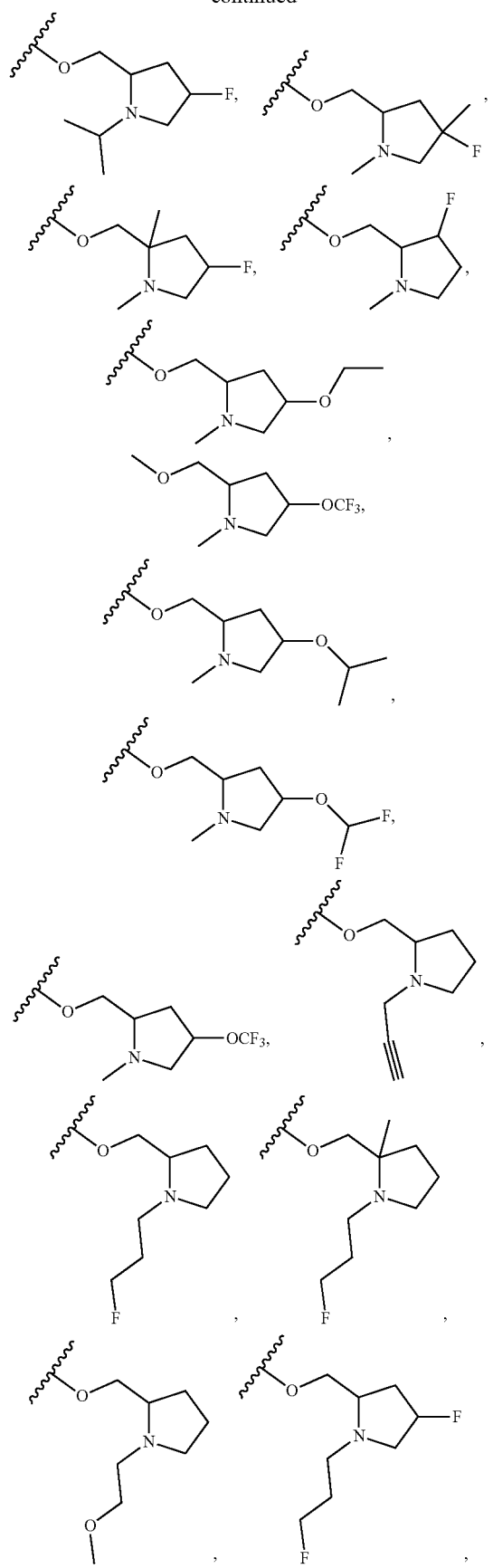
152
-continued
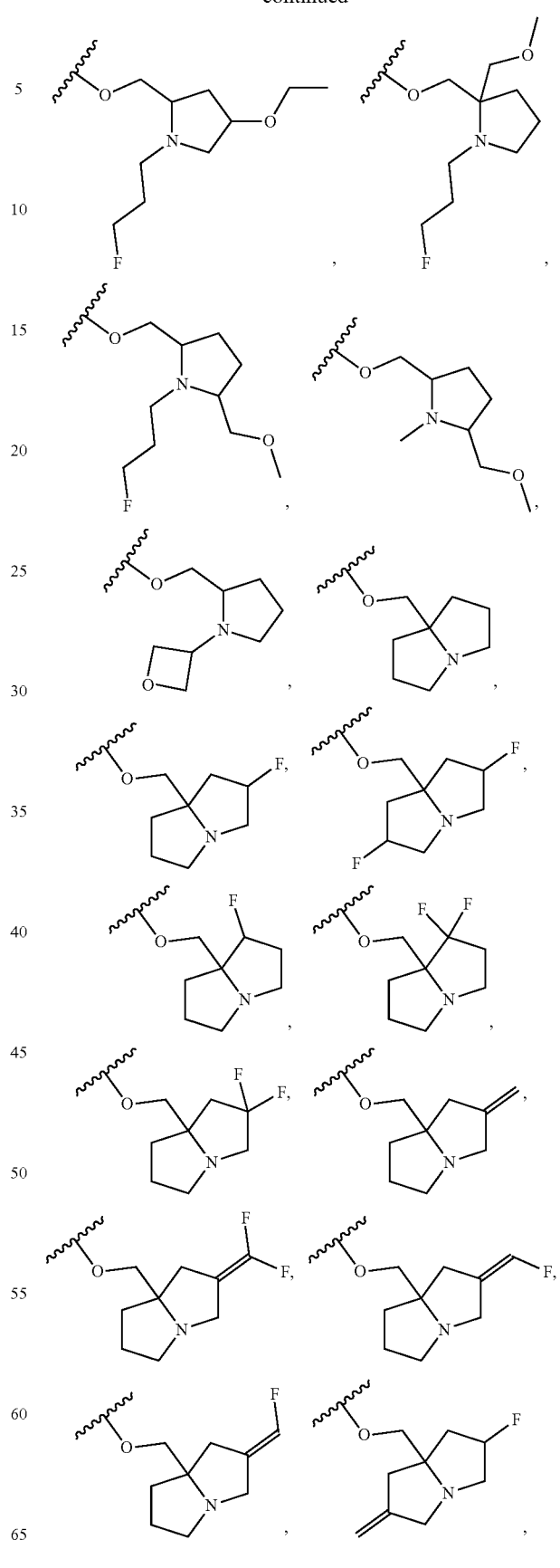

-continued

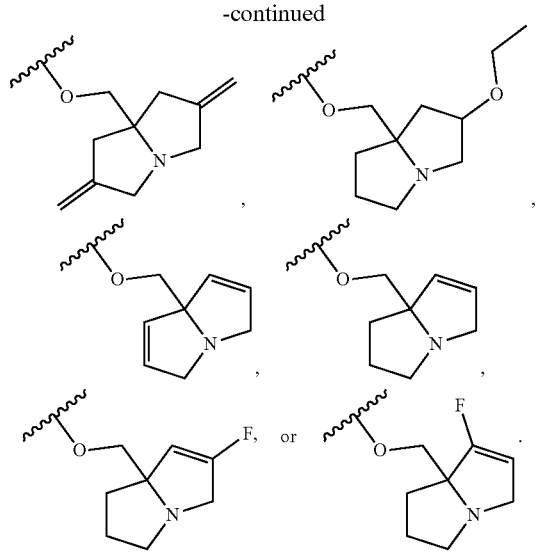

Embodiment No 69. A compound having formula (Pd);

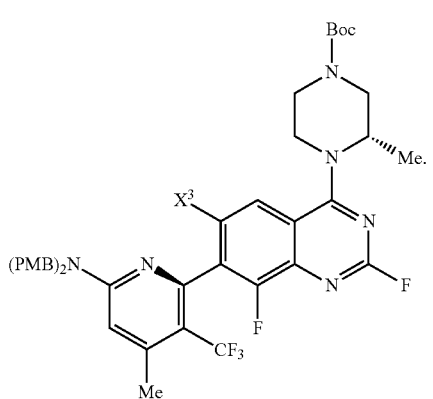
(Id)

wherein $X^3$ is halogen.

Embodiment No 70. A compound having formula (1):

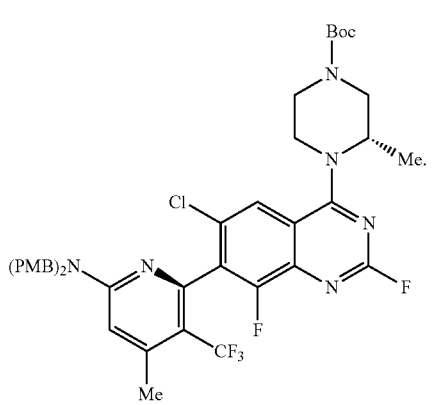
(1)

Embodiment No 71. The process of embodiment 2, wherein step (f) further comprises:

step (g) fluorinating the compound of formula (IIa) to a compound of formula (IIa1)

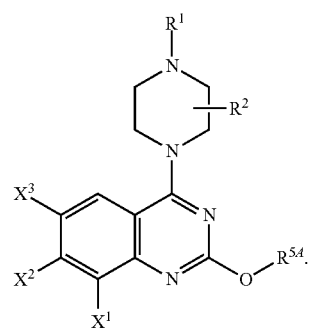
(IIa1)

Embodiment No 72. The process of embodiment 2, wherein step (f) further comprises:

step (h) alkoxylating the compound of formula (IIa) to a compound of formula (IIa2)

(IIa2)

Embodiment No 73. The process of embodiment 2, wherein step (f) further comprises:

step (j) thiolating the compound of formula (IIa) to a compound of formula (IIe):

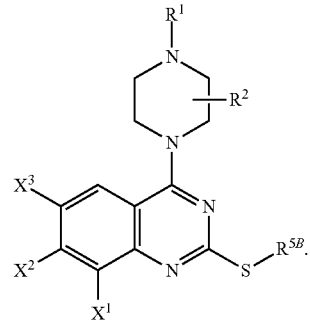
(IIa3)

Embodiment No 74. The process of any one of embodiments 1-6, wherein the compound of formula (I) is a compound of Table 1.

Embodiment No 75. A process for the synthesis of a compound having formula

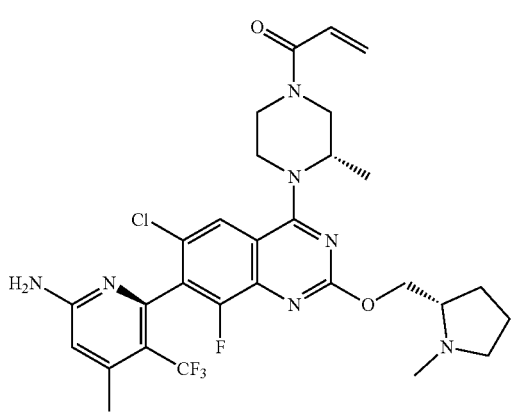
(A)

or a pharmaceutically acceptable salt thereof, the process comprising (a) contacting a compound of formula (2)

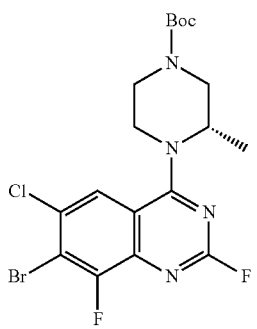

or a salt thereof with of ZnCl$_2$ and i-PrMgCl·LiCl, with a compound of formula (3)

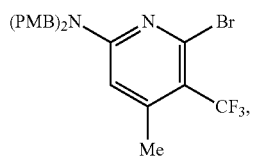

(b) contacting the mixture of step (a) or a salt thereof with a transition metal (e.g. Pd or Ni) catalyst precursor and a chiral ligand thereby synthesizing a compound of formula (1)

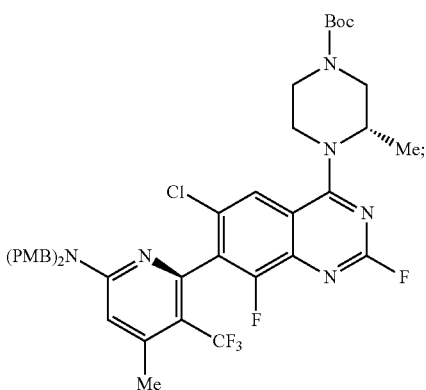
(1)

or a solvate or salt thereof, (c) contacting the compound of formula (1) or a solvate or salt thereof, with a compound of formula HO—X$^A$, wherein X$^A$ has formula

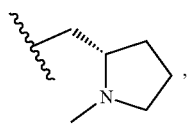

and a base thereby synthesizing a compound of formula (1d);

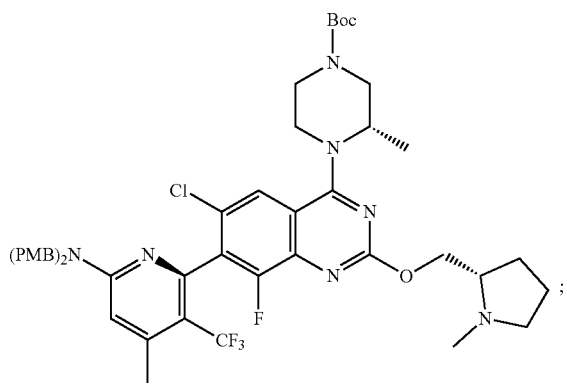
(1d)

or a solvate or pharmaceutically acceptable salt thereof;

(d) contacting the compound of formula (1d) with MsOH in an acid thereby synthesizing a compound of formula (1e);

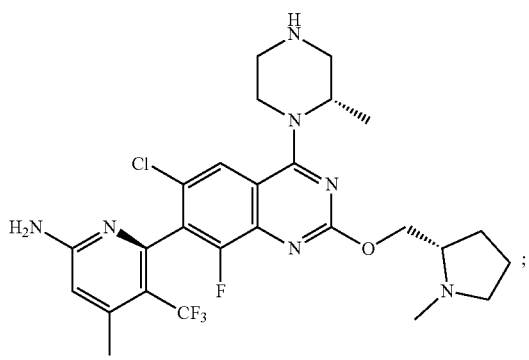

(1e)

or a solvate or pharmaceutically acceptable salt thereof; and (e) contacting the compound of formula (1e) or a solvate or pharmaceutically acceptable salt thereof with

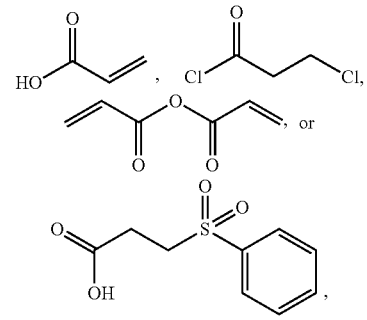

in the presence of a base and optionally an activating agent described herein, thereby making a compound of formula (A) or a pharmaceutically acceptable salt thereof.

Embodiment No 76. The process of embodiment 75, wherein the acid of step (d) is AcOH, trifluoroacetic acid, chlorosulfonic acid, sulfuric acid, HCl, HBr, p-toluenesulfonic acid, or trifluoromethanesulfonic acid.

Embodiment No 77. The process of embodiment 75, wherein step (e) comprises contacting the compound of formula (1e) or a solvate or pharmaceutically acceptable salt thereof with

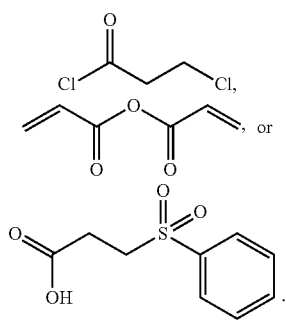

Embodiment No 78. In one embodiment of the process (P9) described herein, step (e) comprises contacting the compound of formula (1e) or a solvate or pharmaceutically acceptable salt thereof with

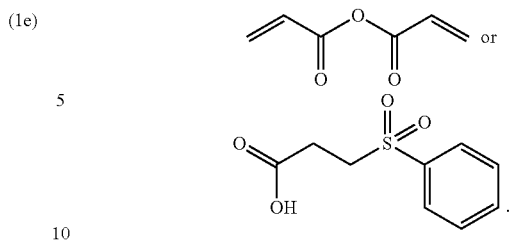

The following Examples are presented by way of illustration, not limitation.

EXAMPLES

Example 1

Synthesis of 2-amino-4-bromo-3-fluorobenzoic Acid. Compound 4a

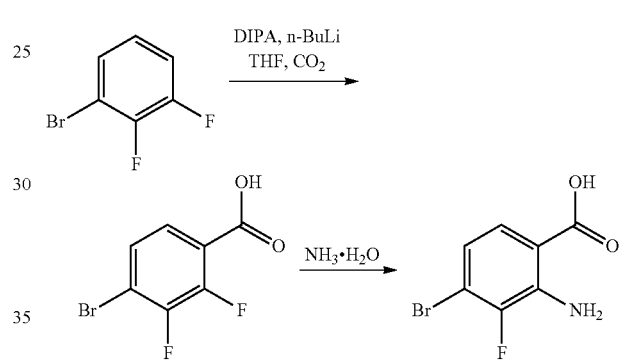

Step 1, Route 1: 4-bromo-2,3-difluorobenzoic Acid

To a solution of dry diisopropylamine (440 g, 4.352 mol) in dry THF (4 L) was added n-BuLi (1.6 L, 3.990 mol, 2.5 M in hexane) dropwise between −65° C. to −50° C. over 1 hour under $N_2$. The mixture was stirred for 1 h at −65° C. A solution of 1-bromo-2,3-difluorobenzene (700 g, 3.627 mol) in dry THF (1.2 L) was added dropwise over 1 hour while maintaining the internal temperature between −65° C. and −50° C. The mixture was stirred for 1.5 h at −65° C. Solid dry ice (2.8 kg) was added into a dry basin and the above reaction mixture was poured into the basin slowly over 10 min with stirring. After that the resulting mixture was stirred for 30 min, quenched with $H_2O$ (2 L) slowly, then acidified with aq. HCl (6 M, 1.6 L) to pH=3 and extracted with EA (3.5 L×2). Combined organic layers were washed with brine (4 L), dried over $Na_2SO_4$ (500 g), filtered and concentrated in vacuum to give 4-bromo-2,3-difluorobenzoic acid (790 g, 92%) as an off-white solid. HPLC: 90%, RT=4.507 min.

Step 2: 2-amino-4-bromo-3-fluorobenzoic Acid

A mixture of 4-bromo-2,3-difluorobenzoic acid (500 g, 2.11 mol) in $NH_3 \cdot H_2O$ (1500 mL, 25% w/w) was heated to 150° C. in a 5 L autoclave and stirred for 35 hours. The reaction mixture was cooled to 0° C. and acidified with conc. HCl to pH=3 in an ice bath. The solids were collected by filtration, washed with water and dried at 50° C. in air to give crude product. The crude solid was dissolved in EtOH (5 volumes) at 75° C. and then water (5 volumes) was added dropwise. The mixture was cooled to room temperature and the precipitates were filtered and dried at 50° C. in air overnight. The resulting solids were triturated with DCM (5 volumes) overnight at room temperature, filtered and dried at 50° C. in air overnight to give 2-amino-4-bromo-3-fluorobenzoic acid (307 g, 61%) as an off-white solid. HPLC: 99%, RT=4.502 min; $^1$H NMR (400 MHz, DMSO-$d_6$) δ 13.09 (brs, 1H), 7.50 (dd, J=8.8 Hz, 1.6 Hz, 1H), 6.80 (brs, 1H), 6.78 (dd, J=8.8 Hz, 6.4 Hz, 1H).

Example 2 tert-butyl (S)-4-(7-bromo-6-chloro-2,8-difluoroquinazolin-4-yl)-3-methylpiperazine-1-carboxylate
Compound 2

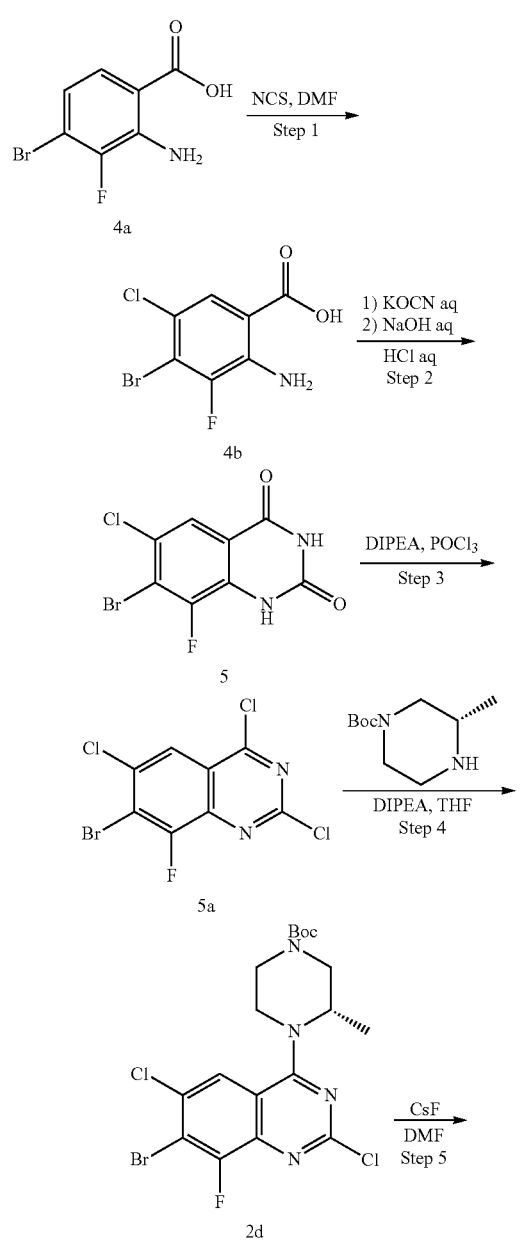

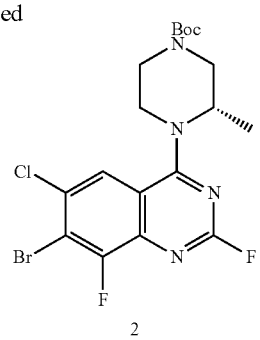

Step 1

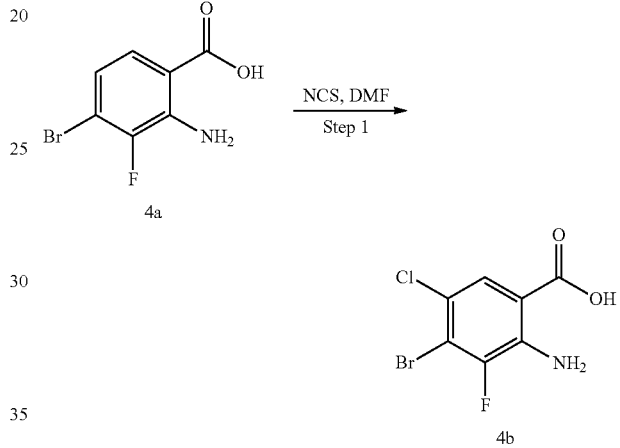

To a 500 L reactor was charged Compound 4a (128.2 mol) under and N$_2$ atmosphere. EtOH was charged to the 500 L reactor under N$_2$ atmosphere and the mixture was heated to 55~60° C. NCS (154.3 mol) was charged to a 500 L reactor in five portions at 55-60° C. over 3 h under N$_2$ atmosphere and the mixture was stirred at 50-55° C. for 0.5 h.

To a separate 1500 L reactor was charged 900 kg water and the water heated to 45~50° C. The reaction mixture was added to the hot water and slurried at 55~60° C. for 1-2 h. The reaction was filtered and about 50 kg of wet 4b was obtained. The wet cake was slurried with hot water at 45-50° C. for 0.5-1.0 h and filtered and washed with hot water. The cake was slurried with DCM at 15-30° C. for 1-2 h filtered and washed with DCM. The cake was dried under high vacuum at 30-40° C. for 16 h. 25.8 kg of Compound 4b (97.5 A %) was isolated as a light brown solid in 80-81% yield.

Step 2

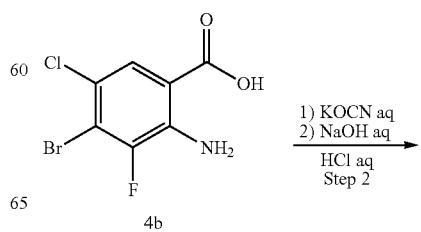

161

-continued

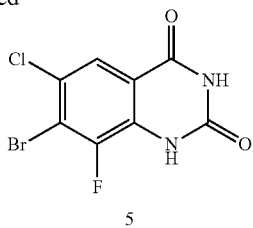

5

To a 3000 L reactor was charged 164 kg water, 28.6 kg Compound 4b (106.5 mol) and 4.85 kg NaOH (dissolved in 32.5 kg water). The reaction was stirred at RT for 5 min. KOCN (188.9 mol) was dissolved in 392 kg water and charged to the 3000 L reactor before stirring at RT for 5 min. The mixture was heated to 39~42° C. and the pH adjusted to 6.3-6.7 with concentrated hydrochloric acid. The mixture was stirred at 39~42° C. for 3 h. KOCN (94.4 mol) was dissolved in 398 kg water and charged to the 3000 L reactor and stirred at RT for 5 min. The mixture was heated to 39~42° C. for 3 h and the pH adjusted to 6.3-6.7 with concentrated hydrochloric acid. KOCN (94.4 mol) was dissolved in 398 kg water and charged to a 3000 L reactor and stirred at RT for 5 min before heating to 39~42° C. for 2.5 h and the pH adjusted to 6.3-6.7 with concentrated hydrochloric acid. The mixture was then stirred at 39~42° C. for 1.0 h and the pH adjusted to 5.3-5.7 with concentrated hydrochloric acid. NaOH (442 mol) dissolved in 35.4 kg water and charged to the 3000 L reactor and stirred at 45-50° C. for 1 h.

The mixture was cooled to 10-15° C. and stirred at 10-15° C. for 0.5 h. The cake was filtered and washed with water (5 vol.) before centrifuging. Acetone and water were charged to a 2000 L reactor and heated to 25-30° C. and the wet cake added and stirred at 25-30° C. for 1.5 h. The pH was adjusted to 1.0 with concentrated hydrochloric acid and the mixture cooled to 5-10° C. The mixture was stirred at 5-10° C. for 0.5 h. The cake was filtered and washed with water (5 vol.×2), centrifuged, and dried at 55-60° C. in vacuum dryer for 48 h. 24 kg of compound 5 (98.4 A %) isolated as an off-white solid in a 72% yield (corrected).

Step 3

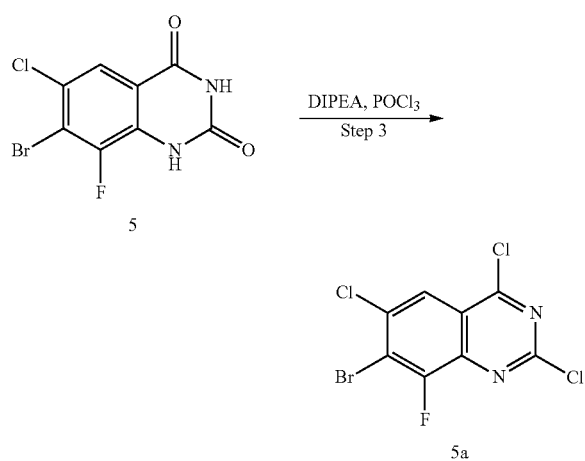

162

POCl₃ (264.8 mol) was charged to a 100 L reactor under N₂ atmosphere and compound 5 (27.3 mol) was added and stirred at RT for 5 min. DIPEA (54.2 mol) was added dropwise over 5-10 min by an elevated tank and the mixture was heated to 80~105° C. and the mixture stirred for 40 min.

The mixture was cooled to 40-50° C. and concentrated to about 10-15 L under vacuum. The mixture was diluted with ACN (14 kg) and the diluted portion added to 105 kg water at 15-30° C. over 1-2 h. The mixture was stirred at 25-30° C. for 0.5 h, filtered and the cake was washed with water (2.5 vol.×3). The wet cake was dried at 45-50° C. in vacuum dryer for 12 h. 8.5 kg of Compound 5a (98.1 A %) was isolated as a yellow solid in 100% yield (corrected).

Step 4

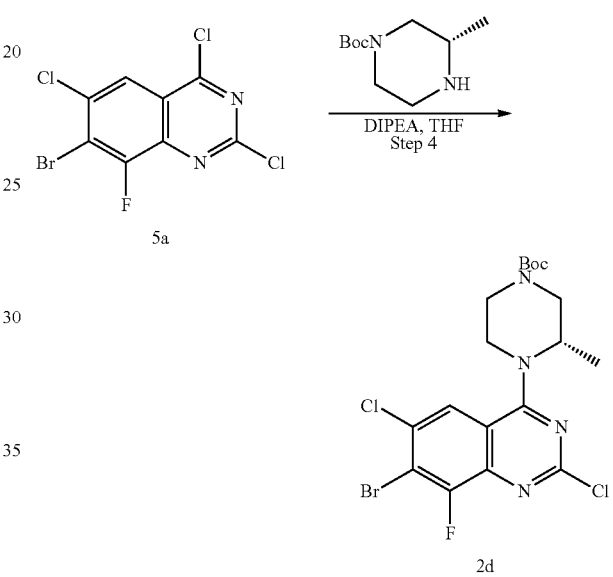

THF was charged to a 500 L reactor under N₂ atmosphere. DIPEA (141.6 mol) was added followed by Compound 5a (5.7 mol) and the mixture stirred at RT for 5 min. The mixture was cooled to 5-10° C.

THF was charged to a 100 L reactor under N₂ atmosphere. tert-Butyl (S)-3-methyl-1-piperazinecarboxylate (83.4 mol) was added to the reactor and stirred at RT for 5 min before transferring the THF solution in 100 L reactor to an elevated tank of 100 L reactor. The THF solution of compound 5a was added dropwise into a 500 L reactor over 60 min by an elevated tank. The mixture was then stirred at 5~10° C. for 30 min.

About 500 kg water was charged to a 1000 L reactor and cooled to 0-10° C. The reaction containing 5a was added to the water and stirred at 0-10° C. for 1 h. The cake was filtered and washed with water (4 vol.×2) then dissolved in DCM (10 vol.) and the phases separated. The organic phase was washed with water (5 vol.) and the aqueous extracted with DCM. The combined organic phase was added to a 500 L reactor and concentrated to about 20-25 L at 45-50° C. under vacuum. About 53 kg of N-heptane was charged to the reactor the contents concentrated to about 50-60 L at 45-50° C. under vacuum and repeated. Another 53 kg of N-heptane was added dropwise to the 500 L reactor at 20-30° C. slowly over 10 min. The mixture was stirred at 20-30° C. for 0.5 h. The mixture was cooled to 5-10° C. and stirred at 5-10° C.

for 0.5 h. The cake was filtered and washed with n-heptane (5 vol.) before drying at 45-50° C. in vacuum dryer for 10 h. 35.8 kg of compound 2d (98.0 A %) was isolated as an off-white solid in a 94% yield (corrected).

Step 5

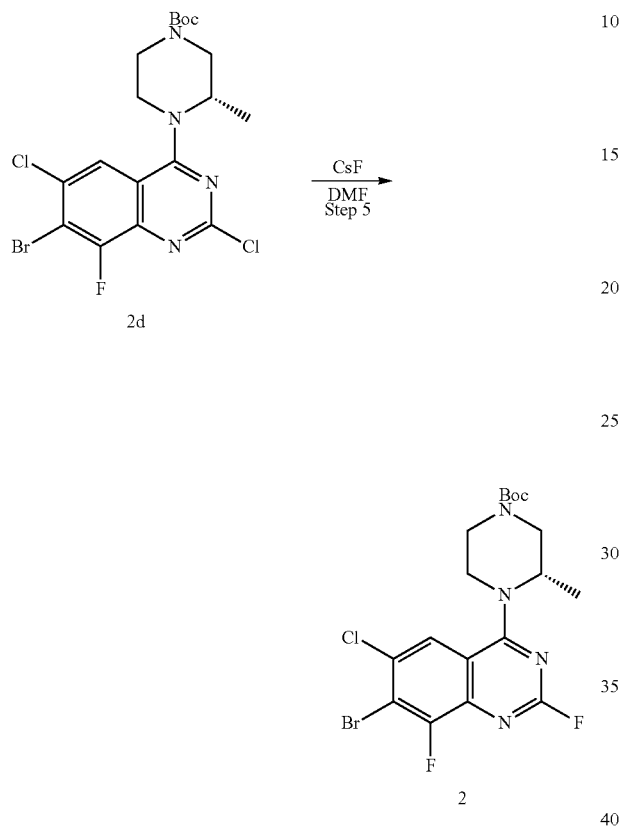

To a 500 L reactor was added 274 kg of DMF under N₂ atmosphere and purged with N₂ twice. Compound 2d (70.8 mol) was added followed by CsF (184.3 mol) and the reactor purged with N₂ three more times before stirred at RT for 5 min. The mixture was heated to 51.5-52.5° C. and stirred for 10 h. Additional CsF (23.7 mol) was added and the mixture stirred at 51.5-52.5° C. under N₂ atmosphere for 16 h.

About 870 kg of water was charged to a 1500 L reactor and cooled to 5-10° C. The reaction mixture was added to the reactor below 15° C. and stirred at 5-10° C. for 0.5 h. The product was filtered before adding a 1000 L reactor containing 320 L each of MeCN and water. The mixture was stirred at 20-25° C. for 5 h. The we cake was dissolved in DCM and the phases separated. The aqueous layer was extracted with DCM (100 L, 3 vol.) and the organic layers were combined and concentrated to about 80 L at 45-50° C. under vacuum. About 59 kg of n-heptane was charged to a 500 L reactor the combined, concentrated organic phase added. The mixture was concentrated to about 80 L at 45-50° C. under vacuum and stirred at 20-30° C. for 0.5 h. The mixture was then cooled to 10-15° C. and stirred for 0.5 h. The cake was filtered and washed with n-heptane (5 vol.) before drying at 45-50° C. in vacuum dryer for 10 h. 28.2 kg of compound 2 (97.2 A %) was isolated as an off-white solid in 82% yield (corrected).

Example 3

Compound 3 (6-bromo-N,N-bis(4-methoxybenzyl)-4-methyl-5-(trifluoromethyl) pyridin-2-amine)

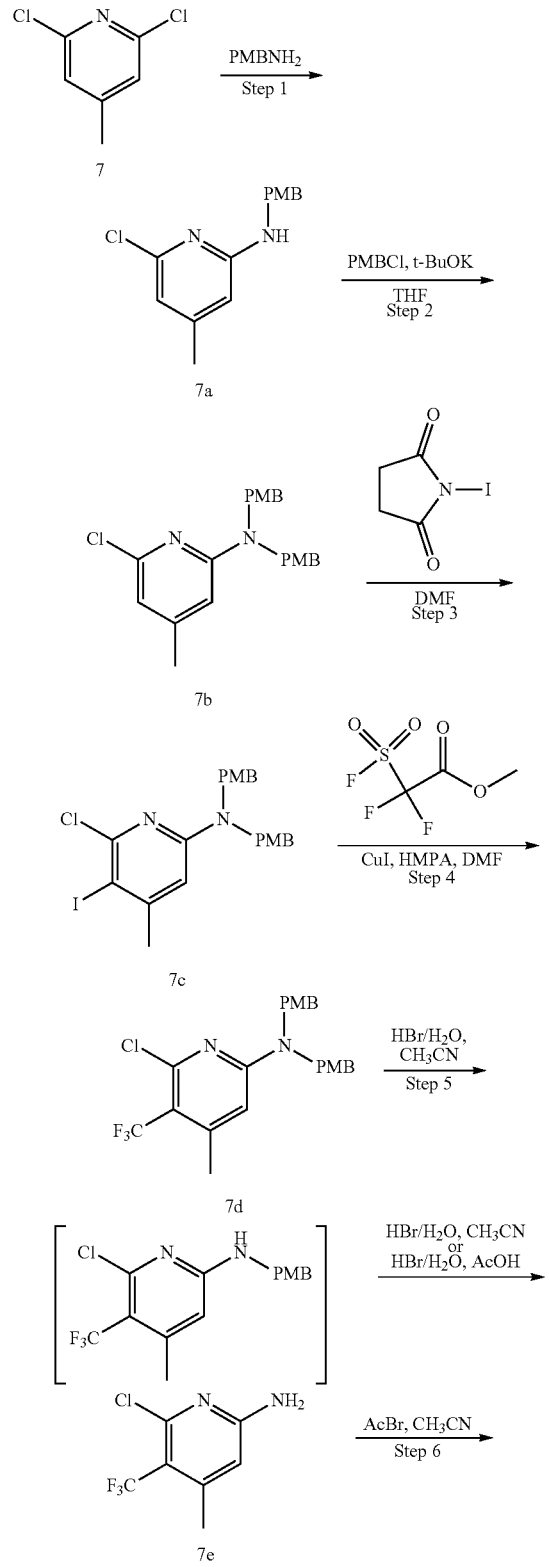

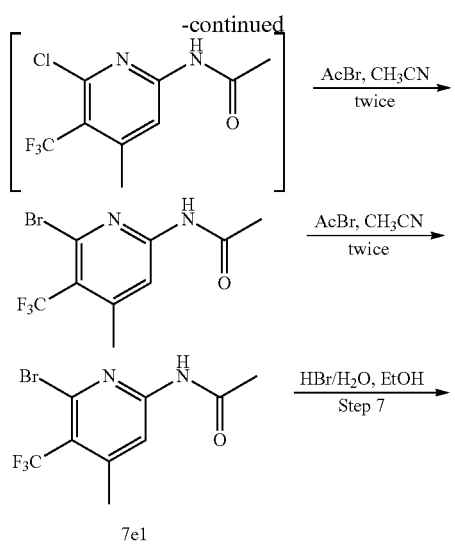

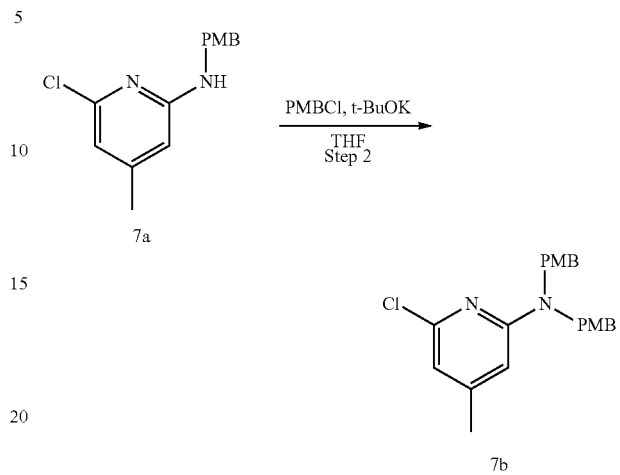

Step 1: 6-chloro-N-(4-methoxybenzyl)-4-methylpyridin-2-amine (Compound 7a)

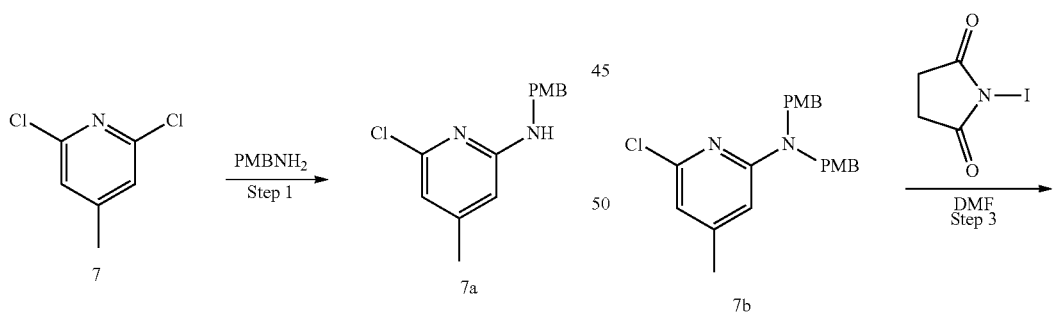

Charged PMBNH₂ (175.0 L, 183.75 kg, 5 V) to the reactor. Charged 2,6-dichloro-4-methylpyridine (Compound 7, 35.0 kg, 1.0 eq.) to the reactor and stirred below 30° C. Heated to 120±10° C. and stirred for 32 hours at 120±10° C. Cooled the reaction to sample for LCMS before adding dropwise soften water/isopropanol=2/1 (350.0 L, 10 V) at 85~130° C. Cooled the reaction to 85~95° C. and stirred for 30~60 min. Cooled to 5±5° C. (Cool down 10±5° C. every hour) and stirred for at least 1 hour at 5±5° C. Centrifuged and washed cake with water/isopropanol=2/1 (3V) for two times. The cake was collected and dried for at least 16 hours at 45±5° C. Yield: 52.0 kg, 91.6%

Step 2: 6-chloro-N,N-bis(4-methoxybenzyl)-4-methylpyridin-2-amine (Compound 7b)

Charged THF (208.0 L, 4.0 V) to the reactor in N₂. Charged Compound 7a (52.0 kg, 1.0 eq.), PMBCl (37.4 kg, 1.2 eq.) to the reactor in N₂ and stirred to suspension at 0±5° C. Added dropwise a solution of t-BuOK in THF (166.4 kg, 1.5 eq, 20 wt % in THF) at 0±5° C. and stirred for at least 6.0 hours at 0±5° C. Added dropwise water (780.0 L, 15.0 V) below 10° C. and stirred for at least 2 hours at 5±5° C. Centrifuged and washed the cake with water. The cake was collected and slurried with water/isopropanol=2/1 (208.0 L, 5.0 V) for at least 6 hours at 25±5° C. Centrifuged again and washed cake with water/isopropanol=2/1 (2V) for two times. The cake was collected and the solids dried at least 16 hours at 45±5° C. Yield: 70.74 kg, 93.4%.

Step 3: 6-chloro-5-iodo-N,N-bis(4-methoxybenzyl)-4-methylpyridin-2-amine

Charged DMF (353.5 L, 5.0 V), Compound 7b (70.70 kg, 1.0 eq.) to the reactor and stirred to clarification at 25±5° C. Charged the solid of NIS (49.9 kg, 1.2 eq.) to the reactor in 10 batches, charging one batch at least every three hours. Stirred for at least 8 hours at 25±5° C. Cooled to 0±5° C. before adding dropwise 5 wt % aq. Na$_2$SO$_3$ (353.5 L, 5.0 V) at −5~25° C. Stirred for at least 30 min at 5±5° C. Centrifuged and washed the cake with soften water for two times, the volume of elution is 2 V every time. Collected the figure cake and slurried with soften water/isopropanol=2/1 (373.5 L, 5.0 V) for at least 30 min at 70±5° C. Cooled to 20±5° C., stir for at least 1 hour at 20±5° C. Centrifuged again and washed the cake with water/isopropanol=2/1 for two times, the volume of elution is 3 V every time. Collected the solids and dried at least 16 hours at 45±5° C. Yield: 86.56 kg, 92.1%.

Step 4: 6-(1,3-bis(4-methoxyphenyl)propan-2-yl)-2-chloro-4-methyl-3-(trifluoromethyl)pyridine (Compound 7d)

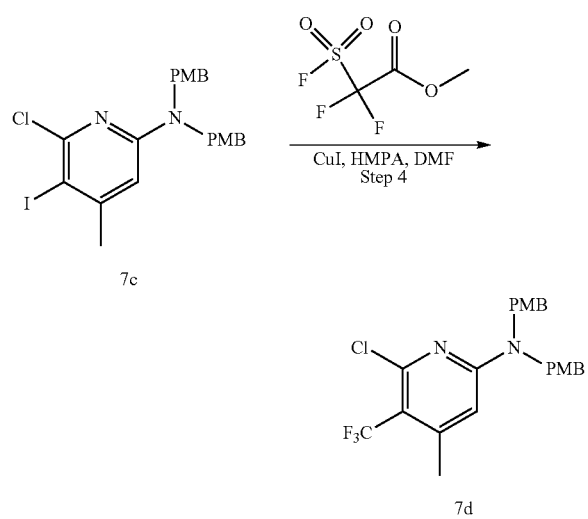

Charged DMF (432.5 L, 5.0 V) and HMPA (152.3 kg, 5.0 eq.) to the reactor. Under nitrogen atmosphere, charged Compound 7c (86.5 kg, 1.0 eq.) to reactor. Charged CuI (80.9 kg, 2.5 eq.) to reactor. Bubbled N$_2$ for at least 40 min at 25±5° C. Heated to 90±5° and charged dropwise methyl 2,2-difluoro-2-(fluorosulfonyl)acetate (98.0 kg, 3.0 eq.) to the reactor. Stirred for at least 2 hours at 90±5° C. Cooled down and filtered through diatomite. Washed with EtOAc (865.0 L, 10.0 V). Evaporated to 4~8 V in vacuum. Cooled to 5±5° C. before adding dropwise soften water (865.0 L, 10.0 V) to reactor at 0~25° C. Stirred for at least 30 min at 20±5° C. Centrifuged and washed cake with water for two times, the volume of elution is 4 V every time. The cake was collected and EtOAc (865.0 L, 10.0 V) added. Stirred for at least 30 min at 25±5° C. and filtered through diatomite before washing with EtOAc (865.0 L, 10.0 V). Held, separated, collected the organic phases and concentrated to 2~4 V. Charged isopropanol (432.5 L, 5.0 V) to reactor and concentrated to 2~4 V. Repeated charging isopropanol (432.5 L, 5.0 V), and concentrating to 2~4 V until the area % of EtOAc ≤ 5.0% was determined by GC. Heated to 60±5° C. and added dropwise water (4~6 V) to the vessel and stirred for at least 0.5 hour at 60±5° C. Cooled to 20±5° C. and stirred for at least 1 hour at 25±5° C. Centrifuged and washed cake with water/isopropanol=2/1 (3V) for two times. Collected and dried the solid at least 16 hours at 50±5° C. Yield: 70.45 kg, 91.9%.

Step 5: 6-bromo-4-methyl-5-(trifluoromethyl)pyridin-2-amine

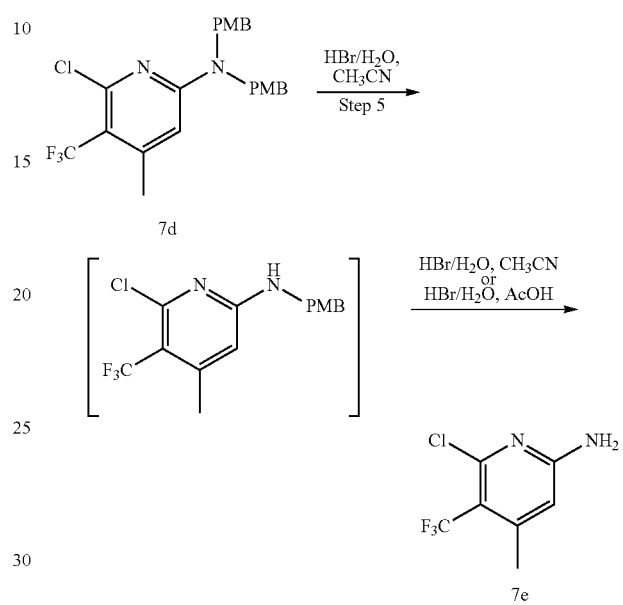

Charged MeCN (176.0 L, 2.5 V), Compound 7d (70.4 kg, 1.0 eq.) to reactor and stirred to suspension at 15±5° C. Added dropwise HBr (176.0 L, 2.5 V, 48% in water) to the reactor at 10~40° C. Adjusted to 80±5° C., stir for at least 2 hours. Cooled before charging IPAC (211.2 L, 3.0 V). Cooled to 0±5° C. and neutralized with 15 wt. % aq. NaOH to pH=7~8 at T≤25° C. Extracted the aqueous layer with IPAC (211.2 L, 3.0 V) for three times and collected and concentrated the organic layers to 2~4 V at T≤45° C. Added MeCN (352.0 L, 5.0 V) to the reactor and concentrated to 2~4 V at T≤45° C. to obtain a solution of 6-chloro-4-methyl-5-(trifluoromethyl)pyridin-2-amine in MeCN.

Step 6: N-(6-bromo-4-methyl-5-(trifluoromethyl)pyridin-2-yl)acetamide

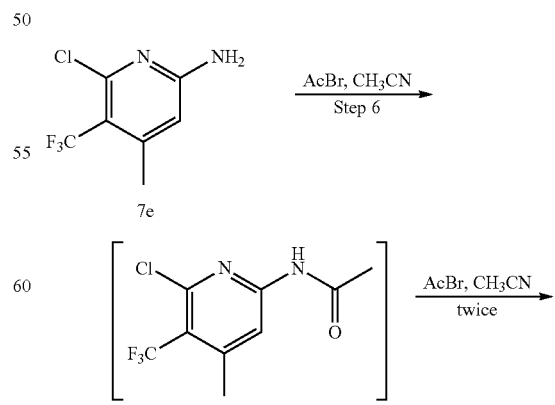

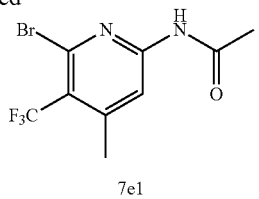

7e1

Charged AcBr (287.9 kg, 15.0 eq.) to the reactor at −10~40° C. and adjusted to 70±5° C. before stirring for at least 10 hours. Cool to 0±5° C. and quenched by EtOH (176.0 L, 2.5 V) at T≤25° C. Cooled to 0±5° C. and neutralized with 15 wt % aq. NaOH to pH=7~8 at T≤25° C. Extracted with EtOAc (281.6 L, 3.0 V) for three times and collected and concentrated the organic layers to 2~4 V at T≤45° C. Added MeCN (352.0 L, 5.0 V) to the reactor and concentrated to 2~4 V at T≤45° C. Charge AcBr (287.9 kg, 15.0 eq.) to the reactor at −10~40° C. and adjusted to 70±5° C. before stirring for at least 10 hours. Cooled to 0±5° C. and quenched by EtOH (176.0 L, 2.5 V) at T≤25° C. Cooled to 0±5° C. and neutralized with 15 wt % aq. NaOH to pH=7~8 at T≤25° C. Extracted with EtOAc (281.6 L, 3 V) three times and collected and concentrated the organic layers to 1~4 V at T≤45° C. Cooled to 5~10° C. and stirred for 1~2 hours at 5~10° C. Centrifuged and washed the cake with EtOAc (1V) twice, and collected the cake for next step without further purification. Yield: 34.50 kg crude product Step 7: 6-bromo-4-methyl-5-(trifluoromethyl)pyridin-2-amine (Compound 7e)

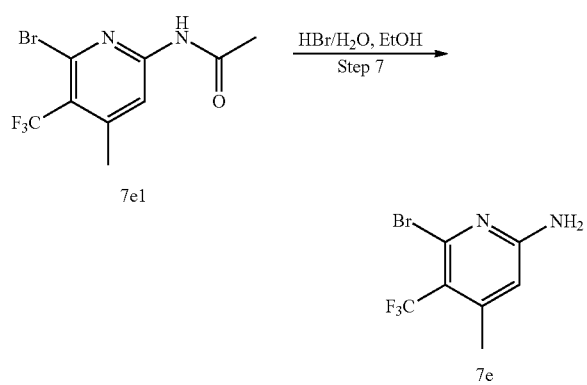

Charged the starting compound, HBr (70.4 L, 1.0 V, 48 wt % in water), EtOH (35.2 L, 0.5 V) and MeCN (70.4 L, 1.0 V) to the reactor. Adjusted to 70±5° C. and stirred for at least 8 hours. Adjusted to 70±5° C. and stirred for at least 4 hours. Cooled to 0±5° C. and neutralized with 15 wt. % aq. NaOH to pH=7~8 at T≤25° C. Centrifuged and washed the cake with soften water. Extracted the filtrate with MTBE four times, the volume of extract is 3.0 V every time and collected the organic layer. Charge the above cake and the above organic layer to the reactor. Adjusted to 45~50° C. and stirred for 1~2 hours. Cooled to 25~30° C. before filtering through diatomite and washing with MTBE (353.0 L, 5.0 V). Collected the filter liquor to 2~4 V. Added isopropanol (353.0 L, 5.0 V) and concentrated under vacuum to 2~4 V. Added a second addition of isopropanol (353.0 L, 5.0 V) and concentrated under vacuum to 2~4 V. Adjusted to 50±5° C. and added dropwise water (3~5 V) to the reactor before stirring for at least for 30 min at 50±5° C. Cooled to 5±5° C. and stirred for at least for 2 hours at 5±5° C. Centrifuged and washed the cake with water/isopropanol=2/1 (2V) twice. Collected and dried the solids at least 16 hours at 45±5° C. Yield: 25.50 kg, 64.0%.

Step 8: 6-bromo-N,N-bis(4-methoxybenzyl)-4-methyl-5-(trifluoromethyl)pyridin-2-amine (Compound 3)

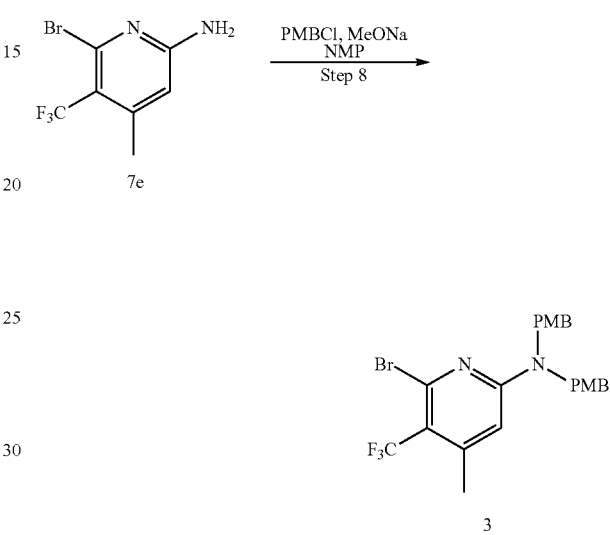

Charged NMP (255.0 L, 10.0 V), PMBCl (47.0 kg, 3.0 eq.), and Compound 7e (25.5 kg, 1.0 eq.) to the reactor in N₂. Cooled to 0±5° C. Charged solid CH₃ONa (16.2 kg, 3.0 eq.) at 0±5° C. in 5 batches. Added one batch at least every 0.5 hour. Stirred for at least 4 hours at 0±5° C. Added dropwise water (20.0 V) at −10~10° C. and stirred for at least 30 mins at 5±5° C. Filtered and washed the filter cake with water (3V) twice. Collected the filter cake and slurried with water/isopropanol=1/1 (127.5 L, 5.0 V) for at least 2 hours at 60±5° C. Cooled to 20±5° C. (Cool down 10±5° C. every hour) and stirred for at least 1 hour at 20±5° C. Centrifuged and washed the cake with water/isopropanol=1/1 (3V) twice. Collected the cake and added and DCM (255.0 L, 10.0 V) to the reactor. Adjust to 25±10° C. and stirred for at least 0.5 hour. Filtered through strainer with activated carbon and washed with DCM (51.0 L, 2.0 V). Collected and concentrated filter liquor to 2~4 V at T≤45° C. Added n-Heptane (255.0 L, 10.0 V) to the reactor and concentrated to 2~4 V at T≤45° C. Added n-Heptane (255.0 L, 10.0 V) to the reactor and adjusted to 70±5° C. Stirred for at least 10 min at 70±5° C. Cooled to 20±5° C. (Cool down 10±5° C. every hour) and stirred for at least 1 hour at 20±5° C. Centrifuged and washed the cake with n-heptane (3V) for two times. Centrifuged and washed the cake with n-Heptane/EtOAc=10/1 (51.0 L, 2 V). Collected and dried the solids at least 16 hours at 45±5° C. Yield: 31.20 kg, 63.0%.

Step 8: 6-bromo-N,N-bis(4-methoxybenzyl)-4-methyl-5-(trifluoromethyl)pyridin-2-amine (Compound 3)

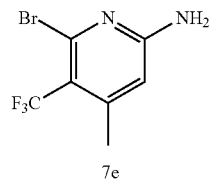

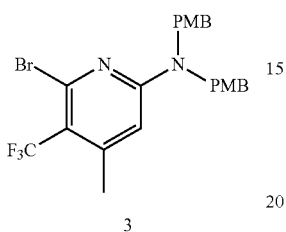

Compound 7e (29 kg, 113 mol, 1 eq) and PMBCl (40.5 kg, 258 mol, 2.4 eq) were dissolved in 213 kg THF (213 kg, 240 L, 8.2 v). ᵗBuOK solution (31.5 kg, 280 mol. 2.5 eq in 132 kg THF, 148 L, 5.1 v) was added into the solution in 9 h at 15-25° C. and the mixture was stirred at 10-25° C. for 18 h.

The mixture was filtered and treated with CUNO cartridge for 8 h. After concentrated to 120 L below 40° C., EtOH (109 kg, 140 L, 4.8 v) and water (250 kg, 250 L, 8.6 v) was added into the residue at 15-25° C. The mixture was cooled to 5-15° C. and stirred for 2-4 h. The solid was filter and washed with water (120 kg, 120 L, 4.1 v) twice. The wet cake was reslurried with 135 kg EtOH (135 kg, 173 L, 6.0 v) at 15-25° C. for 6 h. The solid was filtered and washed with EtOH (15 kg, 19 L, 0.7 v) twice. The wet cake was again reslurried with n-heptane (269 kg, 396 L, 13.7 v) and THF (11 kg, 12 L, 0.4 v) at 15-25° C. for 4 h. The solid was filtered and washed with n-heptane (30 kg, 44 L, 1.5 v) twice. The wet cake was dried under vacuum at 45-55° C. for 44 h to give Compound 3 (39.4 kg, 96.9 A % purity, 101 wt % assay, 70% yield.

Example 4

Compound 3 (6-bromo-N,N-bis(4-methoxybenzyl)-4-methyl-5-(trifluoromethyl) pyridin-2-amine)

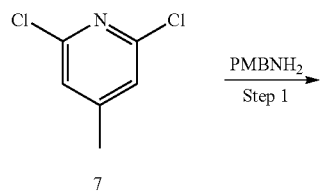

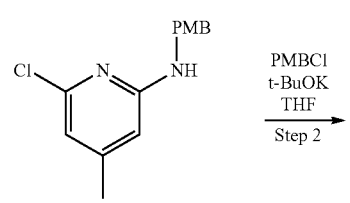

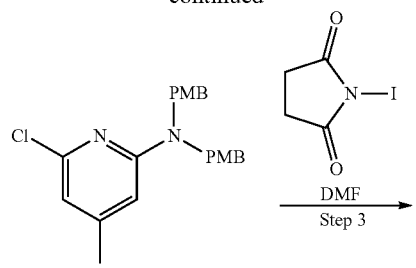

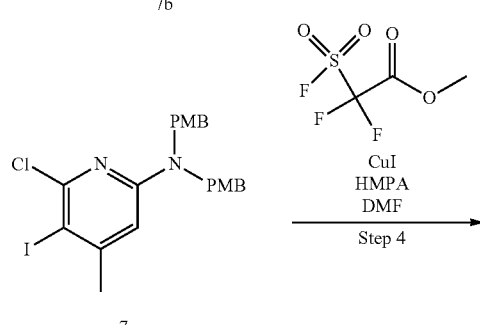

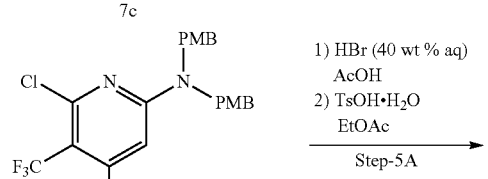

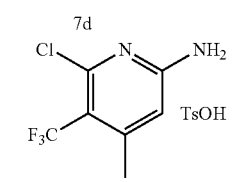

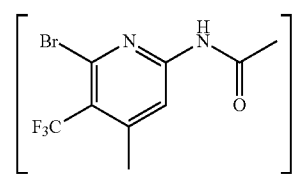

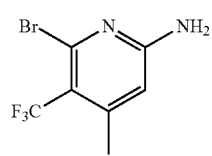

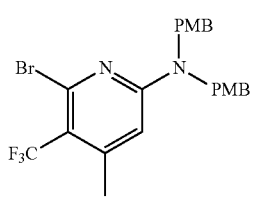

Step 1: 6-chloro-N-(4-methoxybenzyl)-4-methylpyridin-2-amine (Compound 7a)

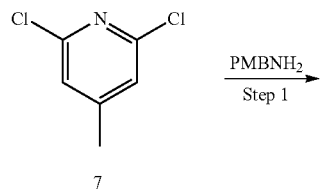

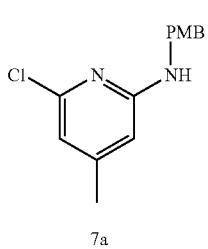

Compound 7 (103 kg, 0.51 X, 0.51 equiv) and 4-Methoxybenzylamine (964 kg, 4.68 X, 5.64 equiv) were added into 5000 L-SS lined reactor R1. R1 was adjusted to 20-30° C. and the reaction was stirred for 1 h. Then R1 was heated to 80-90° C. in 3 h. The reaction was stirred for 1 h. Then R1 was heated to 110-130° C. in 5 h and stirred for 24 h. R1 was cooled to 35-45° C. A second portion Compound 7 (99 kg, 0.49 X, 0.49 equiv) and 4-Methoxybenzylamine (43.0 kg, 0.21 X, 0.25 equiv) were added in R1. R1 was heated to 110-130° C. in 6 h and stirred for 24 h. R1 was cooled to 85-95° C. R1 was heated to 110-130° C. and stirred for another 10 h. R1 was cooled to 85-95° C. 28 wt % IPA/water solution (~2224 kg) was charged into R1 at 85-95° C., the mixture was stirred at 85-95° C. for 3 h. R1 was then cooled to 0-10° C. in 7 h and stirred for 3 h. The wet cake was filtered and washed with 28 wt % IPA/water solution (~485 kg) twice for each load (6 loads in total) to afford 337.55 kg of wet cake (purity of A wet cake: 99.6%, spec: ≥95.0%). The wet cake was divided into two portions to dry. After dried at 40-50° C. for 24 h, 158.55 kg of Compound 7a was obtained with 97.0 wt % assay, 99.3 A % purity and 149.40 kg of Compound 7a was obtained with 97.6 wt % assay, 99.3 A % purity, respectively.

Step 2: 6-chloro-N,N-bis(4-methoxybenzyl)-4-methylpyridin-2-amine (Compound 7b)

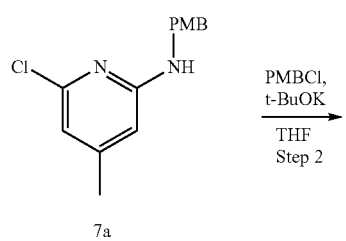

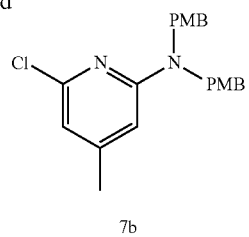

Compound 7a (13.8 kg assay corrected, 0.99 X, 1.00 equiv) and t-BuOK (9.0 kg, 0.65 X, 1.53 equiv) and THF (~139 kg) were charged into R1 and 4-methoxybenzyl chloride (10.1 kg 0.73 X, 1.23 equiv) was charged dropwise into R1 at 15-25° C. The solution was stirred at 15-25° C. for 18 h. The solution was concentrated under vacuum to 4-5× below 40° C. The concentrated solution was cooled to −5-5° C. and water (~112 kg) was added slowly. The mixture was stirred at −5-5° C. for 4 h. IPC of residual B in the supernatant was 0.0%. The wet cake was filtered and washed with water (~54 kg) to give 21.80 kg of wet cake. The wet cake was charged into 28 wt % i-PrOH aq. solution (~82 kg) and then the mixture was stirred at 20-30° C. for 8 h. The wet cake was filtered and washed with 28 wt % i-PrOH aq. solution (~50 kg) to afford 20.60 kg of wet cake. After dried at 40-50° C. for 21 h, 17.90 kg of Compound 7b was obtained with 98.4 wt % assay, 98.9 A % purity in 88% corrected yield.

Step 3: 6-chloro-5-iodo-N,N-bis(4-methoxybenzyl)-4-methylpyridin-2-amine

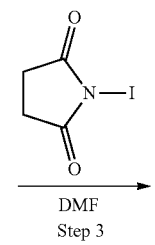

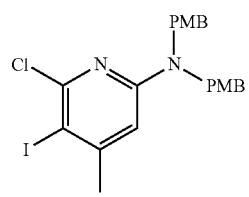

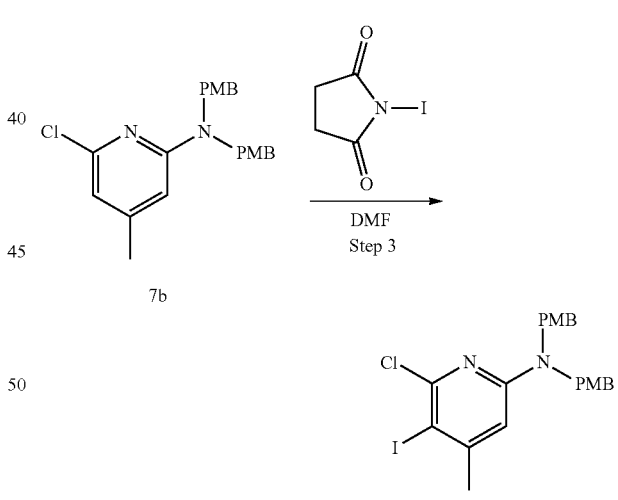

To a solution of Compound 7b (assay corrected 150 kg, 1.00 X, 1.00 equiv) in DMF (802 kg 5.3 X) was added the NIS (108 kg 0.72 X, 1.23 equiv). The solution was stirred at 15-25° C. for 24 h. NIS (3 kg, 0.02 X, 0.03 equiv) was added into the reaction. The solution was stirred at 15-25° C. for 20 h. The solution was stirred at 15-25° C. for another 4.5 h. The reaction was cooled to 0-10° C. and 5 wt % aq. Na$_2$SO$_3$ solution (~845 kg) was added. The mixture was stirred for 2 h at 0-10° C. The wet cake was filtered and washed with water (~466 kg) to give 224.85 kg of wet cake. The wet cake was charged into EtOH (~768 kg) and stirred at 45-55° C. for 2 h. After the mixture was cooled to 15-25° C. for 3 h and stirred for 3 h, the wet cake was filtered and washed with EtOH (~460 kg) to give 208.25 kg of wet cake. After dried at 45-55° C. for 18.5 h, 198.15 kg of Compound 7c was obtained with 98.3 wt % assay, 99.4 A % purity in 98% corrected yield.

Step 4: 6-(1,3-bis(4-methoxyphenyl)propan-2-yl)-2-chloro-4-methyl-3-(trifluoromethyl)pyridine (Compound 7d)

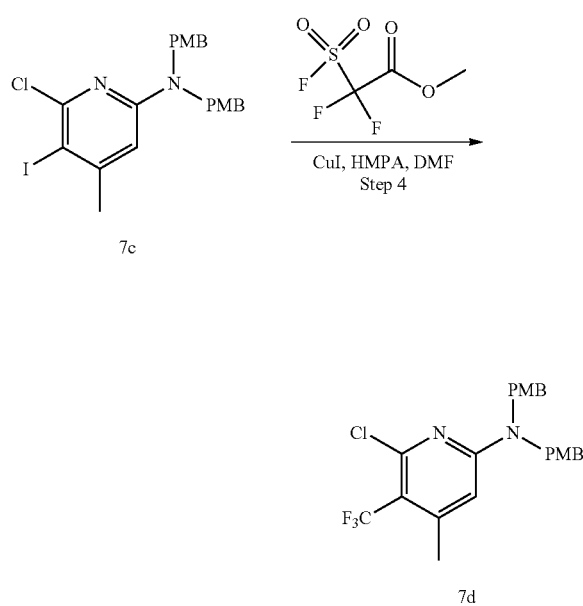

To a solution of Compound 7c (assay corrected 103 kg, 1.00 equiv 1.00 X) in DMF (~364 kg, 3.5 X) was added CuI (98 kg, 2.5 eq, 0.95 X), Methyl 2,2-difluoro-2-(fluorosulfonyl)acetate (113 kg, 2.9 eq, 1.1 X), HMPA (180 kg, 5.0 equiv, 1.75 X) and 30 kg of DMF was rinsed after each material charging. After DMF (~352 kg, 3.48 X) was charged into the reaction, the mixture was heated to 75-85° C. over 3 h and stirred for 8 h. R1 was cooled to 20-30° C. The mixture was heated to 75-85° C. over 3 h and stirred for 4.5 h. R1 was cooled to 20-30° C. The reaction mixture was filtered. 25 wt % aq. NH₃ solution (~411 kg, 4.0 X) was charged dropwise into the filtrate over 2 h at 30-40° C. The mixture was stirred at 30-40° C. for 5 h. Then water (~702 kg, 6.8 X) was added over 1 h at 30-40° C. The mixture was stirred at 30-40° C. for 6 h. The mixture was heated to IT=30-40° C. and pH of the mixture was adjust to 11-12 by adding aq. NH₃ solution (~142 kg). The mixture was stirred at 30-40° C. for 10 h. The mixture was cooled to 10-25° C. Residual of MeI in mother liquor was 168 ppm. The solid was filtered and washed with water (total: ~1004 kg) twice to afford 112.05 kg of wet cake (92.4 A % purity). After dried for about 45 h at 45-55° C., 100.00 kg of Compound 7d was obtained with 83.7 wt % assay, 91.1 A % purity in 92% corrected yield.

Step 5A: 6-bromo-4-methyl-5-(trifluoromethyl)pyridin-2-amine

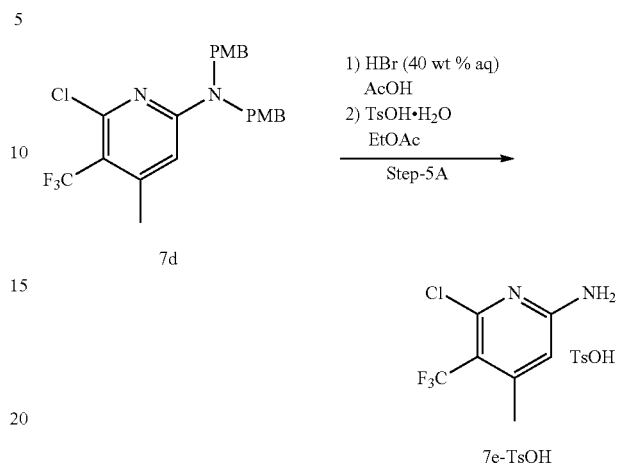

HOAc (~190 kg), Compound 7d (97 kg, 1.00 X) were added into R1. After adjusted R1 to 20-30° C., 40 wt % aq. HBr solution (~180 kg 1.86 X) and water (~12 kg) were added. The reaction solution was adjusted to 45-55° C. in 2 h and then heated to 80-90° C. in 2 h. The reaction was stirred at 80-90° C. for 6.5 h. R1 was cooled to 60-70° C. EtOAc (~370 kg) was added into the mixture and then cooled to 30-40° C. 30 wt % NaOH solution (~489 kg) was added below 45° C. to adjust pH to 7-8. Water (13 kg) was rinsed into the mixture. R1 was cooled to 20-30° C. and the aqueous layer was separated and extracted with EtOAc (~388 kg, 384 kg) twice. The combined organic layers were combined and washed with 2.2 wt % aq. Na₂SO₄ solution (water: ~369 kg+6 kg for rinse; Na₂SO₄: ~8.7 kg). Due to emulsification, the mixture was heated to 30-40° C. and stand for 8 h. The organic layer was separated and azeotropic distillated with EtOAc twice (~470 kg, ~484 kg) to 3-4× to remove water (KF=0.4%). EtOAc (~366 kg) and TsOH·H₂O (~68 kg, 0.70 X) were charged into the mixture. R1 was adjusted to 20-25° C. and stirred for 2 h. The mixture was then cooled to 0-5° C. and stirred for about 3 h. The wet cake was filtered to afford 70.90 kg wet cake. The wet cake was slurry with EtOAc (~472 kg) for 3 h at 20-25° C. The wet cake was filtered and rinsed with EtOAc (total: ~120 kg) to afford 69.45 kg of wet cake. The wet cake was directly used for next step.

Step 5B & 5C: N-(6-bromo-4-methyl-5-(trifluoromethyl)pyridin-2-yl)acetamide

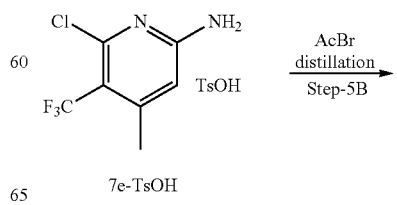

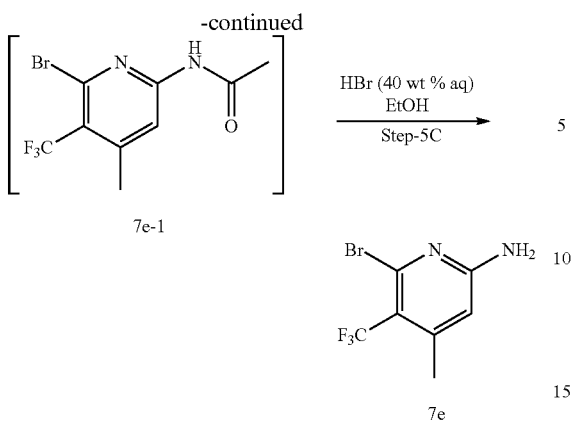

EtOAc (~341 kg), Compound 7e-TsOH wet cake and water (~337 kg) were added into R1. R1 was adjusted to 15-25° C. Then the pH of the aqueous layer was adjusted to 7-8 by adding 30 wt % aq. NaOH solution (~30 kg) below 45° C. Water (~10 kg) was rinsed into R1. R1 was adjusted to 15-25° C. and stirred for 3 h. The organic layer was separated and washed with water (~298 kg). The organic layer was concentrated to 1-3× below 45° C. under vacuum. After adding EtOAc (~578 kg), the organic layer was concentrated to 1-3× below 45° C. under vacuum. R1 was adjusted to 20-30° C. and AcBr (~411 kg) and EtOAc (~14 kg) were charged into R1 below 40° C. R1 was heated to IT=45-55° C. in 2 h and then heated to 65-75° C. in 2 h and stirred for 16 h at 65-75° C. R1 was cooled to 30-40° C. After R1 was heated to 65-75° C., the mixture was distill to 1.0-3.0× below 75° C. R1 was cooled to 20-30° C. AcBr (~224 kg) and EtOAc (~24 kg) were charged into R1 below 40° C. EtOAc (~42 kg) was rinsed into R1. R1 was heated to 45-55° C. in 2 h and then heated to 65-75° C. in 2 h. R1 was stirred for 9.5 h at 65-75° C. and then cooled to 30-40° C. R1 was heated to 65-75° C. and the mixture was distilled to 1-3× below 75° C. R1 was adjusted to 60-75° C. AcBr (~108.4 kg) and EtOAc (~10 kg) were charged into R1 below 75° C. EtOAc (~16 kg) was rinsed into R1. R1 was heated to 70-75° C. in 2 h. The mixture was distilled to 1-3× below 75° C. and stirred for 3 h at 65-75° C. The mixture was cooled to 0-10° C. EtOH (~248 kg) and water (~98 kg) were added below 45° C. in portions. R1 was adjusted to 40-45° C. for 3 h and stirred for 8 h. R1 was then cooled to 30-40° C. R1 was adjusted to IT=40-55° C. and stirred for 8 h. R1 was cooled to 30-40° C. R1 was adjusted to 40-55° C. and stirred for 10 h. 40 wt % HBr aq. solution (~46 kg) was charged into R1 below 40° C. EtOAc (~100 kg) was charged into R1. R1 was adjusted to 40-55° C. and stirred for 5 h. R1 was cooled to 30-40° C. and EtOH (~196 kg) was added and the mixture was stirred for about 2.5 h. R1 was adjusted to 40-55° C. The material was cycled for about 8 h by a diatomite filter. The filtrate was distilled to 1.0-2.0× below 45° C. Water (~572 kg) was added. After R1 was cooled to 0-10° C., 30 wt % aq. NaOH solution (~238 kg) was added below 45° C. to adjust the pH to 7-8. Water (6 kg) was rinsed into R1. R1 was cooled to 0-10° C. and the mixture was stirred for 3 h. The wet cake was filtered and washed with water (total: ~200 kg) to afford 40.80 kg of wet cake (93.7 A %). The wet cake was added in EtOAc (~320 kg). R1 was adjusted to 20-30° C. and stirred for 30 min. The mixture was concentrated to 2.5-5× below 45° C. and then EtOAc (~32 kg) was added. After R1 was cooled to 0-10° C., AcBr (~200 kg) was charged into R1 by vacuum. EtOAc (~28 kg) was charged into R1. R1 was adjusted to 45-55° C. for 2 h and then heated to 65-75° C. in 1.5 h and stirred for 11 h. R1 was cooled to 30-40° C. then R1 was heated to 65-75° C., the mixture was distilled to 2.5-5.0× below 75° C. R1 was cooled to 0-10° C. EtOH (~276 kg) and water (~104 kg) were added below 45° C. in portions. R1 was adjusted to 40-45° C. in 3 h and stirred for 12 h. R1 was cooled to 30-40° C. R1 was cooled to 0-10° C. and 30% NaOH solution (~213 kg) was added below 45° C. to adjust the pH to 7-8. R1 was distilled under vacuum below 45° C. until no distillate. Water (~449 kg) was added and the mixture was cooled to 0-10° C. and stirred for about 2 h. The wet cake was filtered and washed with water (total: ~80 kg) to afford 41.50 kg wet cake. The wet cake was dried at 20-30° C. for 4 h and then dried at 45-55° C. for 44 h. 35.85 kg of Compound 7e1 was obtained with 95.1 wt % assay, 97.4 A % purity in 53% corrected yield.

Step 6: 6-bromo-N,N-bis(4-methoxybenzyl)-4-methyl-5-(trifluoromethyl)pyridin-2-amine (Compound 3)

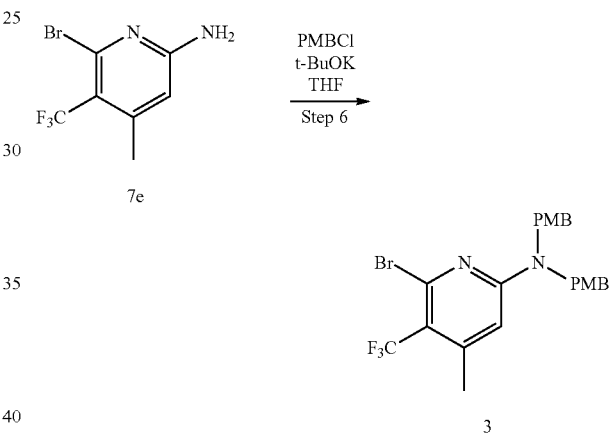

THF (~292 kg), Compound 7e (33.8 kg, assay corrected, 0.97 X) and 4-methoxybenzyl chloride (51.0 kg, 1.5 X) were charged into R1 and the mixture was stirred for 1 h at 15-25° C. t-BuOK (36.0 kg, 1.03 X) was added via three portions. Then the reaction solution was stirred at 15-25° C. for about 21 h. Water (~200 kg) and Na$_2$SO$_4$ (~6.8 kg) were added. The solution was adjusted to 20-25° C. and stirred for 2 h. After filter through diatomite filter, the filtrate was stand and separated. The aqueous phase was extracted with THF twice (total: ~193 kg). The combined organic layers was filtered through diatomite filter and cartridge filter. The filtrate was cycled for 20 h via CUNO (3M-R55SP) and cartridge filter. 29 kg of THF was rinsed into R1. The solution was adjusted to 30-40° C. and distilled to 2-5 vol under vacuum below 40° C. R1 was cooled to 15-25° C. and EtOH (~175 kg) was charged dropwise into R1 for 4.5 h. The mixture was stirred at 15-25° C. for 3 h. Water (~152 kg) was added. R1 was cooled to 5-15° C. and the mixture was stirred for 3 h. After filtration, the wet cake was slurred with EtOH (~102 kg) at 15-25° C. for 8 h. After filtration, the purity of wet cake was 95.6 A %. The wet cake, n-heptane (~82 kg) and THF (~2 kg) were charged into R1. The mixture was adjusted to 40-50° C. and stirred for 8 h. R1 was cooled to 0-10° C. in 3 h and the mixture was stirred for about 1.5 h. The wet cake filtered and washed with n-heptane (~65 kg). After dried at 55-65° C. for 26.5 h, the dry cake was sieved (20 mesh). 51.65 kg of Compound 3 was obtained with 97.2 w % assay, 97.0 A % purity in 76% corrected yield.

Example 5

2,6-dibromo-4-methyl-3-(trifluoromethyl)pyridine
(Compound 8b)

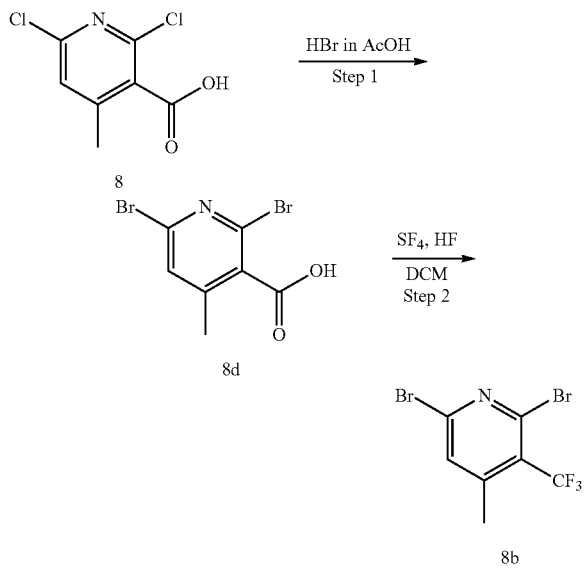

Step 1: To a Hastelloy autoclave reactor were charged 2,6-dichloro-4-methylnicotinic acid (Compound 8, 100 g, 2.06 mol, 100 mol %) and HBr in acetic acid (33 wt %, 1.00 L, 10 v) at 20° C. The reaction mixture was gradually heated and stirred for 32 h. The mixture was quenched with water (1.00 L, 10 v) and the organic layer was extracted with methyl tert-butyl ether (300 mL, 3 v) three times. The organic layers were then combined and concentrated under reduced pressure. The resulting residue was then slurried with heptane (500 mL, 5 v) and subsequently filtered and dried to afford 2,6-dibromo-4-methylnicotinic acid (Compound 8d, 133 g, 92.9% yield) as a grey solid. $^1$H NMR (400 MHz, DMSO-$d_6$) δ 14.16 (s, 1H), 7.74 (d, 1H), 2.31-2.51 (m, 3H). $^{13}$C NMR (101 MHz, DMSO-$d_6$) δ 166.7, 149.5, 139.5, 135.6, 133.8, 128.7, 18.6. MS ([M+H]$^+$) calculated for $C_7H_5Br_2NO_2$ 293.8757, found 293.876.

Step 2: To a Hastelloy autoclave reactor was charged Compound 8d (130 g, 2.27 mol, 100 mol %) at 20° C. The reaction mixture was cooled down to −20° C. and anhydrous hydrogen fluoride was charged (178 g, 8.90 mol, 392 mol %). The reaction mixture was further cooled down to −78° C. and sulfur tetrafluoride was charged (761 g, 7.04 mol, 310 mol %). The stirred reaction mixture was allowed to warm up to 20° C. under ambient conditions and was then further heated and stirred for 24 h. The mixture was then cooled to 0° C., diluted with dichloromethane, and neutralized to pH 10-12 with a solution of potassium carbonate in water. The resulting mixture was then filtered through celite, and the aqueous layer extracted with dichloromethane (390 mL, 3 v) three times. The organic layers were then combined and concentrated under reduced pressure to afford Compound 8b (135 g, 96.0% yield) as a black solid.

Example 6

Step 1:
2,6-dichloro-4-methyl-3-(trifluoromethyl)pyridine
(Compound 8a)

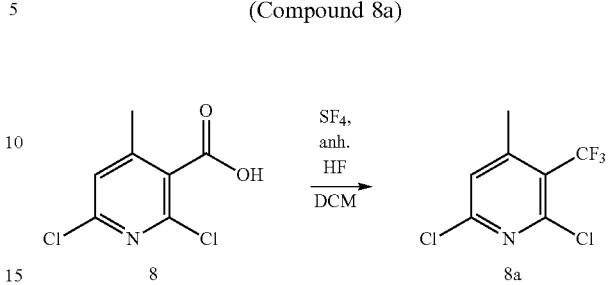

2,6-Dichloro-4-methylnicotinic acid (Compound 8, 1.0 equiv) was charged to an autoclave at ambient temperature (20-30° C.), followed by anhydrous HF (1.37 rel. wt) at −20° C. and SF$_4$ (2.5 equiv) at −78° C., sequentially. The reaction mixture was allowed to warm to ambient temperature and then heated at 70-80° C. for 17-24 h. The reaction was cooled to ambient temperature (25-30° C.) before purging into a KOH (alkaline scrubber). Exchanged solvent to MTBE and cooled the reaction to 0-10° C. and added DM water (1 rel. vol.) and K$_2$CO$_3$ (4 rel. weight) in DM water (8 rel. vol.).

The temperature of the reaction was set to about 20-30° C. before filtering and washing with 2.5 vol. MTBE. Separated the layers and washed aqueous layer with 2.5 vol. MTBE. Separated the layers and combined the organic layers before washing with twice with 2.5 vol. water at ambient temperature (20-30° C.). Distilled the organic layer to obtain a slurry before washing with methanol (1 rel. vol.). The mixture was distilled and dissolved in methanol (4 rel. vol.) before adding to activated charcoal (Norit CG1 10% w/w). The mixture was stirred for at least 60 min before filtering with celite or cellulose pad. The filtrate was added to a new reactor with water (1.3 rel. vol.) and stirred 10-15 min at 20-25° C. Compound 8a seeds (1% w/w) was added and the contents stirred for 10-15 min before adding 1.7 vol. DM water. Cooled the contents to 0-5° C. and stirred for at least 60 min before filtering. The filtrate was washed with 1 vol. water and the wet cake was dried under pressure to provide compound 8a (94.88 kg, 86.3% yield).

2,6-dichloro-4-methyl-3-(trifluoromethyl)pyridine
(Compound 8a)

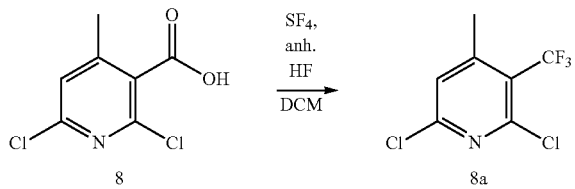

Nicotinic acid substrate (Compound 8, 1.0 equiv) was charged to an autoclave at ambient temperature, followed by anhydrous HF (1.37 rel. wt) at −20° C. and SF$_4$ (3.5 equiv) at −78° C., sequentially. The reaction mixture was allowed to warm to ambient temperature and then heated at 90-100° C. for 24 h. A check for conversion was performed by HPLC analysis. Upon completion, DCM was charged to the reaction, then the mixture was unloaded over ice, neutralized using $K_2CO_3$, filtered through celite, and extracted with DCM (3×3 V). The combined organic layers were concentrated to give a black semi-solid.

Charcoal Treatment: The crude product mixture was dissolved in MeOH (5 V), treated with charcoal (10% w/w), and stirred at 50° C. for 1 h. The resulting slurry was filtered through a celite bed, washed with MeOH (2 V) and concentrated under reduced pressure to provide compound 8a as a brown solid (96.97 A % by HPLC after charcoal treatment; 91.2% yield on 500 g scale).

6-bromo-N,N-bis(4-methoxybenzyl)-4-methyl-5-(trifluoromethyl)pyridin-2-amine (Compound 3)

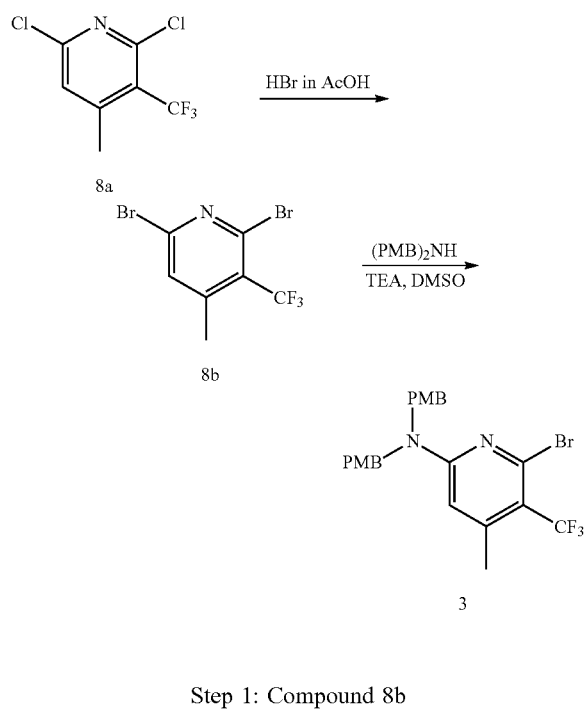

Step 1: Compound 8b

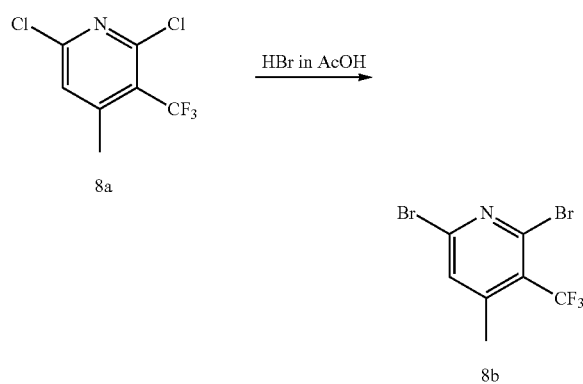

To a reactor was added Compound 8a (977 g, 1 eq.) and 33 wt % HBr/AcOH (600 g, 0.5 v). The mixture solution was heated to 115° C. 33 wt % HBr/AcOH (9700 g) was added dropwise to the mixture solution at 115° C. over 24 h. After complete addition, the reaction solution was cooled to 40° C., then bubbled with $N_2$ for 2 h. The mixture was heated to 115° C., and 33 wt % HBr/AcOH (1300 g) was added dropwise to the mixture solution at 115° C. over 2.5 h. 33 wt % HBr/AcOH (1200 g) was added dropwise to the mixture solution at 115° C. over 2.5 h. 33 wt % HBr/AcOH (1246 g) was added dropwise to the mixture solution at 115° C. over 2.5 h. The complete reaction solution was cooled to 20° C., and water (8000 mL, 8 v) was added below 30° C. The mixture solution was extracted with MTBE twice (8 L/3 L, 8 v/3 v). The organic phases were combined and adjusted to pH 7~8 with 15 wt % aq. NaOH below 30° C. Then the organic phase was washed with water (2 L, 2 v) and dried with anhydrous $Na_2SO_4$ (500 g, 0.5 X). After filtration, the filtrate was concentrated to dryness under reduced pressure (0.06~0.1 MPa) at 40~45° C., product as brown oil was obtained (HPLC purity: 97.6%, assay: 94.3%, yield: 93.3%).
$^1$H NMR (400 MHz, CHLOROFORM-d) δ 2.42-2.61 (m, 3H), 7.31-7.48 (s, 1H).

Step 2

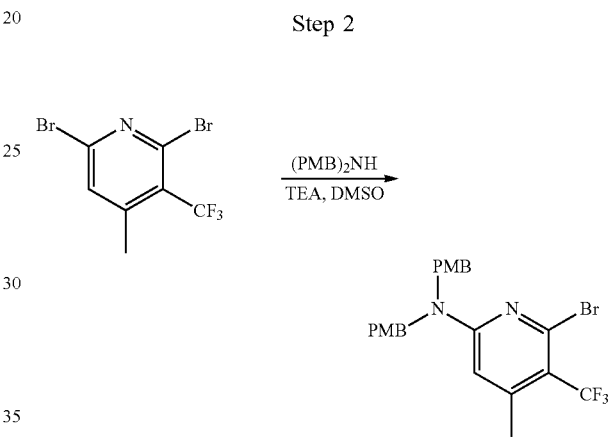

To a mixture solution of Compound 8b (877 g, 1 eq.) and triethylamine (TEA) (414 g, 1.5 eq.) in N-butylpyrrolidinone (NBP) (4650 mL, 5 v) $(PMB)_2NH$ (1080 g, 1.5 eq.) was added. The mixture solution was heated to 70° C. and stirred at that temperature for 24 h. The complete reaction solution was cooled to 50° C., and 20 wt % aq. Citric acid (10 L, 10 v) was added dropwise at 50° C. over 1 h. Then the mixture solution was cooled to 20° C. over 1 h. The suspension was filtered and washed with water (2 L, 2 v) and MeOH (2 L, 2 v) subsequently. The filter cake was dried under reduced pressure at 25° C. for 20 h to obtain crude product (1115 g, assay: 88.2%, residual MeOH: 0.01%).

Recrystallization: To a reactor was added crude product (1115 g) and THF (4.46 L, 4 L), and the mixture solution was stirred to be clear and then decolorized by active carbon (110 g, 10 wt %). The decolorized solution was concentrated under reduced pressure below 40° C. to 1.2 v, then methanol (2.23 L, 1.2 v) was added. The mixture solution was heated to 50° C. and stirred at that time for 0.5 h to obtain a clear solution. MeOH (4.65 L, 4.2 v) was charged to the solution, then crystal seed (1 wt %) was added. The mixture solution was stirred at 50° C. for 1 h. MeOH (2.23 L, 1.2 v) was added to the suspension at 50° C. and stirred at that temperature for 0.5 h. The suspension was then cooled to 0° C. over 1 h and stirred at that temperature for 16 h. The suspension was filtered and washed with MeOH (2.23 L, 1.2 v). The filter cake was dried under reduced pressure at 45° C. for 20 h to obtain product as off-white solid (931.6 g, HPLC purity: 99.7 A %, assay: 102.3 wt %, yield: 68.4%).
$^1$H NMR (400 MHz, CHLOROFORM-d) δ 2.24-2.45 (m, 3H), 3.73-3.90 (s, 6H), 4.57-4.85 (s, 4H), 6.11-6.22 (s, 1H), 6.80-6.93 (m, 4H), 7.10-7.23 (m, 4H), 7.24-7.34 (s, 1H)

Example 7

Compound 1: tert-butyl (S)-4-((R)-7-(6-(bis(4-methoxybenzyl)amino)-4-methyl-3-(trifluoromethyl)pyridin-2-yl)-6-chloro-2,8-difluoroquinazolin-4-yl)-3-methylpiperazine-1-carboxylate

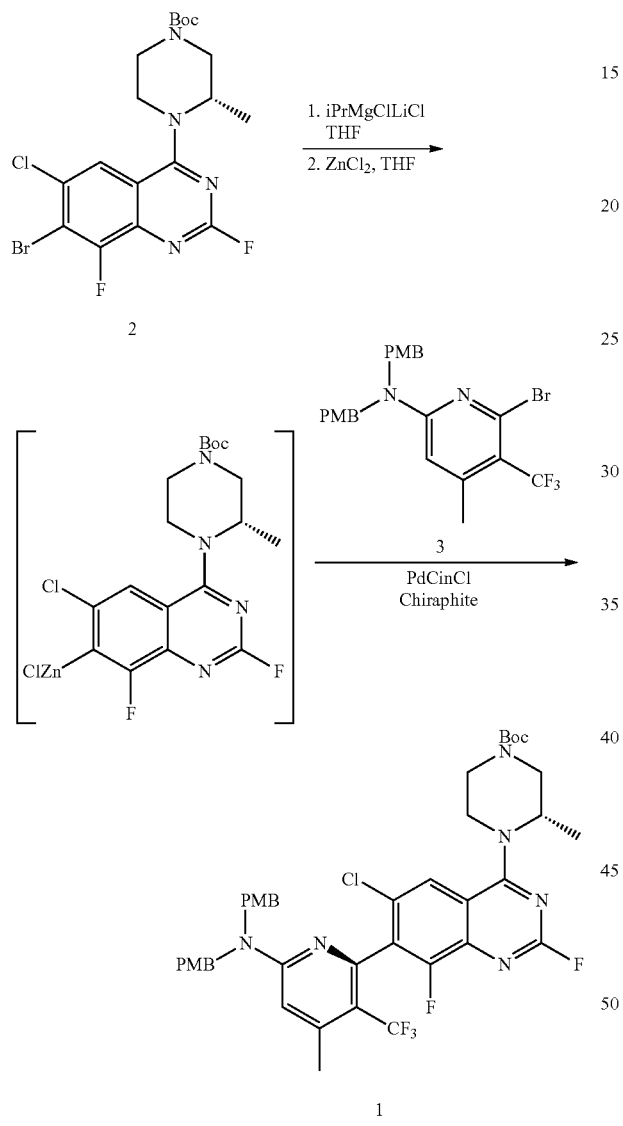

To a dry flask (1 L) was added compound 2 (50.0 g, 104.7 mmol, 1.1 equiv) and THF (350 mL, 7 v, 100-200 ppm of H₂O). i-PrMgCl·LiCl (1.3 M in THF, 93.0 mL, 1.265 equiv) was added dropwise under argon at −78 to −70° C. over 30 min. The reaction mixture was stirred at −78° C. for 10 min. ZnCl₂ (1.9 M in Me-THF, 72 mL, 1.43 equiv, ~230 ppm H₂O) was added dropwise at −78 to −70° C. over 20 min and then warmed to 10° C. gradually over 2 h. The mixture was stirred at 10° C. for ~0.5 h. The reaction mixture was stirred at −70 to −30° C. for at least 1 h after addition of ZnCl₂. To another dry flask (1 L) was added compound 3 (47.1 g, 95.2 mmol, 1.0 equiv) and 1,4-dioxane (8 v). Zn reagent was added under argon atmosphere. The reaction mixture was bubbled with argon for 2 h at 0.3 L/min. A solution of [PdCinnamylCl]₂ (0.5 mol %), (R,R)-chiraphite ligand (1.0 mol %) in 1,4-dioxane (~14 mL, ~0.27 v) was added under argon atmosphere. The mixture was stirred at ~48° C. for 21 h.

The reaction mixture was cooled to 10~20° C. The reaction mixture was added dropwise to saturated aq NH₄Cl (~471 mL, 10 v) below 20° C., then the resulting mixture was stirred for 30 min. Filtered with diatomite (~1 wt) and the cake was washed with toluene (236 mL, 5 v). Two phases (the filtrate) were separated, and the aqueous was extracted with toluene (236 mL, 5 v). The combined organic phase was washed with brine (236 mL, 5 v). Then the toluene was concentrated under vacuum at 40~50° C. to 4 vol. (~200 mL). Toluene (200 mL, 4 v) was added and then concentrated to about ~200 mL (4 v). Toluene (200 ml, 4 v) was added and then concentrated to about ~200 mL (279 g, 4 v). The solution was cooled to 15~20° C. N-heptane (6 v, 637 mL) was added dropwise at 15~20° C. over 50 min. Stirred at rt (15~20° C.) for ~1 h. Filtered and the cake was washed with toluene/n-heptane (~2.5 v×2, n-heptane/toluene=2/6). Dried the solids. Yield: 60.7 g of crude product=98.6/1.4, pale-yellow solid in ~69% corrected yield.

Example 8

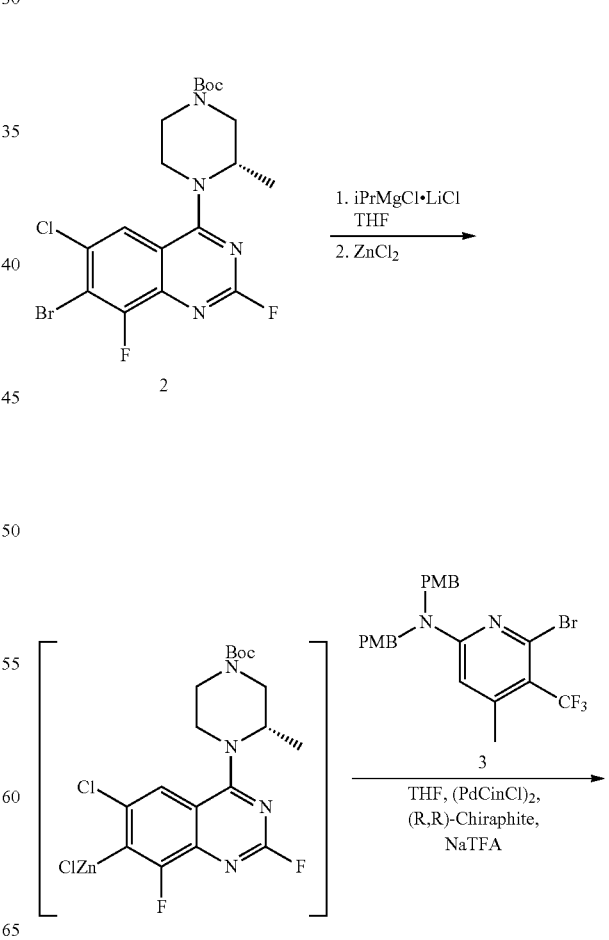

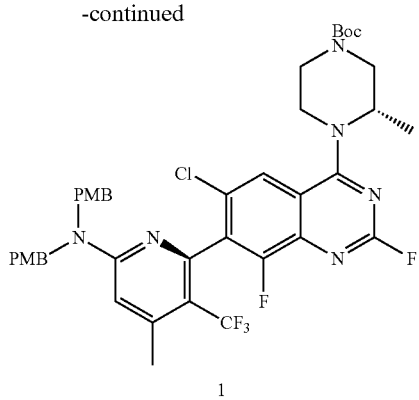

To a solution of compound 2 (42.0 g, 88 mmol, 1.1 equiv.) in THF (200 mL) was added at −70±5° C. i-PrMgCl·LiCl (1.14 M in THF, 77.78 g, 92 mmol, 1.15 equiv.) and the corresponding mixture was stirred for 30 minutes. Then, a ZnCl₂ solution (50.0 g, 94 mmol, 1.18 equiv.) was added at −70±5° C. After complete addition, the reaction mixture was heated −10° C. followed by portionwise addition of NaTFA (32.6 g, 240 mmol, 3.0 eq.). The mixture was then heated to 50° C. followed by the addition of a solution of bromopyridine Compound 3 (39.6 g, 80 mmol, 1.0 equiv.) in THF (80 mL). The mixture was stirred for about 15 minutes followed by the addition of a solution of palladium(π-cinnamyl) chloride dimer (0.201 g, 0.4 mmol, 0.005 equiv.) and (R,R)-Chiraphite (0.77 g, 0.88 mmol, 0.011 equiv.) in THF (16 mL) and the reaction mixture was stirred until full conversion was achieved. The reaction mixture was cooled to 20° C. and quenched upon addition to an aqueous solution of trisodium citrate (300 g, 20% w/w) and toluene (200 mL). The reactor was rinsed with THF (20 mL) and the biphasic mixture was stirred for 15 minutes. After phase separation an aqueous solution of trisodium citrate (300 g, 20% w/w) was added and the biphasic mixture was stirred for 15 minutes. After phase separation, water (100 mL) was added the biphasic mixture was stirred for 15 minutes. After phase separation, water, THF and 2-Me-THF were replaced by toluene (200 mL) at a constant volume under vacuum. Then the solution was filtered at 50±2° C. over a charcoal filter, the reactor and the filter were rinsed with toluene (42 g) the reaction volume was reduced under vacuum to about 130-150 mL. The reactor was cooled to 20° C., n-heptane (27.1 g) and 0.04 g of seeds were added and the resulting thin suspension was aged for 1 h. Then n-heptane (301 g) was added over 2 h and the resulting suspension was stirred for at least 12 h. The crystals were filtered off and washed three times with 100 mL toluene/n-heptane (1:1) to yield the crude title compound as yellowish crystals. The crude title compound may be recrystallized from toluene/n-heptane following the above described crystallization procedure yielding the title compound as off-white crystals in 70-75% yield.

Exemplary Chiral Ligand Conversions and Selectivies

| Ligand | Conversion | Selectivity (dr) |
|---|---|---|
|  | 97% | 97:3 |
|  | 97% | 95:5 |

Exemplary Chiral Ligand Conversions and Selectivies

| Ligand | Conversion | Selectivity (dr) |
|---|---|---|
| (structure) | 100% | 88:12 |
| (structure) | 100% | 95:5 |
| (structure) | 100% | 61:39 |
| (structure) | 100% | 78:22 |

Exemplary Chiral Ligand Conversions and Selectivies
| Ligand | Conversion | Selectivity (dr) |
|---|---|---|
| | 100% | 82:18 |
| | 99% | 72:28 |
| | 46% | 85:15 |
Example 9
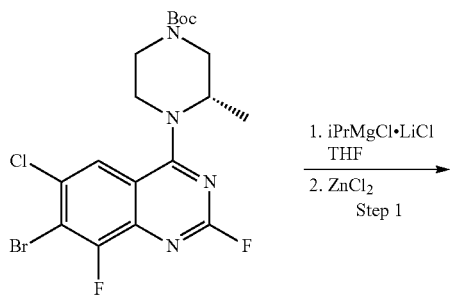
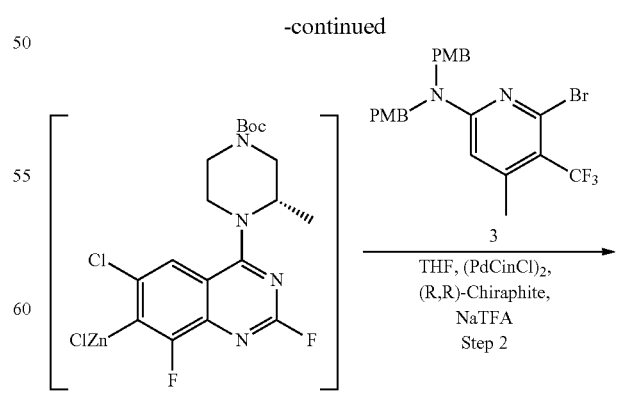

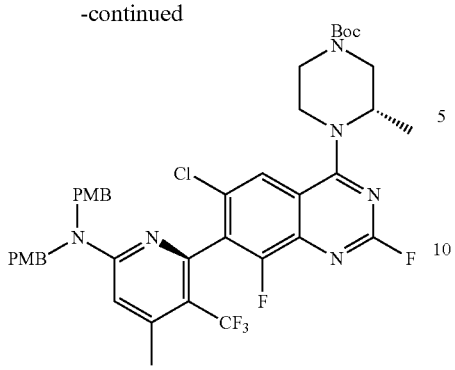

1

Compound 2 (53 g, 111 mmol, 1.10 eq) was dissolved in THF (223 g, 250 mL, 5 v) and then cooled to −78 to −70° C. under $N_2$ protection. i-PrMgCl·LiCl (98 g, 122 mmol, 1.21 eq, 97 mL, 1.9 v, 1.26 M in THF) was dropped into the solution at −78 to −70° C. under $N_2$ protection in 1 h and stirred for 1 h. $ZnCl_2$ (70 g, 126 mmol, 1.25 eq, 63 mL, 1.3 v, 2.0 M in 2-MeTHF) was dropped into the solution in 1 h at −78 to −70° C. under $N_2$ protection and stirred for 1 h. The solution was adjusted to 0 to 10° C. during 2-3 h gradually under $N_2$ protection. NaTFA (41 g, 301 mmol, 3.0 eq) was added into the solution under $N_2$ protection. The suspension was stirred at 15-25° C. for 30 min and then heated to 50 to 55° C. After stirred at 50 to 55° C. for 1 h, the suspension was directly used for Negishi coupling (step-2). Compound 3 (50 g, 101 mmol, 1.0 eq) was dissolved in THF (142 g, 160 mL, 3.2 v) and then the solution was sparged with $N_2$ for 2 h at 15-25° C. $(PdCinCl)_2$ (390 mg, 0.765 mmol, 0.75 mol %) and (R,R)-Chiraphite (1.4 g, 1.60 mmol, 1.5 mol %) were added into the solution under $N_2$ protection. The solution was sparged with $N_2$ for another 1 h. That solution was dropped into the solution of compound 2 at 50 to 55° C. under $N_2$ protection. The reaction mixture was stirred at 50 to 55° C. for 11 h.

The reaction mixture was cooled to 15-25° C. and 20 wt % aq $NH_4Cl$ (300 mL, 6 v) was charged into and stir for 1 h. The organic layer was separated and the aqueous layer was extracted with toluene (250 mL, 5 v). 5 wt % $Na_2SO_4$ (250 mL, 5 v) was changed into the combined organic phase and the mixture was filtered with diatomite and wash with THF (250 mL, 5 v). The crude THF/toluene solution was passed through charcoal (CUNO) at 15-25° C. for 5 h (flow rate 80 mL/min) and the CUNO channel was washed with THF 50 mL (1 v). The THF/toluene solution was again passed through consecutive diatomite pad and charcoal pad (CUNO) at 15-25° C. for 16 h (flow rate 80 mL/min). The solution was concentrated to 2 v and toluene (200 mL, 4 v) was added. The solution was again passed through consecutive diatomite pad and charcoal (CUNO) at 15-25° C. for 16 h (flow rate 80 mL/min). The CUNO channel was washed with toluene (50 mL, 1 v) and concentrated to (4 v) under vacuum at 40-50° C. Toluene (200 mL, 4 v) was charged into the residue and the solution was concentrated again to 4 v under vacuum at 40-50° C.

The residue was cooled to 15-25° C. and then n-heptane (50 mL, 1 v) was added to the crude solution. 150 mg seed was added into the mixture. The mixture was stirred for 1 hr at 15-25° C. and then n-heptane (11 v) was added to the crude solution drop wise over 2 h. The wet cake was filtered and washed with toluene/n-heptane 2×125 mL (2×2.5 v, toluene/n-heptane=1:3). 90.8 g crude wet 1 was obtained with 85.4 wt % assay.

The wet cake was charged into toluene (131 g, 150 mL, 3 v) and then heptane (408 g, 600 mL, 12 v) was dropped into the suspension. The suspension was stirred for 19 h at 15-25° C. The wet cake was filtered and rinsed with n-heptane (34 g, 50 mL, 1 v). 81.8 g wet cake was obtained and dried in vacuum below 45° C. for 16 h. Finally, 65.2 g product toluene solvate was obtained with 98.5 A % purity in 68.9 wt % assay yield. Purity: 98.5 A %; assay: 86.8 wt %; toluene: 11.0 wt %; chiral purity: 99.1 A %.

Example 10

Compound 1: tert-butyl (S)-4-((R)-7-(6-(bis(4-methoxybenzyl)amino)-4-methyl-3-(trifluoromethyl)pyridin-2-yl)-6-chloro-2,8-difluoroquinazolin-4-yl)-3-methylpiperazine-1-carboxylate

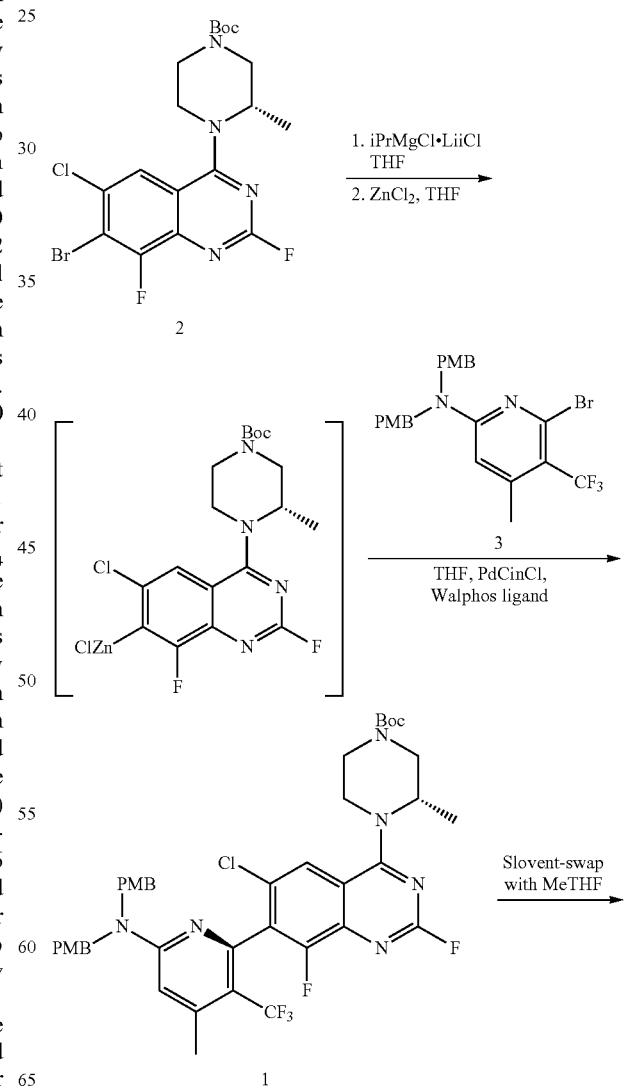

-continued

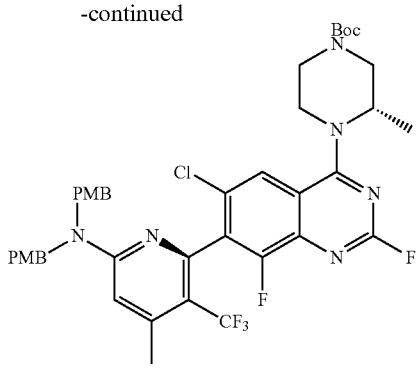

1

To a reactor was added ultra-dry THF (53 L, 8.4 v) and compound 2 (8.5 kg, 17.79 mol, 1.4 equiv) under argon atmosphere. The mixture was degassed by 3 cycles of vacuum/argon and cooled to −78° C. by a liquid N$_2$ bath. A solution of i-PrMgCl·LiCl (1.3 M in THF, 15.74 L, 20.46 mol, 1.61 equiv) was added drop-wise under argon at −78 to −70° C. over 15 min. The reaction mixture was stirred at −78° C. for 15 min. ZnCl$_2$ (1.9 M in Me-THF, 12.2 L, 23.18 mmol, 1.82 equiv., ~1300 ppm) was added dropwise at −78 to −70° C. over 15 min and then warmed to −10° C. gradually over 3.0 h. The reaction mixture was stirred at −70 to −30° C. for at least 1 h after addition of ZnCl$_2$.

To another reactor was added ultra-dry THF (44.4 L, 7.0 v) and compound 3 (6.3 kg, 12.71 mol, 1.0 equiv.) under argon atmosphere. The mixture in the first reactor was added to the second reactor under argon pressure and the resulting mixture was bubbled with argon for 2 h. A solution of PdCinCl (65.9 g, 0.13 mol, 1.0 mol % of Pd) and Walphos ligand (88.3 g, 0.13 mol, 1.0 mol %) in degassed THF (1.7 L, 0.27 v) was added under argon pressure via PFA tube and the mixture was bubbled with argon for 2 h. Heated to 40-45° C. and stirred for 3 h under argon.

Cooled to 20° C. and then added to saturated NH$_4$Cl (64 L, 10 v) solution at <20° C. Filtered through 3.2 kg of diatomite and two phases (filtrate) were separated. The aqueous was extracted twice with EtOAc (32 L, 5 vol.). The combined organic phase was washed with brine (32 L, 5 v) and then concentrated at 40° C. to ~2 v (~17 L) and then solvent-swapped with EtOAc (~30 L×3) to provide an EtOAc solution (~17 L). Above solution was concentrated under high vacuum at ~40° C. to remove most of EtOAc and then solvent-swapped with DCM (~30 L×3) to provide a DCM solution (~17 L, DCM/EtOAc=5-6/1).

About 14 kg of silica (60-100 M, ~2.2 x) was added to above solution and the resulting mixture was agitated at −15° C. for ~1 h. The resulting mixture was added to the column filled with ~74 kg of silica (wet packing column, 200-300 M, ~11 x) and then eluted with ~200 L of n-heptane followed by a total amount of ~2000 L of n-heptane/EtOAc=4/1. The desired fraction was concentrated under vacuum at ~40 C to ~2-3 v (17-25 L).

About 60 L of EtOAc was added and the resulting mixture was warmed to −40° C. to become a solution (EtOAc/n-heptane=~2/1) after ~1 h. Then, the solution was cooled to ~15° C. naturally. About 680 g of C941 (8 w %, related to the amount of compound) was added and the resulting mixture was agitated at ~15° C. for ~1 h. Filtered and the cake was washed with EtOAc (2.5 L×2), the filtrate and washes were concentrated to 2-3 v (17-25 L) and then further dried in a rotary evaporator at 40° C. to dryness to provide a final compound 1. $^1$H NMR (600 MHz, DMSO-d6) δ ppm 7.97 (s, 1H), 7.15 (d, J=8.7 Hz, 4H), 6.87 (br d, J=8.2 Hz, 4H), 6.84 (s, 1H), 4.71-4.88 (m, 3H), 4.56 (br d, J=15.7 Hz, 2H), 4.19-4.25 (m, 1H), 3.86-4.02 (m, 1H), 3.79-3.86 (m, 1H), 3.74 (br d, J=5.8 Hz, 1H), 3.72 (s, 6H), 2.94-3.30 (m, 2H), 2.40 (d, J=1.7 Hz, 3H), 1.43 (s, 8H), 1.33-1.36 (m, 3H). HR-MS (ESI): calc. for $C_{41}H_{42}ClF_5N_6$ m/z ([M+H]+) 813.2965; found 813.2963.

Example 11

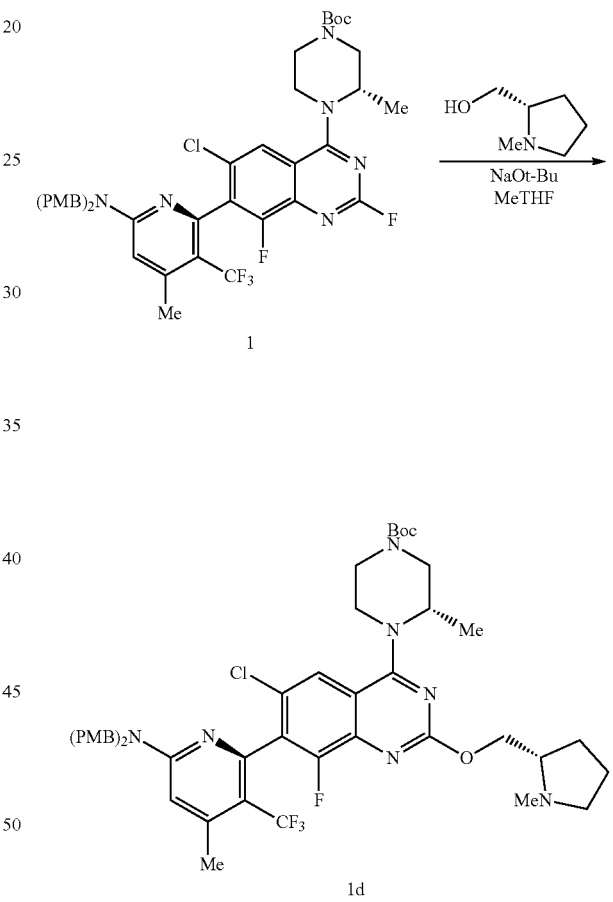

A solution of tert-butyl (3S)-4-[7-[6-[bis[(4-methoxyphenyl)methyl]amino]-4-methyl-3-(trifluoromethyl)-2-pyridyl]-6-chloro-2,8-difluoro-quinazolin-4-yl]-3-methyl-piperazine-1-carboxylate (50.0 g, 53.7 mmol, 1.00 equiv., 87.3% assay) and [(2S)-1-methylpyrrolidin-2-yl]methanol (7.44 g, 64.6 mmol, 1.20 equiv.) in 2-Me-THF (320 g) was concentrated under reduced pressure (235 mbar) to a 250 mL solution. The solution was cooled down to −10° C. Sodium tert-pentoxide as a solution in toluene (27.5 g, 64.6 mmol, 1.20 equiv., 25% w/w) was then dosed over 10 to 20 min. The reaction mixture was stirred at 0° C. until full conversion was achieved (typically 1 h). Then, the reaction mixture was diluted with 2-Me-THF (214 g), warmed up to 15-25° C. and quenched by the addition of aqueous potassium carbonate (200 g, 10% w/w solution). The biphasic mixture was stirred for 1 h and the layers separated. The organic layer was further washed with aqueous potassium carbonate (200 g, 10% w/w). The biphasic mixture was stirred for 15 min and the layers separated. The organic layer was concentrated under reduced pressure (235 mbar) to a 250 mL solution, cooled down to 20-25° C. and polish filtered. The filtrate was further concentrated under reduced pressure (235 mbar) to a 175 mL solution. 1-PrOH (100 g) was added and a continuous exchange of 2-Me-THF to 1-PrOH was performed under reduced pressure (150 to 60 mbar). Then, water (100 g) was added at 50° C. and the solution was seeded at this temperature. The resulting mixture was further stirred at this temperature for 2 h and water (100 g) was added over at least 2 h. The crystal slurry was cooled down to 20° C. over at least 3 h and further stirred at this temperature for at least 5 h. The crystals were filtered off, washed with a solution of 1-PrOH/water and dried under reduced pressure until constant weight was attained. The title compound is isolated in 96% yield (47.5 g) as off-white crystals. $^1$H NMR (600 MHz, DMSO-d6) δ ppm 7.82 (s, 1H), 7.16 (d, J=8.7 Hz, 4H), 6.87 (br d, J=8.3 Hz, 4H), 6.82 (s, 1H), 4.62-4.89 (m, 3H), 4.56 (br d, J=15.6 Hz, 2H), 4.39 (dd, J=10.7, 4.7 Hz, 1H), 4.12-4.25 (m, 1H), 4.05 (br d, J=13.4 Hz, 1H), 3.89-4.00 (m, 1H), 3.76-3.84 (m, 1H), 3.51-3.67 (m, 1H), 2.88-3.18 (m, 2H), 2.55-2.84 (m, 1H), 2.27-2.43 (m, 5H), 2.07-2.31 (m, 1H), 1.85-2.00 (m, 1H), 1.68 (br dd, J=13.3, 7.9 Hz, 3H), 1.42 (s, 9H), 1.28 (br d, J=6.6 Hz, 3H) ppm. HR-MS (ESI): calc. for C47H54ClF4N7O5 907.3811. found: 907.3808.

Example 12

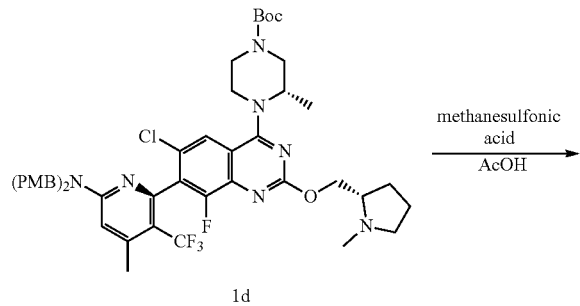

1d methanesulfonic acid
⟶
AcOH

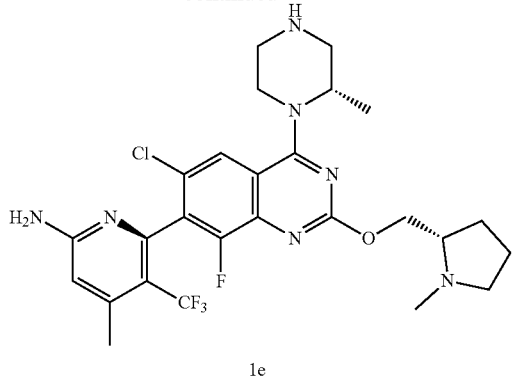

1e

To a mixture of acetic acid (46.2 g), methanesulfonic acid (52.9 g) and toluene (34.7 g) at 40° C. was added a solution of tert-butyl (3S)-4-[7-[6-[bis[(4-methoxyphenyl)methyl]amino]-4-methyl-3-(trifluoromethyl)-2-pyridyl]-6-chloro-8-fluoro-2-[[(2S)-1-methylpyrrolidin-2-yl]methoxy]quinazolin-4-yl]-3-methyl-piperazine-1-carboxylate (20.0 g, 22.0 mmol) in toluene (86.7 g) over at least 15 min. The reaction mixture was then heated to 52° C. until full conversion is achieved (typically 2 h). Then, the reaction mixture was cooled down to 25° C. and the layers separated. The acidic layer slowly quenched (typically over 1 h) over a mixture of aqueous sodium hydroxide (211.5 g, 28% w/w), water (80.0 g) and toluene (121.4 g) at 40° C. Upon completion of the quench, acetic acid (10.0 g) added to rinse the line. The biphasic mixture warmed up to 50° C. and the layers separated. The organic layer was washed two times with aqueous sodium hydroxide (2×90.0 g, 0.1N solution). Then, distillation under reduced pressure at constant volume (90 mbar; typically 69 g of toluene is exchanged) of the toluene layer was performed. After polish filtration, the resulting toluene solution was concentrated under reduced pressure (90 mbar) to a 94 mL solution, which was then warmed up to 60° C. Then, n-heptane (34.6 g) was added over at least 30 min and the solution was seeded at this temperature. The resulting mixture was further stirred at this temperature for at least 1 h and the crystal slurry was cooled down to 0° C. over at least 4 h and further stirred at this temperature for at least 1 h. The crystals were filtered off, washed with a solution of toluene/n-heptane (1:1 v/v) and dried under reduced pressure until constant weight was attained. The title compound was isolated in 89% yield (11.7 g) as off-white crystals. $^1$H NMR (600 MHz, DMSO-d6) δ ppm 7.74 (d, J=0.9 Hz, 1H), 6.84 (s, 2H), 6.49 (s, 1H), 4.54-4.65 (m, 1H), 4.38 (dd, J=10.8, 4.6 Hz, 1H), 4.14 (dd, J=10.7, 6.5 Hz, 1H), 3.96 (br d, J=13.1 Hz, 1H), 3.47-3.57 (m, 1H), 2.89-3.00 (m, 3H), 2.73-2.82 (m, 2H), 2.55-2.60 (m, 1H), 2.32-2.40 (m, 7H), 2.12-2.20 (m, 1H), 1.94 (dd, J=11.9, 7.6 Hz, 1H), 1.67 (br d, J=8.3 Hz, 3H), 1.40 (d, J=6.9 Hz, 3H) ppm. HR-MS (ESI): calc. for C26H30ClF4N7O 567.2136; found: 567.2141.

Example 13

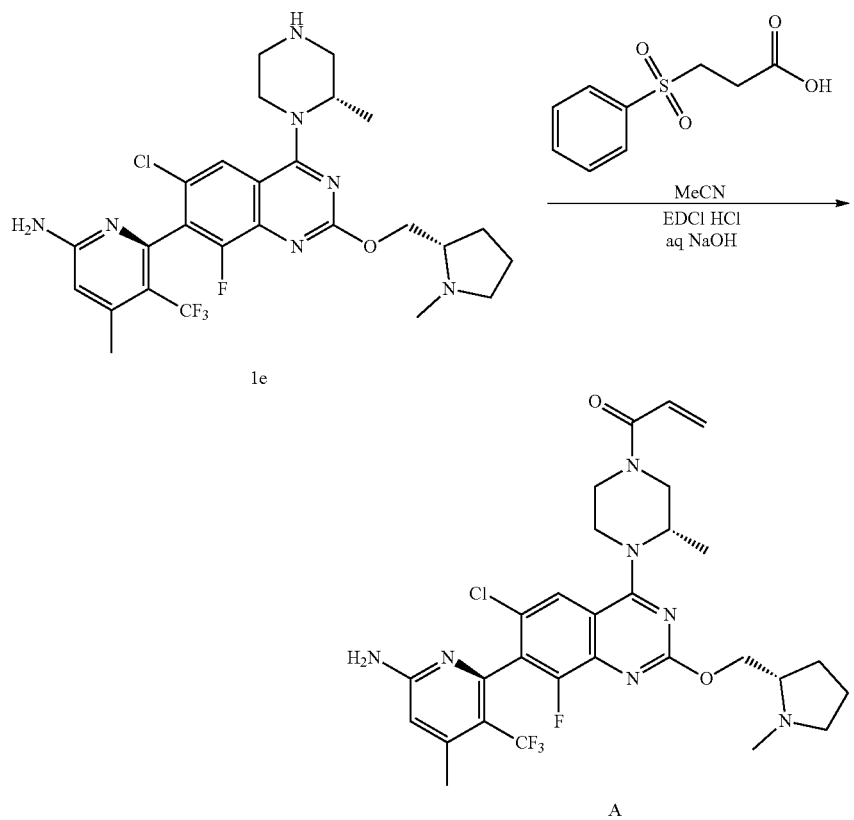

To a 250 mL round bottom flask equipped with overhead agitation and nitrogen line was charged Compound 1e (8.00 g, 14.1 mmol, 1.0 equiv), 3-(phenylsulfonyl)propanoic acid (3.66 g, 16.9 mmol, 1.20 equiv) and acetonitrile (48 mL, 6 v). The mixture was agitated for 5 min before N-(3-dimethylaminopropyl)-N'-ethylcarbodiimide hydrochloride (EDCl·HCl) (3.11 g, 16.2 mmol, 1.15 equiv) was added, and rinsed forward with acetonitrile (16 mL, 2 v). The reaction was stirred at 20° C. for a minimum of three h. Upon reaction completion to form sulfone intermediate, water (32 mL, 4 v) and sodium hydroxide pellets (1.60 g, 39.9 mmol, 2.85 equiv) were added to adjust to pH 13.0-13.5. The reaction mixture was stirred for a minimum of two hours to give Compound A, which was isolated by first adding water (24 mL, 3 v) and seed crystals (0.5 wt %). The precipitation was then completed by dosing more water (24 mL, 3 v) slowly over 2 h, aging at 20° C. for 2 h followed by dosing of water (64 mL, 8 v) slowly over 5 h. The resulting slurry was held at 20° C. for 2 h, filtered, washed with 1:1 acetonitrile/water (64 mL, 8 v) followed by water (64 mL, 8 v). Upon drying, Compound A (7.42 g) was obtained as an off-white solid in 89.6% yield (corrected for purity).

Example 14

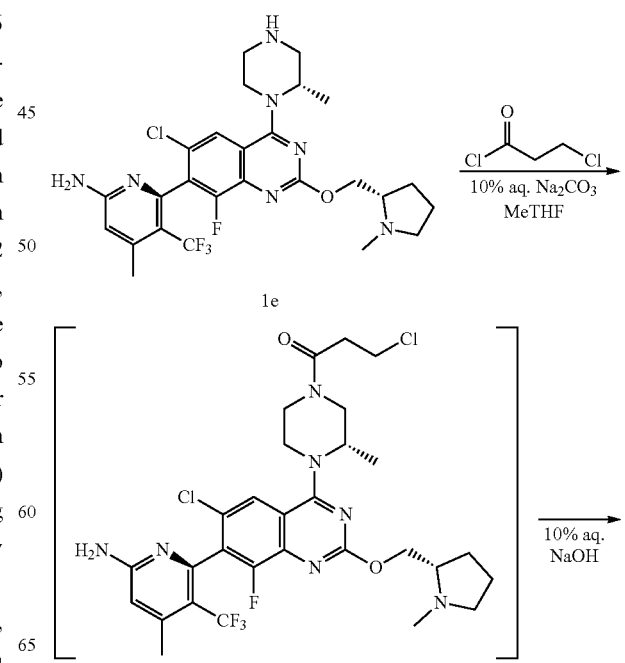

-continued

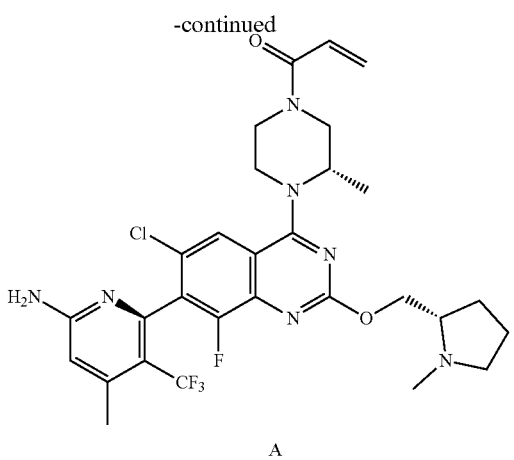

A

To a 400 mL reactor was added compound 1e (10.0 g, 17.6 mmol, 1.00 equiv) followed by 2-MeTHF (50.0 mL, 5 mL/g) and the material was stirred at rt until complete dissolution was observed. Next, 10% aq. Na₂CO₃ (50.0 mL, 5 mL/g) was added and the reactor was cooled to 0° C. (internal temperature control) and the overhead stirrer was set to 350 RPM. Once the internal temperature of the reactor reached 0° C., a solution of 3-chloropropionyl chloride (4.47 g, 35.2 mmol, 2.00 equiv) dissolved in MeTHF (50.0 mL, 5 mL/g) was added dropwise to the biphasic solution over 30 minutes while maintaining an internal temperature of 0° C. This mixture was then allowed to stir at 0° C. for 1 hour (97.8% conversion).

Next, a 10% aq. NaOH solution (50.0 mL/5 mL/g) was added and the reactor was set to 40° C. (internal temperature control) and stirred for 16 hours. Then, the reactor was cooled to 25° C. and the mixture was transferred to a 500 mL separatory funnel and the lower (aq) layer was removed. The upper (organic) layer was transferred back to the 400 mL reactor and a 10% aq. NaOH solution (50.0 mL/5 mL/g) was added and the reactor was set to 40° C. (internal temperature control) and stirred for 4 h (350 RPM). Then, the reactor was cooled to 25° C. and the mixture was transferred to a 500 mL separatory funnel and the lower (aq) layer was removed. Next, the organic layer was transferred to a 250 mL round bottom flask and concentrated to ~20 mL and refilled with 60 mL MeCN, this process was repeated 6 times and the solvent composition was checked via headspace GC (0.03% MeTHF after solvent swap). The mixture in the round bottom flask was then placed in a 5° C. fridge for two days, filtered and washed with two 20 mL portions of MeCN (pre-cooled to −10° C.).

The wetcake was then dried under vacuum with nitrogen sweep at ambient temperature for 24 h. Compound A was isolated in 69% yield (7.52 g, 12.1 mmol) as an off-white solid.

Example 15

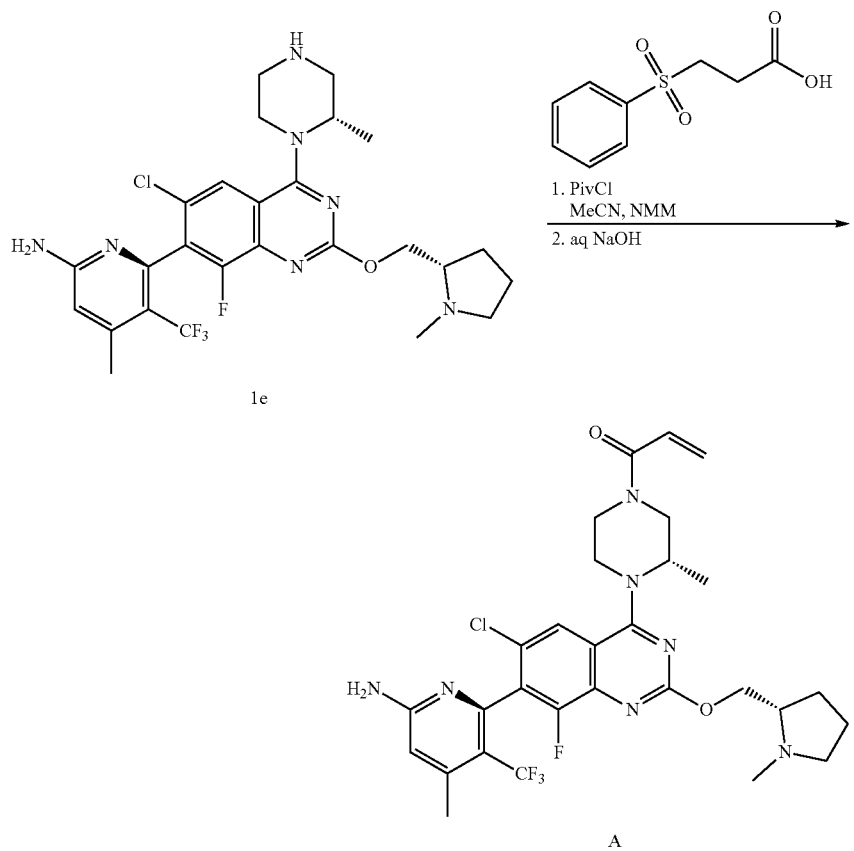

To a 250 mL round bottom flask equipped with overhead agitation and nitrogen line was charged 3-(phenylsulfonyl) propanoic acid (3.66 g, 16.9 mmol, 1.20 equiv), acetonitrile (32 mL, 4 v), N-methyl morpholine (2.33 mL, 21.1 mmol, 1.50 equiv) and a forward acetonitrile rinse (8 mL, 1 v). The mixture was cooled to −10° C. before pivaloyl chloride (1.90 mL, 15.5 mmol, 1.10 equiv) was added over 5 min, and rinsed forward with acetonitrile (8 mL, 1 v). The mixture was stirred at −10 C for a minimum of 1 h before adding Compound 1e (8.00 g, 14.1 mmol, 1.0 equiv), and rinsed forward with acetonitrile (8 mL, 1 v). The reaction was stirred at −10° C. for a minimum of 30 min. Upon reaction completion to form sulfone intermediate, the mixture was warmed to 20° C. Water (32 mL, 4 v) and sodium hydroxide pellets (2.11 g, 52.8 mmol, 3.75 equiv) were added to adjust to pH 13.0-13.5. The reaction mixture was stirred for a minimum of 2 h to give Compound A, which was isolated by first adding water (24 mL, 3 v) and seed crystals (0.5 wt %). The precipitation was then completed by dosing more water (24 mL, 3 v) slowly over 2 h, aging at 20° C. for 2 h followed by dosing of water (48 mL, 6 v) slowly over 4 h. The resulting slurry was held at 20° C. for 2 h, filtered, washed with 1:1 acetonitrile/water (64 mL, 8 v) followed by water (64 mL, 8 v). Upon drying, Compound A (7.10 g) was obtained as an off-white solid in 87.4% yield (corrected for purity).

Example 16

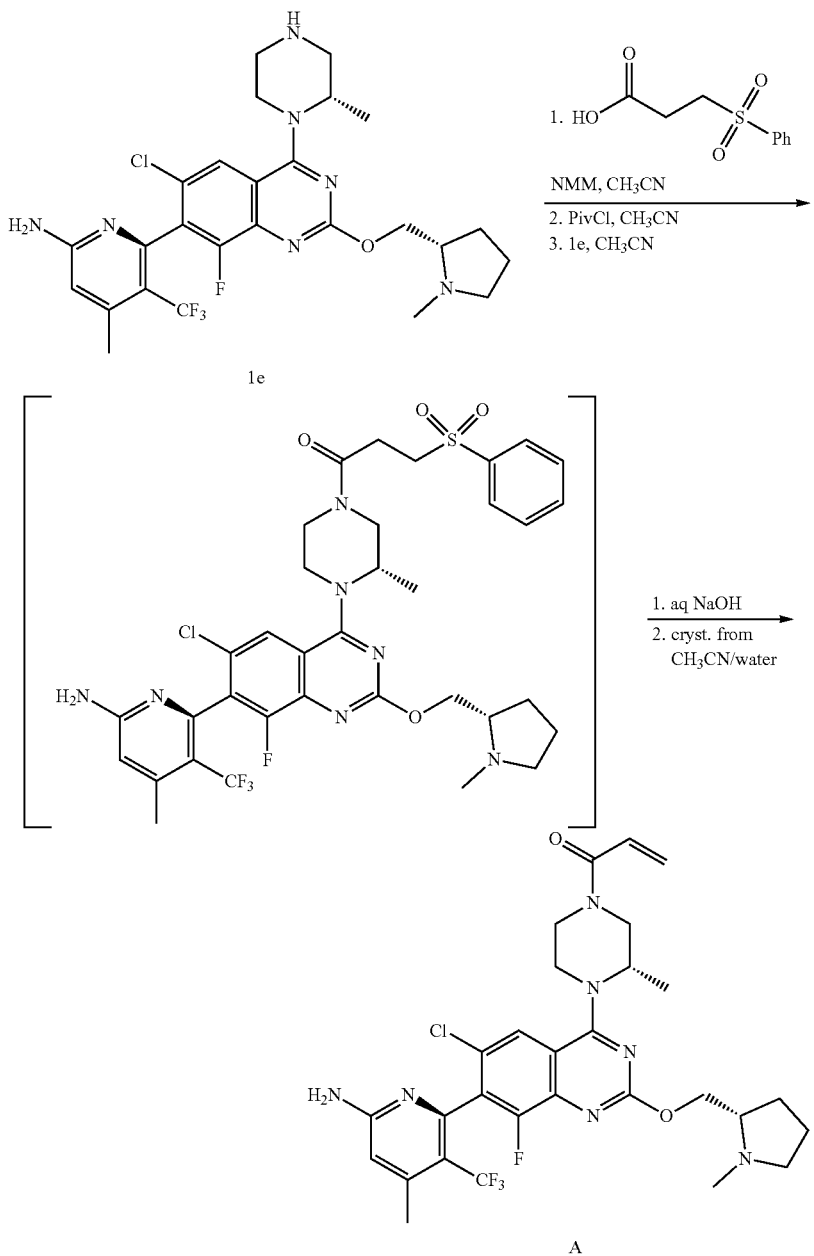

A solution of 3-(phenylsulfonyl)propionic acid (24.1 g, 112 mmol, 1.40 equiv), N-methylmorpholine (13.4 g, 133 mmol, 1.65 equiv) in acetonitrile (180.7 g) was cooled down to −10° C. Pivaloyl chloride (11.8 g, 97.9 mmol, 1.22 equiv.) was dosed over 30 min. The reaction mixture was further stirred for 1 h at this temperature. Then, a solution of 6-[6-chloro-8-fluoro-4-[(2S)-2-methylpiperazin-1-yl]-2-[[(2S)-1-methylpyrrolidin-2-yl]methoxy]quinazolin-7-yl]-4-methyl-5-(trifluoromethyl)pyridin-2-amine (50.0 g, 80.4 mmol, 1.00 equiv.) in acetonitrile (176.9 g) was added onto the cold reaction mixture over 1 h and further stirred at −10° C. until full conversion to the sulfone intermediate was achieved (typically 1 h). The reaction mixture was warmed up to 20° C. and quenched by the addition of water (62.5 g) and aqueous sodium hydroxide (51.7 g, 362 mmol, 4.5 equiv, 28% w/w solution). Stirring was continued until full conversion was obtained (typically 8 h) and the mixture was seeded followed by the addition of water (865 g) over at least 2 h. The crystal slurry was further stirred at this temperature for at least 4 h and the crystals were filtered off, washed with a solution of acetonitrile/water (3:7 v/v), washed with water and then dried under reduced pressure until constant weight was attained. The title compound was isolated in 91% yield (45.6 g) as off-white crystals. $^1$H NMR (600 MHz, DMSO-d6) δ 7.82 (s, 1H), 6.73-6.98 (m, 3H), 6.50 (s, 1H), 6.10-6.28 (m, 1H), 5.68-5.81 (m, 1H), 4.66-4.85 (m, 1H), 4.32-4.46 (m, 1H), 4.25 (br d, J=13.5 Hz, 1H), 4.06-4.21 (m, 2H), 3.98 (br d, J=13.4 Hz, 1H), 3.38-3.76 (m, 2H), 2.91-3.27 (m, 2H), 2.53-2.68 (m, 1H), 2.37 (br d, J=1.4 Hz, 6H), 2.11-2.26 (m, 1H), 1.87-2.00 (m, 1H), 1.56-1.79 (m, 3H), 1.27 (br dd, J=11.7, 6.7 Hz, 3H) ppm. HR-MS (ESI): calc. for C29H32ClF4N7O2 621.2242. found: 621.2257.

To the solution of Compound 1e (3.02 kg, 5.32 mol, 1.0 equiv) in DCM (in 100 L reactor) was charged DIPEA (2.05 kg, 15.86 mol, 2.98 equiv). The mixture was cooled to −25° C., and a solution of acrylic anhydride (0.87 kg, 6.90 mol, 1.30 equiv) in DCM (28.30 kg, 7V) was slowly added over 140 min while maintaining the temperature below −20° C. The reaction mixture was agitated for a minimum of 10 min, warmed to 5° C. and quenched with 10 wt % aqueous potassium bicarbonate solution (12.1 kg, 4V).

The organic layer was washed with 20 wt % aqueous ammonium chloride solution (12.2 kg, 4V), followed by 10 wt % aqueous solution of monobasic potassium phosphate and dried with magnesium sulfate (1.50 kg, 50 wt %). The slurry was filtered and rinsed with DCM (8.05 kg, 2V) before passed through CUNO filter housing containing E-Pak Graver C-941 (850 g). The filtrate was then concentrated to 19 L (6V) and diluted with acetonitrile (9.60 kg, 4V). The solution was transferred to a 25 L reactor through in-line polish filter. Distillation was continued to remove DCM while replacing with acetonitrile (8.80 kg, 4V) to reach a final volume of 18 L before cooling the thick slurry to 0° C. After holding at 0° C. for a minimum of 3 h, the slurry was filtered, rinsed with pre-cooled (temperature=0° C.) acetonitrile (4.65 kg, 2V) and dried at 20° C. to give Compound A (2.32 kg) in 69.7% yield. $^1$H NMR (400 MHz, DMSO-d$_6$) δ 7.84 (d, J=1.6 Hz, 1H), 6.87 (s, 2H), 6.83 (m, 1H), 6.52 (m, 1H), 6.20 (dd, J=16.8, 6.8 Hz, 1H), 5.75 (dd, J=10.4, 2.4 Hz, 1H), 4.76 (m, 1H), 4.41 (dd, J=10.8, 4.7 Hz, 1H), 4.24 (m, 1H), 4.18 (dd, J=10.8, 6.5 Hz, 1H), 4.13 (m, 2H), 3.67 (m, 1H), 3.47 (m, 1H), 3.25 (m, 1H), 2.95 (m, 1H), 2.58 (m, 1H), 2.39 (m, 3H), 2.37 (s, 3H), 2.17 (m, 1H), 1.94 (m, 1H), 1.68 (m, 3H), 1.29 (t, J=6.6 Hz, 3H); $^{13}$C NMR Example 17

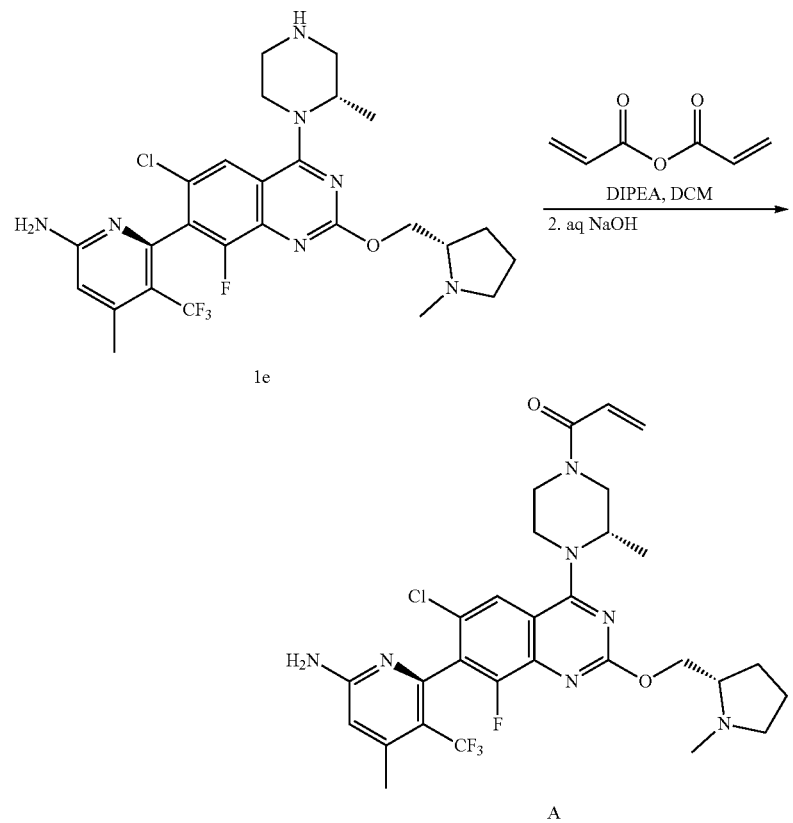

(101 MHz, DMSO-$d_6$): δ 165.4, 164.8, 164.7, 162.2, 161.3, 154.4, 151.8, 148.7, 148.7, 147.6, 143.0, 142.8, 131.1, 130.9, 129.6, 128.4, 128.4, 128.3, 128.2, 128.1, 126.9, 125.2, 125.2, 124.2, 121.5, 120.9, 120.9, 114.6, 114.6, 112.5, 112.2, 111.9, 111.7, 110.5, 69.8, 63.8, 57.4, 52.4, 52.3, 49.3, 45.8, 45.1, 44.8, 44.2, 42.0, 41.6, 40.6, 40.4, 40.2, 40.0, 39.8, 39.6, 39.4, 29.0, 23.1, 20.3, 20.2, 15.8, 15.2; $^{19}$F NMR (376 MHz, DMSO-$d_6$): δ −53.7, −125.9.

Example 18

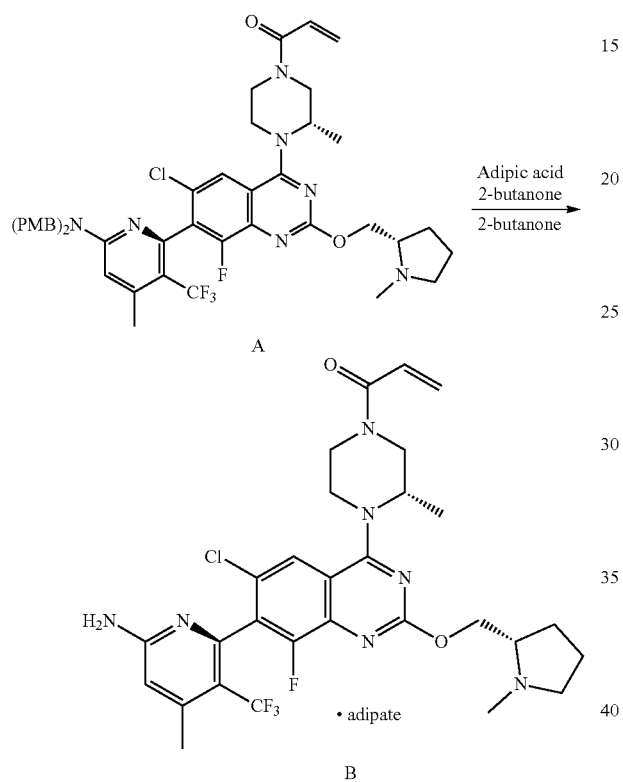

To a 25 L reactor equipped with an active nitrogen line, overhead agitation, and temperature probe was combined Compound A (2.32 kg, 3.53 mol) and polish-filtered 2-butanone (17.42 L, 7.5 L/kg). In a separate 5 L glass bottle was charged adipic acid (0.46 kg, 3.17 mol, 0.9 equiv) and polish-filtered 2-butanone (1.16 L, 0.5 L/kg). The reactor was then heated to 50° C.±10° C. and upon reaching the desired internal temperature target of >45° C., the adipic acid slurry in 2-butanone was charged to the reactor by vacuum pull. Compound B seeds (0.02 kg, 1 wt %) were charged to the 5 L glass bottle followed by polish-filtered butanone (2.32 L, 1.0 L/kg). Again, the slurry was charged to the reactor by vacuum pull. Finally, the 5 L glass bottle was rinsed with polish-filtered 2-butanone (1.16 L, 0.5 L/kg) then charged to the reactor via vacuum pull. The reactor contents were aged for a minimum of 1 h, cooled to 0° C. over a minimum of 2 h, then aged at 0° C. overnight (15 h). The contents were transferred to the pre-cooled filter dryer at 0° C. In parallel, polish-filtered 2-butanone (9.29 L, 4.0 L/kg) was charged to the reactor at 0° C. then stirred for 30 min. The material in the filter dryer was then filtered and the resulting cake washed with the chilled 2-butanone. After drying for a minimum of 8 h with vacuum pull and nitrogen sweep, the filter dryer contents were discharged to afford Compound B (2.137 kg, 77%) as an off-white solid. $^1$H NMR (600 MHz, DMSO-$d_6$) δ 7.77 (s, 1H), 6.81 (s, 2H), 6.76 (dd, J=16.8, 10.6 Hz, 1H), 6.45 (s, 1H), 6.18-6.10 (m, 1H), 5.70 (dd, J=10.4, 2.3 Hz, 1H), 4.75-4.66 (m, 1H), 4.38-4.30 (m, 2H), 4.25-3.89 (m, 4H), 3.61 (dq, J=21.3, 12.4, 10.9 Hz, 2H), 3.20 (dd, J=13.4, 3.8 Hz, 1H), 3.00 (td, J=12.6, 3.7 Hz, 1H), 2.91 (ddd, J=9.0, 6.0, 2.8 Hz, 1H), 2.59-2.51 (m, 1H), 2.32 (d, J=6.2 Hz, 6H), 2.15 (td, J=8.6, 7.7, 4.7 Hz, 5H), 1.94-1.85 (m, 1H), 1.61 (dddd, J=20.8, 12.3, 8.0, 4.1 Hz, 3H), 1.45 (h, J=3.4 Hz, 4H), 1.22 (dd, J=12.4, 6.6 Hz, 3H); $^{13}$C{$^1$H, $^{19}$F} NMR (151 MHz, DMSO-$d_6$) δ 174.9, 165.5, 164.8, 162.2, 161.4, 153.2, 148.8, 147.7, 143.0, 131.1, 128.5, 128.4, 128.3, 128.2, 125.6, 125.3, 121.0, 114.7, 112.2, 110.5, 69.8, 63.9, 57.4, 52.5, 52.4, 49.4, 45.9, 45.2, 44.9, 44.3, 42.0, 41.7, 40.6, 34.0, 29.1, 24.6, 23.1, 20.3, 15.9, 15.3; $^{19}$F NMR (565 MHz, DMSO-$d_6$) δ −53.5, −125.9.

Example 19

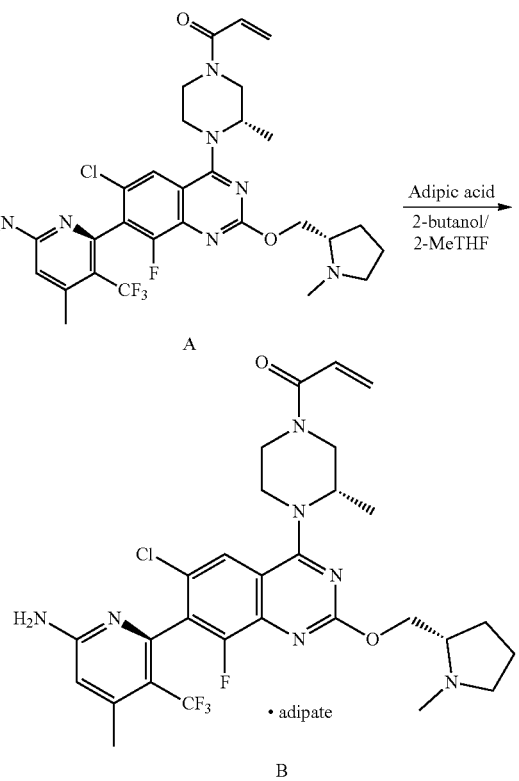

Compound A (1 mol-equiv) and adipic acid (1 mol-equiv) were suspended in 2-butanol and 2-methyltetrahydrofuran and dissolved upon heating to about 70° C. The polish-filtered solution was cooled to approx. 25° C. For seeding jet-milled Compound B material was used. Seeding material Compound B material suspended in 2-butanol/n-heptane. This suspension was used for seeding the solution at approx. 25° C. The seeding equipment was rinsed with n-heptane which then was added to the seeded suspension. N-Heptane was added at approx. 25° C. within 15-30 min. The suspension was stirred at approx. 25° C. for approx. 3 hours. The suspension was cooled to approx. 0° C. and stirred for at least 5 hours. The solid was isolated by solid/liquid separation and rinsed with a mixture of 2-butanol/n-heptane followed by n-heptane. The solid was dried at approx. 40° C. under reduced pressure to yield a white to off-white powder in a yield of 88-95%.

In another procedure, Compound A (1 mol-equiv) and adipic acid (1 mol-equiv or an excess) were suspended in 2-butanol and 2-methyltetrahydrofuran and dissolved upon heating, to about 70° C. The polish-filtered solution was cooled to the seeding temperature (about 25° C.). For seeding Compound B was used either without pretreatment, or after impact-milling, jet-milling, or wet-milling. Seeding material Compound B was suspended in a solvent (n-heptane, or 2-butanol/n-heptane mixtures, or 2-butanol). This suspension was used for seeding at the seeding temperature. The seeding equipment was rinsed with solvent (n-heptane, or 2-butanol/n-heptane mixtures, or 2-butanol, respectively) which then was added to the seeded suspension. N-Heptane was added at the seeding temperature or at a lower temperature (typically, at approx. 25° C.) for about 15-30 min. The suspension was stirred at the temperature of n-heptane addition for at least 3 hours. The suspension was cooled to approx. 0° C. and stirred for at least 5 hours. The solid was isolated by solid/liquid separation and rinsed with a mixture of 2-butanol/n-heptane followed by n-heptane. The solid was dried at approx. 40° C. under reduced pressure to yield a white to off-white powder in a yield of 88-95%.

Example 20: Cyclohexane Crystalline Solvate Compound 1

X-ray quality crystals were grown from a hot cyclohexane solution that was allowed to slowly cool to room temperature and sit for 72 hours to deposit the crystal diffracted. A colorless rod 0.110×0.090×0.050 mm in size was mounted on a Cryoloop with Paratone oil. Data were collected in a nitrogen gas stream at 90(2) K using phi and omega scans. Crystal-to-detector distance was 40 mm and exposure time was 0.15 seconds per frame using a scan width of 0.5°. Data collection was 100.0% complete to 67.000° in θ. A total of 112434 reflections were collected covering the indices, −11<=h<=11, −16<=k<=17, −40<=l<=41. 8888 reflections were found to be symmetry independent, with an $R_{int}$ of 0.0352. Indexing and unit cell refinement indicated a primitive, orthorhombic lattice. The space group was found to be P 21 21 21 (No. 19). The data were integrated and scaled using CrysAlisPro 1.171.41.72a. Solution by iterative methods (SHELXT-2014) produced a complete heavy-atom phasing model. All non-hydrogen atoms were refined anisotropically by full-matrix least-squares (SHELXL-2018). All hydrogen atoms were placed using a riding model. Their positions were constrained relative to their parent atom using the appropriate HFIX command in SHELXL-2018. Absolute stereochemistry was unambiguously determined to be S at all chiral centers.

TABLE 2

Crystal data and structure refinement for cyclohexane solvate.

| Identification code | cyclohexane solvate |
|---|---|
| Empirical formula | C47 H54 Cl F5 N6 O4 |
| Formula weight | 897.41 |
| Temperature | 90(2) K |
| Wavelength | 1.54184 Å |
| Crystal system | Orthorhombic |
| Space group | P 21 21 21 |

TABLE 2-continued

Crystal data and structure refinement for cyclohexane solvate.

| Identification code | cyclohexane solvate |
|---|---|
| Unit cell dimensions | a = 9.83870(10) Å α = 90°. |
| | b = 13.66880(10) Å β = 90°. |
| | c = 33.36080(10) Å γ = 90°. |
| Volume | 4486.47(6) Å$^3$ |
| Z | 4 |
| Density (calculated) | 1.329 Mg/m$^3$ |
| Absorption coefficient | 1.359 mm$^{-1}$ |
| F (000) | 1888 |
| Crystal size | 0.110 × 0.090 × 0.050 mm$^3$ |
| Theta range for data collection | 2.649 to 75.169°. |
| Index ranges | −11 <= h <= 11, −16 <= k <= 17, −40 <= l <= 41 |
| Reflections collected | 112434 |
| Independent reflections | 8888 [R(int) = 0.0352] |
| Completeness to theta = 67.000° | 100.0% |
| Absorption correction | Gaussian |
| Max. and min. transmission | 1.000 and 0.880 |
| Refinement method | Full-matrix least-squares on F$^2$ |
| Data/restraints/parameters | 8888/0/575 |
| Goodness-of-fit on F$^2$ | 1.062 |
| Final R indices [I >2 sigma(I)] | R1 = 0.0248, wR2 = 0.0632 |
| R indices (all data) | R1 = 0.0253, wR2 = 0.0635 |
| Absolute structure parameter | 0.003 (2) |
| Extinction coefficient | n/a |
| Largest diff. peak and hole | 0.188 and −0.155 e.Å$^{-3}$ |

Example 21: Methylcyclohexane Crystalline Solvate Compound 1

X-ray quality crystals were grown from a hot methylcyclohexane solution that was allowed to slowly cool to room temperature and sit for 48 hours. A colorless prism 0.206×0.097×0.068 mm in size was mounted on a Cryoloop with Paratone oil. Data were collected in a nitrogen gas stream at 90(2) K using phi and omega scans. Crystal-to-detector distance was 40 mm and exposure time was 0.1 seconds per frame using a scan width of 0.5°. Data collection was 100.0% complete to 67.000° in θ. A total of 128902 reflections were collected covering the indices, −17<=h<=17, −11<=k<=12, −41<=l<=40. 17535 reflections were found to be symmetry independent, with an $R_{int}$ of 0.0912. Indexing and unit cell refinement indicated a primitive, monoclinic lattice. The space group was found to be P 21 (No. 4). The data were integrated and scaled using CrysAlisPro 1.171.41.72a. Solution by iterative methods (SHELXT-2014) produced a complete heavy-atom phasing model. All non-hydrogen atoms were refined anisotropically by full-matrix least-squares (SHELXL-2018). All hydrogen atoms were placed using a riding model. Their positions were constrained relative to their parent atom using the appropriate HFIX command in SHELXL-2018. Absolute stereochemistry was unambiguously determined to be S at all chiral centers.

TABLE 3

Crystal data and structure refinement for methylcyclohexane solvate.

| Identification code | methylcyclohexane solvate |
|---|---|
| Empirical formula | C48 H56 Cl F5 N6 O4 |
| Formula weight | 911.43 |
| Temperature | 90(2) K |
| Wavelength | 1.54184 Å |
| Crystal system | Monoclinic |
| Space group | P21 |

TABLE 3-continued

Crystal data and structure refinement for methylcyclohexane solvate.

| Identification code | methylcyclohexane solvate |
|---|---|
| Unit cell dimensions | a = 13.7661(2) Å α = 90°. |
| | b = 9.8704(2) Å β = 90.473(2)°. |
| | c = 33.4547(6) Å γ = 90°. |
| Volume | 4545.57(14) Å$^3$ |
| Z | 4 |
| Density (calculated) | 1.332 Mg/m$^3$ |
| Absorption coefficient | 1.350 mm$^{-1}$ |
| F(000) | 1920 |
| Crystal size | 0.206 × 0.097 × 0.068 mm$^3$ |
| Theta range for data collection | 2.642 to 75.168°. |
| Index ranges | −17 <= h <= 17, −11 <= k <= 12, −41 <= l <= 40 |
| Reflections collected | 128902 |
| Independent reflections | 17535 [R(int) = 0.0912] |
| Completeness to theta = 67.000° | 100.0% |
| Absorption correction | Gaussian |
| Max. and min. transmission | 1.000 and 0.708 |
| Refinement method | Full-matrix least-squares on F$^2$ |
| Data/restraints/parameters | 17535/12/1128 |
| Goodness-of-fit on F$^2$ | 1.067 |
| Final R indices [I >2 sigma(I)] | R1 = 0.0666, wR2 = 0.1773 |
| R indices (all data) | R1 = 0.0684, wR2 = 0.1810 |
| Absolute structure parameter | −0.010(9) |
| Extinction coefficient | n/a |
| Largest diff. peak and hole | 0.704 and −0.636 e.Å$^{-3}$ |

Example 22: Chlorobenzene Crystalline Solvate Compound 1

X-ray quality crystals were grown from a saturated chlorobenzene solution followed by the slow vapor diffusion of heptane to deposit the crystal diffracted. A colorless prism 0.130×0.110×0.060 mm in size was mounted on a Cryoloop with Paratone oil. Data were collected in a nitrogen gas stream at 90(2) K using phi and omega scans. Crystal-to-detector distance was 40 mm and exposure time was 0.05 seconds per frame using a scan width of 0.5°. Data collection was 100.0% complete to 67.000° in θ. A total of 110828 reflections were collected covering the indices, −12<=h<=12, −16<=k<=16, −41<=l<=41. 8734 reflections were found to be symmetry independent, with an R$_{int}$ of 0.0384. Indexing and unit cell refinement indicated a primitive, orthorhombic lattice. The space group was found to be P 21 21 21 (No. 19). The data were integrated and scaled using CrysAlisPro 1.171.41.71a. Solution by iterative methods (SHELXT-2014) produced a complete heavy-atom phasing model. All non-hydrogen atoms were refined anisotropically by full-matrix least-squares (SHELXL-2018). All hydrogen atoms were placed using a riding model. Their positions were constrained relative to their parent atom using the appropriate HFIX command in SHELXL-2018. Absolute stereochemistry was unambiguously determined to be S at all chiral centers.

TABLE 4

Crystal data and structure refinement for chlorobenzene solvate

| Identification code | chlorobenzene solvate |
|---|---|
| Empirical formula | C47 H47 Cl2 F5 N6 O4 |
| Formula weight | 925.80 |
| Temperature | 90(2) K |
| Wavelength | 1.54184 Å |
| Crystal system | Orthorhombic |
| Space group | P 21 21 21 |

TABLE 4-continued

Crystal data and structure refinement for chlorobenzene solvate

| Identification code | chlorobenzene solvate |
|---|---|
| Unit cell dimensions | a = 9.93180(10) Å α = 90°. |
| | b = 13.17100(10) Å β = 90°. |
| | c = 33.7092(2) Å γ = 90°. |
| Volume | 4409.56(6) Å$^3$ |
| Z | 4 |
| Density (calculated) | 1.395 Mg/m$^3$ |
| Absorption coefficient | 1.949 mm$^{-1}$ |
| F(000) | 1928 |
| Crystal size | 0.130 × 0.110 × 0.060 mm$^3$ |
| Theta range for data collection | 2.622 to 75.118°. |
| Index ranges | −12 <= h <= 12, −16 <= k <= 16, −41 <= l <= 41 |
| Reflections collected | 110828 |
| Independent reflections | 8734 [R(int) = 0.0384] |
| Completeness to theta = 67.000° | 100.0% |
| Absorption correction | Gaussian |
| Max. and min. transmission | 1.000 and 0.792 |
| Refinement method | Full-matrix least-squares on F$^2$ |
| Data/restraints/parameters | 8734/0/626 |
| Goodness-of-fit on F$^2$ | 1.028 |
| Final R indices [I >2 sigma(I)] | R1 = 0.0381, wR2 = 0.0936 |
| R indices (all data) | R1 = 0.0389, wR2 = 0.0943 |
| Absolute structure parameter | 0.003(3) |
| Extinction coefficient | n/a |
| Largest diff. peak and hole | 0.488 and −0.479 e.Å$^{-3}$ |

Example 23: Ethylbenzene Crystalline Solvate Compound 1

X-ray quality crystals were grown from a saturated ethylbenzene solution followed by the slow vapor diffusion of heptane to deposit the crystal diffracted. A colorless prism 0.162×0.103×0.067 mm in size was mounted on a Cryoloop with Paratone oil. Data were collected in a nitrogen gas stream at 90(2) K using phi and omega scans. Crystal-to-detector distance was 40 mm and exposure time was 0.25 seconds per frame using a scan width of 0.5°. Data collection was 100.0% complete to 67.000° in θ. A total of 20385 reflections were collected covering the indices, −16<=h<=16, −12<=k<=12, −42<=l<=42. 20385 reflections were found to be symmetry independent, with an R$_{int}$ of 0.1540. Indexing and unit cell refinement indicated a primitive, monoclinic lattice. The space group was found to be P 21 (No. 4). The data were integrated and scaled using CrysAlisPro 1.171.41.71a. Solution by iterative methods (SHELXT-2014) produced a complete heavy-atom phasing model. All non-hydrogen atoms were refined anisotropically by full-matrix least-squares (SHELXL-2018). All hydrogen atoms were placed using a riding model. Their positions were constrained relative to their parent atom using the appropriate HFIX command in SHELXL-2018. Absolute stereochemistry was unambiguously determined to be S at all chiral centers.

TABLE 5

Crystal data and structure refinement for ethylbenzene solvate

| Identification code | ethylbenzene |
|---|---|
| Empirical formula | C49 H52 Cl F5 N6 O4 |
| Formula weight | 919.41 |
| Temperature | 90(2) K |
| Wavelength | 1.54184 Å |

TABLE 5-continued

Crystal data and structure refinement for ethylbenzene solvate

| Identification code | ethylbenzene |
|---|---|
| Crystal system | Monoclinic |
| Space group | P21 |
| Unit cell dimensions | a = 13.4759(2) Å α = 90°. |
| | b = 9.93500(10) Å β = 91.7320(10)°. |
| | c = 33.8955(4) Å γ = 90°. |
| Volume | 4535.96(10) Å$^3$ |
| Z | 4 |
| Density (calculated) | 1.346 Mg/m$^3$ |
| Absorption coefficient | 1.360 mm$^{-1}$ |
| F(000) | 1928 |
| Crystal size | 0.162 × 0.103 × 0.067 mm$^3$ |
| Theta range for data collection | 2.608 to 75.040°. |
| Index ranges | −16 <= h <= 16, −12 <= k <= 12, |
| | −42 <= l <= 42 |
| Reflections collected | 20385 |
| Independent reflections | 20385 [R(int) = 0.1540] |
| Completeness to theta = 67.000° | 100.0% |
| Absorption correction | Gaussian |
| Max. and min. transmission | 1.000 and 0.760 |
| Refinement method | Full-matrix least-squares on F$^2$ |
| Data/restraints/parameters | 20385/1/1188 |
| Goodness-of-fit on F$^2$ | 1.047 |
| Final R indices [I >2 sigma(I)] | R1 = 0.0538, wR2 = 0.1519 |
| R indices (all data) | R1 = 0.0544, wR2 = 0.1531 |
| Absolute structure parameter | 0.000(13) |
| Extinction coefficient | n/a |
| Largest diff. peak and hole | 0.725 and −0.362 e.Å$^{-3}$ |

Example 24: m-Xylene Crystalline Solvate Compound 1

X-ray quality crystals were grown from a saturated m-xylene solution followed by the slow vapor diffusion of heptane to deposit the crystal diffracted. A colorless prism 0.190×0.170×0.130 mm in size was mounted on a Cryoloop with Paratone oil. Data were collected in a nitrogen gas stream at 90(2) K using phi and omega scans. Crystal-to-detector distance was 40 mm and exposure time was 0.1 seconds per frame using a scan width of 0.5°. Data collection was 100.0% complete to 67.000° in θ. A total of 115184 reflections were collected covering the indices, −11<=h<=12, −16<=k<=16, −40<=l<=40. 8996 reflections were found to be symmetry independent, with an R$_{int}$ of 0.0373. Indexing and unit cell refinement indicated a primitive, orthorhombic lattice. The space group was found to be P 21 21 21 (No. 19). The data were integrated and scaled using CrysAlisPro 1.171.41.71a. Solution by iterative methods (SHELXT-2014) produced a complete heavy-atom phasing model. All non-hydrogen atoms were refined anisotropically by full-matrix least-squares (SHELXL-2018). All hydrogen atoms were placed using a riding model. Their positions were constrained relative to their parent atom using the appropriate HFIX command in SHELXL-2018. Absolute stereochemistry was determined to be S at O12.

TABLE 6

Crystal data and structure refinement for m-xylene solvate

| Identification code | m-xylene solvate |
|---|---|
| Empirical formula | C49 H52 Cl F5 N6 O4 |
| Formula weight | 919.41 |
| Temperature | 90(2) K |
| Wavelength | 1.54184 Å |
| Crystal system | Orthorhombic |
| Space group | P 21 21 21 |

TABLE 6-continued

Crystal data and structure refinement for m-xylene solvate

| Identification code | m-xylene solvate |
|---|---|
| Unit cell dimensions | a = 9.97450(10) Å α = 90°. |
| | b = 13.72000(10) Å β = 90°. |
| | c = 33.30730(10) Å γ = 90°. |
| Volume | 4558.11(4) Å$^3$ |
| Z | 4 |
| Density (calculated) | 1.340 Mg/m$^3$ |
| Absorption coefficient | 1.353 mm$^{-1}$ |
| F(000) | 1928 |
| Crystal size | 0.190 × 0.170 × 0.130 mm$^3$ |
| Theta range for data collection | 2.653 to 75.116°. |
| Index ranges | −11 <= h <= 12, −16 <= k <= 16, |
| | −40 <= l <= 40 |
| Reflections collected | 115184 |
| Independent reflections | 8996 [R(int) = 0.0373] |
| Completeness to theta = 67.000° | 100.0% |
| Absorption correction | Gaussian |
| Max. and min. transmission | 1.000 and 0.620 |
| Refinement method | Full-matrix least-squares on F$^2$ |
| Data/restraints/parameters | 8996/0/595 |
| Goodness-of-fit on F$^2$ | 1.020 |
| Final R indices [I >2 sigma(I)] | R1 = 0.0252, wR2 = 0.0672 |
| R indices (all data) | R1 = 0.0256, wR2 = 0.0675 |
| Absolute structure parameter | 0.003(2) |
| Extinction coefficient | n/a |
| Largest diff. peak and hole | 0.239 and −0.200 e.Å$^{-3}$ |

Example 25: Toluene Crystalline Solvate Compound 1

X-ray quality crystals were grown from a saturated toluene solution followed by the slow vapor diffusion of heptane to deposit the crystal diffracted. A colorless prism 0.150×0.130×0.110 mm in size was mounted on a Cryoloop with Paratone oil. Data were collected in a nitrogen gas stream at 90(2) K using phi and omega scans. Crystal-to-detector distance was 40 mm and exposure time was 0.1 seconds per frame using a scan width of 0.5°. Data collection was 100.0% complete to 67.000° in θ. A total of 329491 reflections were collected covering the indices, −12<=h<=12, −41<=k<=41, −50<=l<=49. 26769 reflections were found to be symmetry independent, with an R$_{int}$ of 0.0335. Indexing and unit cell refinement indicated a primitive, orthorhombic lattice. The space group was found to be P 21 21 21 (No. 19). The data were integrated and scaled using CrysAlisPro 1.171.41.70a. Solution by iterative methods (SHELXT-2014) produced a complete heavy-atom phasing model. All non-hydrogen atoms were refined anisotropically by full-matrix least-squares (SHELXL-2018). All hydrogen atoms were placed using a riding model. Their positions were constrained relative to their parent atom using the appropriate HFIX command in SHELXL-2018. Absolute stereochemistry was unambiguously determined to be S at all chiral centers.

TABLE 7

Crystal data and structure refinement for toluene solvate

| Identification code | toluene |
|---|---|
| Empirical formula | C48 H50 Cl F5 N6 O4 |
| Formula weight | 905.39 |
| Temperature | 90(2) K |
| Wavelength | 1.54184 Å |
| Crystal system | Orthorhombic |
| Space group | P 21 21 21 |

TABLE 7-continued

Crystal data and structure refinement for toluene solvate

| Identification code | toluene |
|---|---|
| Unit cell dimensions | a = 9.90500(1) Å α = 90°. |
| | b = 33.55390(10) Å β = 90°. |
| | c = 40.28230(10) Å γ = 90°. |
| Volume | 13387.88(5) Å$^3$ |
| Z | 12 |
| Density (calculated) | 1.348 Mg/m$^3$ |
| Absorption coefficient | 1.374 mm$^{-1}$ |
| F(000) | 5688 |
| Crystal size | 0.150 × 0.130 × 0.110 mm$^3$ |
| Theta range for data collection | 2.194 to 75.133°. |
| Index ranges | −12 <= h <= 12, −41 <= k <= 41, |
| | −50 <= l <= 49 |
| Reflections collected | 329491 |
| Independent reflections | 26769 [R(int) = 0.0335] |
| Completeness to theta = 67.000° | 100.0% |
| Absorption correction | Gaussian |
| Max. and min. transmission | 1.000 and 0.839 |
| Refinement method | Full-matrix least-squares on F$^2$ |
| Data/restraints/parameters | 26769/0/1753 |
| Goodness-of-fit on F$^2$ | 1.024 |
| Final R indices [I >2 sigma(I)] | R1 = 0.0321, wR2 = 0.0950 |
| R indices (all data) | R1 = 0.0330, wR2 = 0.0968 |
| Absolute structure parameter | 0.0022(16) |
| Extinction coefficient | n/a |
| Largest diff. peak and hole | 0.525 and −0.265 e.Å$^{-3}$ |

All technical and scientific terms used herein have the same meaning. Efforts have been made to ensure accuracy with respect to numbers used (e.g. amounts, temperature, etc.) but some experimental errors and deviations should be accounted for.

Throughout this specification and the claims, the words "comprise," "comprises," and "comprising" are used in a non-exclusive sense, except where the context requires otherwise. It is understood that embodiments described herein include "consisting of" and/or "consisting essentially of" embodiments.

Where a range of values is provided, it is understood that each intervening value, to the tenth of the unit of the lower limit, unless the context clearly dictates otherwise, between the upper and lower limit of the range and any other stated or intervening value in that stated range, is encompassed herein. The upper and lower limits of these small ranges which can independently be included in the smaller rangers is also encompassed herein, subject to any specifically excluded limit in the stated range. Where the stated range includes one or both of the limits, ranges excluding either or both of those included limits are also included herein.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation.

What is claimed is:

1. A process for the preparation of a compound or a solvate, tautomer, stereoisomer, or salt thereof of formula;

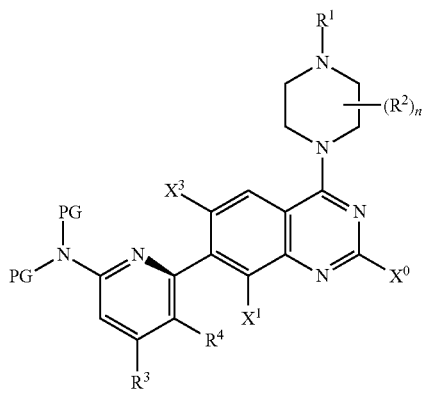

wherein;

$X^0$ is hydrogen, halogen, OR$^{5A}$, or R$^5$-substituted or unsubstituted C$_{1-6}$ haloalkyl;

$X^1$ is hydrogen or halogen;

$X^3$ is hydrogen, halogen, R$^6$-substituted or unsubstituted C$_{1-3}$ alkyl, R$^6$-substituted or unsubstituted C$_{1-3}$ haloalkyl, R$^6$-substituted or unsubstituted C$_{1-3}$ alkoxy, or R$^6$-substituted or unsubstituted cyclopropyl;

$R^1$ is hydrogen or PG$^1$;

each $R^2$ is independently halogen, cyano, unsubstituted C$_{1-6}$ alkyl, unsubstituted C$_{1-6}$ cyanoalkyl, or unsubstituted C$_{1-6}$ haloalkyl;

$R^3$ is hydrogen, halogen, R$^{3A}$-substituted or unsubstituted C$_{1-3}$ alkyl, R$^{3A}$-substituted or unsubstituted C$_{1-3}$ haloalkyl, or R$^{3A}$-substituted or unsubstituted C$_{3-6}$ cycloalkyl;

$R^{3A}$ is halogen, OH, CN, unsubstituted C$_{1-3}$ alkyl or unsubstituted C$_{1-3}$ haloalkyl;

$R^4$ is R$^{4A}$-substituted or unsubstituted C$_{1-3}$ haloalkyl;

$R^{4A}$ is unsubstituted C$_{1-3}$ alkyl;

$R^5$ is halogen, cyano, OH, NO$_2$, R$^{5A}$-substituted or unsubstituted C$_{1-6}$ alkyl, R$^{5A}$-substituted or unsubstituted C$_{1-6}$ haloalkyl, R$^{5A}$-substituted or unsubstituted C$_{1-6}$ cyanoalkyl, R$^{5A}$-substituted or unsubstituted C$_{3-6}$ cycloalkyl, R$^{5A}$-substituted or unsubstituted 3-6 membered heterocycle, R$^{5A}$-substituted or unsubstituted phenyl, or R$^{5A}$-substituted or unsubstituted 6 membered heteroaryl;

$R^{5A}$ and $R^{5B}$ are each independently R$^{5C}$-substituted or unsubstituted C$_{1-6}$ alkyl, R$^{5C}$-substituted or unsubstituted C$_{1-6}$ haloalkyl, R$^{5C}$-substituted or unsubstituted C$_{3-7}$ cycloalkyl; R$^{5C}$-substituted or unsubstituted 3-7 membered heterocycle; R$^{5C}$-substituted or unsubstituted C$_{5-7}$ aryl, or R$^{5C}$-substituted or unsubstituted C$_{5-7}$ heteroaryl;

$R^{5C}$ is independently halogen, OH, CN, NO$_2$, R$^{5D}$-substituted or unsubstituted C$_{1-6}$ alkyl, R$^{5D}$-substituted or unsubstituted C$_{1-6}$ haloalkyl, R$^{5D}$-substituted or unsubstituted C$_{3-7}$ cycloalkyl; R$^{5D}$-substituted or unsubstituted C$_{3-7}$ heterocycle; R$^{5D}$-substituted or unsubstituted C$_{5-7}$ aryl, or R$^{5D}$-substituted or unsubstituted C$_{5-7}$ heteroaryl;

$R^{5D}$ is independently halogen, OH, CN, NO$_2$, unsubstituted C$_{1-6}$ alkyl, unsubstituted C$_{1-6}$ haloalkyl, unsubstituted $C_{3-7}$ cycloalkyl; unsubstituted $C_{3-7}$ heterocycle; unsubstituted $C_{5-7}$ aryl, or unsubstituted $C_{5-7}$ heteroaryl;

$R^6$ is halogen, OH, CN, $NO_2$, unsubstituted $C_{1-6}$ alkyl, unsubstituted $C_{1-6}$ haloalkyl, or unsubstituted $C_{3-7}$ cycloalkyl;

n is 0, 1, or 2;

each PG is independently Ac (acetyl), trifluoroacetyl, phthalimide, Bn (benzyl), Tr (triphenylmethyl or trityl), benzylidenyl, p-toluenesulfonyl, DMB (dimethoxybenzyl), PMB (p-methoxybenzyl), Boc (tert-butyloxycarbonyl), Fmoc (9-fluorenylmethyloxycarbonyl) or Cbz (carbobenzyloxy); and $PG^1$ is Ac (acetyl), trifluoroacetyl, Bn (benzyl), Tr (triphenylmethyl or trityl), benzylidenyl, p-toluenesulfonyl, PMB (p-methoxybenzyl), Boc (tert-butyloxycarbonyl), Fmoc (9-fluorenylmethyloxycarbonyl) or Cbz (carbobenzyloxy);

the process comprising the steps:

(a) contacting a compound of formula (II)

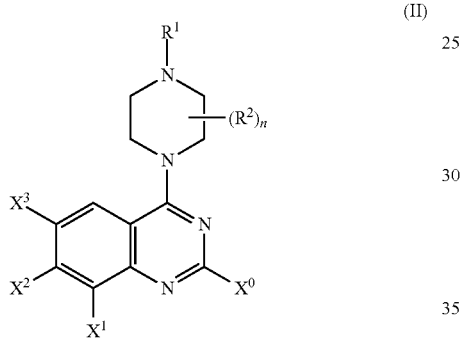

(II)

wherein $X^2$ is halogen;

with (i) an organomagnesium compound selected from the group consisting of isopropylmagnesium chloride, isopropylmagnesium bromide, isopropylmagnesium iodide, isopropylmagnesium chloride lithium chloride complex, sec-butylmagnesium chloride, lithium tri-n-butylmagnesiate, lithium triisopropylmagnesiate, and lithium (isopropyl) (di-n-butyl) magnesiate) and (ii) a zinc complex selected from the group consisting of $ZnCl_2$, $ZnBr_2$, $ZnI_2$, $Zn(OAc)_2$, and $Zn(OPiv)_2$; and (b) contacting the mixture of step (a) with (i) a compound of formula (III),

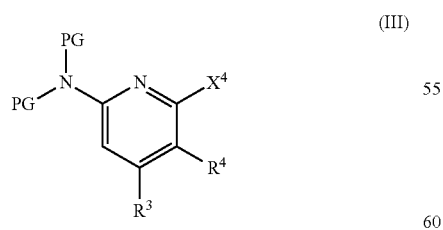

(III)

wherein $X^4$ is halogen;

(ii) a Pd catalyst precursor selected from the group consisting of $Pd(OAc)_2$, $PdCl_2$, $PdCl_2(MeCN)_2$, $Pd(benzonitrile)_2Cl_2$, $Pd(dba)_2$, $Pd_2(dba)_3$, $Pd(PPh_3)_4$, $Pd(PCy_3)_2$, $Pd(PtBu_3)_2$, $Pd(TFA)_2$, $[Pd(allyl)Cl]_2$, $[Pd(cinammyl)Cl]_2$, $[PdCl(crotyl)]_2$, $PdCl(\eta5$-cyclopentadienyl), or $[(\eta3$-allyl$)(\eta5$-cyclopentadienyl$)$ palladium (II)]; and (iii) a chiral ligand comprising a compound of formula:

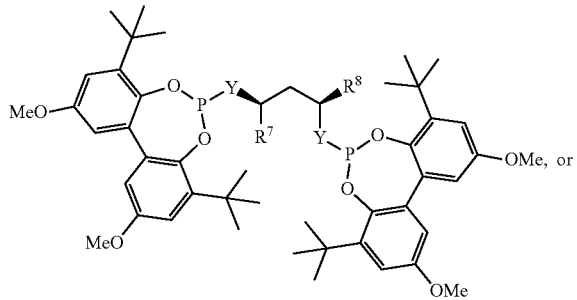

(L1)

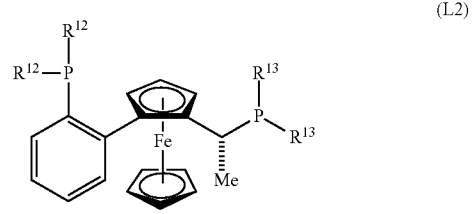

(L2)

wherein

Y is O or $NR^7$;

$R^7$ and $R^8$ are independently unsubstituted $C_{1-6}$ alkyl;

$R^{12}$ and $R^{13}$ are each independently $R^{14}$-substituted or unsubstituted $C_{1-6}$ alky, $R^{14}$-substituted or unsubstituted $C_{3-7}$ cycloalkyl, $R^{14}$-substituted or unsubstituted aryl, or $R^{14}$-substituted or unsubstituted $C_{5-7}$ heteroaryl; and each $R^{14}$ is independently unsubstituted $C_{1-4}$ alkyl;

thereby synthesizing a compound of formula

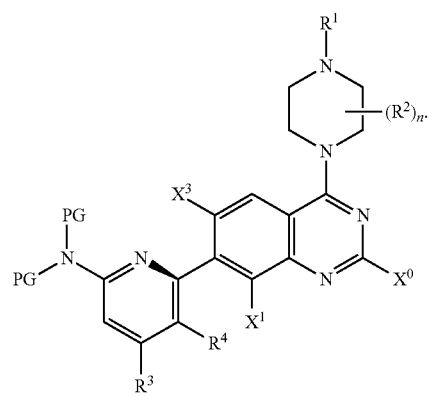

2. The process of claim 1, wherein the compound of formula (II) is prepared according to the method:
(a) contacting the compound of formula (IVa)

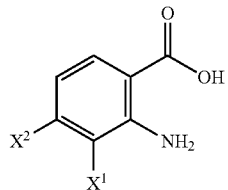
(IVa)

with a halogenating agent having formula

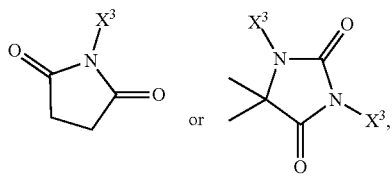

wherein $X^3$ is halogen, to make a compound of formula (IVb)

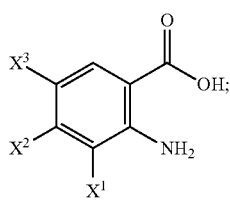
(IVb)

(b) cyclizing the compound of formula (IVb) to a compound of formula (V)

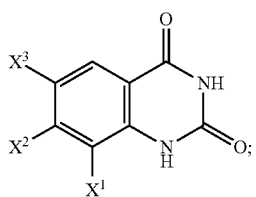
(V)

(c) contacting the compound of formula (V) with a chlorinating agent to make a compound of formula (Va)

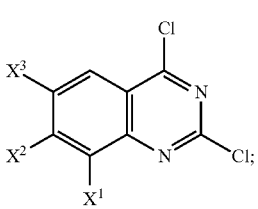
(Va)

and
(d) contacting the compound of formula (Va) with a piperazinyl moiety having formula

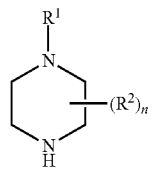
(VI)

to make a compound of formula (IIa)

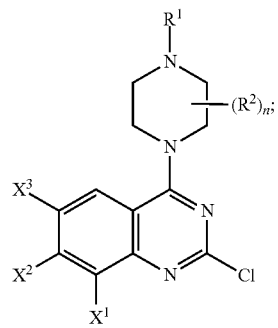
(IIa)

and
(e) contacting the compound of formula (IIa) with a moiety comprising $X^0$ for form a compound of formula (II).

3. The process of claim 2 further comprising step:
(a0) contacting a compound of formula (IV)

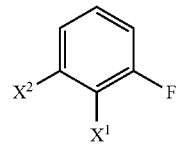

with a base in the presence of $CO_2$ gas and aminating the compound to form the compound of formula (IVa)

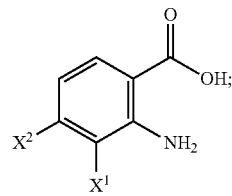
(IVa)

4. The process of claim 2, wherein:
the halogenating agent is NCS or 1,3-dichloro-5,5-dimethylhydantoin; and
the chlorinating agent is $POCl_3$, $PCl_3$, $PCl_5$, or $SOCl_2$.

5. The process of claim 2, wherein step (e) further comprises:
step (g) fluorinating the compound of formula (IIa) to a compound of formula (IIa1)

(IIa1)

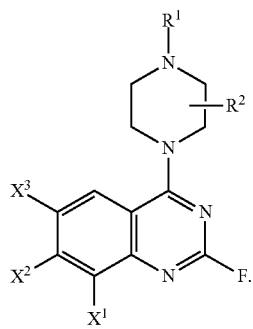

6. The process of claim 2, wherein step (e) further comprises:
    step (h) alkoxylating the compound of formula (IIa) to a compound of formula (IId)

(IIa2)

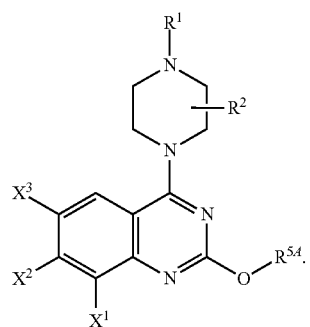

7. The process of claim 1, wherein the compound of formula (III) is prepared according to the method:
    (a) contacting a compound of formula (VII)

(VII)

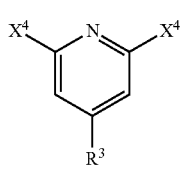

with a compound having formula $NH_2(PG)$ thereby making a compound of formula (VIIa)

(VIIa)

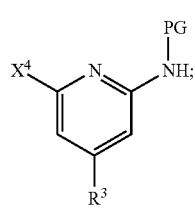

(b) contacting the compound of formula (VIIa) with a compound having formula $X^aPG$, wherein $X^a$ is halogen, to make a compound of formula (VIIb)

(VIIb)

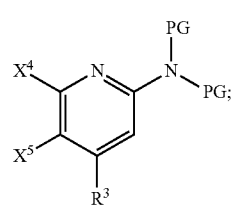

(c) contacting the compound of formula (VIIb) with a halogenating agent having formula

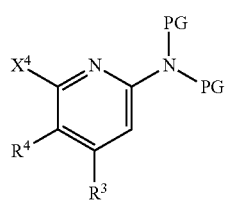

wherein $X^5$ is halogen, to make a compound of formula of formula (VIIc)

(VIIc)

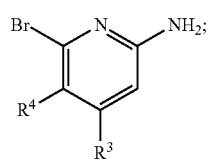

(d) haloalkylating the compound of formula (VIIc) with a haloalkylation agent to make a compound of formula (VIId)

(VIId)

(e) brominating the compound of formula (VIId) to make a compound of formula (VIIe)

(VIIe)

and
(f) contacting the compound of formula (VIIe) with $X^aPG$ to make a compound of formula (III).

8. The process of claim 7, wherein:

the halogenating agent is NIS or 1,3-diiodomo-5,5-dimethylhydantoin;

and the haloalkylation agent is a fluoroalkylation agent.

9. The process of claim 7, wherein the haloalkylation agent is methyl 2,2-difluoro-2-(fluorosulfonyl)acetate.

10. The process of claim 1, wherein the compound of formula (III) is prepared according to the method:

(a) contacting a compound of formula (VIII)

wherein $X^6$ is Cl or I, with a halogenating agent to form a compound of formula (VIIIa)

(b) brominating the compound of formula (VIIIa) to form a compound of formula (VIIIb)

and (c) contacting the compound of formula (VIIIb) with a compound having formula $NH(PG)_2$ thereby making a compound of formula (III).

11. The process of claim 1, wherein the compound of formula (III) is prepared according to the method:

(a) contacting a compound of formula (VIIIc)

with a brominating agent to form a compound of formula (VIIId)

(b) contacting the compound of formula (VIIId) with a halogenating agent to form a compound of formula (VIIIb)

(c) contacting the compound of formula (VIIIb) with a compound having formula $NH(PG)_2$ thereby making a compound of formula (III).

12. The process of claim 11, wherein the halogenating agent is $SF_4$ in HF.

13. The process of claim 1, wherein $X^1$ is halogen.

14. The process of claim 13, wherein $X^1$ is F or Cl.

15. The process of claim 1, wherein $X^3$ is halogen, unsubstituted $C_{1-4}$ alkyl, or unsubstituted $C_{1-3}$ haloalkyl.

16. The process of claim 1, wherein $X^3$ is Cl, F, $CF_3$, $CHF_2$, or $CH_2F$.

17. The process of claim 1, wherein $R^1$ is $PG^1$ and $PG^1$ is Boc (tert-butyloxycarbonyl).

18. The process of claim 1, wherein $R^2$ is unsubstituted $C_{1-6}$ alkyl, unsubstituted $C_{1-6}$ cyanoalkyl, or unsubstituted $C_{1-6}$ haloalkyl.

19. The process of claim 1, wherein $R^2$ is methyl, ethyl, $CH_2CN$, $CF_3$, $CHF_2$, or $CH_2F$.

20. The process of claim 1, wherein $R^3$ is hydrogen or $R^{3A}$-substituted or unsubstituted $C_{1-3}$ alkyl.

21. The process of claim 1, wherein $R^4$ is $CF_3$, $CHF_2$, or $CH_2F$.

22. The process of claim 1, wherein each PG is PMB (p-methoxybenzyl).

23. The process of claim 1, wherein $R^1$ is $PG^1$ and $PG^1$ is Boc and each PG is p-methoxybenzyl.

24. The process of claim 1, wherein the organomagnesium compound is selected from the group consisting of isopropylmagnesium chloride, isopropylmagnesium bromide, or isopropylmagnesium chloride lithium chloride complex.

25. The process of claim 1, wherein the zinc complex is $ZnCl_2$ or $Zn(OPiv)_2$.

26. The process of claim 1, wherein the Pd catalyst precursor is selected from the group consisting of $Pd(OAc)_2$, $PdCl_2$, $[Pd(allyl)Cl]_2$, or $[Pd(cinammyl)Cl]_2$.

27. The process of claim 1, wherein the chiral ligand is

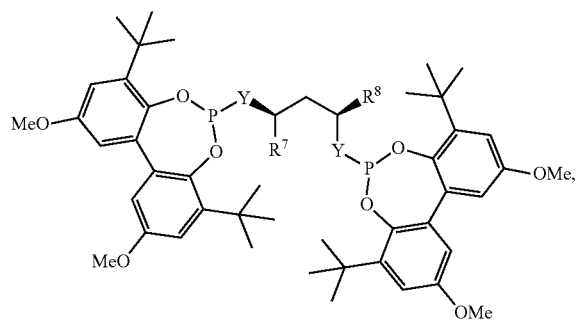
(L1)

wherein
Y is O;
$R^7$ and $R^8$ are independently unsubstituted $C_{1-6}$ alkyl;
$R^{12}$ and $R^{13}$ are each independently $R^{14}$-substituted or unsubstituted $C_{1-6}$ alky, $R^{14}$-substituted or unsubstituted $C_{3-7}$ cycloalkyl, $R^{14}$-substituted or unsubstituted aryl, or $R^{14}$-substituted or unsubstituted $C_{5-7}$ heteroaryl;
each $R^{14}$ is independently unsubstituted $C_{1-4}$ alkyl.

28. The process of claim 27, wherein $R^7$ and $R^8$ are the same.

29. The process of claim 28, wherein $R^7$ and $R^8$ are each methyl, ethyl, or phenyl.

30. The process claim 1, wherein the chiral ligand is:

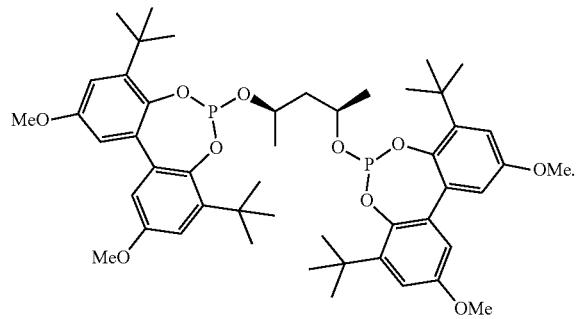 [SMILES: COc1cc(C(C)(C)C)c2op(O[C@H](C)C[C@@H](C)Op3oc4c(C(C)(C)C)cc(OC)cc4c4cc(OC)cc(C(C)(C)C)c4o3)oc3c(C(C)(C)C)cc(OC)cc3c2c1]

31. The process of claim 1, wherein the compound of formula (II) has the formula:

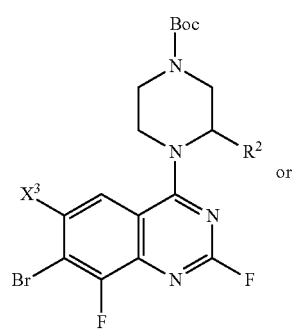
(IIe1)

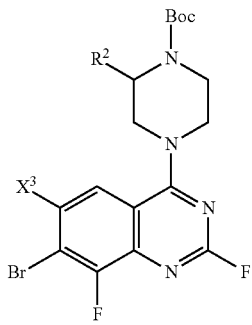
(IIe2)

wherein $X^3$ is halogen.

32. The process of claim 1, wherein the compound of formula (II) has the formula:

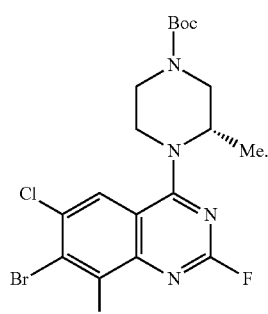
(2)

33. The process of claim 1, wherein the compound of formula (III) has the formula:

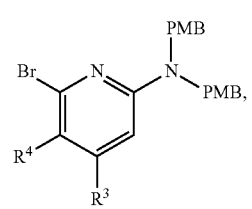
(III2)

wherein $R^3$ is unsubstituted $C_{1-3}$ alkyl and $R^4$ is unsubstituted $C_{1-3}$ haloalkyl.

34. The process of claim 1, wherein the compound of formula (III) has the formula:

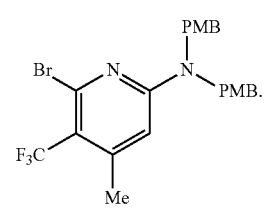
(3)

35. The process of claim 1, wherein the compound or a solvate, tautomer, stereoisomer, or salt thereof has the formula:

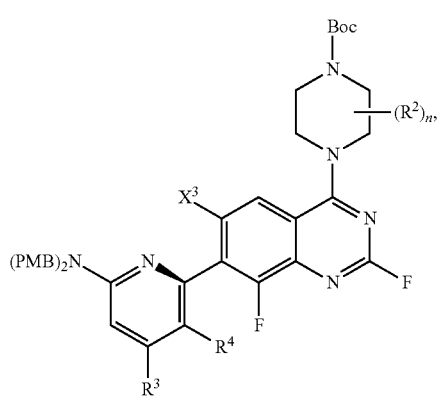

(Ib3)

wherein
R² is unsubstituted $C_{1-6}$ alkyl, unsubstituted $C_{1-6}$ cyanoalkyl, or unsubstituted $C_{1-6}$ haloalkyl; and
R³ is unsubstituted $C_{1-3}$ alkyl; and
R⁴ is unsubstituted $C_{1-3}$ haloalkyl.

36. The process claim 35, wherein the solvate is a cyclohexane, methylcyclohexane, chlorobenzene, ethylbenzene, m-xylene, or toluene solvate thereof of the compound of formula Ib3.

37. The process of claim 1, wherein the compound of formula or a solvate, tautomer, stereoisomer, or salt thereof has the formula:

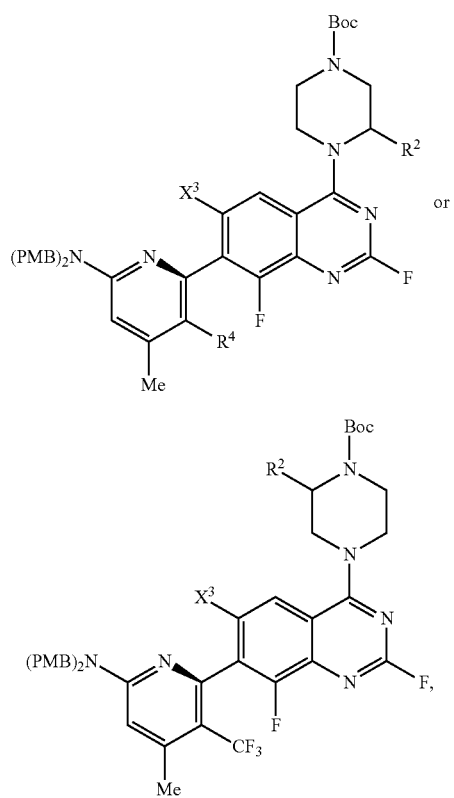

wherein R² is unsubstituted $C_{1-6}$ alkyl, unsubstituted $C_{1-6}$ cyanoalkyl, or unsubstituted $C_{1-6}$ haloalkyl; and X³ is halogen.

38. The process of claim 37, wherein R² is methyl, ethyl, CN, CH₂CN, CF₃, CHF₂, or CH₂F.

39. The process claim 37, wherein the solvate is a cyclohexane, methylcyclohexane, chlorobenzene, ethylbenzene, m-xylene, or toluene solvate thereof of the compound of formula Ic1 or Ic2.

40. The process of claim 1, wherein the compound or a solvate, tautomer, stereoisomer, or salt thereof has the formula:

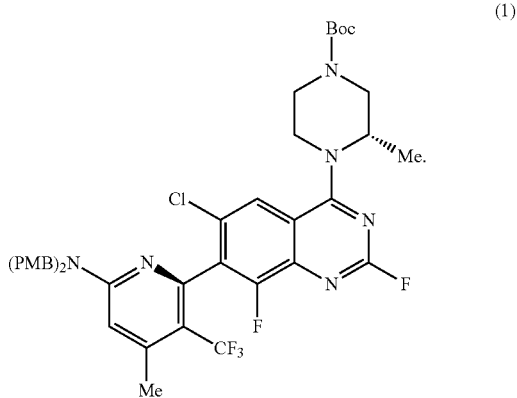

41. The process claim 40, wherein the solvate is a cyclohexane, methylcyclohexane, chlorobenzene, ethylbenzene, m-xylene, or toluene solvate thereof of the compound of formula 1.

42. The process of claim 1, wherein X⁰ is hydrogen, halogen, CF₃, CHF₂, CH₂F, or a moiety having structure:

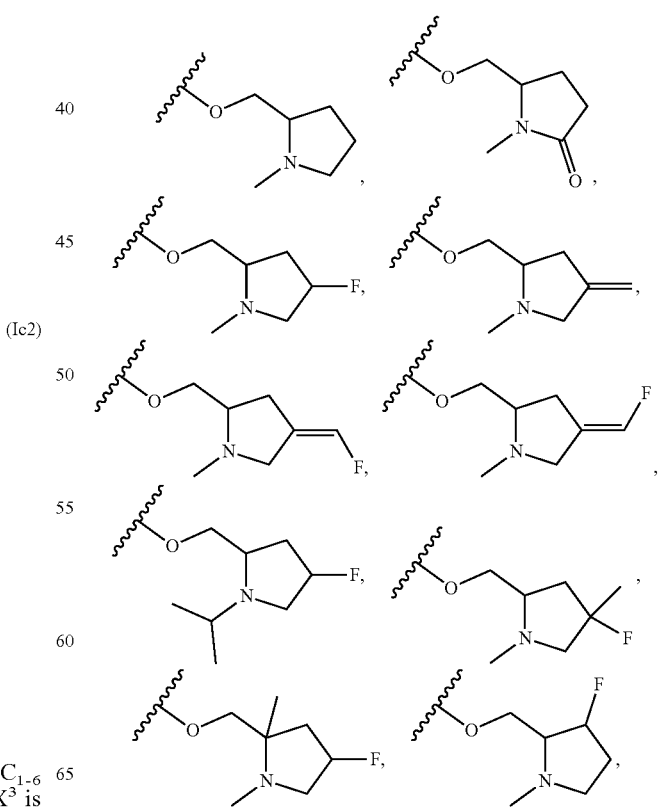

227
-continued
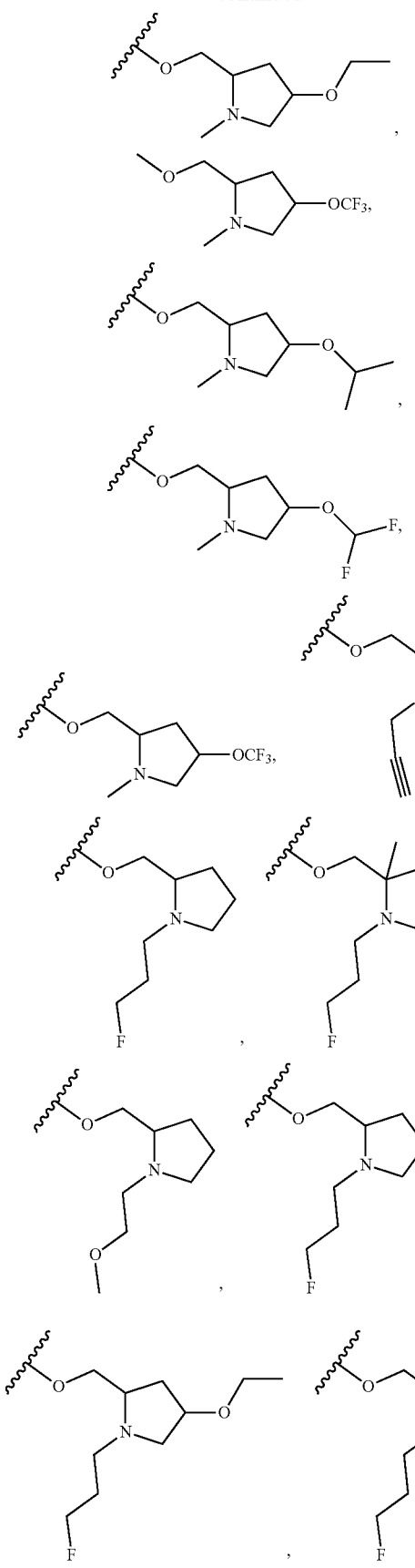
228
-continued
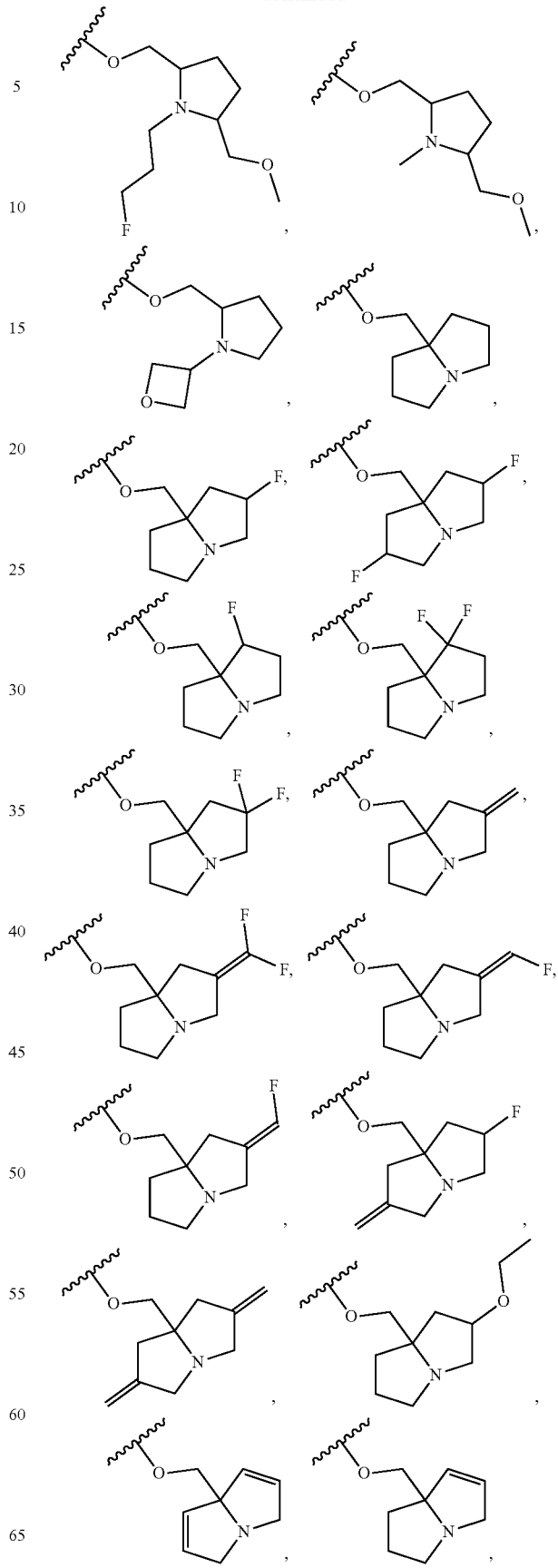

229
-continued
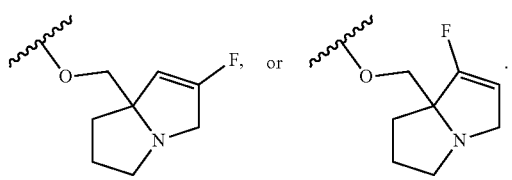
43. The process of claim 1, wherein the compound or a solvate, tautomer, stereoisomer, or salt thereof has the structure:
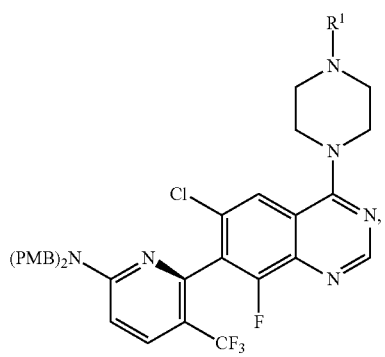
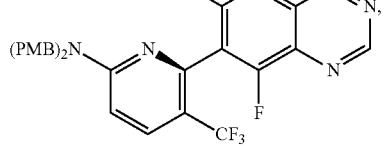
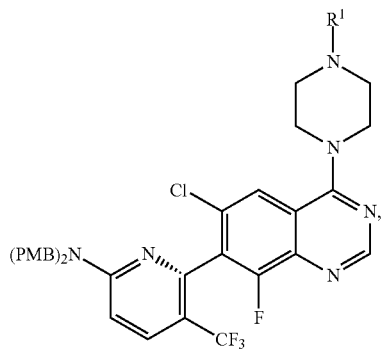
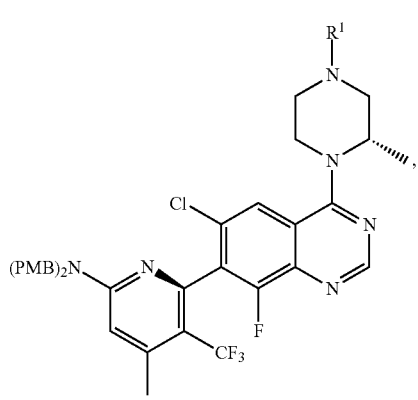
230
-continued
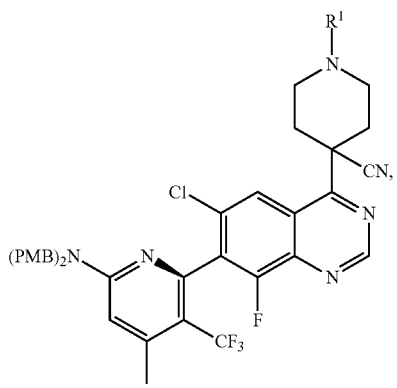
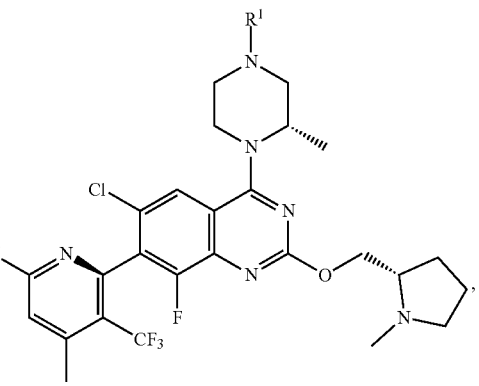
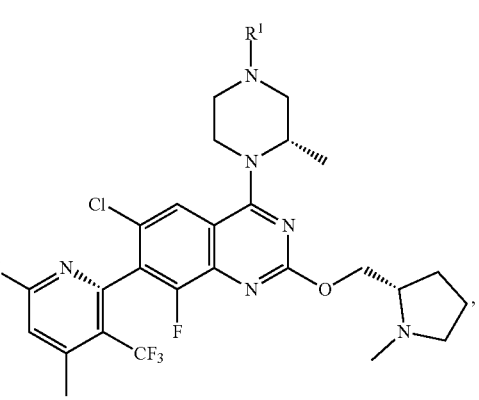
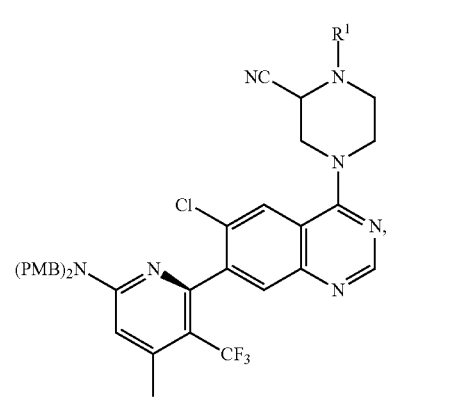

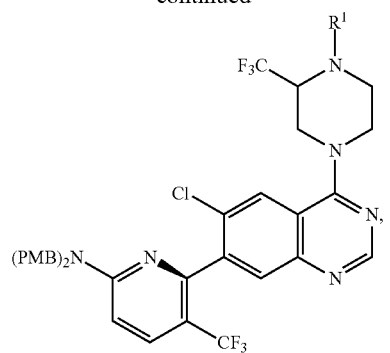
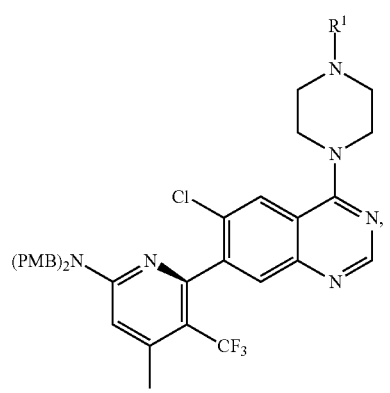
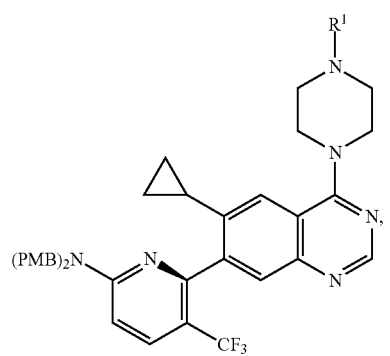
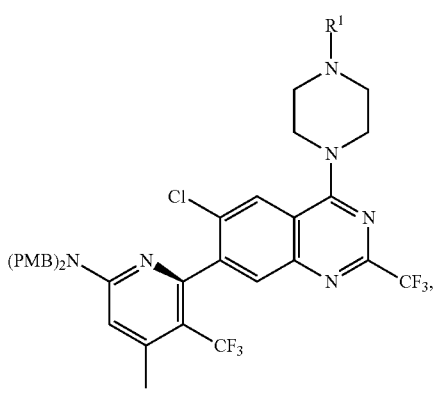
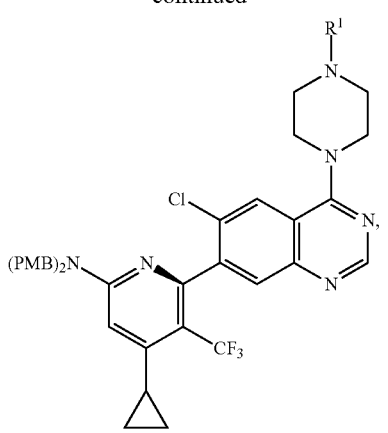
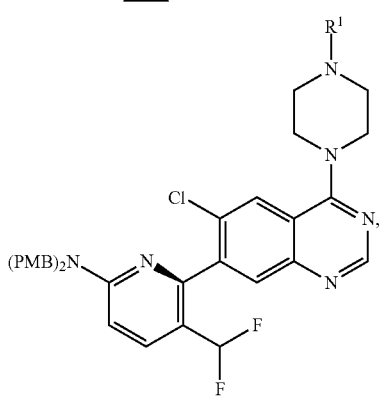
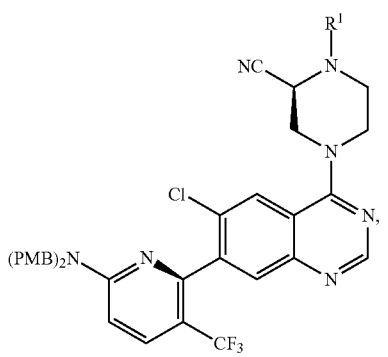
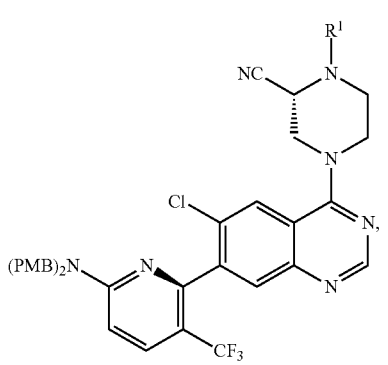

233
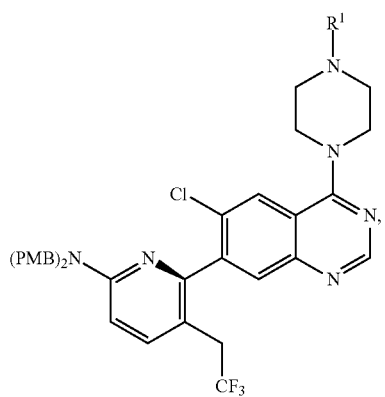
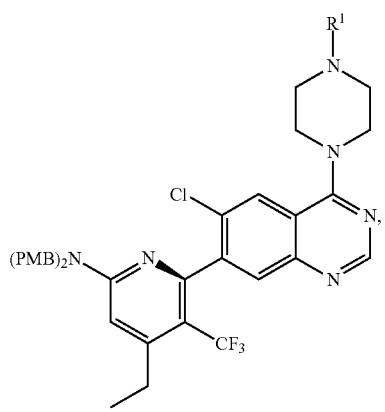
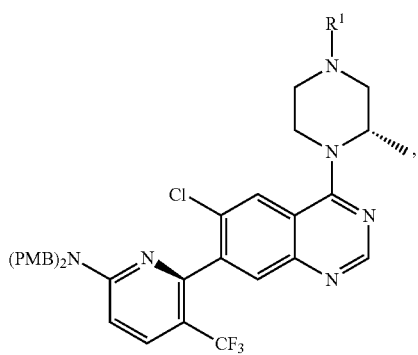
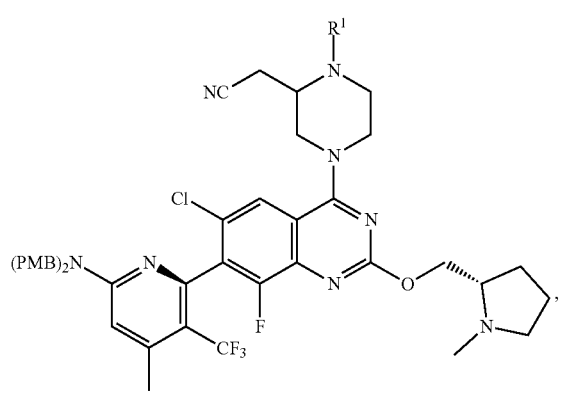
234
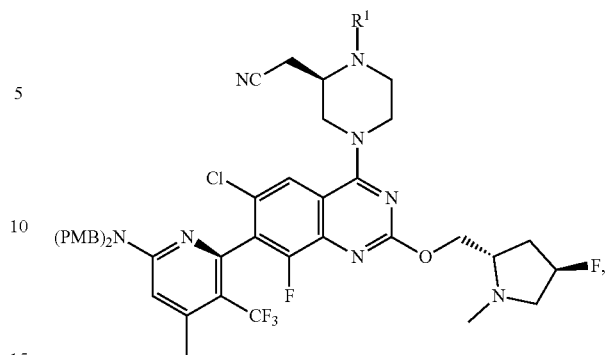
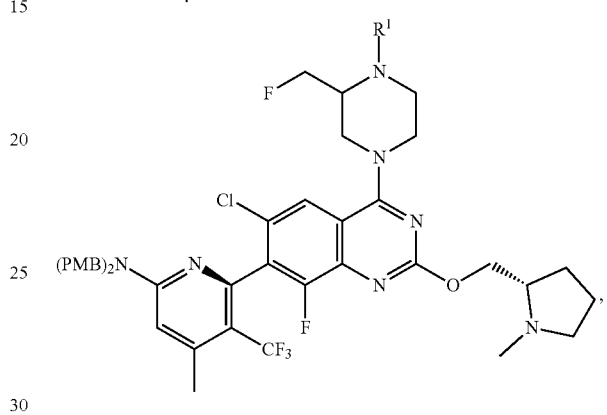
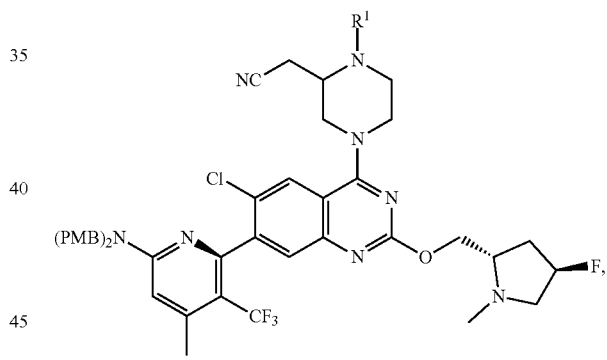
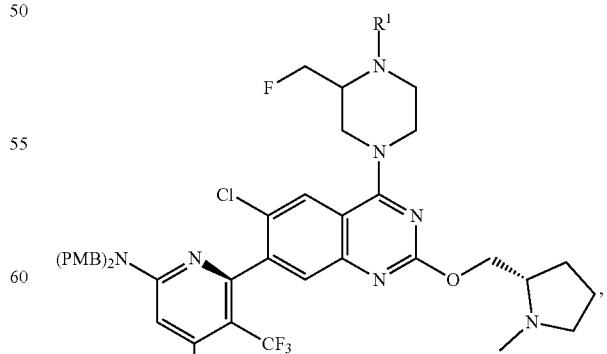

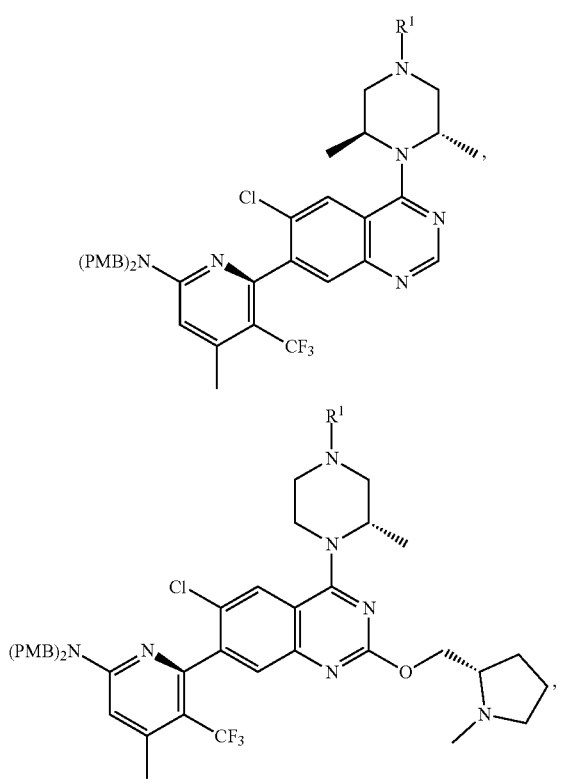
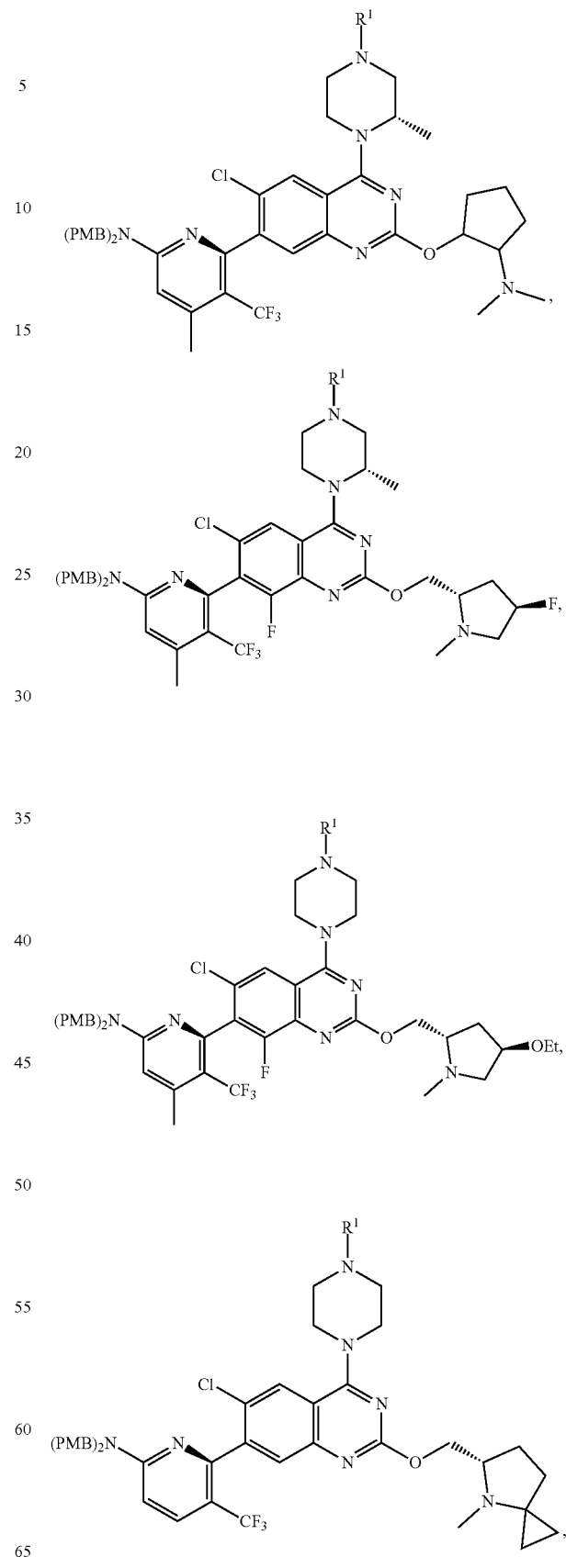

-continued
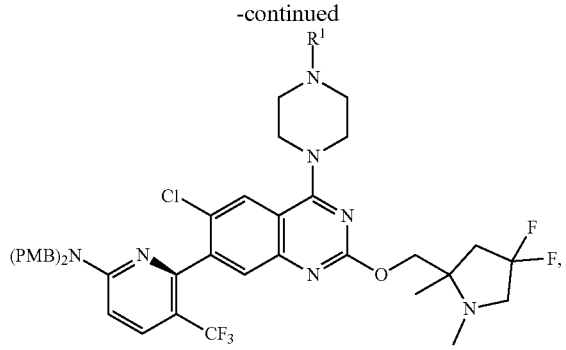
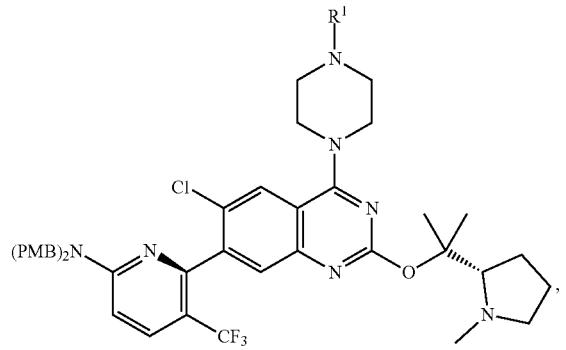
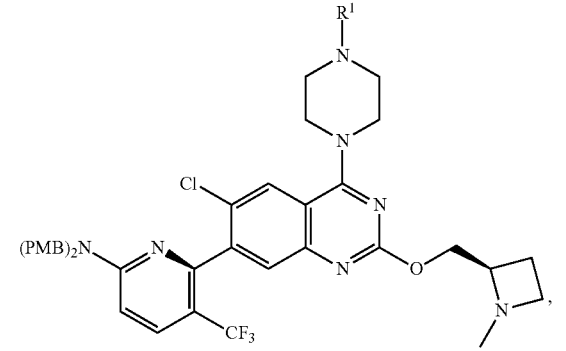
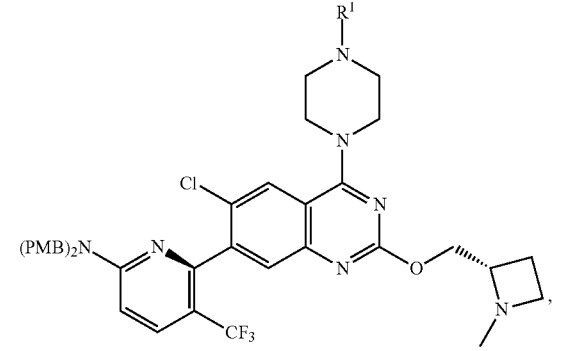
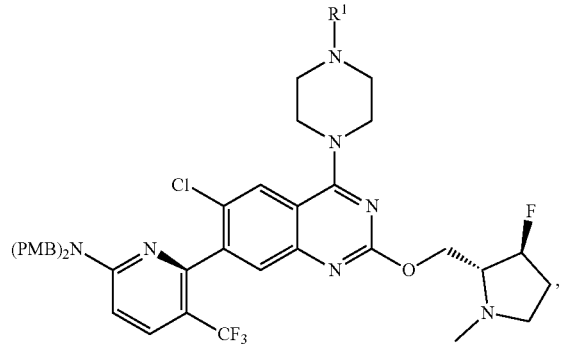
-continued
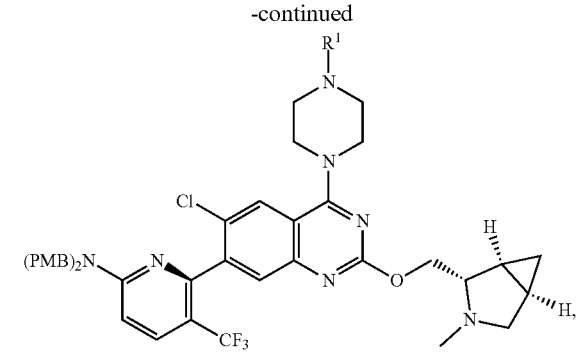
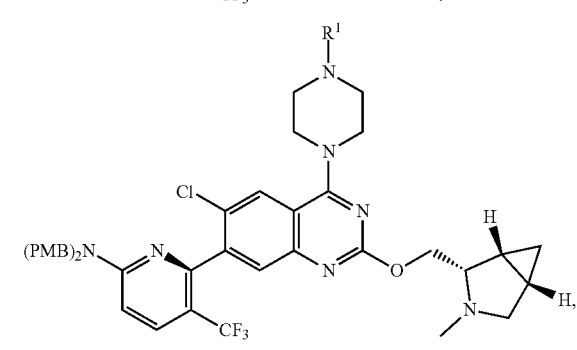
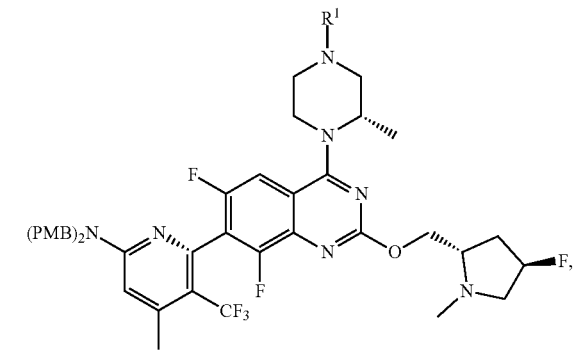
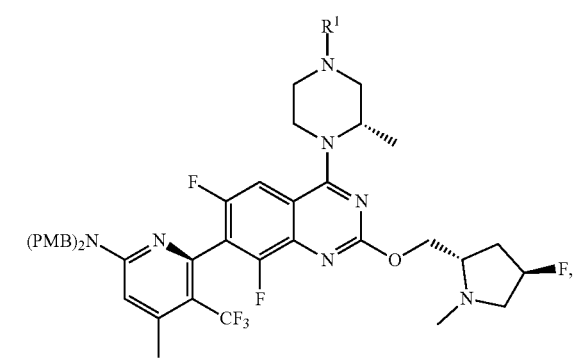
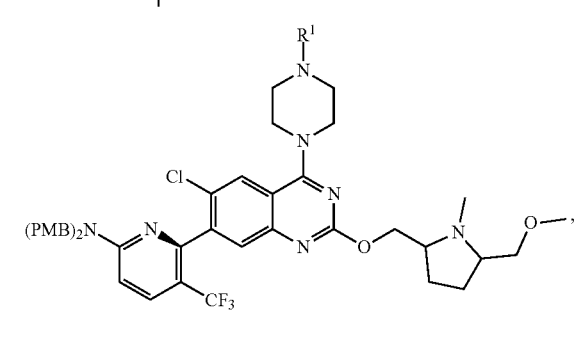

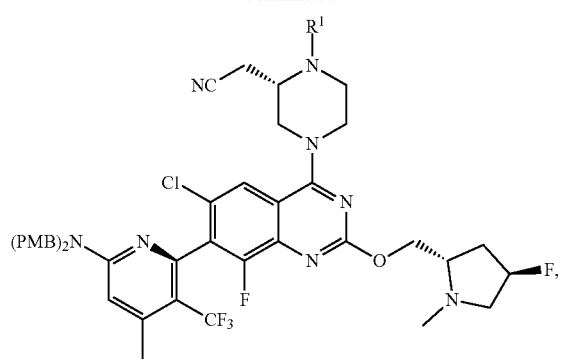
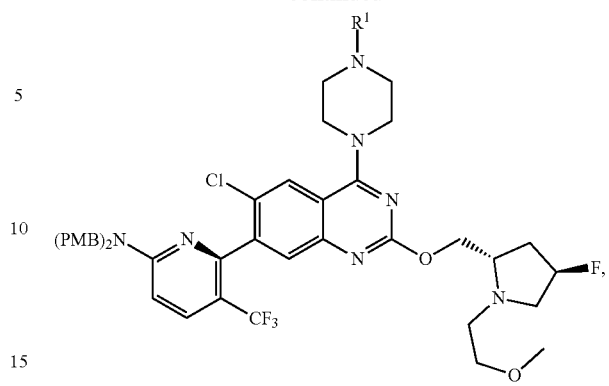
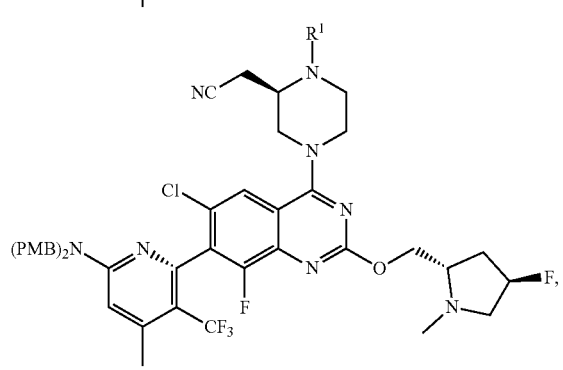
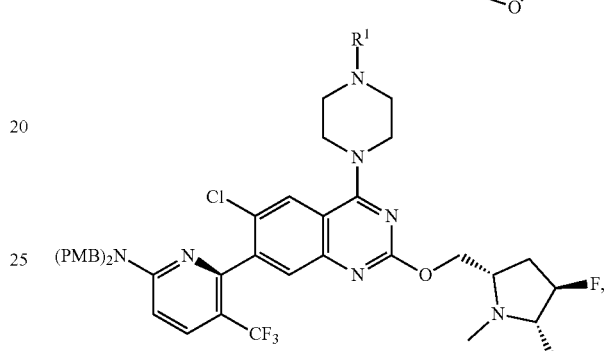
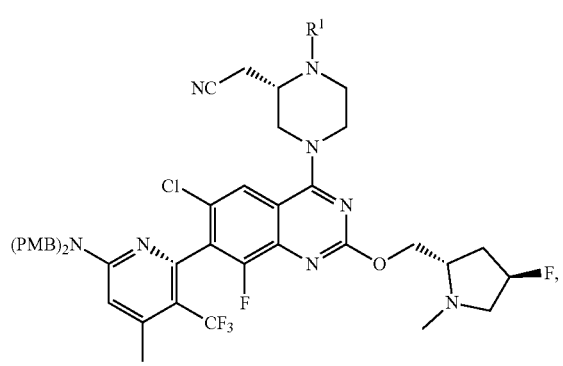
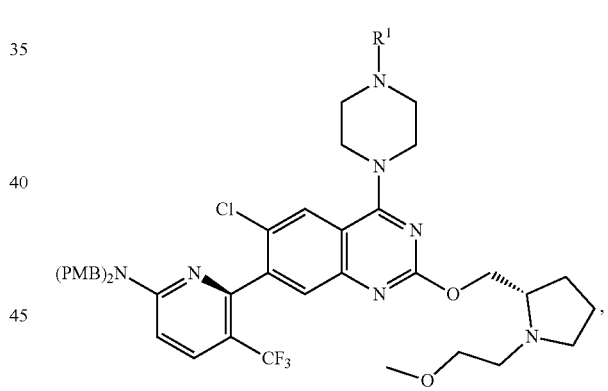
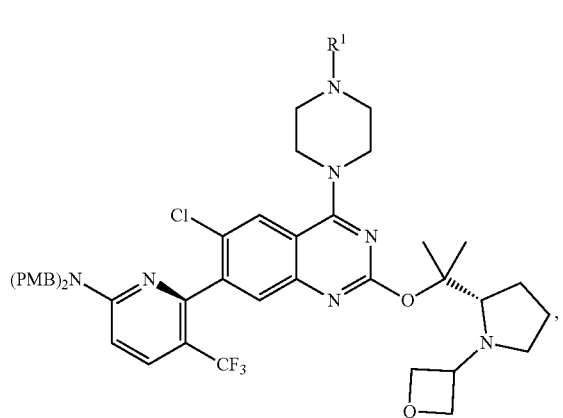
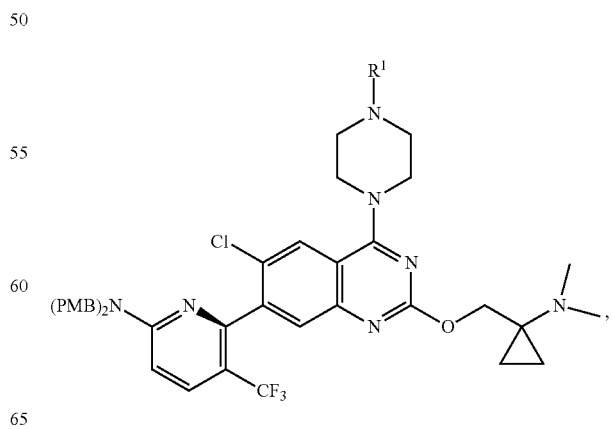

241

-continued

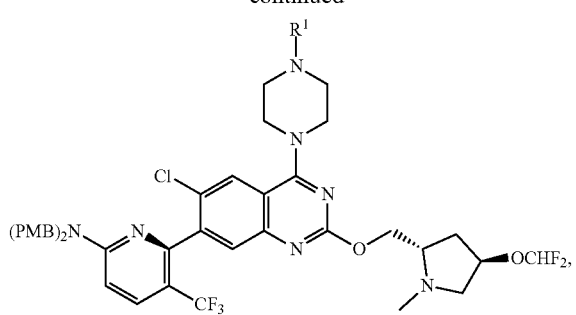

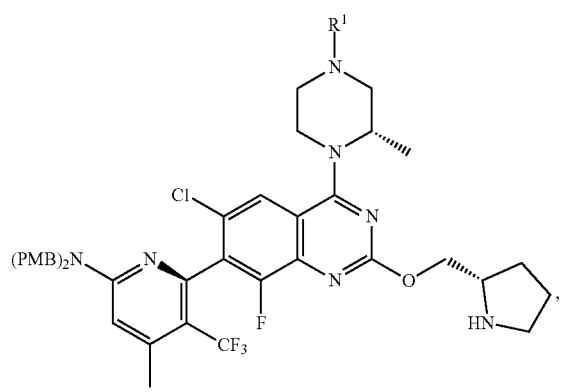

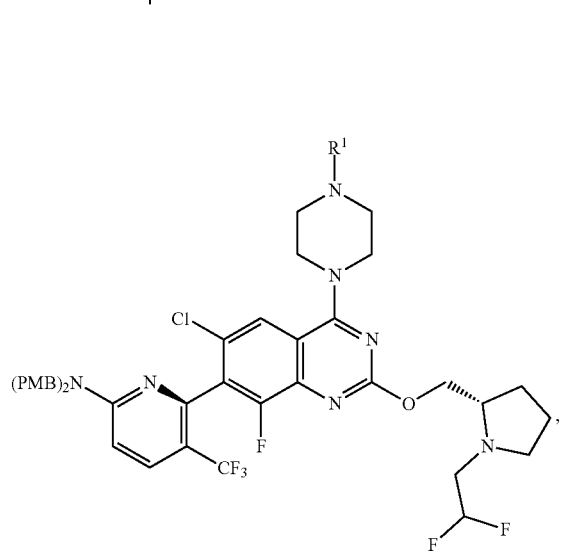

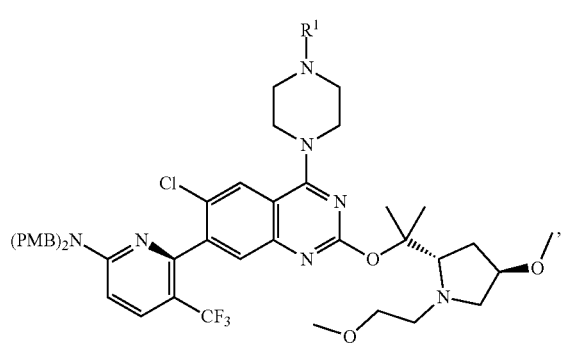

242

-continued

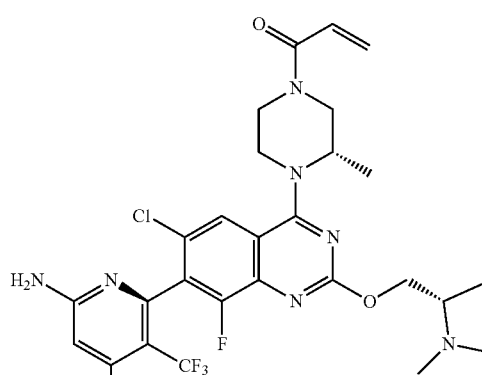, or

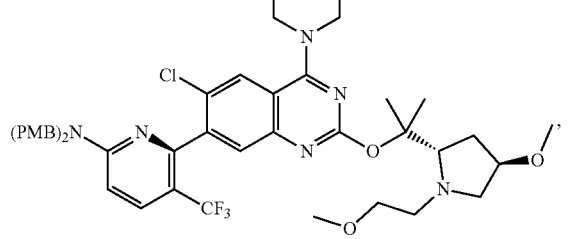

44. The process claim 43, wherein the solvate is a cyclohexane, methylcyclohexane, chlorobenzene, ethylbenzene, m-xylene, or toluene solvate thereof.

45. The process claim 1, wherein the solvate is a cyclohexane, methylcyclohexane, chlorobenzene, ethylbenzene, m-xylene, or toluene solvate thereof.

46. A process for the synthesis of a compound having formula

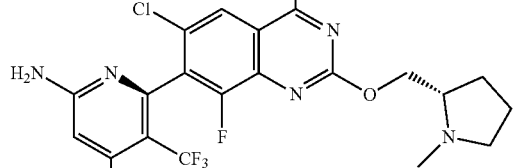

(A)

or a pharmaceutically acceptable salt thereof, the process comprising (a) contacting a compound of formula (2)

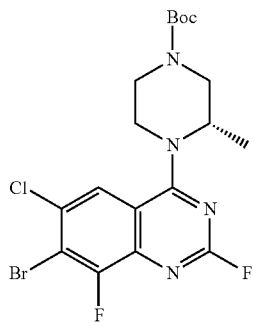

or a salt thereof with i-PrMgCl·LiCl and ZnCl$_2$, followed by NaTFA and a compound of formula (3)

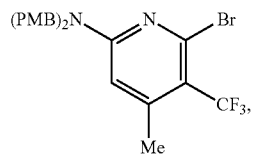

(b) contacting the mixture of step (a) or a salt thereof with a Pd or Ni catalyst precursor and a chiral ligand thereby synthesizing a compound of formula (1)

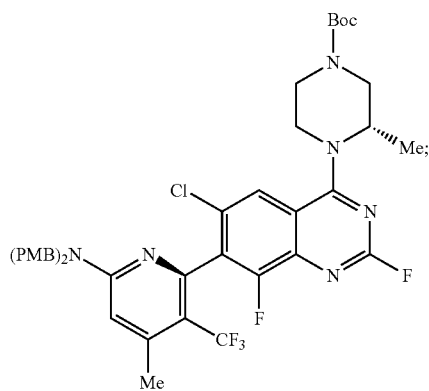
(1)

or a solvate or salt thereof, (c) contacting the compound of formula (1) or a solvate or salt thereof, with a compound of formula HO—X$^A$, wherein X$^A$ has formula

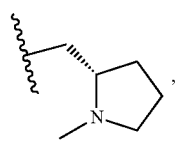 [SMILES: *C[C@@H]1CCCN1C]

and a base thereby synthesizing a compound of formula (1d);

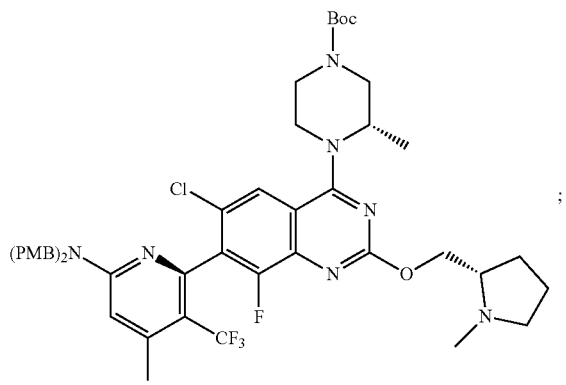
(1d)

or a solvate or pharmaceutically acceptable salt thereof;

(d) contacting the compound of formula (1d) with MsOH in an acid thereby synthesizing a compound of formula (1e);

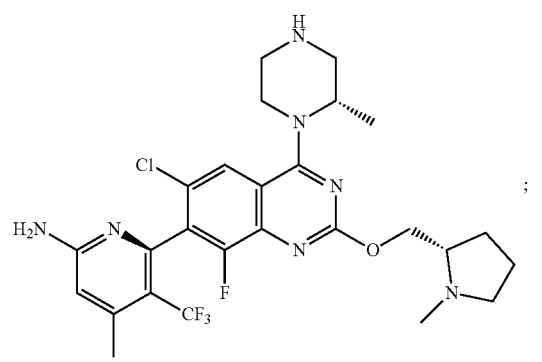
(1e)

or a solvate or pharmaceutically acceptable salt thereof; and (e) contacting the compound of formula (1e) or a solvate or pharmaceutically acceptable salt thereof with

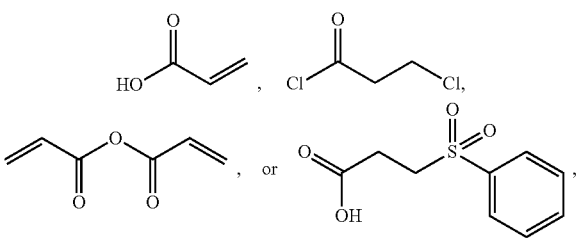

in the presence of a base and optionally an activating agent, thereby making a compound of formula (A) or a pharmaceutically acceptable salt thereof.

47. The process of claim 46, wherein the acid of step (d) is AcOH, trifluoroacetic acid, chlorosulfonic acid, sulfuric acid, HCl, HBr, p-toluenesulfonic acid, or trifluoromethanesulfonic acid.

48. The process of claim 46, wherein step (e) comprises contacting the compound of formula (1e) or a solvate or pharmaceutically acceptable salt thereof with 245
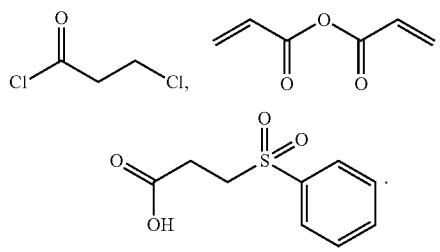
49. The process of claim 46 wherein step (e) comprises the compound of formula
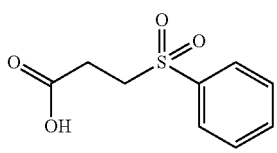 [SMILES: O=C(O)CCS(=O)(=O)c1ccccc1]
in the presence of a base and an activating agent.
50. The process claim 46, further comprising step:
(f) contacting the compound of formula (A) with adipic acid in a solvent according to the method of:
Scheme 1
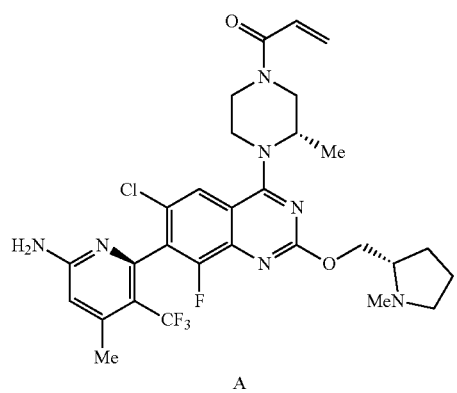
246
Scheme 2
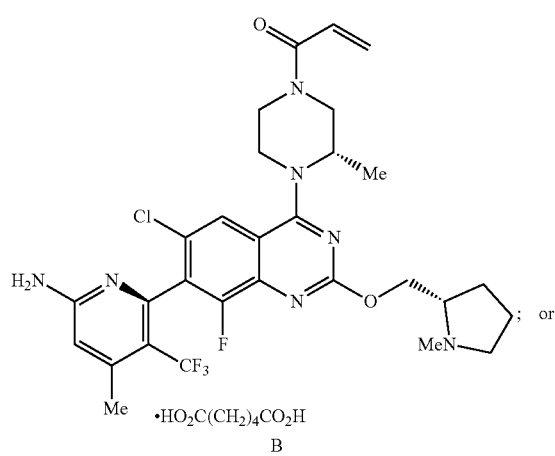
Scheme 3
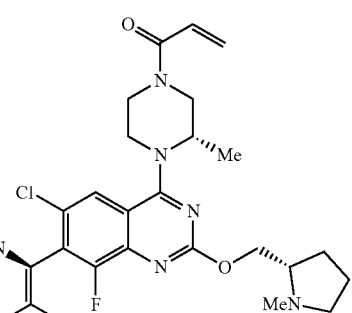
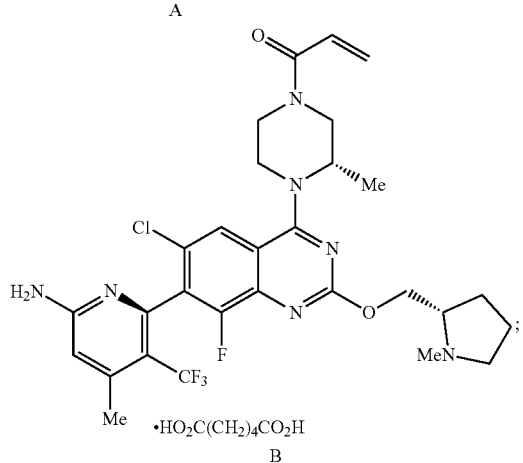

-continued
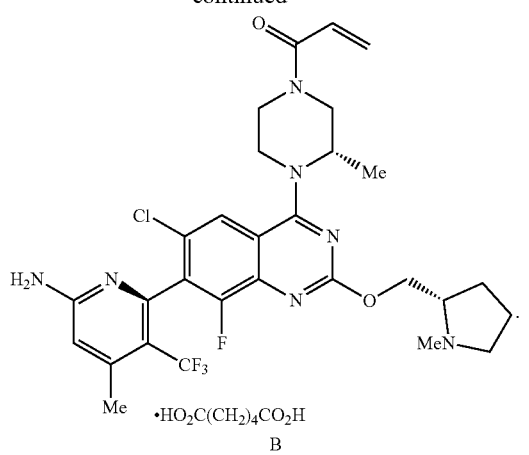
B
51. The process claim 46, wherein the chiral ligand is:
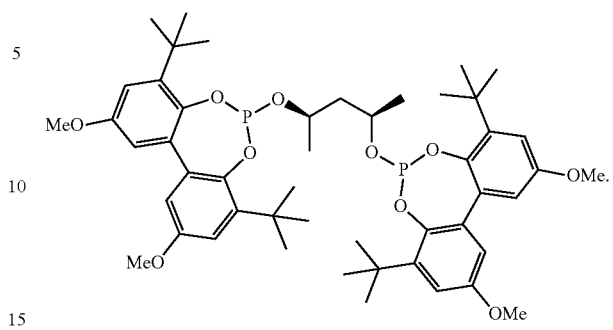
52. The process claim 46, wherein the solvate is a cyclohexane, methylcyclohexane, chlorobenzene, ethylbenzene, m-xylene, or toluene solvate thereof of the compound of formula 1.
* * * * *